US009127060B2

(12) United States Patent
Geles et al.

(10) Patent No.: US 9,127,060 B2
(45) Date of Patent: Sep. 8, 2015

(54) ANTI-NOTCH1 ANTIBODIES

(75) Inventors: Kenneth G. Geles, Nyack, NY (US);
Bin-Bing Stephen Zhou, Rohnert Park, CA (US); Lioudmila Gennadievna Tchistiakova, Stoneham, MA (US);
Yijie Gao, Chestnut Hill, MA (US); Joel Bard, Newton, MA (US)

(73) Assignee: Wyeth LLC, New York, NY (US)

( * ) Notice: Subject to any disclaimer, the term of this patent is extended or adjusted under 35 U.S.C. 154(b) by 0 days.

(21) Appl. No.: 13/994,349

(22) PCT Filed: Dec. 9, 2011

(86) PCT No.: PCT/IB2011/055595
§ 371 (c)(1),
(2), (4) Date: Jun. 14, 2013

(87) PCT Pub. No.: WO2012/080926
PCT Pub. Date: Jun. 21, 2012

(65) Prior Publication Data
US 2013/0266594 A1 Oct. 10, 2013

Related U.S. Application Data

(60) Provisional application No. 61/423,578, filed on Dec. 15, 2010, provisional application No. 61/552,578, filed on Oct. 28, 2011.

(51) Int. Cl.
C07K 16/28 (2006.01)
A61K 39/00 (2006.01)

(52) U.S. Cl.
CPC .......... *C07K 16/28* (2013.01); *A61K 2039/505* (2013.01); *C07K 2317/34* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| 4,683,195 | A | 7/1987 | Mullis et al. |
|---|---|---|---|
| 4,683,202 | A | 7/1987 | Mullis et al. |
| 4,754,065 | A | 6/1988 | Levenson et al. |
| 4,800,159 | A | 1/1989 | Mullis et al. |
| 4,816,567 | A | 3/1989 | Cabilly et al. |
| 5,047,335 | A | 9/1991 | Paulson et al. |
| 5,225,539 | A | 7/1993 | Winter et al. |
| 5,278,299 | A | 1/1994 | Wong et al. |
| 5,510,261 | A | 4/1996 | Goochee et al. |
| 5,530,101 | A | 6/1996 | Queen et al. |
| 5,565,332 | A | 10/1996 | Hoogenboom |
| 5,580,717 | A | 12/1996 | Dower et al. |
| 5,585,089 | A | 12/1996 | Queen et al. |
| 5,624,821 | A | 4/1997 | Winter et al. |
| 5,648,260 | A | 7/1997 | Winter et al. |
| 5,677,425 | A | 10/1997 | Bodmer et al. |
| 5,693,761 | A | 12/1997 | Queen et al. |
| 5,693,762 | A | 12/1997 | Queen et al. |
| 5,714,350 | A | 2/1998 | Co et al. |
| 5,733,743 | A | 3/1998 | Johnson et al. |
| 5,786,158 | A | 7/1998 | Artavanis-Tsakonas et al. |
| 5,807,715 | A | 9/1998 | Morrison et al. |
| 5,866,692 | A | 2/1999 | Shitara et al. |
| 5,869,046 | A | 2/1999 | Presta et al. |
| 5,997,867 | A | 12/1999 | Waldmann et al. |
| 6,054,297 | A | 4/2000 | Carter et al. |
| 6,121,022 | A | 9/2000 | Presta et al. |
| 6,165,745 | A | 12/2000 | Ward et al. |
| 6,180,370 | B1 | 1/2001 | Queen et al. |
| 6,180,377 | B1 | 1/2001 | Morgan et al. |
| 6,194,551 | B1 | 2/2001 | Idusogie et al. |
| 6,210,671 | B1 | 4/2001 | Co et al. |
| 6,265,150 | B1 | 7/2001 | Terstappen et al. |
| 6,277,375 | B1 | 8/2001 | Ward |
| 6,331,415 | B1 | 12/2001 | Cabilly et al. |
| 6,350,861 | B1 | 2/2002 | Co et al. |
| 7,666,982 | B2 | 2/2010 | Okochi et al. |
| 7,919,092 | B2 | 4/2011 | Lewicki et al. |
| 2003/0148954 | A1 | 8/2003 | Bresnick et al. |
| 2004/0110704 | A1 | 6/2004 | Yamane et al. |
| 2005/0026831 | A1 | 2/2005 | Bodmer et al. |
| 2007/0071742 | A1 | 3/2007 | Fang et al. |
| 2007/0072222 | A1 | 3/2007 | Boess et al. |
| 2008/0206753 | A1 | 8/2008 | Egan et al. |
| 2008/0220416 | A1 | 9/2008 | Miele et al. |
| 2008/0241150 | A1 | 10/2008 | Blacklow et al. |
| 2008/0267971 | A1 | 10/2008 | Green et al. |
| 2009/0081238 | A1 | 3/2009 | Siebel et al. |
| 2009/0137470 | A1 | 5/2009 | Stylianou |

(Continued)

FOREIGN PATENT DOCUMENTS

| EP | 0154316 B1 | 9/1985 |
|---|---|---|
| EP | 0401384 B1 | 12/1990 |

(Continued)

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
McCafferty et al, "Phage Antibodies: Filamentous Phage Displaying Antibody Variable Domains", Nature 348:552-554 (1990).
Morgan et al, "The N-Terminal End of the CH2 Domain of Chimeric Human IgG1 Anti-HLA-DR is Necessary for C1q, FcγRI and FcγRIII Binding", Immunology 86:319-324 (1995).

(Continued)

*Primary Examiner* — Brian J Gangle
*Assistant Examiner* — Andrea McCollum
(74) *Attorney, Agent, or Firm* — Carol A. McKeever

(57) ABSTRACT

The present invention provides for antibodies that bind to Notch1. The present disclosure also provides methods of making the antibodies, pharmaceutical compositions comprising these antibodies and methods of treating disorders with the antibodies and pharmaceutical compositions.

9 Claims, 28 Drawing Sheets

(56) References Cited

U.S. PATENT DOCUMENTS

| | | | |
|---|---|---|---|
| 2009/0155256 A1 | 6/2009 | Black et al. | |
| 2010/0062012 A1 | 3/2010 | Ioannides et al. | |
| 2012/0093813 A1 | 4/2012 | Li et al. | |

FOREIGN PATENT DOCUMENTS

| | | | |
|---|---|---|---|
| EP | 0519596 A1 | 12/1992 | |
| EP | 1176195 A1 | 1/2002 | |
| WO | 87/04462 A1 | 7/1987 | |
| WO | 93/06213 A1 | 4/1993 | |
| WO | WO 94/07474 A1 | 4/1994 | |
| WO | 94/29351 A2 | 12/1994 | |
| WO | 99/54342 A1 | 10/1999 | |
| WO | 99/58572 A1 | 11/1999 | |
| WO | WO 00/20576 A2 | 4/2000 | |
| WO | 00/42072 A2 | 7/2000 | |
| WO | 01/27160 A1 | 4/2001 | |
| WO | 02/059285 A1 | 8/2002 | |
| WO | 03/035835 A2 | 5/2003 | |
| WO | 2004/058184 A2 | 7/2004 | |
| WO | WO 2005/054434 A2 | 6/2005 | |
| WO | WO 2006/015375 A2 | 2/2006 | |
| WO | WO 2006/053063 A2 | 5/2006 | |
| WO | WO 2007/061988 A2 | 5/2007 | |
| WO | 2008/150525 A1 | 12/2008 | |
| WO | WO 2008150525 A1 * | 12/2008 | |
| WO | 2010/005567 A2 | 1/2010 | |
| WO | 2010/059543 A1 | 5/2010 | |
| WO | 2010/146550 A1 | 12/2010 | |
| WO | WO 2011/041336 A2 | 4/2011 | |
| WO | 2011/088215 A2 | 7/2011 | |
| WO | 2012/080891 A1 | 6/2012 | |
| WO | WO 2012/080926 A2 | 6/2012 | |

OTHER PUBLICATIONS

Morikawa et al, "Two E-Rosette-Forming Lymphoid Cell Lines", Int. J. Cancer 21:166-170 (1978).

Morrison et al, "Chimeric Human Antibody Molecules: Mouse Antigen-Binding Domains With Human Constant Region Domains", Proc. Natl. Acad. Sci. USA 81:6851-6855 (1984).

Ngo et al; "Computational Complexity, Protein Structure Prediction, and the Levinthal Paradox"; The Protein Folding Problem and Tertiary Structure Prediction; K. Merz, Jr. and S. Le Grand, Editors; Birkhauser Boston; Chapter 14, pp. 492-495 (1994).

Ohno et al, "Antigen-binding specificities of antibodies are primarily determined by seven residues of VH", Proc. Natl. Acad. Sci. USA 82:2945-2949 (1985).

Osipo et al, "ErbB-2 Inhibition Activates Notch-1 and Sensitizes Breast Cancer Cells to a y-Secretase Inhibitor", Oncogene 27:5019-5032 (2008).

Paes et al, "Atomic-Level Mapping of Antibody Epitopes on a GPCR", J. Am. Chem. Soc. 131:6952-6954 (2009).

Pakula et al, "Genetic Analysis of Protein Stability and Function", Annual Review of Genetics 23:289-310 (1989).

PCT International Search Report and Written Opinion for International Patent Application No. PCT/IB2011/055595 issued Jul. 13, 2012.

Peeters et al, "Production of Antibodies and Antibody Fragments in Plants", Vaccine 19:2756-2761 (2001).

Pollock et al, "Transgenic Milk as a Method for the Production of Recombinant Antibodies", Journal of Immunological Methods 231:147-157 (1999).

Queen et al, "A Humanized Antibody that Binds to theh Interleukin 2 Receptor", Proc. Natl. Acad. Sci. USA 86:10029-10033 (1989).

Ravetch et al, "Fc receptors", Annu. Rev. Immunol. 9:457-492 (1991).

Reedijk et al, "High-level Coexpression of JAG1 and NOTCH1 is Observed in Human Breast Cancer and is Associated with Poor Overall Survival", Cancer Research 65:8530-8537 (2005).

Riechmann et al, "Reshaping Human Antibodies for Therapy", Nature 332:323-327 (1998).

Rockberg et al, "Epitope Mapping of Antibodies Using Bacterial Surface Display", Nature Methods 5(12):1039-1045 (2008).

Rudikoff et al, "Single amino acid substitution altering antigen-binding specificity", Proc. Natl. Acad. Sci. USA 79:1979-1983 (1982).

Sanchez-Irizarry et al, "Notch Subunit Heterodimerization andn Prevention of Ligand-Independent Proteolytic Activation Depend, Respectively, on a Novel Domain and the LNR Repeats", Molecular and Cell Biology 24(21):9265-9273 (2004).

Schier et al, "Identification of Functional and Structural Amino-Acid Residues by Parsimonious Mutagenesis", Gene 169:147-155 (1996).

Schildbach et al, "Modulation of antibody affinity by a non-contact residue", Protein Science 2:206-214 (1993).

Shaw et al, "Characterization of a Mouse/Human Chimeric Monoclonal Antibody (17-1a) to a Colon Cancer Tumor-Associated Antigen", The Journal of Immunology 138(12):4534-4538 (1987).

Shields et al, "High Resolution Mapping of the Binding Site on Human IgG1 for FcyRI, FcyRII, FcyRIII, and FcRn and Design of IgG1 Variants with Improved Binding to the FcyR", The Journal of Biological Chemistry 276(9):6591-6604 (2001).

Shields et al, "Lack of Fucose on Human IgG1 N-Linked Oligosaccharide Improves Binding to Human FcyRIII and Antibody-dependent Cellular Toxicity", The Journal of Biological Chemistry 277(30):26733-26740 (2002).

Skolnick et al, "From genes to protein structure and function: novel applications of computational approaches in the genomic era", Trends in Biotech 18(1):34-39 (2000).

Smith et al, "The challenges of genome sequence annotation or the devil is in the details", Nature Biotechnology 15:1222-1223 (1997).

Tao et al, "Studies of Aglycosylated Chimeric Mouse-Human IgG Role of Carbohydrate in the Structure and Effector Functions Mediated by the Human IgG Constant Region", The Journal of Immunology 143(8):2595-2601 (1989).

Tokuriki et al, "Stability effects of mutations and protein evolvability", Current Opinion in Structural Biology 19:596-604 (2009).

Tramontano et al, "Framework Residue 71 is a Major Determinant of the Position and Conformation of the Second Hypervariable Region in the VH Domains of Immunoglobulins", J. Mol. Biol. 215:175-182 (1990).

Tun et al, "Recognition Sequence of a Highly Conserved DNA Binding Protein RBP-Jx", Nucleic Acids Research 22(6):965-971 (1994).

Umaña et al, "Engineered Glycoforms of an Antineuroblastoma IgG1 with Optimized Antibody-dependent Cellular Cytotoxic Activity", Nature Biotechnology 17:176-180 (1999).

Vardar et al, "Nuclear Magnetic Resonance Structure of a Prototype Lin12-Notch Repeat Module from Human Notch1", Biochemistry 42:7061-7067 (2003).

Verhoeyen et al, "Reshaping Human Antibodies: Grafting an Antilysozyme Activity", Science 239:1534-1536 (1988).

Waterhouse et al, "Combinatorial Infecction and In Vivo Recombination: a Strategy for Making Large Phage Antibody Repertoires", Nucleic Acids Research 21(9):2265-2266 (1993).

Wells, "Additivity of Mutational Effects in Proteins", Biochemistry 29(37):8509-8517 (1990).

Winter et al, "Man-Made Antibodies", Nature 349:293-299 (1991).

Winter et al, "Making antibodies by phage display technology", Annu. Rev. Immunol. 12:433-455 (1994).

Wittwer et al, "Glycosylation at Asn-184 Inhibits the Conversion of Single-Chain to Two-Chain Tissue-Type Plasminogen Activator by Plasmin", Biochemistry 29:4175-4180 (1990).

Wu et al, "Therapeutic Antibody Targeting of Individual Notch Receptors", Nature 464:1052-1057 (2010).

Wyss et al, "The Structural Role of Sugars in Glycoproteins", Current Opinion in Biotechnology 7:409-416 (1996).

Yamane-Ohnuki et al, "Establishment of FUT8 Knockout Chinese Hamster Ovary Cells: An Ideal Host Cell Line for Producing Completely Defucosylated Antibodies With Enhanced Antibody-Dependent Cellular Cytotoxicity", Biotechnology and Biogengineering 87(5):614-622 (2004).

Yelton et al, "Affinity Maturation of the BR96 Anti-Carcinoma Antibody by Codon-Based Mutagenesis", The Journal of Immunology 155:1994-2004 (1995).

(56) References Cited

OTHER PUBLICATIONS

Altschuler et al, Uspekhi Biologicheskoi Khimmii, vol. 50, pp. 207-208 (2010) (English Translation).
Aster et al, "The Folding and Structural Integrity of the First LIN-12 Module of Human Notch1 Are Calcium-Dependent", Biochemistry 38:4736-4742 (1999).
Bray, "Notch signalling: a simple pathway becomes complex", Nature Reviews: Molecular Cell Biology 7(9):678-689 (2006).
Chen, J., "Force-induced unfolding simulations of the human Notch1 negative regulatory region: possible roles of the heterodimerization domain in mechanosensing," PLoS One, 6(7):e22837 11 pages (2011).
Falk et al., "Generation of anti-Notch antibodies and their application in blocking Notch signalling in neural stem cells", Methods, 58(1):69-78 (2012).
Harrison et al, "The Manufacturing Process for Recombinant Factor IX", Seminars in Hematology, 35(2 Suppl 2):4-10 (1998).
Hellström et al, "Dll4 signalling through Notch1 regulates formation of tip cells during angiogenesis", Nature 445:776-780 (2007).
Jeffries et al, "Characterization of a High-Molecular-Weight Notch Complex in the Nucleus of Notch$^{ic}$-Transformed RKE Cells and in a Human T-Cell Leukemia Cell Line", Molecular and Cellular Biology 22(11):3927-3941 (2002).
Kidd et al, "Structure and distribution of the Notch protein in developing *Drosophila*", Genes & Development 3(8):1113-1129 (1989).
Klinakis et al, "Myc is a Notch1 transcriptional target and a requisite for Notch1-induced mammary tumorigenesis in mice", Proceedings of the National Academy of Sciences USA 103(24):9262-9267 (2006).
Li et al, "Distinct expression profiles of Notch-1 protein in human solid tumors: Implications for development of targeted therapeutic monoclonal antibodies", Biologics: Targets & Therapy 4(24):163-171 (2010).
Mumm et al. "A Ligand-Induced Extracellular Cleavage Regulates γ-Secretase-like Proteolytic Activation of Notch1". Molecular Cell 5, 197-206 (2000).
Nakatsu et al, "Angiogenic sprouting and capillary lumen formation modeled by human umbilical vein endothelial cells (HUVEC) in fibrin gels: the role of fibroblasts and Angiopoietin-1", Microvascular Research 66:102-112 (2003).
Nam et al, "Notch signaling as a therapeutic target", Current Opinion in Chemical Biology 6:501-509 (2002).
PCT International Search Report and Written Opinion for International Patent Application No. PCT/IB2011/055411 issued Mar. 5, 2012.
PCT International Search Report and Written Opinion for International Patent Application No. PCT/IB2010/052711 issued Oct. 19, 2010.
Ploscariu et al., "Single molecule studies of force-induced S2 site exposure in the Mammalian notch negative regulatory domain", J. Phys. Chem. B, May 8;118(18):4761-70 (2014).
Radtke et al, "The Role of Notch in Tumorigenesis: Oncogene or Tumour Suppressors?", Nature Reviews—Cancer 3:756-767 (2003).
Rand et al, "Calcium Depletion Dissociates and Activates Heterodimeric Notch Receptors", Molecular and Cellular Biology 20(5):1825-1835 (2000).
Ridgway et al, "Inhibition of Dll4 signalling inhibits tumour growth by deregulating angiogenesis", Nature 444:1083-1087 (2006).
Roy et al, "The multifaceted role of Notch in cancer", Current Opinion in Genetics & Development 17:52-59 (2007).
Said et al, "Involucrin in Lung Tumors: A Specific Marker for Squamos Differentiation", Laboratory Investigation 49(5):563-568 (1983).
Schroeter et al. "Notch-1 signaling requires ligand-induced proteolytic release of intracellular domain". Nature 393(6683):382-386 (1998).
Stephenson et al., "Direct observation of proteolytic cleavage at the S2 site upon forced unfolding of the Notch negative regulatory region", Proc. Natl. Acad. Sci. U S A., Sep. 24;109(41):E2757-65 (2012).
Tiyanont et al., "Insights into Notch3 activation and inhibition mediated by antibodies directed against its negative regulatory region", J. Mol. Biol., 9;425(17):3192-204 (2012).
van ES et al, "Notch/γ-secretase inhibition turns proliferative cells in intestinal crypts and adenomas into goblet cells", Nature 435:959-963 (2005).
Weng et al, "Activating Mutations of NOTCH1 in Human T Cell Acute Lymphoblastic Leukemia", Science 306(#5694):269-271 (2004).
Caldas et al, "Humanization of the anti-CD18 antibody 6.7: an unexpected effect of a framework residue in binding to antigen", Molecular Immunology 39:941-952 (2003).
Krauss et al, "Impact of antibody framework residue VH-71 on the stability of a humanised anti-MUC1 scFv and derived immunoenzyme", British Journal of Cancer 90:1863-1870 (2004).
Paul, Fundamental Immunology, Raven Press, New York, p. 270 (1989).
Roitt et al, Immunology, 5th edition, pp. 71 & 73 (1998).
Andresen, "Development of peptide microarrays for epitope mapping of antibodies against the human TSH receptor", Journal of Immunological Methods 315:11-18 (2006).
Armour et al, "Recombinant human IgG molecules lacking Fcγ receptor I binding and monocyte triggering activities", Eur. J. Immunol. 29:2613-2624 (1999).
Aste-Amezaga et al, "Characterization of Notch1 Antibodies That Inhibit Signaling of Both Normal and Mutated Notch1 Receptors", Plos One 5(2):1-13 (2010).
Balint et al, "Antibody engineering by parsimonious mutagenesis", Gene 137:109-118 (1993).
Barbas III et al, "In vitro evolution of a neutralizing human antibody to human immunodeficiency virus type 1 to enhance affinity and broaden strain cross-reactivity", Proc. Nat. Acad. Sci. USA 91:3809-3813 (1994).
Boyd et al, "The effect of the removal of sialic acid, galactose and total carbohydrate on the functional activity of campath-IH", Molecular Immunology 32:1311-1318 (1995).
Bork, "Powers and Pitfalls in Sequence Analysis: The 70% Hurdle", Genome Research 10:398-400 (2000).
Bork et al, "Go hunting in sequence databases but watch out for the traps", Trends in Genet 12(10):425-427 (1996).
Brenner, "Errors in genome annotation", Trends in Genet 15(4):132-133 (1999).
Brorson et al, "Mutational Analysis of Avidity and Fine Specificity of Anti-Levan Antibodies", The Journal of Immunology 163:6694-6701 (1999).
Brown et al, "Tumor-specific Genetically Engineered Murine/Human Chimeric Monoclonal Antibody", Cancer Research 47:3577-3583 (1987).
Brummell et al, "Probing the Combining Site of an Anti-Carbohydrate Antibody by Saturation-Mutagenesis: Role of the Heavy-Chain CDR3 Residues", Biochemistry 32(4):1180-1187 (1993).
Burks et al, "In vitro scanning saturation mutagenesis of an antibody binding pocket", Proc. Natl. Acad. Sci. USA 94:412-417 (1997).
Capel et al, "Heterogeneity of Human IgG Fc Receptors", Immunomethods 4:25-34 (1994).
Colman, "Effects of amino acid sequence changes on antibody-antigen interactions", Research in Immunology 145(1):33-36 (1994).
Daeron, "Fc Receptor Biology", Annu. Rev. Immunol. 15:203-234 (1997).
Daugherty et al, "Polymerase chain reaction facilitates the cloning, CDR-grafting and rapid expression of a murine monoclonal antibody directed against the CD18 component of leukocyte integrins", Nucleic Acids Research 19 (9):2471-2476 (1991).
de Haas et al, "Fcγ receptors of phagocytes", J. Lab. Clin. Med. 126:330-341 (1995).
Dhungana et al, "Epitope Mapping by Proteolysis of Antigen-Antibody Complexes", Methods in Molecular Biology 524:87-101 (2009).
Doerks et al, "Protein annotation: detective work for function prediction", Trends in Genet 14(6):248-250 (1998).

(56) References Cited

OTHER PUBLICATIONS

Duquesnoy et al, "Structural and Functional Definitions of Epitopes Reacting with Mouse Monoclonal Antibodies", URL: HLAMatchmake Website; http://www.hlamatchmaker.net/documents/01structure.pdf, (2012).

Efstratiadis et al, "Notch, Myc and Breast Cancer", Cell Cycle 6(4):418-429 (2007).

Gordon et al, "Structural basis for autoinhibition of Notch", Nature Structural & Molecular Biology 14(4):295-300 (2007).

Gordon et al, "Structure of the Notch1-negative regulatory region: implications for normal activation and pathogenic signaling in T-ALL", Blood 113:4381-4390 (2009).

Guyer et al, "Immunoglobulin binding by mouse intestinal epithelial cell receptors", The Journal of Immunology 117(2):587-593 (1976).

Hawkins et al, "Selection of phage antibodies by binding affinity mimicking affinity maturation", J. Mol. Biol. 226:889-896 (1992).

Hong et al, "Overexpression of Notch 1 signaling associates with the tumorigenesis of gastric adenorna and intestinal type of gastric cancer", Gastroenterology 132(Issue 4-Suppl.2):AGA Abstract # T2084:p. A617 (2007).

Hsu et al, "Differential N-Glycan Patterns of Secreted and Intracellular IgG Produced in Trichoplusia ni Cells", The Journal of Biological Chemistry 272(14):9062-9070 (1997).

Hu et al, "Overexpression of Activated Murine Notch1 and Notch3 in Transgenic Mice Blocks Mammary Gland Development and Induces Mammary Tumors", American Journal of Pathology 168(3):973-990 (2006).

Hwang et al, "Immunogenicity of engineered antibodies", Methods 36:3-10 (2005).

Idusogie et al, "Mapping of theh C1q Binding Site on Rituxan, a Chimeric Antibody with a Human IgG1 Fc", The Journal of Immunology 164:4178-4184 (2000).

Jackson et al, "In vitro antibody maturation, improvement of a high affinity, neutralizing antibody against IL-1β", The Journal of Immunology 154:3310-3319 (1995).

Jang et al, "The structural basis for DNA binding by an anti-DNA autoantibody", Molecular Immunology 35:1207-1217 (1998).

Jefferis et al, "IgG-Fc-mediated effector functions: molecular definition of interaction sites for effector ligands and the role of glycosylation", Immunological Reviews 163:59-76 (1998).

Jones et al, "Replacing the complementarity-determining regions in a human antibody with those from a mouse", Nature 321:522-525 (1986).

Kang et al, "Bacterial cell surface display for epitope mapping of hepatitis C virus core antigen", FEMS Microbiology Letters 226:347-353 (2003).

Kim et al, "Localization of the site of the murine IgGI molecule that is involved in binding to the murine intestinal Fc receptor", Eur. J. Immunol. 24:2429-2434 (1994).

Kipriyanov et al, "Generation and production of engineered antibodies" Molecular Biotechnology 26(1):39-60 (2004).

Kobayashi et al, "Tryptophan H33 plays an important role in pyrimidine (6-4) pyrimidone photoproduct binding by a high-affinity antibody", Protein Engineering 12(10):879-884 (1999).

Kussie et al, "A Single Engineered Amino Acid Substitution Changes Antibody Fine Specificity", Journal of Immunology 152(1):146-152 (1994).

Lee et al, "Epitope Mapping of CCR5 Reveals Multiple Conformational States and Distinct but Overlapping Structures Involved in Chemokine and Coreceptor Function", The Journal of Biological Chemistry 274(14):9617-9626 (1999).
Levy et al, "Fine and Domain-level Epitope Mapping of Botulinum Neurotoxin Type A Neutralizing Antibodies by Yeast Surface Display", Journal of Molecular Biology 365:196-210 (2007).
Li et al, "Modulation of Notch Signaling by antibodies specific for the extracellular negative regulatory region of NOTCH3", Journal of Biological Chemistry 283(12):8046-8054 (2008).
LoBuglio et al, "Mouse/Human Chimeric Monoclonal Antibody in Man: Kinetics and Immune Response", Proc. Natl. Acad. Sci. USA 86:4220-4224 (1989).
Lonberg et al, "Human Antibodies from Transgenic Mice", Intern. Rev. Immunol. 13:65-93 (1995).
Lund et al, "Multiple Interactions of IgG with Its Core Oligosaccharide Can Modulate Recognition by Complement and Human Fcy Receptor I and Influence the Synthesis of Its Oligosaccharide", The Journal of Immunology 157:4963-4960 (1996).
Malecki et al, "Leukemia-Associated Mutations with the NOTCH1 Heterodimerization Domain Fall into at Least Two Distinct Mechanistic Classes", Molecular and Cell Biology 26(12):4642-4651 (2006).
Marks et al, By-Passing Immunization: Building High Affinity Human Antibodies by Chain Shuffling:, Bio/Technology 10:779-783 (1992).

* cited by examiner

| Anti Notch1: | Rat 351-mIgG1 | Rat 438-mIgG1 | A2 |
|---|---|---|---|
| A—B—C—hd1—hd2 | 57 | 51 | 75 |
| A—B—C—hd1—hd2 | 40 | 1 | 1 |
| A—B—C—hd1—hd2 | 78 | 6 | 2 |
| A—B—C—hd1—hd2 | 56 | 2 | 6 |
| A—B—C—hd1—hd2 | 20 | 15 | 6 |
| A—B—C—hd1—hd2 | 55 | 47 | 70 |
| A—B—C—hd1—hd2 | 34 | 29 | 50 |
| A—B—C—hd1—hd2 | 0 | 0 | 0 |
| A—B—C—hd1—hd2 | 60 | 53 | 83 |

Rat 438 epitope on human Notch1 NRR

Rat 351 epitope on human Notch1 NRR

A2 epitope on human Notch1 NRR

Superposition of the structures of human
Notch1 NRR bound to rat 438 and A2

Superposition of the structures of human
Notch1 NRR bound to rat 351 and A2

LNR-A/Heavy Chain Interaction in Complex 1

LNR-A/Heavy Chain Interaction in Complex 2

Neutralization activity of rat 351, mutant rat 351 and A2 in co-culture reporter gene assays Representative confocal images of Isolectin B4-Alexa488 staining in a mouse retinal model of angiogenesis Western blot analysis of protein extracts generated from CCD1076SK human fibroblasts plated on recombinant human DLL4 ligand FIG. 20 Western blot analysis of protein extracts generated from T-ALL cell lines (n.d = not determined)

Western blot analysis of protein extracts
generated in 37622A1 NSCLC patient
derived xenografts Western blot analysis of protein extracts generated in 87393A1 NSCLC patient derived xenografts Immunohistochemical detection of involucrin expression in 87393A1 NSCLC patient derived xenografts Western blot analysis of involucrin expression
in 87393A1 NSCLC patient derived xenografts Histochemical identification of secretory goblet cells using Alcian Blue stain on the ileum section of mouse intestines from Calu-6 efficacy study Anti-Ki67 immunohistochemistry on mouse intestinal crypts from Calu-6 efficacy study Anti-Ki67 immunohistochemistry on mouse intestinal crypts from 87393A1 NSCLC patient derived xenografts efficacy study

ANTI-NOTCH1 ANTIBODIES

CROSS REFERENCE TO RELATED APPLICATIONS

This application is a national stage submission under 35 U.S.C. §371 from International Application No. PCT/IB2011/055595, filed Dec. 9, 2011, which claims the benefit of priority of U.S. Provisional Patent Application No. 61/552,578 filed Oct. 28, 2011 and U.S. Provisional Patent Application No. 61/423,578 filed Dec. 15, 2010, the disclosures of which are incorporated herein by reference in their entirety.

REFERENCE TO SEQUENCE LISTING

This application contains a sequence listing filed electronically via EFS-Web. The sequence listing is provided as a .txt file entitled "PC71751A$_{13}$ SeqListing.txt" created on Jun. 14, 2013 and having a size of 112 KB. The sequence listing contained in the .txt file is part of the specification and is incorporated herein by reference in its entirety.

FIELD OF THE INVENTION

The present invention relates to anti-notch1 antibodies. The present invention further relates to the methods of using such antibodies in the treatment of cancer.

BACKGROUND

Notch receptors control normal cell growth, differentiation, and death in multicellular organisms through a signaling pathway that is triggered by ligand-induced proteolysis (Bray, Nat. Rev. Mol. Cell Biol. 7(9):678-689, 2006). The mature Notch heterodimer after furin-like protease cleavage at site S1 is held in an auto-inhibited state by a juxtamembrane negative regulatory region (NRR) consisting of three Lin12/Notch repeats (LNR-A, B, C) and the heterodimerization (HD) domain. The HD domain is divided into N-terminal (HD1) and C-terminal (HD2) halves by cleavage at site S1. Through an uncertain mechanism, binding of ligands of the Delta/Serrate/Lag-2 (DSL) family to the N-terminal, EGF-repeat region relieves this inhibition and induces two successive additional cleavages at S2 near the C-terminal region HD-2, and S3 within transmembrane domain in Notch that are catalyzed by ADAM-type metalloproteinase and gamma-Secretase, respectively (Gordon, W. R., et. al, Nature Structural & Molecular Biology, 2007, volume 14, 295-300). The latter cleavage releases the intracellular domain of Notch (Notch$^{ICD}$), permitting it to translocate to the nucleus and activate the transcription of target genes.

In mammalian cells, there are four known Notch receptors. Notch1-4 have broad, overlapping patterns of expression in embryonic and adult tissues, and fulfill non-redundant roles during hematopoietic stem cell specification, T cell development, intestinal crypt cell specification and vascular development. Acquired abnormalities involving specific Notch1 receptors have been implicated in cancers, such as T cell acute lymphoblastic leukemia (T-ALL), breast cancer and lung cancer. In addition, activated Notch1 is a potent inducer of leukemia in murine models and is over-expressed in various solid tumors, including non-small cell lung cancer, breast cancer and ovarian cancer.

Over 50% of T-ALL patients harbor mutations in the Notch1 receptor some of which result in constitutive cleavage of the receptor and production of the Notch1$^{ICD}$ due in part to Notch1 ligand-hypersenstivity or ligand-independent activation caused by alterations in or near the NRR auto-inhibitory domain. These mutations are categorized into 3 major classes. Class 1 mutations are single amino acid substitutions and small in-frame deletions or insertions in HD1. Class 2 mutations are longer insertions in the distal region of HD2 that relocate the S2-metalloprotease cleavage site beyond the auto-inhibitory NRR domain. Class 3 mutations, also called juxtamembrane expansion (JMEs) mutations, occur from large insertions that displace the NRR away from the cell membrane.

Several strategies are in development to inhibit Notch signaling for therapeutic purposes in cancer. One approach is to block the proteolytic release of intracellular Notch from the membrane by treatment with inhibitors of gamma-secretase (GSIs). Although GSIs have progressed into the clinic, they cannot distinguish individual Notch receptors and cause intestinal toxicity attributed to the inhibition of both Notch1 and Notch2. There is still a need in the art for novel anti-Notch1 therapies for the treatment of cancer while providing reduced side effects, in particular, intestinal toxicity.

SUMMARY

In one embodiment, the present invention provides for antibodies that bind to Notch1, having a heavy chain variable region having a CDR1 region, a CDR2 region, and a CDR3 region from the heavy chain variable region comprising SEQ ID NO: 71.

In another embodiment, the present invention provides for antibodies that bind to Notch1, having a light chain variable region having a CDR1 region, a CDR2 region, and a CDR3 region from the light chain variable region comprising SEQ ID NO: 97.

The present invention also provides for antibodies that bind to Notch1 having 1) a heavy chain variable region having a CDR1 region, a CDR2 region, and a CDR3 region from the heavy chain variable region comprising SEQ ID NO: 71, and 2) a light chain variable region having a CDR1 region, a CDR2 region, and a CDR3 region from the light chain variable region comprising SEQ ID NO: 97.

Also provided are antibodies that bind to Notch1 having a heavy chain variable region amino acid sequence that is at least 90% identical to SEQ ID NO: 71. Further provided are antibodies that bind to Notch1 having a heavy chain variable region amino acid sequence as set forth in SEQ ID NO: 71.

Also provided are antibodies that bind to Notch1 having a light chain variable region amino acid sequence that is at least 90% identical to SEQ ID NO: 97. Further provided are antibodies that bind to Notch1 having a light chain variable region amino acid sequence as set forth in SEQ ID NO: 97.

Also provided are antibodies that bind to Notch1 having a heavy chain amino acid sequence that is at least 90% identical to SEQ ID NO: 111. Further provided are antibodies that bind to Notch1 having a heavy chain amino acid sequence as set forth in SEQ ID NO: 111.

Also provided are antibodies having a light chain amino acid sequence that is at least 90% identical to SEQ ID NO: 113. Further provided are antibodies having a light chain amino acid sequence as set forth in SEQ ID NO: 113.

In a further embodiment, the invention provides for antibodies that bind to Notch1, having a heavy chain variable region amino acid sequence that is at least 90% identical to SEQ ID NO: 71; and a light chain variable amino acid sequence that is at least 90% identical to SEQ ID NO: 97. Further provided are antibodies that bind to Notch1 having a heavy chain variable region amino acid sequence as forth in SEQ ID NO: 71; and a light chain variable region amino acid sequence as set forth in SEQ ID NO: 97.

In a further embodiment, the invention provides for antibodies that bind to Notch1, having a heavy chain amino acid sequence that is at least 90% identical to SEQ ID NO: 111; and a light chain amino acid sequence that is at least 90% identical to SEQ ID NO: 113. Further provided are antibodies that bind to Notch1 having a heavy chain amino acid sequence as set forth in SEQ ID NO: 111, and a light chain amino acid sequence as set forth in SEQ ID NO: 113.

In a further embodiment, the invention provides for antibodies, that bind to human Notch1, wherein the antibodies bind an epitope having at least 8 amino acid residues selected from Asn 1461, Lys 1462, Val 1463, Cys 1464, Leu 1466, Leu 1580, Tyr 1621, Gly 1622, Met 1670, Asp 1671, Val 1672, Arg 1673, Leu 1707, Ala 1708, Leu 1710, Gly 1711, Ser 1712, Leu 1713, Pro 1716 and Lys 1718.

In another embodiment, the present invention provides for antibodies that bind to Notch1, having a heavy chain variable region having a CDR1 region, a CDR2 region, and a CDR3 region from the heavy chain variable region comprising SEQ ID NO: 115.

In another embodiment, the present invention provides for antibodies that bind to Notch1, having a light chain variable region having a CDR1 region, a CDR2 region, and a CDR3 region from the light chain variable region comprising SEQ ID NO: 129.

The present invention also provides for antibodies that bind to Notch1 having 1) a heavy chain variable region having a CDR1 region, a CDR2 region, and a CDR3 region from the heavy chain variable region comprising SEQ ID NO: 115, and 2) a light chain variable region having a CDR1 region, a CDR2 region, and a CDR3 region from the light chain variable region comprising SEQ ID NO: 129.

Also provided are antibodies that bind to Notch1 having a heavy chain variable region amino acid sequence that is at least 90% identical to SEQ ID NO: 115. Further provided are antibodies that bind to Notch1 having a heavy chain variable region amino acid sequence as set forth in SEQ ID NO: 115.

Also provided are antibodies that bind to Notch1 having a light chain variable region amino acid sequence that is at least 90% identical to SEQ ID NO: 129.

Further provided are antibodies that bind to Notch1 having a light chain variable region amino acid sequence as set forth in SEQ ID NO: 129.

Also provided are antibodies that bind to Notch1 having a heavy chain amino acid sequence that is at least 90% identical to SEQ ID NO: 149. Further provided are antibodies that bind to Notch1 having a heavy chain amino acid sequence as set forth in SEQ ID NO: 149.

Also provided are antibodies having a light chain amino acid sequence that is at least 90% identical to SEQ ID NO: 151. Further provided are antibodies having a light chain amino acid sequence as set forth in SEQ ID NO: 151.

In a further embodiment, the invention provides for antibodies that bind to Notch1, having a heavy chain variable region amino acid sequence that is at least 90% identical to SEQ ID NO: 115; and a light chain variable amino acid sequence that is at least 90% identical to SEQ ID NO: 129. Further provided are antibodies that bind to Notch1 having a heavy chain variable region amino acid sequence as forth in SEQ ID NO: 115; and a light chain variable region amino acid sequence as set forth in SEQ ID NO: 129.

In a further embodiment, the invention provides for antibodies that bind to Notch1, having a heavy chain amino acid sequence that is at least 90% identical to SEQ ID NO: 149; and a light chain amino acid sequence that is at least 90% identical to SEQ ID NO: 151. Further provided are antibodies that bind to Notch1 having a heavy chain amino acid sequence as set forth in SEQ ID NO: 149, and a light chain amino acid sequence as set forth in SEQ ID NO: 151.

In a further embodiment, the invention provides for antibodies, that bind to human Notch1, wherein the antibodies bind an epitope having at least 8 amino acid residues selected from Asp 1458, Asn 1461, Val 1463, Cys 1464, Leu 1466, Leu 1580, Met 1581, Pro 1582, Tyr 1621, Gly 1622, Arg 1623, Asp 1671, Val 1672, Arg 1673, Gly 1674, Leu 1710, Gly 1711, Ser 1712, Leu 1713, Asn 1714, Ile 1715, Pro 1716 and Lys 1718.

In another embodiment, the invention provides for antibodies that demonstrate higher inhibition of Notch1 activation of a mutant Notch1 receptor compared to inhibition of Notch1 activation of a native Notch1 receptor. It is further provided that the mutant Notch1 receptor has a mutation in the negative regulatory region (NRR). In a further embodiment, the mutation in the NRR is selected from the group consisting of a class 1, a class 2, and a class 3 mutation. In a further embodiment, the mutation in the NRR is associated with cells having abnormal activation of Notch1. It is further provided that the cells are T-cell acute lymphoblastic leukemia (T-ALL) cells. It is also provided that the T-ALL cells are selected from the group consisting of HPB-ALL, ALL-SIL, CCRF-CEM, MOLT-4 and DND-41 cells.

Also provided are antibodies that bind to Notch1 and compete for binding to Notch1 with any of the antibodies described herein.

In a further embodiment, the invention provides for antibodies that bind to Notch1 where the antibodies are of isotype IgA, IgD, IgE, IgG, or IgM. Further provided are antibodies that bind to Notch1 where the isotype is IgG, and wherein the subclass is IgG1, IgG2, IgG3 or IgG4, or is derived therefrom. Also provided are antibodies that bind to Notch1 where the subclass is derived from IgG1.

In a further embodiment, the invention provides nucleic acids that encode any of the antibodies described herein, or that encode any of the heavy chains and/or light chains of antibodies described herein. For example, in one embodiment, the invention provides nucleic acids having the sequence as set forth in SEQ ID NO: 112. In a further embodiment, the invention provides nucleic acids having the sequence as set forth in SEQ ID NO: 114. In another embodiment, the invention provides nucleic acids having the sequence as set forth in SEQ ID NO: 150. In a further embodiment, the invention provides nucleic acids having the sequence as set forth in SEQ ID NO: 152.

In a further embodiment, the invention provides for a vector comprising any of the nucleic acids described herein. In a further embodiment, the invention provides for host cells comprising any of the vectors described herein. In a further embodiment, the invention provides a process for producing any of the antibodies described herein comprising cultivating any host cells described herein and recovering the antibodies from the culture media. In a further embodiment, the invention provides host cells that recombinantly produce any of the antibodies described herein. In one embodiment, any of the host cells described herein are isolated.

In a further embodiment, the present invention provides pharmaceutical compositions comprising any of the antibodies described herein and pharmaceutically acceptable carriers. In a further embodiment, the invention provides methods of treating disorders in subjects in need thereof, comprising administering to the subjects any of the antibodies or pharmaceutical compositions described herein. The invention further provides methods of treating disorders that are associated with abnormal activation of Notch1 in subjects in need thereof, comprising administering to the subjects any of the antibodies or pharmaceutical compositions described herein. In a further embodiment, the invention provides methods of treating disorders, such as T-cell acute lymphoblastic leukemia (T-ALL), non-small cell lung cancer (NSCLC), breast cancer and colon cancer, in subjects in need thereof, comprising administering to the subjects any of the antibodies or pharmaceutical compositions described herein. The invention further provides for a method of treating disorders in subjects in need thereof, comprising administering to the subjects any of the antibodies or pharmaceutical compositions described herein in combination with one or more therapeutic agent.

In another embodiment, the invention provides for any of the antibodies disclosed herein for use in therapy. In a further embodiment, the invention provides the use of any of the antibodies disclosed herein for the manufacture of medicaments for therapy. In a further embodiment, the invention provides for any of the antibodies disclosed herein for use in treating disorders that are associated with abnormal activation of Notch1 in subjects in need thereof. In a further embodiment, the invention provides for any of the antibodies disclosed herein for use in treating disorders, such as T-cell acute lymphoblastic leukemia (T-ALL), non-small cell lung cancer (NSCLC), breast cancer and colon cancer, in subjects in need thereof.

In a further embodiment, the invention provides for antibodies that bind to human, mouse and cynomolgus (hereinafter "cyno") Notch1, but do not bind to human Notch2. In another embodiment, the invention provides for antibodies that bind to human, mouse and cyno Notch1, but do not bind to human and mouse Notch3.

DETAILED DESCRIPTION OF THE INVENTION

Figure 1:
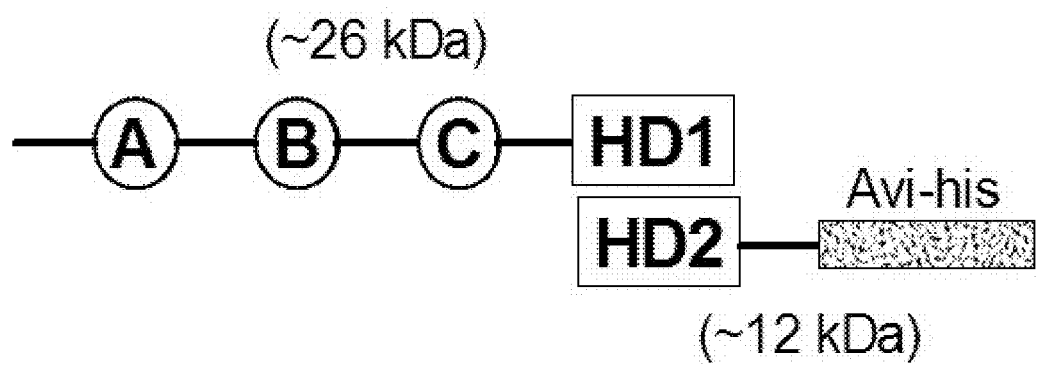
FIG. 1 shows a schematic diagram of recombinant, S1-cleaved, heterodimeric Notch1 NRR protein immunogen with Avi and His tags.

The present invention relates to isolated antibodies, particularly human, humanized, chimeric and rat monoclonal antibodies that bind to Notch1. Further, the present disclosure provides for isolated antibodies that demonstrate higher inhibition of Notch1 activation of a mutant Notch1 receptor compared to inhibition of Notch1 activation of a native Notch1 receptor. The disclosure provides for isolated antibodies and methods of making such antibodies and pharmaceutical compositions containing the antibodies. The present disclosure further relates to immunoconjugates and bispecific molecules containing such antibodies. The disclosure also relates to methods of using the antibodies to inhibit Notch1 activation, and treat various diseases related to abnormal cell growth, such as cancer (e.g. T-cell acute lymphoblastic leukemia (T-ALL), non-small cell lung cancer (NSCLC), colon cancer, breast cancer and ovarian cancer.

General Techniques

Unless otherwise indicated the methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference.

Definitions

"Notch1" or "Notch-1" refers to native, variants, isoforms and species homologs of human Notch1 protein. Native human Notch1 protein, for example, is made up of a leader peptide, a large epidermal growth factor (EGF)-like repeat region, three Lin12 repeats, a N terminal heterodimerization domain (HD-1), a C terminal heterodimerization domain (HD-2), a transmembrane (TM) sequence and an intracellular domain (Notch1$^{ICD}$). The NCBI/GenBank accession number of the full length human Notch1 is NM_017617.2

"Notch1 negative regulatory region", or "Notch1 NRR" as used herein, unless otherwise indicated, refers to any native or synthetic polypeptide region of Notch1 consisting of the three Lin12 domains and the amino acid sequence or sequences located between the three Lin12 domains, plus the HD1 and HD2 domains of Notch1. In one embodiment, the "Notch1 NRR" includes the three Lin12 domains and two heterodimerization domains HD-1, and HD-2, wherein the HD-1 and HD-2 domains of Notch1 are covalently bonded and not yet cleaved by the furin-like protease (before S1 cleavage). In another embodiment, the "Notch1 NRR" includes the three Lin12 domains and the two heterodimerization domains HD-1, and HD-2, wherein the HD-1 and HD-2 domains are non-covalently bonded (after S1 cleavage). In one aspect of this embodiment, the S2 site within the HD-2 domain has not been cleaved by the ADAM-type metalloproteases. In another particular aspect of this embodiment, the S2 site within the HD-2 domain is being cleaved or has already been cleaved by the ADAM-type metalloproteases. (Gordon, W. R., et. al, Nature Structural & Molecular Biology, 2007, volume 14, 295-300).

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments (e.g., antigen binding portions) thereof (such as Fab, Fab', F(ab')$_2$, Fv), single chain (ScFv) and domain antibodies such as shark and camelid antibodies), and fusion proteins comprising an antibody portion (such as domain antibodies), and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes (isotypes) of immunoglobulins: IgA, IgD, IgE, IgG, and IgM, and several of these may be further divided into subclasses, e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

An "isolated antibody", as used herein, is intended to refer to an antibody that is substantially free of other antibodies having different antigenic specificities (e.g., an isolated antibody that specifically binds Notch1 is substantially free of antibodies that specifically bind antigens other than Notch1). An isolated antibody that specifically binds Notch1 may, however, have cross-reactivity to other antigens, such as Notch-1 molecules from other species. Moreover, an isolated antibody may be substantially free of other cellular material and/or chemicals.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site.

"Humanized" antibody refers to forms of non-human (e.g. murine) antibodies that are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Preferably, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FW) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FW regions are those of a human immunoglobulin consensus sequence. The humanized antibody optimally also will comprise at least a portion of an immunoglobulin constant region or domain (Fc), typically that of a human immunoglobulin. Other forms of humanized antibodies have one or more CDRs (L-CDR1, L-CDR2, L-CDR3, H-CDR1, H-CDR2, or H-CDR3) which are altered with respect to the original antibody, which are also termed one or more CDRs "derived from" one or more CDRs from the original antibody.

"Human antibody" or "fully human antibody" is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo). This definition of a human antibody includes antibodies comprising at least one human heavy chain polypeptide or at least one human light chain polypeptide. Human antibodies can be produced using various techniques known in the art.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "recombinant antibody", as used herein, includes all antibodies that are prepared, expressed, created or isolated by recombinant means. Such recombinant antibodies have variable regions in which the framework and CDR regions are derived from germline immunoglobulin sequences. In certain embodiments, however, such recombinant antibodies can be subjected to in vitro mutagenesis (or, when an animal transgenic for Ig sequences is used, in vivo somatic mutagenesis) and thus the amino acid sequences of the VH and VL regions of the recombinant antibodies are sequences that, while derived from and related to germline VH and VL sequences, may not naturally exist within the antibody germline repertoire in vivo.

The phrases "an antibody recognizing an antigen" and "an antibody specific for an antigen" are used interchangeably herein with the term "an antibody which binds specifically to an antigen."

As known in the art, the term "Fc region" is used to define a C-terminal region of an immunoglobulin heavy chain (CH2+CH3). The "Fc region" may be a native sequence Fc region or a variant Fc region.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one function of the native sequence Fc region.

The terms "Fc receptor" or "FcR" are used to describe a receptor that binds to the Fc region of an antibody. For example, the FcR can be a native sequence human FcR. Furthermore, the FcR can be one that binds an IgG antibody (a gamma receptor) and includes receptors of the FcγRI, FcγRII, FcγRIII, and FcγRIV subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. As will be appreciated by those of skill in the art, inhibiting receptor FcγRIIB contains an immunoreceptor tyrosine-based inhibition motif (ITIM) in its cytoplasmic domain. FcRs have been extensively reviewed and are well known to those of skill in the art. Other FcRs, including those to be identified in the future, are encompassed by the term "FcR" herein. The term also includes the neonatal receptor, FcRn, which is responsible for the transfer of maternal IgGs to the fetus, and the extended half life of IgGs.

The term "binds" refers to an affinity between two molecules, for example, an antigen and an antibody. An antibody that "specifically binds to Notch1" refers to a preferential binding of an antibody to Notch1 antigen in a sample comprising multiple different antigens, with a difference in $K_D$ of at least 100 fold or preferably 1,000 fold.

The term "high affinity" refers to an antibody having a $K_D$ of $1 \times 10^{-6}$ M or less, more preferably having a $K_D$ of $1 \times 10^{-8}$ M or less. Affinity can be measured using, for example, surface Plasmon resonance.

"Epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics.

The term "$k_{on}$", as used herein, is intended to refer to the on-rate, or association rate of a particular antibody-antigen interaction, whereas the term "$k_{off}$" as used herein, is intended to refer to the off-rate, or dissociation rate of a particular antibody-antigen interaction. The term "$K_D$", as used herein, is intended to refer to the equilibrium dissociation constant, which is obtained from the ratio of $k_{off}$ to $k_{on}$ (i.e., $k_{off}/k_{on}$) and is expressed as a molar concentration (M). $K_D$ values for antibodies can be determined using methods well established in the art. One method for determining the $K_D$ of an antibody is by using surface plasmon resonance, typically using a biosensor system such as a Biacore® system.

The terms "polypeptide", "oligopeptide", "peptide" and "protein" are used interchangeably herein to refer to chains of amino acids of any length, preferably, relatively short (e.g., 10-100 amino acids). The chain may be linear or branched, it may comprise modified amino acids, and/or may be interrupted by non-amino acids. It is understood that the polypeptides can occur as single chains or associated chains.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase.

A "variable region" of an antibody refers to the variable region of the antibody light chain or the variable region of the antibody heavy chain, either alone or in combination. As known in the art, the variable regions of the heavy and light chain each consist of four framework regions (FW) connected by three complementarity determining regions (CDRs) also known as hypervariable regions. The CDRs in each chain are held together in close proximity by the FWs and, with the CDRs from the other chain, contribute to the formation of the antigen-binding site of antibodies.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop originally described by Chothia and others. See, e.g., Chothia et al., 1989, Nature 342:877-883. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

A "constant region" of an antibody refers to the constant region of the antibody light chain or the constant region of the antibody heavy chain, either alone or in combination.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of the present disclosure.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods.

An "individual" or a "subject" is a mammal, more preferably, a human. Mammals also include, but are not limited to, farm animals, sport animals, pets, primates, horses, dogs, cats, mice and rats.

An "isolated protein", "isolated polypeptide" or "isolated antibody" is a protein, polypeptide or antibody that by virtue of its origin or source of derivation (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

Notch1 Receptor

Human Notch1 cDNA encodes a protein of 2556 amino acid residues consisting of a leader peptide, 36 EGF-like repeats, negative regulatory region (NRR), a transmembrane (TM) sequence and an intracellular domain (Notch1$^{ICD}$).

Anti-Notch1 Antibodies that Bind to the NRR

It is within the contemplation of the current disclosure that antibodies that bind to the Notch1 domain with a high affinity may reduce Notch1 signal transduction, and therefore may demonstrate biological activity in vitro and in vivo to inhibit cancer cell growth, in particular, T-cell acute lymphoblastic leukemia (T-ALL), non-small cell lung cancer (NSCLC), breast cancer, colon cancer and ovarian cancer. Such antibodies may be produced following general methods known to those of ordinary skill in the art. In one embodiment, such antibodies can be produced through immunization of a rat with an immunogen followed by hybridoma cloning of the antibodies thus generated and assaying the cloned antibodies by a variety of assays. For example, solid-phase ELISA immunoassay, immunoprecipitation, Biacore®, FACS, and Western blot analysis are among many assays that may be used to identify an antibody that specifically reacts with Notch1. The Notch1 binding affinity of the antibodies selected according to the ELISA assay can be measured on a surface plasma resonance Biacore® instrument.

The anti-Notch1 antibodies of the current disclosure can be produced by any other methods known in the art other than described in the above paragraph. The route and schedule of immunization of the host animal are generally in keeping with established and conventional techniques for antibody stimulation and production, as further described herein. General techniques for production of human and mouse antibodies are known in the art and/or are described herein.

Anti-Notch1 Antibodies Generated by Hybridoma Technologies.

It is within the contemplation of the current disclosure that any mammalian subject including humans or antibody producing cells therefrom can be manipulated to serve as the basis for production of mammalian, including human, hybridoma cell lines.

Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Hybridomas that may be used as a source of antibodies encompass all derivatives, progeny cells of the parent hybridomas that produce monoclonal antibodies specific for Notch1, or a portion thereof.

Hybridomas that produce such antibodies may be grown in vitro or in vivo using known procedures. The monoclonal antibodies may be isolated from the culture media or body fluids, by conventional immunoglobulin purification procedures.

Humanization of Anti-Notch1 Antibodies Generated by Immunization in a Host Animal.

It is within the contemplation of the current disclosure that anti Notch1 antibodies of the disclosure, wherein the antibodies are generated by immunization in a host animal can be manipulated in many ways to improve their biological activity and pharmaceutical properties. One way of such manipulation is humanization.

Methods of humanizing antibodies are well known to those of ordinary skill in the art. In general, there are four basic steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody.

A number of "humanized" antibody molecules comprising an antigen-binding site derived from a non-human immunoglobulin have been described in the literature, including chimeric antibodies having rodent or modified rodent V regions and their associated CDRs fused to human constant domains; rodent CDRs grafted into a human supporting framework region (FR) prior to fusion with an appropriate human antibody constant domain; and rodent CDRs supported by recombinantly engineered rodent framework regions. Such "humanized" molecules are designed to minimize unwanted immunological response toward rodent anti-human antibody molecules which limits the duration and effectiveness of therapeutic applications of those moieties in human recipients.

Human Anti-Notch1 Antibodies

It is within the contemplation of the current disclosure that fully human anti-Notch1 antibodies may be obtained by using commercially available mice that have been engineered to express specific human immunoglobulin proteins. Transgenic animals that are designed to produce a more desirable (e.g., fully human antibody) or more robust immune response may also be used for generation of humanized or human antibodies. Examples of such technologies are Xenomouse™ from Abgenix, Inc. (Fremont, Calif.) and HuMAb-Mouse® and TC Mouse™ from Medarex, Inc. (Princeton, N.J.).

It is also within the contemplation of the current disclosure that fully human anti-Notch1 antibodies may be obtained recombinantly following general methods of phage display technology, as will be readily apparent to those of skill in the art. Alternatively, the phage display technology can be used to produce human antibodies and antibody fragments in vitro, from immunoglobulin variable (V) domain gene repertoires from unimmunized donors.

Gene shuffling can also be used to derive human antibodies from rodent antibodies, where the human antibody has similar affinities and specificities to the starting rodent antibody. Although the above discussion pertains to humanized and human antibodies, the general principles discussed are applicable to customizing antibodies for use, for example, in dogs, cats, primate, equines and bovines. One or more aspects of humanizing an antibody described herein may be combined, e.g., CDR grafting, framework mutation and CDR mutation.

Engineered and Modified Anti-Notch1 Antibodies Made Recombinantly

In general, antibodies may be made recombinantly by placing the DNA sequences of the desired antibody into expression vectors followed by transfection and expression in host cells, including but not limited to E. coli cells, simian COS cells, Chinese hamster ovary (CHO) cells, or myeloma cells that do not otherwise produce immunoglobulin protein. Other host cells, such as transgenic plant cells or transgenic milk cells may also be used.

An antibody may also be modified recombinantly. For example, the DNA of the human heavy and light chain constant regions may be used in place of the homologous murine sequences of the murine antibody DNA, or by covalently joining to the immunoglobulin coding sequence all or part of the coding sequence for a non-immunoglobulin polypeptide. In similar manner, "chimeric" or "hybrid" antibodies can be prepared that have the binding specificity of an anti-Notch1 monoclonal antibody herein.

Antibody variable regions can also be modified by CDR grafting. Because CDR sequences are predominantly responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties.

Accordingly, another aspect of the disclosure pertains to an isolated monoclonal antibody, comprising a heavy chain variable region comprising CDR1, CDR2, and CDR3 sequences as described herein, and a light chain variable region comprising CDR1, CDR2, and CDR3 sequences as described herein. Thus, such antibodies contain the VH and VL CDR sequences of the monoclonal antibodies described herein, yet may contain different framework sequences from these antibodies. Such framework sequences can be obtained from public DNA databases or published references that include germline antibody gene sequences.

Another type of variable region modification is to mutate amino acid residues within the VH and/or VL CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated using in vitro or in vivo assays as described herein. Typically, conservative modifications (as discussed below) are introduced. The mutations may be amino acid substitutions, additions or deletions. Moreover, typically no more than one, two, three, four or five residues within a CDR region are modified.

Epitope Mapping

The binding epitopes of monoclonal antibodies on an antigen may be mapped by a number of methods depending on the type of antigen-antibody interactions.

If an antibody binds to a single epitope consisting of sequential amino acid residues in an antigen, whose binding usually is not affected by antigen conformational changes, the binding epitope is called a linear epitope. Determining the amino acid sequence of a linear epitope can be accomplished by utilizing techniques well known in the art. A non-linear epitope which is constituted by several sequentially discontinuous segments or noncontiguous residues that are brought together by the folding of the antigen to its native structure is known as a conformational epitope.

Mapping of conformational epitopes depends on the interaction of antibody to antigen in its native conformation. A number of techniques well known in the art are useful in determining conformational epitopes. For example, co-crystallization of antigen-antibody complex, X-ray diffraction and structural analysis gives direction visualization of antigen-antibody interaction. When combined with amino acid mutagenesis, the technologies can provide powerful evidence and a vivid picture for antibody binding epitopes. The epitope or the set of epitopes that each of the anti-Notch1 antibodies bind to may be determined according to the above mapping methods or others generally known in the art.

Conservative Substitutions

An antibody may also be modified recombinantly by conservative substitution of one or more of the amino acid residues of the antibody or by one or more deletions or additions of amino acids to that of the antibody. Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated.

Affinity Matured Anti-Notch1 Antibodies

The disclosure includes affinity matured embodiments. For example, affinity matured antibodies can be produced by procedures known in the art (such as Marks et al. (1992) Bio/Technology, 10:779-783; Barbas et al. (1994) Proc Nat. Acad. Sci, USA 91:3809-3813; Schier et al. (1995) Gene, 169:147-155; Yelton et al. (1995) J. Immunol., 155:1994-2004; Jackson et al. (1995) J. Immunol., 154(7):3310-9; Hawkins et al. (1992) J. Mol. Biol., 226:889-896; and PCT Publication No. WO2004/058184). Such methods may be used for adjusting the affinity of an antibody and for characterizing a CDR.

Post Translational Modification of Anti-Notch1 Antibodies

Antibodies can also be modified by post translational modifications, including, but not limited to glycosylation with different sugars, acetylation, and phosphorylation by techniques are well known in the art.

Other methods of post translational modification include using coupling techniques known in the art, including, but not limited to, enzymatic means, oxidative substitution and chelation. Modifications can be used, for example, for attachment of labels for immunoassay.

Anti-Notch1 Antibodies with Modified Constant Region

In some embodiments of the disclosure, the antibody comprises a modified constant region, such as a constant region that is immunologically inert or partially inert, e.g., does not trigger complement mediated lysis, does not stimulate antibody-dependent cell mediated cytotoxicity (ADCC), or does not activate microglia; or have reduced activities (compared to the unmodified antibody) in any one or more of the following: triggering complement mediated lysis, stimulating antibody-dependent cell mediated cytotoxicity (ADCC), or activating microglia. Different modifications of the constant region may be used to achieve optimal level and/or combination of effector functions. See, for example, Morgan et al., Immunology 86:319-324 (1995); Lund et al., J. Immunology 157:4963-9 157:4963-4969 (1996); Idusogie et al., J. Immunology 164:4178-4184 (2000); Tao et al., J. Immunology 143: 2595-2601 (1989); and Jefferis et al., Immunological Reviews 163:59-76 (1998).

In some embodiments, the antibody comprises a human heavy chain IgG1 constant region comprising the following mutations: L234A/L235A/G237A in the lower hinge region resulting in substantially reduced ADCC and CDC activities. See for example US20090155256.

Modifications within the Fc region can typically be used to alter one or more functional properties of the antibody, such as serum half-life, complement fixation, Fc receptor binding, and/or antigen-dependent cellular cytotoxicity. Furthermore, an antibody of the disclosure may be chemically modified (e.g., one or more chemical moieties can be attached to the antibody) or be modified to alter its glycosylation pattern, again to alter one or more functional properties of the antibody.

Another modification of the antibodies herein that is contemplated by the disclosure is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Typically, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1 to C10) alkoxy- or aryloxy-polyethylene glycol or polyethylene glycol-maleimide. In certain cases, the antibody to be pegylated is an aglycosylated antibody. Methods for pegylating proteins are known in the art and can be applied to the antibodies of the present disclosure.

Fusion Protein

The disclosure also encompasses fusion proteins comprising one or more fragments or regions from the antibodies or polypeptides of this disclosure. In one embodiment, a fusion polypeptide is provided that comprises at least 10 contiguous amino acids of the variable light chain region and/or at least 10 amino acids of the variable heavy chain region of the antibodies of the current disclosure. In other embodiments, a fusion polypeptide is provided that comprises at least about 10, at least about 15, at least about 20, at least about 25, or at least about 30 contiguous amino acids of the variable light chain region and/or at least about 10, at least about 15, at least about 20, at least about 25, or at least about 30 contiguous amino acids of the variable heavy chain region. In another embodiment, the fusion polypeptide comprises a light chain variable region and/or a heavy chain variable region, of the antibodies of the current disclosure. In another embodiment, the fusion polypeptide comprises one or more CDR(s) of the antibodies of the current disclosure. For purposes of this disclosure, a fusion protein contains one or more antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag.

A fusion polypeptide can be created by methods known in the art, for example, synthetically or recombinantly.

Bispecific Molecules

An antibody of the disclosure, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the disclosure may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the disclosure, an antibody of the disclosure can be functionally linked (e.g., by chemical coupling, genetic fusion, noncovalent association or otherwise) to one or more other binding molecules, such as another antibody, antibody fragment, peptide or binding mimetic, such that a bispecific molecule results.

Single-Chain Antibodies

An antibody of the disclosure can be a single-chain antibody (scFv) in which the heavy and light chain variable regions (Fv region) have been connected by a flexible linker to form a single polypeptide chain, which forms an antigen-binding region. Such single-chain antibodies may be prepared by fusing DNA encoding a peptide linker between DNAs encoding the two variable domain polypeptides (VL and VH). The resulting polypeptides can fold back on themselves to form antigen-binding monomers, or they can form multimers (e.g., dimers, trimers, or tetramers), depending on the length of a flexible linker between the two variable domains (Kortt et al. (1997) Prot. Eng. 10:423; Kortt et al. (2001) Biomol. Eng. 18:95-108). By combining different VL and VH-comprising polypeptides, one can form multimeric scFvs that bind to different epitopes (Kriangkum et al. (2001) Biomol. Eng. 18:31-40). Single chain antibodies can be produced using various techniques known in the art.

Immunoconjugates

An antibody of the disclosure can be an immunoconjugate or antibody-drug conjugates (ADC). Immunoconjugates combine the binding specificity of monoclonal antibodies with the potency of chemotherapeutic agents.

Polynucleotides Encoding the Anti-Notch1 Antibodies

The disclosure also provides isolated polynucleotides encoding the antibodies and peptides of the disclosure, and vectors and host cells comprising the polynucleotide.

In one aspect, the disclosure provides compositions, such as a pharmaceutical composition, comprising any of the polynucleotides of the disclosure. In some embodiments, the composition comprises an expression vector comprising a polynucleotide encoding the antibody of the disclosure. In other embodiment, the composition comprises an expression vector comprising a polynucleotide encoding any of the antibodies or polypeptides of the disclosure.

In another aspect, the disclosure provides a method of making any of the polynucleotides described herein.

Polynucleotides complementary to any such sequences are also encompassed by the present disclosure. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present disclosure, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably, at least about 80% identity, yet more preferably, at least about 90% identity, and most preferably, at least about 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present disclosure. Further, alleles of the genes comprising the polynucleotide sequences provided herein are within the scope of the present disclosure. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this disclosure can be obtained using chemical synthesis, recombinant methods, or PCR.

For preparing polynucleotides using recombinant methods, a polynucleotide comprising a desired sequence can be inserted into a suitable vector, and the vector in turn can be introduced into a suitable host cell for replication and amplification. Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector.

Expression vectors generally are replicable polynucleotide constructs that contain a polynucleotide according to the disclosure. It is implied that an expression vector must be replicable in the host cells either as episomes or as an integral part of the chromosomal DNA. Vector components may generally include, but are not limited to, one or more of the following: a signal sequence; an origin of replication; one or more marker genes; suitable transcriptional controlling elements (such as promoters, enhancers and terminator).

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The disclosure also provides host cells comprising any of the polynucleotides described herein. Any host cells capable of over-expressing heterologous DNAs can be used for the purpose of isolating the genes encoding the antibody, polypeptide or protein of interest. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably, 10 fold higher, even more preferably, 20 fold higher than that of the corresponding endogenous antibody or protein of interest, if present, in the host cells.

Pharmaceutical Compositions

In another aspect, the present disclosure provides a composition, e.g., a pharmaceutical composition, containing one or a combination of monoclonal antibodies, or antigen-binding portion(s) thereof, of the present disclosure, formulated together with a pharmaceutically acceptable carrier. Such compositions may include one or a combination of (e.g., two or more different) antibodies, or immunoconjugates or bispecific molecules of the disclosure. For example, a pharmaceutical composition of the disclosure can comprise a combination of antibodies (or immunoconjugates or bispecifics) that bind to different epitopes on the target antigen or that have complementary activities.

Pharmaceutical compositions of the disclosure also can be administered in combination therapy, i.e., combined with other agents. For example, the combination therapy can include an anti-Notch1 antibody of the present disclosure combined with at least one other anti-inflammatory, anticancer or immunosuppressant agent. Examples of therapeutic agents that can be used in combination therapy are described in greater detail below in the section on uses of the antibodies of the disclosure.

As used herein, "pharmaceutically acceptable carrier" includes any and all solvents, dispersion media, coatings, antibacterial and antifungal agents, isotonic and absorption delaying agents, and the like that are physiologically compatible. Typically, the carrier is suitable for intravenous, intramuscular, subcutaneous, parenteral, spinal or epidermal administration (e.g., by injection or infusion). Depending on the route of administration, the active compound, i.e., antibody, antigen-binding portion thereof, immunoconjuage, or bispecific molecule, may be coated in a material to protect the compound from the action of acids and other natural conditions that may inactivate the compound.

In certain embodiments, the antibodies of the present disclosure may be present in a neutral form (including zwitter ionic forms) or as a positively or negatively-charged species. In some cases, the antibodies may be complexed with a counterion to form a pharmaceutically acceptable salt. Thus, the pharmaceutical compounds of the disclosure may include one or more pharmaceutically acceptable salts.

A "pharmaceutically acceptable salt" refers to a salt that retains the desired biological activity of the parent compound (e.g. antibody) and does not impart undesired toxicological effects (see e.g., Berge, S. M., et al. (1977) J. Pharm. Sci. 66:1-19). For example, the term "pharmaceutically acceptable salt" includes a complex comprising one or more antibodies and one or more counterions, where the counterions are derived from pharmaceutically acceptable inorganic and organic acids and bases.

Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Furthermore, pharmaceutically acceptable inorganic bases include metallic ions. Metallic ions include, but are not limited to, appropriate alkali metal salts, alkaline earth metal salts and other physiological acceptable metal ions. Salts derived from inorganic bases include aluminum, ammonium, calcium, cobalt, nickel, molybdenum, vanadium, manganese, chromium, selenium, tin, copper, ferric, ferrous, lithium, magnesium, manganic salts, manganous, potassium, rubidium, sodium, and zinc, and in their usual valences.

Pharmaceutically acceptable acid addition salts of the antibodies of the present disclosure can be prepared from the following acids, including, without limitation formic, acetic, acetamidobenzoic, adipic, ascorbic, boric, propionic, benzoic, camphoric, carbonic, cyclamic, dehydrocholic, malonic, edetic, ethylsulfuric, fendizoic, metaphosphoric, succinic, glycolic, gluconic, lactic, malic, tartaric, tannic, citric, nitric, ascorbic, glucuronic, maleic, folic, fumaric, propionic, pyruvic, aspartic, glutamic, benzoic, hydrochloric, hydrobromic, hydroiodic, lysine, isocitric, trifluoroacetic, pamoic, propionic, anthranilic, mesylic, orotic, oxalic, oxalacetic, oleic, stearic, salicylic, aminosalicylic, silicate, p-hydroxybenzoic, nicotinic, phenylacetic, mandelic, embonic, sulfonic, methanesulfonic, phosphoric, phosphonic, ethanesulfonic, ethanedisulfonic, ammonium, benzenesulfonic, pantothenic, naphthalenesulfonic, toluenesulfonic, 2-hydroxyethanesulfonic, sulfanilic, sulfuric, nitric, nitrous, sulfuric acid monomethyl ester, cyclohexylaminosulfonic, β-hydroxybutyric, glycine, glycylglycine, glutamic, cacodylate, diaminohexanoic, camphorsulfonic, gluconic, thiocyanic, oxoglutaric, pyridoxal 5-phosphate, chlorophenoxyacetic, undecanoic, N-acetyl-L-aspartic, galactaric and galacturonic acids.

Pharmaceutically acceptable organic bases include trimethylamine, diethylamine, N,N'-dibenzylethylenediamine, chloroprocaine, choline, dibenzylamine, diethanolamine, ethylenediamine, meglumine (N-methylglucamine), procaine, cyclic amines, quaternary ammonium cations, arginine, betaine, caffeine, clemizole, 2-ethylaminoethanol, 2-diethylaminoethanol, 2-dimethylaminoethanol, ethanediamine, butylamine, ethanolamine, ethylenediamine, N-ethylmorpholine, N-ethylpiperidine, ethylglucamine, glucamine, glucosamine, histidine, hydrabamine, imidazole, isopropylamine, methylglucamine, morpholine, piperazine, pyridine, pyridoxine, neodymium, piperidine, polyamine resins, procaine, purines, theobromine, triethylamine, tripropylamine, triethanolamine, tromethamine, methylamine, taurine, cholate, 6-amino-2-methyl-2-heptanol, 2-amino-2-methyl-1,3-propanediol, 2-amino-2-methyl-1-propanol, aliphatic mono- and dicarboxylic acids, phenyl-substituted alkanoic acids, hydroxy alkanoic acids, aromatic acids, aliphatic and aromatic sulfonic acids, strontium, tricine, hydrazine, phenylcyclohexylamine, 2-(N-morpholino)ethanesulfonic acid, bis(2-hydroxyethyl)amino-tris (hydroxymethyl)methane, N-(2-acetamido)-2-aminoethanesulfonic acid, 1,4-piperazinediethanesulfonic acid, 3-morpholino-2-hydroxypropanesulfonic acid, 1,3-bis[tris(hydroxymethyl)methylamino]propane, 4-morpholinepropanesulfonic acid, 4-(2-hydroxyethyl)piperazine-1-ethanesulfonic acid, 2-[(2-hydroxy-1,1-bis(hydroxymethyl)ethyl)amino]ethanesulfonic acid, N,N-bis(2-hydroxyethyl)-2-aminoethanesulfonic acid, 4-(N-morpholino)butanesulfonic acid, 3-(N,N-bis[2-hydroxyethyl]amino)-2-hydroxypropanesulfonic acid, 2-hydroxy-3-[tris(hydroxymethyl)methylamino]-1-propanesulfonic acid, 4-(2-hydroxyethyl)piperazine-1-(2-hydroxypropanesulfonic acid), piperazine-1,4-bis(2-hydroxypropanesulfonic acid)dihydrate, 4-(2-hydroxyethyl)-1-piperazinepropanesulfonic acid, N,N-bis(2-hydroxyethyl)glycine, N-(2-hydroxyethyl)piperazine-N'-(4-butanesulfonic acid), N-[tris(hydroxymethyl)methyl]-3-aminopropanesulfonic acid, N-tris(Hydroxymethyl)methyl-4-aminobutanesulfonic acid, N-(1,1-dimethyl-2-hydroxyethyl)-3-amino-2-hydroxypropanesulfonic acid, 2-(cyclohexylamino)ethanesulfonic acid, 3-(cyclohexylamino)-2-hydroxy-1-propanesulfonic acid, 3-(cyclohexylamino)-1-propanesulfonic acid, N-(2-acetamido)iminodiacetic acid, 4-(cyclohexylamino)-1-butanesulfonic acid, N-[tris(hydroxymethyl)methyl]glycine, 2-amino-2-(hydroxymethyl)-1,3-propanediol, and trometamol.

A pharmaceutical composition of the disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation include, but are not limited to, vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1 to 10 mg/kg. An exemplary treatment regime entails administration once per week, once every two weeks, once every three weeks, once every four weeks, once per month, once every 3 months or once every three to 6 months. Dosage regimens for an anti-Notch1 antibody of the disclosure include, for example, 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1 to 1000 µg/ml and in some methods about 25 to 300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-Notch antibody of the disclosure preferably results in a decrease in severity of disease symptoms, an increase in frequency and duration of disease symptom-free periods, or a prevention of impairment or disability due to the disease affliction. For example, for the treatment of Notch1-positive tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present disclosure can be administered via one or more routes of administration using one or more of a variety of methods known in the art. As will be appreciated by the skilled artisan, the route and/or mode of administration will vary depending upon the desired results. Routes of administration for antibodies of the disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody or antigen biding portion thereof of the disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Uses and Methods of the Disclosure

The antibodies, particularly the human antibodies, antibody compositions and methods of the present disclosure have numerous in vitro and in vivo diagnostic and therapeutic utilities involving the diagnosis and treatment of Notch1 mediated disorders. For example, these molecules can be administered to cells in culture, in vitro or ex vivo, or to human subjects, e.g., in vivo, to treat, prevent and to diagnose a variety of disorders. As used herein, the term "subject" is intended to include human and non-human animals. Non-human animals include all vertebrates, e.g., mammals and non-mammals, such as non-human primates, sheep, dogs, cats, cows, horses, chickens, amphibians, and reptiles. Preferred subjects include human patients having disorders mediated by Notch1 activity. The methods are particularly suitable for treating human patients having a disorder associated with abnormal Notch1 expression or activation. When antibodies to Notch1 are administered together with another agent, the two can be administered in either order or simultaneously.

Given the specific binding of the antibodies of the disclosure for Notch1, the antibodies of the disclosure can be used to specifically detect Notch1 expression on the surface of cells and, moreover, can be used to purify Notch1 via immunoaffinity purification.

Furthermore, the antibodies, antibody compositions and methods of the present disclosure can be used to treat a subject with abnormal Notch1 expression, e.g., a cancer. In one particular embodiment, the cancer is T-cell acute lymphoblastic leukemia (T-ALL). In another particular embodiment, the cancer is non-small cell lung cancer (NSCLC), breast cancer, colon cancer or ovarian cancer.

Other types of abnormal Notch1 expression that may be treated by the antibodies of the disclosure include, for example, mesothelioma, hepatobilliary (hepatic and billiary duct), a primary or secondary CNS tumor, a primary or secondary brain tumor, lung cancer (NSCLC and SCLC), bone cancer, pancreatic cancer, skin cancer, cancer of the head or neck, cutaneous or intraocular melanoma, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

Suitable routes of administering the antibody compositions (e.g., human monoclonal antibodies, multispecific and bispecific molecules and immunoconjugates) of the disclosure in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

Human anti-Notch1 antibodies of the disclosure can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. The antibody and the agent can be prepared for simultaneous, sequential or separate administration. Such therapeutic agents include, among others, anti-neoplastic agents such as docetaxel, doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin can be intravenously administered as a 100 mg/dose once every four weeks and adriamycin is intravenously administered as a 60 to 75 mg/ml dose once every 21 days. Co-administration of the human anti-Notch1 antibodies of the present disclosure with chemotherapeutic agents provides two anti-cancer agents which operate via different mechanisms which yield a cytotoxic effect to human tumor cells.

Kits

Also within the scope of the present disclosure are kits comprising the antibody compositions of the disclosure (e.g., human antibodies, bispecific or multispecific molecules, or immunoconjugates) and instructions for use. The kit can further contain one or more additional reagents, such as an immunosuppressive reagent, a cytotoxic agent or a radiotoxic agent, or one or more additional antibodies of the disclosure (e.g., a human antibody having a complementary activity which binds to an epitope in the Notch1 antigen distinct from the first human antibody).

Accordingly, patients treated with antibody compositions of the disclosure can be additionally administered (prior to, simultaneously with, or following administration of a human antibody of the disclosure) another therapeutic agent, such as a cytotoxic or radiotoxic agent, which enhances or augments the therapeutic effect of the human antibodies.

The present disclosure is further illustrated by the following examples which should not be construed as further limiting. The contents of all figures and all references, patents and published patent applications cited throughout this application are expressly incorporated herein by reference.

EXAMPLES

Example 1

Generation of Recombinant Human and Mouse Notch1 Protein Immunogens

A. Expression and Purification of Human and Mouse Notch1 NRR Proteins cDNA constructs encoding the Notch1 NRR region, amino acids of SEQ ID 2 for human Notch1 and amino acids of SEQ ID 6 for mouse Notch1 shown in Table 1, with a signal peptide at the N-terminus and Avi and His6 tag at the C-terminus, were cloned into the expression vector pSMED2. These constructs were transiently transfected into COS or Chinese hamster ovary (CHO) cells and the secreted protein in conditioned media were analyzed on SDS-PAGE. After processing at the S1 cleavage site, the N-terminal ~26 kDa (LNR-A, B, C and HD1) and C-terminal ~12 kDa (HD2 and Avi_His tag) halves of the Notch1 NRR domain remain associated through non-covalent interactions to form a heterodimeric complex, as shown in FIG. 1. S1 processing of the Notch1 NRR was determined to be about 50% or less in samples prepared from CHO cells.

To enhance processing at the S1 cleavage site, the Notch1 NRR expression construct was transfected into CHO-PACE cells (Harrison et, al, Semin Hematol. 1998 Apr; 35(2 Suppl 2):4-10) and stable cell lines with the highest expression and complete processing of Notch1 NRR were selected. Culture of these cell lines was scaled up for the collection of conditioned media (CM) from which Notch1 NRR proteins were purified.

Concentrated CHO-PACE CM was loaded onto a 27 ml Qiagen Ni-NTA Superflow column that was equilibrated with PBS at a flow rate of 1 ml/min at 4° C. After loading, the column was washed with 10 Column Volumes (CV) of PBS, followed by 10 CV of Buffer A (300 mM NaCl, 50 mM $Na_2HPO_4$, pH 8.0), and followed by 10 CV 4% Buffer B (500 mM imidazole, 300 mM NaCl, 50 mM $Na_2HPO_4$, pH 8.0). The human Notch1 Avi_His was eluted using a linear gradient to 100% Buffer B over 10 CV. Fractions containing human Notch1 Avi_His were pooled, filtered and dialyzed to PBS calcium magnesium free (CMF). The protein was further purified with two rounds of size exclusion chromatography on a tandem SUPERDEX-200 and SUPERDEX-75 columns (total CV=600 ml) equilibrated with TBS +1 mM $CaCl_2$, 0.1 mM $ZnCl_2$. SDS-PAGE analysis of purified human and mouse Notch1 NRR_Avi_His tag proteins show that >90% of the purified protein was correctly cleaved into the predicted Notch1 NRR N-terminal and C-terminal peptide sizes. Light scattering (SEC-MALs) analysis of purified human and mouse Notch1 NRR proteins showed a peak at the expected molecular weight of 40 kDa on a size exclusion column under native conditions, indicating proper formation of an intact Notch1 NRR heterodimer.

B. Expression and Purification of Cyno-Notch1 NRR-Fc Fusion Protein

A cDNA construct encoding the cyno Notch1 NRR region, amino acids of SEQ ID 10 for cyno Notch1 shown in Table 1, with a signal peptide at the N-terminus and human IgG1 Fc fragment at the C-terminus, was cloned into the expression vector pSMED2. This construct was transiently co-transfected into 293 (Invitrogen) cells with a soluble PACE over-expressing construct (Harrison et, al, Semin Hematol. 1998 April; 35(2 Suppl 2):4-10) to ensure complete processing of the cyno-Notch1 NRR region. Conditioned medium was harvested from transfected cells and the cyno-Notch1 NRR-Fc fusion protein was purified via protein A affinity purification. Purified protein was then dialyzed into TBS containing 1 mM $CaCl_2$. SDS-PAGE analysis showed two polypeptide fragments at expected sizes of 12 Kd (HD1) and 37 Kd (HD2+Fc), with >95% purity of the protein preparation. Analytical SEC under native conditions showed a single peak around 50 $K_D$, representing a heterodimer of the two fragments described above, with minimal amount of aggregates (<1%) in the preparation.

Table 1 below provides the amino acid and nucleotide sequences of human, mouse and cyno Notch1 NRR regions.

TABLE 1

Amino acid and nucleotide sequences of human, mouse and cyno Notch1 NRR regions.

| SEQ ID NO: | | |
|---|---|---|
| 1 | Human Notch1 NRR amino acid sequence (amino acids in lower case type represent the Gp1b signal sequence and Avi_His tag) | mplllllllllpsplhpGGAGRDIPPPLIEEACELPECQE DAGNKVCSLQCNNHACGWDGGDCSLNFNDP WKNCTQSLQCWKYFSDGHCDSQCNSAGCLF DGFDCQRAEGQCNPLYDQYCKDHFSDGHCD QGCNSAECEWDGLDCAEHVPERLAAGTLVVV VLMPPEQLRNSSFHFLRELSRVLHTNVVFKRD AHGQQMIFPYYGREEELRKHPIKRAAEGWAAP DALLGQVKASLLPGGSEGGRRRRELDPMDVR GSIVYLEIDNRQCVQASSQCFQSATDVAAFLG ALASLGSLNIPYKIEAVQSETVEPPPPAQLHFM gggsgglndifeaqkiewheggpphhhhhh |
| 2 | Human Notch1 NRR amino acid sequence | GGAGRDIPPPLIEEACELPECQEDAGNKVCSL QCNNHACGWDGGDCSLNFNDPWKNCTQSLQ CWKYFSDGHCDSQCNSAGCLFDGFDCQRAE GQCNPLYDQYCKDHFSDGHCDQGCNSAECE WDGLDCAEHVPERLAAGTLVVVVLMPPEQLR NSSFHFLRELSRVLHTNVVFKRDAHGQQMIFP YYGREEELRKHPIKRAAEGWAAPDALLGQVKA SLLPGGSEGGRRRRELDPMDVRGSIVYLEIDN RQCVQASSQCFQSATDVAAFLGALASLGSLNI PYKIEAVQSETVEPPPPAQLHFM |
| 3 | Human Notch1 NRR nucleotide sequence (nucleotides in lower case type represent the signal peptide Avi_His tag coding sequence) | atgcctctcctcctcttgctgctcctgctgccaagcccttacacgc gGGTGGGGCCGGGCGCGACATCCCCCCGC CGCTGATCGAGGAGGCGTGCGAGCTGCCCG AGTGCCAGGAGGACGCGGGCAACAAGGTCT GCAGCCTGCAGTGCAACAACCACGCGTGCG GCTGGGACGGCGGTGACTGCTCCCTCAACT TCAATGACCCCTGGAAGAACTGCACGCAGTC TCTGCAGTGCTGGAAGTACTTCAGTGACGGC CACTGTGACAGCCAGTGCAACTCAGCCGGC TGCCTCTTCGACGGCTTTGACTGCCAGCGTG CGGAAGGCCAGTGCAACCCCCTGTACGACC AGTACTGCAAGGACCACTTCAGCGACGGGC ACTGCGACCAGGGCTGCAACAGCGCGGAGT GCGAGTGGGACGGGCTGGACTGTGCGGAG CATGTACCCGAGAGGCTGGCGGCCGGCACG CTGGTGGTGGTGGTGCTGATGCCGCCGGAG CAGCTGCGCAACAGCTCCTTCCACTTCCTGC GGGAGCTCAGCCGCGTGCTGCACACCAACG TGGTCTTCAAGCGTGACGCACACGGCCAGC AGATGATCTTCCCCTACTACGGCCGCGAGGA GGAGCTGCGCAAGCACCCCATCAAGCGTGC CGCCGAGGGCTGGGCCGCACCTGACGCCCT GCTGGGCCAGGTGAAGGCCTCGCTGCTCCC TGGTGGCAGCGAGGGTGGCCGGCGGCGGA GGGAGCTGGACCCCATGGACGTCCGCGGCT CCATCGTCTACCTGGAGATTGACAACCGGCA GTGTGTGCAGGCCTCCTCGCAGTGCTTCCA GAGTGCCACCGACGTGGCCGCATTCCTGGG AGCGCTCGCCTCGCTGGGCAGCCTCAACAT CCCCTACAAGATCGAGGCCGTGCAGAGTGA GACCGTGGAGCCGCCCCCGCCGGCGCAGC TGCACTTCATGGgaggggggaagcggaggcggactgaa cgacatcttcgaggctcagaaaatcgaatggcacgaaggtggc ccaccacatcatcatcatcac |

TABLE 1-continued

Amino acid and nucleotide sequences of human, mouse and cyno Notch1 NRR regions.

| SEQ ID NO: | | |
|---|---|---|
| 4 | Human Notch1 NRR nucleotide sequence | GGTGGGGCCGGGCGCGACATCCCCCCGCC GCTGATCGAGGAGGCGTGCGAGCTGCCCGA GTGCCAGGAGGACGCGGGCAACAAGGTCTG CAGCCTGCAGTGCAACAACCACGCGTGCGG CTGGGACGGCGGTGACTGCTCCCTCAACTT CAATGACCCCTGGAAGAACTGCACGCAGTCT CTGCAGTGCTGGAAGTACTTCAGTGACGGC CACTGTGACAGCCAGTGCAACTCAGCCGGC TGCCTCTTCGACGGCTTTGACTGCCAGCGTG CGGAAGGCCAGTGCAACCCCCTGTACGACC AGTACTGCAAGGACCACTTCAGCGACGGGC ACTGCGACCAGGGCTGCAACAGCGCGGAGT GCGAGTGGGACGGGCTGGACTGTGCGGAG CATGTACCCGAGAGGCTGGCGGCCGGCACG CTGGTGGTGGTGGTGCTGATGCCGCCGGAG CAGCTGCGCAACAGCTCCTTCCACTTCCTGC GGGAGCTCAGCCGCGTGCTGCACACCAACG TGGTCTTCAAGCGTGACGCACACGGCCAGC AGATGATCTTCCCCTACTACGGCCGCGAGGA GGAGCTGCGCAAGCACCCCATCAAGCGTGC CGCCGAGGGCTGGGCCCACCTGACGCCCT GCTGGGCCAGGTGAAGGCCTCGCTGCTCCC TGGTGGCAGCGAGGGTGGGCGGCGGCGGA GGGAGCTGGACCCCATGGACGTCCGCGGCT CCATCGTCTACCTGGAGATTGACAACCGGCA GTGTGTGCAGGCCTCCTCGCAGTGCTTCCA GAGTGCCACCGACGTGGCCGCATTCCTGGG AGCGCTCGCCTCGCTGGGCAGCCTCAACAT CCCCTACAAGATCGAGGCCGTGCAGAGTGA GACCGTGGAGCCGCCCCCGCCGGCGCAGC TGCACTTCATG |
| 5 | Mouse Notch1 NRR amino acid sequence (amino acids in lower case type represent the Gp1b signal sequence and Avi_His tag of purified protein) | mpllllllllpsplhoGGAGRDIPPPQIEEACELPECQV DAGNKVCNLQCNNHACGWDGGDCSLNFNDP WKNCTQSLQCWKYFSDGHCDSQCNSAGCLF DGFDCQLTEGQCNPLYDQYCKDHFSDGHCDQ GCNSAECEWDGLDCAEHVPERLAAGTLVLVVL LPPDQLRNNSFHFLRELSHVLHTNVVFKRDAQ GQQMIFPYYGHEEELRKHPIKRSTVGWATSSL LPGTSGGRQRRELDPMDIRGSIVYLEIDNRQC VQSSSQCFQSATDVAAFLGALASLGSLNIPYKI EAVKSEPVEPPLPSQLHLMgggsggglndifeaqkie wheggpphhhhhh |
| 6 | Mouse Notch1 NRR amino acid sequence | GGAGRDIPPPQIEEACELPECQVDAGNKVCNL QCNNHACGWDGGDCSLNFNDPWKNCTQSLQ CWKYFSDGHCDSQCNSAGCLFDGFDCQLTEG QCNPLYDQYCKDHFSDGHCDQGCNSAECEW DGLDCAEHVPERLAAGTLVLVVLLPPDQLRNN SFHFLRELSHVLHTNVVFKRDAQGQQMIFPYY GHEEELRKHPIKRSTVGWATSSLLPGTSGGRQ RRELDPMDIRGSIVYLEIDNRQCVQSSSQCFQ SATDVAAFLGALASLGSLNIPYKIEAVKSEPVEP PLPSQLHLM |
| 7 | Mouse Notch1 NRR nucleotide sequence (nucleotides in lower case type represent the Gp1b signal sequence and Avi_His tag of purified protein) | atgcctctcctcctcttgctgctcctgctgccaagccccttacacgc gGGTGGCGCTGGGCGCGACATTCCCCCACC GCAGATTGAGGAGGCCTGTGAGCTGCCTGA GTGCCAGGTGGATGCAGGCAATAAGGTCTG CAACCTGCAGTGTAATAATCACGCATGTGGC TGGGATGGTGGCGACTGCTCCCTCAACTTCA ATGACCCCTGGAAGAACTGCACGCAGTCTCT ACAGTGCTGGAAGTATTTTAGCGACGGCCAC TGTGACAGCCAGTGCAACTCGGCCGGCTGC CTCTTTGATGGCTTCGACTGCCAGCTCACCG AGGGACAGTGCAACCCCCTGTATGACCAGTA CTGCAAGGACCACTTCAGTGATGGCCACTGC GACCAGGGCTGTAACAGTGCCGAATGTGAG TGGGATGGCCTAGACTGTGCTGAGCATGTAC CCGAGCGGCTGGCAGCCGGCACCCTGGTG CTGGTGGTGCTGCTTCCACCCGACCAGCTA CGGAACAACTCCTTCCACTTTCTGCGGGAGC TCAGCCACGTGCTGCACACCAACGTGGTCTT CAAGCGTGATGCGCAAGGCCAGCAGATGAT CTTCCCGTACTATGGCCACGAGGAAGAGCT |

TABLE 1-continued

Amino acid and nucleotide sequences of human, mouse and cyno Notch1 NRR regions.

SEQ ID NO:

| | | |
|---|---|---|
| | | GCGCAAGCACCCAATCAAGCGCTCTACAGT<br>GGGTTGGGCCACCTCTTCACTGCTTCCTGGT<br>ACCAGTGGTGGGCGCCAGCGCAGGGAGCT<br>GGACCCCATGGACATCCGTGGCTCCATTGTC<br>TACCTGGAGATCGACAACCGGCAATGTGTGC<br>AGTCATCCTCGCAGTGCTTCCAGAGTGCCAC<br>CGATGTGGCTGCCTTCCTAGGTGCTCTTGCG<br>TCACTTGGCAGCCTCAATATTCCTTACAAGAT<br>TGAGGCCGTGAAGAGTGAGCCGGTGGAGCC<br>TCCGCTGCCCTCGCAGCTGCACCTCATGgga<br>gggggaagcggaggcggactgaacgacatcttcgaggctcag<br>aaaatcgaatggcacgaaggtggcccaccacatcatcatcatca<br>tcac |
| 8 | Mouse Notch1 NRR nucleotide sequence | GGTGGCGCTGGGCGCGACATTCCCCCACCG<br>CAGATTGAGGAGGCCTGTGAGCTGCCTGAG<br>TGCCAGGTGGATGCAGGCAATAAGGTCTGC<br>AACCTGCAGTGTAATAATCACGCATGTGGCT<br>GGGATGGTGGCGACTGCTCCCTCAACTTCAA<br>TGACCCCTGGAAGAACTGCACGCAGTCTCTA<br>CAGTGCTGGAAGTATTTTAGCGACGGCCACT<br>GTGACAGCCAGTGCAACTCGGCCGGCTGCC<br>TCTTTGATGGCTTCGACTGCCAGCTCACCGA<br>GGGACAGTGCAACCCCCTGTATGACCAGTA<br>CTGCAAGGACCACTTCAGTGATGGCCACTGC<br>GACCAGGGCTGTAACAGTGCCGAATGTGAG<br>TGGGATGGCCTAGACTGTGCTGAGCATGTAC<br>CCGAGCGGCTGGCAGCCGGCACCCTGGTG<br>CTGGTGGTGCTGCTTCCACCCGACCAGCTA<br>CGGAACAACTCCTTCCACTTTCTGCGGGAGC<br>TCAGCCACGTGCTGCACACCAACGTGGTCTT<br>CAAGCGTGATGCGCAAGGCCAGCAGATGAT<br>CTTCCCGTACTATGGCCACGAGGAAGAGCT<br>GCGCAAGCACCCAATCAAGCGCTCTACAGT<br>GGGTTGGGCCACCTCTTCACTGCTTCCTGGT<br>ACCAGTGGTGGGCGCCAGCGCAGGGAGCT<br>GGACCCCATGGACATCCGTGGCTCCATTGTC<br>TACCTGGAGATCGACAACCGGCAATGTGTGC<br>AGTCATCCTCGCAGTGCTTCCAGAGTGCCAC<br>CGATGTGGCTGCCTTCCTAGGTGCTCTTGCG<br>TCACTTGGCAGCCTCAATATTCCTTACAAGAT<br>TGAGGCCGTGAAGAGTGAGCCGGTGGAGCC<br>TCCGCTGCCCTCGCAGCTGCACCTCATG |
| 9 | Cyno-Notch1 NRR-Fc amino acid sequence (amino acids in lower case type represent the signal sequence and hIgG1 Fc fragment of purified protein) | mgwsciilflvatatgahsGGAGRDIPPPLIEEACELPE<br>CQEDAGNKVCSLQCNNHACGWDGGDCSLNF<br>NDPWKNCTQSLQCWKYFSDGHCDSQCNSAG<br>CLFDGFDCQRAEGQCNPLYDQYCKDHFSDGH<br>CDQGCNSAECEWDGLDCAEHVPERLAAGTLV<br>VVVLMPPEQLRNSSFHFLRELSRVLHTNVVFK<br>RDAHGQQMIFPYYGREEELRKHPIKRAAEGWA<br>APEALLGQVKASLLPGGGGGGRRRRELDPMD<br>VRGSIVYLEIDNRQCVQASSQCFQSATDVAAFL<br>GALASLGSLNIPYKIEAVQSETVEPPPPAQLHF<br>Mggggsggggepkssdkthtcppcpapellggpsvflfppkpk<br>dtlmisrtpevtcvvvdvshedpevkfnwyvdgvevhnaktkpr<br>eeqynstyrvvsvltvlhqdwlngkeykckvsnkalpapiektisk<br>akgqprepqvytlppsreemtknqvsltclvkgfypsdiavewes<br>ngqpennykttppvldsdgsfflyskltvdksrwqqgnvfscsvm<br>healhnhytqkslslspgk |
| 10 | Cyno-Notch1 NRR amino acid sequence | GGAGRDIPPPLIEEACELPECQEDAGNKVCSL<br>QCNNHACGWDGGDCSLNFNDPWKNCTQSLQ<br>CWKYFSDGHCDSQCNSAGCLFDGFDCQRAE<br>GQCNPLYDQYCKDHFSDGHCDQGCNSAECE<br>WDGLDCAEHVPERLAAGTLVVVVLMPPEQLR<br>NSSFHFLRELSRVLHTNVVFKRDAHGQQMIFP<br>YYGREEELRKHPIKRAAEGWAAPEALLGQVKA<br>SLLPGGGGGGRRRRELDPMDVRGSIVYLEIDN<br>RQCVQASSQCFQSATDVAAFLGALASLGSLNI<br>PYKIEAVQSETVEPPPPAQLHFM |
| 11 | Cyno-Notch1 NRR-Fc nucleotide sequence (nucleotides in lower case type | atgggatggagctgtatcatcctcttcttggtagcaacagctacag<br>gcgcgcactccGGTGGGGCCGGGCGCGACATCC<br>CCCCGCCGCTGATCGAGGAGGCGTGCGAGC |

TABLE 1-continued

Amino acid and nucleotide sequences of human, mouse and cyno Notch1 NRR regions.

| SEQ ID NO: | | |
|---|---|---|
| | represent the signal sequence and hIgG1 Fc fragment of purified protein) | TGCCCGAGTGCCAGGAGGACGCGGGCAACA<br>AGGTCTGCAGCCTGCAGTGCAACAACCACG<br>CGTGCGGCTGGGACGGCGGTGACTGCTCCC<br>TCAACTTCAATGACCCCTGGAAGAACTGCAC<br>GCAGTCTCTGCAGTGCTGGAAGTACTTCAGT<br>GACGGCCACTGTGACAGCCAGTGCAACTCA<br>GCCGGCTGCCTCTTCGACGGCTTTGACTGC<br>CAGCGTGCGGAAGGCCAGTGCAACCCCCTG<br>TACGACCAGTACTGCAAGGACCACTTCAGCG<br>ACGGGCACTGCGACCAGGGCTGCAACAGCG<br>CGGAGTGCGAGTGGGACGGGCTGGACTGTG<br>CGGAGCATGTACCCGAGAGGCTGGCGGCCG<br>GCACGCTGGTGGTGGTGCTGATGCCGC<br>CGGAGCAGCTGCGCAACAGCTCCTTCCACTT<br>CCTGCGGGAGCTCAGCCGCGTGCTGCACAC<br>CAACGTGGTCTTCAAGCGTGACGCACACGG<br>CCAGCAGATGATCTTCCCCTACTACGGCCGC<br>GAGGAGGAGCTGCGCAAGCACCCCATCAAG<br>CGTGCCGCCGAGGGCTGGGCCGCACCTGAA<br>GCCCTGCTGGGCCAGGTGAAGGCCTCGCTG<br>CTCCCTGGTGGCGGTGGAGGTGGGCGGCG<br>GCGGAGGGAGCTGGACCCCATGGACGTCCG<br>CGGCTCCATCGTCTACCTGGAGATTGACAAC<br>CGGCAGTGTGTGCAGGCCTCCTCGCAGTGC<br>TTCCAGAGTGCCACCGACGTGGCCGCATTC<br>CTGGGAGCGCTCGCCTCGCTGGGCAGCCTC<br>AACATCCCCTACAAGATCGAGGCCGTGCAGA<br>GTGAGACCGTGGAGCCGCCCCCGCCGGCG<br>CAGCTGCACTTCATGggaggggcggatccggcgga<br>ggcggagagcccaaatcttctgacaaaactcacacatgcccac<br>cgtgcccagcacctgaactcctggggggaccgtcagtcttcctctt<br>ccccccaaaacccaaggacaccctcatgatctcccggacccct<br>gaggtcacatgcgtggtggtggacgtgagccacgaagaccctg<br>aggtcaagttcaactggtacgtggacggcgtggaggtgcataat<br>gccaagacaaagccgcgggaggagcagtacaacagcacgta<br>ccgtgtggtcagcgtcctcaccgtcctgcaccaggactggctgaa<br>tggcaaggagtacaagtgcaaggtctccaacaaagccctccca<br>gcccccatcgagaaaaccatctccaaagccaaagggcagccc<br>cgagaaccacaggtgtacaccctgcccccatcccgggaggag<br>atgaccaagaaccaggtcagcctgacctgcctggtcaaaggctt<br>ctatcccagcgacatcgccgtggagtgggagagcaatgggcag<br>ccggagaacaactacaagaccacgcctcccgtgctggactccg<br>acggctccttcttcctctatagcaagctcaccgtggacaagagca<br>ggtggcagcaggggaacgtcttctcatgctccgtgatgcatgagg<br>ctctgcacaaccactacacgcagaagagcctctccctgtccccg<br>ggtaaa |
| 12 | Cyno-Notch1 NRR nucleotide sequence | GGTGGGGCCGGGCGCGACATCCCCCCGCC<br>GCTGATCGAGGAGGCGTGCGAGCTGCCCGA<br>GTGCCAGGAGGACGCGGGCAACAAGGTCTG<br>CAGCCTGCAGTGCAACAACCACGCGTGCGG<br>CTGGGACGGCGGTGACTGCTCCCTCAACTT<br>CAATGACCCCTGGAAGAACTGCACGCAGTCT<br>CTGCAGTGCTGGAAGTACTTCAGTGACGGC<br>CACTGTGACAGCCAGTGCAACTCAGCCGGC<br>TGCCTCTTCGACGGCTTTGACTGCCAGCGTG<br>CGGAAGGCCAGTGCAACCCCCTGTACGACC<br>AGTACTGCAAGGACCACTTCAGCGACGGGC<br>ACTGCGACCAGGGCTGCAACAGCGCGGAGT<br>GCGAGTGGGACGGGCTGGACTGTGCGGAG<br>CATGTACCCGAGAGGCTGGCGGCCGGCACG<br>CTGGTGGTGGTGCTGATGCCGCCGGAG<br>CAGCTGCGCAACAGCTCCTTCCACTTCCTGC<br>GGGAGCTCAGCCGCGTGCTGCACACCAACG<br>TGGTCTTCAAGCGTGACGCACACGGCCAGC<br>AGATGATCTTCCCCTACTACGGCCGCGAGGA<br>GGAGCTGCGCAAGCACCCCATCAAGCGTGC<br>CGCCGAGGGCTGGGCCGCACCTGAAGCCCT<br>GCTGGGCCAGGTGAAGGCCTCGCTGCTCCC<br>TGGTGGCGGTGGAGGTGGGCGGCGGCGGA<br>GGGAGCTGGACCCCATGGACGTCCGCGGCT<br>CCATCGTCTACCTGGAGATTGACAACCGGCA<br>GTGTGTGCAGGCCTCCTCGCAGTGCTTCCA<br>GAGTGCCACCGACGTGGCCGCATTCCTGGG<br>AGCGCTCGCCTCGCTGGGCAGCCTCAACAT |

TABLE 1-continued

Amino acid and nucleotide sequences of human, mouse and cyno Notch1 NRR regions.

SEQ ID
NO:

```
CCCCTACAAGATCGAGGCCGTGCAGAGTGA
GACCGTGGAGCCGCCCCCGCCGGCGCAGC
TGCACTTCATG
```

Example 2

Generation, Cloning and Humanization of Rat Anti-Notch1 Inhibitory Antibodies

A. Immunization and Hybridoma Generation

The human and mouse immunogens described in Example 1 were co-injected into Sprague-Dawley rats for the generation of hybridomas. Sprague-Dawley rats were immunized by subcutaneous injections of a mixture containing 20 µg each of human and mouse Notch1 NRR_Avi_His recombinant proteins in Freund's complete adjuvant. Immunizations were repeated at 2-week intervals for 12 weeks. Collected sera samples at day 0, 35, 49, and 63 after the 1$^{st}$ injection were tested for circulating anti-Notch1 antibody titer activity by enzyme-linked immunosorbent assay (ELISA), as described below.

When optimal titers were reached, a final dose of the protein mixture was injected intravenously (tail vein) into a rat having optimal antibody titer 4 days before it was to be sacrificed for splenocyte collection. Total splenocytes (2×10E08) from the rat were fused with mouse myeloma cell line P3×63.Ag8.653 (2.5×10E07) using PEG 4000. Fused cells were plated out in 96-well plates (0.2 ml/well) and subjected to HAT selection (RPMI 1640 containing 5×10E-04 M Hypoxanthine, 1.6×10E-05 M Thymidine, 4×10E-04 M Aminopterin, and 20% Heat Inactivated FCS).

Fourteen days post fusion, hybridoma supernatants were harvested and tested for the presence of rat IgGs that exhibit binding activity to human and/or mouse Notch1 NRR recombinant protein, and full length Notch1 expressed on the surface of U-2 OS cells by ELISA, as described below. Supernatants that showed binding activity to Notch1 targets were further tested for their ability to block Notch1 mediated signaling activity in a reporter gene assay, as described below. Selected Notch1 signaling blocking clones were then subcloned for further analysis.

B. Screening and Selection of Notch1 Specific Antibodies

1. Recombinant Protein Binding ELISA

Supernatants from hybridoma cultures were first screened for binding to recombinant human and mouse immunogens by ELISA. Purified human or mouse Notch1 NRR_Avi_His tag proteins were coated on CoStar hi-bound 96-well ELISA plates in 100 µl of PBS with Mg/Ca at a concentration of 1 µg/ml overnight. The plates were washed with PBS-Mg/Ca and blocked for 1 hour with 1% BSA in PBS-Mg/Ca. Blocking solution was decanted from the plate and hybridoma culture supernatants were applied to the plate. After incubation at room temperature for 1 hour, plates were washed again with PBS-Mg/Ca before HRP-conjugated secondary antibody diluted (1:20,000) in blocking buffer was applied. When the primary antibody tested was rat IgG, the secondary antibody was goat anti-rat IgG Fc (Bethyl Biotech); and when the primary antibody was mouse IgG, the secondary antibody was goat anti-mouse IgG Fc (Thermal Scientific).

After 1 hour incubation with the secondary antibody, plates were washed again, as described above, and TMB substrate solution was added. The developing reaction was allowed for 10 minutes before the stopping solution, 0.18M $H_2SO_4$, was added. Absorbance at O. D. 450 nM was measured and data was plotted and analyzed with Microsoft Excel and Graphpad-Prizm software. The antibodies exhibiting binding activity to human and/or mouse Notch1 NRR were selected for further cell based ELISA, as described below.

2. Cell Based ELISA

Supernatants from clones displaying positive binding to immunogens in recombinant Notch1 NRR based ELISAs described above were then screened for cell surface Notch1 binding in a cell-based ELISA. U-2 OS cells stably overexpressing human or mouse full length Notch1 protein on cell surface were plated at 50,000 cells/well in 96 well plates (white opaque, BD/VWR) the day before ELISA assay. On the day of the ELISA, culture media were removed from wells and serially diluted (1:3 in blocking buffer) antibody solutions or hybridoma culture supernatants were applied to the plate. Plates were incubated at room temperature for 2 hours before being washed with PBS-Mg/Ca. HRP-conjugated secondary antibody was then applied and incubated with cells for 1 hour as described above for recombinant protein ELISA. Plates were washed with PBS-Mg/Ca before being developed with Pico-Chemiluminescent developing kit (Thermal Scientific), and chemiluminescence measurements were performed per manufacturer's instructions. Data plotting and analyses were performed with Microsoft Excel and Graphpad-Prizm software. This data was used in screening of hybridoma clones and the characterization of a parental rat and humanized antibodies, as described in the Examples below.

3. Reporter Gene Assays

Supernatants from clones displaying positive binding to immunogens were then screened for neutralization activity in human and mouse Notch1 reporter gene co-culture assays (RGA). Results of the screening were used to select primary clones.

Human Notch1 reporter cells were trypinized and harvested from culture plate in complete McCoy's 5A media (McCoy's 5A with 10% FBS and penicillin, streptomycin, Invitrogen) and counted. Appropriate dilutions of cells were made with the same medium to allow for 3,000 cells/well in a total volume of 80 µl/well on a 96 well culture plate (white opaque, BD/VWR), in the presence of serially diluted (1:3 in complete McCoy's 5A media) antibody solutions or hybridoma culture supernatants. The mixture of cells and antibody dilutions were incubated on the plates in a cell culture incubator (37° C., 5% $CO_2$) for 1 hr before 15,000/well of human DLL4-HEK293 cells were added to each well. After addition of hDLL4-HEK293 cells, the plates were further incubated for 20 hrs in the incubator and DUAL-GLO Luciferase assay system (Promega) was used to measure the firefly luciferase and internal control Renilla luciferase activity per manufacturer's instructions. Data was plotted and analyzed using Microsoft Excel and Graphpad-Prism software. Mouse Notch1 reporter gene co-culture assay was performed as described for human Notch1 reporter gene co-culture assay, except 20,000 cells/well of mouse Notch1 reporter cells were co-cultured with 40,000 cells/well of mouse DLL4-HEK293 cells.

C. Cloning and Sequencing

Primary clones with confirmed cell surface binding or neutralizing activities were subcloned, such as clones 438 and 351 further described below. RNAs from the subclones were extracted and the variable region DNA sequences from the expressed antibodies were obtained via RT-PCR cloning, as described below.

One to five million of the subcloned hybridoma cells were homogenized for total RNA isolation with QIAGEN RNAEASY Mini kit. First strand cDNA was then produced using SUPERSCRIPT III RT kit (Invitrogen). Double stranded cDNAs for variable regions of anti-Notch1 IgGs were subsequently generated and amplified by PCR using primers from the rat IgG heavy chain (IgG1, 2a, 2b) and light chain (kappa or lamda) constant regions, as described below. PCR cycling conditions: 1 cycle at 95° C. for 1 min; 25 cycles at 95° C. for 1 min, 63° C. for 1 min and 72° C. for 1 min. The resulting RT-PCR products were cloned into TOPO-BLUNT cloning vector (Invitrogen) and sequenced by conventional methods.

Variable (V) region cDNAs from parental rat 438 and parental rat 351 (hereinafter "rat 438" and "rat 351", respectively) were subcloned into mammalian expression vectors wherein rat Variable Heavy chain (VH) were fused in frame with murine IgG1 (mIgG1), and rat Variable Light chain (VL) were fused with murine kappa. Similarly, for the generation of chimeric antibodies with rat V region and human IgG constant region, rat VH was fused in frame with human IgG1 (hIgG1), and VL with human kappa, respectively. Corresponding chimeric antibodies were generated from these constructs by transient transfection in COS cells and their binding and neutralizing activities were confirmed in assays.

Purified rat variable-mouse constant chimeric antibodies (hereinafter "rat 438-mIgG1" and "rat 351-mIgG1") were further characterized in a series of in vitro and in vivo assays, including recombinant antigen and cell surface target binding, inhibition of Notch1 activity in the RGA and angiogenesis assays, and tumor growth inhibition in mouse models, as described in the Examples below.

The lead antibodies, rat 438 and rat 351 were selected based on these studies. Table 2 lists the amino acid and nucleic acid sequences of various regions of rat 438 and rat 351's variable regions and additional clones 90, 132, 132 (A12/G11) and 137.

TABLE 2

Rat variable region sequences

| SEQ ID NO: | | |
|---|---|---|
| 13 | 438 Heavy Chain Variable Region amino acid sequence | AVQLVESGGGLVQPGRSLKLSCTASGFTFS SFAMAWVRQAPTKGLEWVASISYGGADTY YRDSVKGRFTISRDNAKSSLYLQMDSLRSE DTSTYYCAKDLPYYGYTPFVMDAWGQGTS VTVSS |
| 14 | 438 Heavy Chain Variable Region nucleotide sequence | GCGGTACAGTTGGTGGAGTCTGGGGGAG GCTTAGTGCAGCCTGGAAGGTCCTTGAAA CTCTCCTGTACAGCCTCTGGATTCACTTT CAGTAGCTTTGCAATGGCCTGGGTCCGC CAGGCTCCAACGAAGGGGCTGGAGTGGG TCGCATCCATTAGTTATGGTGGTGCTGAC ACTTACTATCGAGACTCCGTGAAGGGCC GATTCACTATCTCCAGAGATAATGCAAAA AGCAGCCTATATTTGCAAATGGACAGTCT GAGGTCTGAGGACACGTCCACTTATTACT GTGCAAAAGACCTTCCATACTACGGATAT ACCCCCTTTGTTATGGATGCCTGGGGTCA GGGAACTTCAGTCACTGTCTCCTCA |
| 15 | 438 Heavy Chain Variable Region CDR1 amino acid sequence Kabat | SFAMA |
| 16 | 438 Heavy Chain Variable Region CDR1 amino acid sequence Chothia | GFTFSSFAMA |
| 17 | 438 Heavy Chain Variable Region CDR1 nucleotide sequence Kabat | TCCTTCGCCATGGCC |
| 18 | 438 Heavy Chain Variable Region CDR1 nucleotide sequence Chothia | GGATTCACCTTTAGTTCCTTCGCCATGGC C |
| 19 | 438 Heavy Chain Variable Region CDR2 amino acid sequence Kabat | SISYGGADTYYRDSVKG |
| 20 | 438 Heavy Chain Variable Region CDR2 amino acid sequence Chothia | SYGGAD |

TABLE 2 -continued

Rat variable region sequences

| SEQ ID NO: | | |
|---|---|---|
| 21 | 438 Heavy Chain Variable Region CDR2 nucleotide sequence Kabat | TCCATCTCCTATGGAGGCGCTGACACCTA CTACCGGGACTCCGTGAAGGGC |
| 22 | 438 Heavy Chain Variable Region CDR2 nucleotide sequence Chothia | CCTATGGAGGCGCTGAC |
| 23 | 438 Heavy Chain Variable Region CDR3 amino acid sequence Kabat and Chothia | DLPYYGYTPFVMDA |
| 24 | 438 Heavy Chain Variable Region CDR3 nucleotide sequence Kabat and Chotia | GATCTGCCCTACTACGGCTACACCCCCTT CGTGATGGACGCC |
| 25 | 438 Light Chain Variable Region amino acid sequence | DIMLTQSPPTLSVTPGETISLSCRASQRINT DLHWYQQKPNESPRVLIKFASQTISGVPSR FSGSGSGTDFTLNINRVEPEDFSVYYCQQS NSWPYTFGAGTKLELK |
| 26 | 438 Light Chain Variable Region nucleotide sequence | GACATCATGCTGACTCAGTCTCCACCTAC CCTGTCTGTAACTCCAGGAGAGACCATCA GTCTCTCCTGCAGGGCCAGTCAGAGAATT AACACTGACTTACATTGGTATCAGCAAAA ACCAAATGAGTCTCCAAGGGTTCTCATCA AATTTGCTTCCCAGACCATCTCTGGAGTC CCCTCCAGGTTCAGTGGCAGTGGATCAG GGACAGATTTCACTCTCAATATTAACAGA GTAGAGCCTGAAGATTTTTCAGTTTATTAC TGTCAACAGAGTAATAGCTGGCCATACAC GTTTGGCGCTGGGACCAAGCTGGAACTG AAA |
| 27 | 438 Light Chain Variable Region CDR1 amino acid sequence Kabat and Chothia | RASQRINTDLH |
| 28 | 438 Light Chain Variable Region CDR1 nucleotide sequence Kabat and Chothia | CGGGCCTCCCAGCGGATCAACACCGACC TGCAC |
| 29 | 438 Light Chain Variable Region CDR2 amino acid sequence Kabat and Chothia | FASQTIS |
| 30 | 438 Light Chain Variable Region CDR2 nucleotide sequence Kabat and Chothia | TTCGCCAGCCAGACCATCTCC |
| 31 | 438 Light Chain Variable Region CDR3 amino acid sequence Kabat and Chothia | QQSNSWPYT |
| 32 | 438 Light Chain Variable Region CDR3 nucleotide sequence Kabat and Chothia | CAGCAGTCCAACTCCTGGCCCTACACC |
| 33 | 351 Heavy Chain Variable Region amino acid sequence | EVQLVESGGGLVQPGRSLKVSCLASGFTFS HYGMNWIRQAPGKGLDWVASISRSGSYIR YVDTVKGRFTVSRDIAKNTLYLQMTSLRSE DTALYYCAREGQFGDYFEYWGQGVMVTV SS |
| 34 | 351 Heavy Chain Variable Region nucleotide sequence | GAGGTGCAGCTGGTGGAGTCTGGAGGAG GCTTAGTGCAGCCTGGAAGGTCCCTGAA AGTCTCCTGTTTAGCCTCTGGATTCACTTT CAGTCACTATGGAATGAACTGGATTCGCC AGGCTCCAGGGAAGGGGCTGGACTGGGT TGCATCTATTAGTAGGAGTGGCAGTTACA TCCGCTATGTAGACACAGTGAAGGGCCG ATTCACCGTCTCCAGAGACATTGCCAAGA ACACCCTGTACCTGCAAATGACCAGTCTG AGGTCTGAAGACACTGCCTTGTATTACTG |

TABLE 2 -continued

Rat variable region sequences

| SEQ ID NO: | | |
|---|---|---|
| | | TGCAAGAGAGGGACAATTCGGGGACTAC TTTGAGTACTGGGGCCAAGGAGTCATGG TCACAGTCTCCTCA |
| 35 | 351 Heavy Chain Variable Region CDR1 amino acid sequence Kabat | HYGMN |
| 36 | 351 Heavy Chain Variable Region CDR1 amino acid sequence Chothia | GFTFSHYGMN |
| 37 | 351 Heavy Chain Variable Region CDR1 nucleotide sequence Kabat | CACTATGGAATGAAC |
| 38 | 351 Heavy Chain Variable Region CDR1 nucleotide sequence Chothia | GGATTCACTTTCAGTCACTATGGAATGAA C |
| 39 | 351 Heavy Chain Variable Region CDR2 amino acid sequence Kabat | SISRSGSYIRYVDTVKG |
| 40 | 351 Heavy Chain Variable Region CDR2 amino acid sequence Chothia | SRSGSY |
| 41 | 351 Heavy Chain Variable Region CDR2 nucleotide sequence Kabat | TCTATTAGTAGGAGTGGCAGTTACATCCG CTATGTAGACACAGTGAAGGGC |
| 42 | 351 Heavy Chain Variable Region CDR2 nucleotide sequence Chothia | AGTAGGAGTGGCAGTTAC |
| 43 | 351 Heavy Chain Variable Region CDR3 amino acid sequence Kabat and Chothia | EGQFGDYFEY |
| 44 | 351 Heavy Chain Variable Region CDR3 nucleotide sequence Kabat and Chotia | GAGGGACAATTCGGGGACTACTTTGAGTA C |
| 45 | 351 Light Chain Variable Region amino acid sequence | DIMLTQSPATLSVTPGERISLSCRASQKIST NLHWYQQKPNESPRILIKYASQTISGIPSRF SGSGSGTDFTLHINTVEPEDFSVYYCQQTN SWPLTFGSGTKLEIK |
| 46 | 351 Light Chain Variable Region nucleotide sequence | GACATCATGCTGACTCAGTCTCCAGCTAC CCTGTCTGTAACTCCAGGAGAGAGAATCA GTCTCTCCTGCAGGGCCAGTCAGAAAATT AGCACTAACTTACATTGGTATCAGCAAAA GCCAAATGAGTCTCCAAGGATTCTCATCA AATATGCTTCCCAGACCATCTCTGGAATC CCCTCCAGGTTCAGTGGCAGTGGATCAG GGACAGATTTCACTCTCCATATTAACACA GTAGAGCCTGAAGATTTTTCAGTTTATTAC TGTCAACAGACTAATAGTTGGCCGCTCAC GTTCGGTTCTGGGACCAAGCTGGAGATC AAG |
| 47 | 351 Light Chain Variable Region CDR1 amino acid sequence Kabat and Chothia | RASQKISTNLH |
| 48 | 351 Light Chain Variable Region CDR1 nucleotide sequence Kabat and Chothia | AGGGCCAGTCAGAAAATTAGCACTAACTT ACAT |
| 49 | 351 Light Chain Variable Region CDR2 amino acid sequence Kabat and Chothia | YASQTIS |

TABLE 2 -continued

Rat variable region sequences

| SEQ ID NO: | | |
|---|---|---|
| 50 | 351 Light Chain Variable Region CDR2 nucleotide sequence Kabat and Chothia | TATGCTTCCCAGACCATCTCT |
| 51 | 351 Light Chain Variable Region CDR3 amino acid sequence Kabat and Chothia | QQTNSWPLT |
| 52 | 351 Light Chain Variable Region CDR3 nucleotide sequence Kabat and Chothia | CAACAGACTAATAGTTGGCCGCTCACG |
| 53 | 90 Heavy Chain Variable Region amino acid sequence (kabat CDR underlined) | EVQLVESGGGLVQPGRSLKLSCLASGFTFS HYGVNWIRQAPGKGLEWIASISRSSSYIYYA DTVKGRFTISRDNAKNTLFLQLTSLRSEDTA LYYCAREGQFGDYFEYWGRGVMVTVSS |
| 54 | 90 Heavy Chain Variable Region nucleotide sequence | GAGGTGCAGCTAGTGGAGTCTGGAGGAG GCTTAGTGCAGCCTGGAAGGTCCCTGAA ACTCTCCTGTTTAGCCTCTGGATTCACTTT CAGTCACTATGGAGTGAACTGGATTCGCC AGGCTCCAGGGAAGGGGCTGGAATGGAT TGCATCTATTAGTAGAAGTAGCAGTTACA TCTACTATGCAGACACAGTGAAGGGCCG ATTCACCATCTCCAGAGACAATGCCAAGA ACACCCTGTTCCTGCAATTGACCAGTCTG AGGTCTGAAGACACTGCCTTGTATTACTG TGCAAGAGAGGGGCAATTCGGGGACTAC TTTGAATACTGGGGCCGAGGAGTCATGG TCACAGTCTCCTCA |
| 55 | 90 Light Chain Variable Region amino acid sequence (kabat CDR underlined) | DIILTQSPAALSVTPGESISLSCRASQSINTN LHWYQQKPNESPRVLIKYASQTISGIPSRFS GSGSGTDFTLNINRVEPEDFSVYYCQQSNS WPLTFGSGTKLEIK |
| 56 | 90 Light Chain Variable Region nucleotide sequence | GACATCATACTGACTCAGTCTCCAGCTGC CCTGTCTGTAACTCCAGGAGAGAGCATCA GTCTCTCCTGCAGGGCCAGTCAGAGTATT AACACTAACTTGCATTGGTATCAGCAAAA ACCAAATGAGTCTCCAAGGGTTCTCATCA AATATGCTTCCCAGACCATCTCTGGAATC CCCTCCAGGTTCAGTGGCAGTGGATCAG GGACAGATTTCACTCTCAATATTAACAGA GTAGAGCCTGAAGATTTTTCAGTTTATTAC TGTCAACAGAGTAATAGCTGGCCGCTCAC GTTCGGTTCTGGGACCAAGCTGGAGATC AAA |
| 57 | 132 Heavy Chain Variable Region amino acid sequence (kabat CDR underlined) | EVQLVESGGGLVQPGRSLKLSCLASGFTFS HYGMNWIRQAPGKGLEWITSITSSSSYIYYA DTVKGRFTISRDNAKNTLYLQMTSLRSEDT ALYYCAREGQFGDYFDYWGQGVMVTVSS |
| 58 | 132 Heavy Chain Variable Region nucleotide sequence | GAGGTGCAGCTGGTGGAGTCTGGAGGAG GCTTAGTGCAGCCTGGAAGGTCCCTGAA ACTCTCCTGTTTAGCCTCTGGATTCACTTT CAGTCACTATGGAATGAACTGGATTCGCC AGGCTCCAGGGAAGGGGCTGGAGTGGAT TACATCTATTACTAGTAGTAGCAGTTACAT CTACTATGCAGACACAGTGAAGGGCCGA TTCACCATCTCCAGAGACAATGCCAAGAA CACCCTGTACCTGCAAATGACCAGTCTGA GGTCTGAAGACACTGCCTTGTATTACTGT GCAAGAGAGGGGCAATTCGGGGACTACT TTGATTACTGGGGCCAAGGAGTCATGGTC ACAGTCTCCTCA |
| 59 | 132 Light Chain Variable Region amino acid sequence (kabat CDR underlined) | DIMLTQSPATLSVTPGESISLSCRASQSINT NLHWYQQKPNESPRVLIKYASQTISGIPSRF SGSGSGTDFTLNINRVEPEDFSVYYCQQSN SWPLTFGSGTKLEIK |

TABLE 2 -continued

Rat variable region sequences

| SEQ ID NO: | | |
|---|---|---|
| 60 | 132 Light Chain Variable Region nucleotide sequence | GACATCATGCTGACTCAGTCTCCAGCTAC CCTGTCTGTAACTCCAGGAGAGAGCATCA GTCTCTCCTGCAGGGCCAGTCAGAGTATT AACACTAACTTACATTGGTATCAGCAAAAA CCAAATGAGTCTCCAAGGGTTCTCATCAA ATATGCTTCCCAGACCATCTCTGGAATCC CCTCCAGGTTCAGTGGCAGTGGATCAGG GACAGATTTCACTCTCAATATTAACAGAGT AGAGCCTGAAGATTTTTCAGTTTATTACTG TCAACAGAGTAATAGCTGGCCGCTCACGT TCGGTTCTGGGACCAAGCTGGAGATCAA A |
| 61 | 132_A12 Heavy Chain Variable Region amino acid sequence (kabat CDR underlined) | EVQLVESGGGLVQPGRSLKLSCLASGFTFS <u>HYGMN</u>WIRQAPGKGLEWIT<u>SITSSSSYIYYA DTVKG</u>RFTISRDNAKNTLYLQMTSLRSEDT ALYYCAR<u>EGQFGDYFDY</u>WGQGVMVTVSS |
| 62 | 132_A12 Heavy Chain Variable Region nucleotide sequence | GAGGTGCAGCTGGTGGAGTCTGGAGGAG GCTTAGTGCAGCCTGGAAGGTCCCTGAA ACTCTCCTGTTTAGCCTCTGGATTCACTTT CAGTCACTATGGAATGAACTGGATTCGCC AGGCTCCAGGGAAGGGGCTGGAGTGGAT TACATCTATTACTAGTAGTAGCAGTTACAT CTACTATGCAGACACAGTGAAGGGCCGA TTCACCATCTCCAGAGACAATGCCAAGAA CACCCTGTACCTGCAAATGACCAGTCTGA GGTCTGAAGACACTGCCTTGTATTACTGT GCAAGAGAGGGGCAATTCGGGGACTACT TTGATTACTGGGGCCAAGGAGTCATGGTC ACAGTCTCCTCA |
| 63 | 132_G11 Light Chain Variable Region amino acid sequence (kabat CDR underlined) | DIMLTQSPATLSVTPGESISLSC<u>RASQSINT NLH</u>WYQQKPNESPRVLIK<u>YASQTIS</u>GIPSRF SGSGSGTDFTLNINRVEPEDFSVYYC<u>QQSN SWPLT</u>FGSGTKLEIK |
| 64 | 132_G11 Light Chain Variable Region nucleotide sequence | GACATCATGCTGACTCAGTCTCCAGCTAC CCTGTCTGTAACTCCAGGAGAGAGCATCA GTCTCTCCTGCAGGGCCAGTCAGAGTATT AACACTAACTTACATTGGTATCAGCAAAAA CCTCCAGGTTCAGTGGCAGTGGATCAGG GACAGATTTCACTCTCAATATTAACAGAGT AGAGCCTGAAGATTTTTCAGTTTATTACTG TCAACAGAGTAATAGCTGGCCGCTCACGT TCGGTTCTGGGACCAAGCTGGAGATCAA A |
| 65 | 137 Heavy Chain Variable Region amino acid sequence (kabat CDR underlined) | QVQVKESGPGLVQPSQTLSLTCTVSGFSLT <u>SYHVS</u>WVRQPPGKGLEWMG<u>AIWTGGSTA YNSLLKS</u>RLSISRDISKSQVFLKMNSLQTED TATYYCAR<u>ADFYVMDA</u>WGQGASVTVSS |
| 66 | 137 Heavy Chain Variable Region nucleotide sequence | CAGGTGCAGGTGAAGGAGTCAGGACCTG GTCTGGTGCAGCCCTCACAGACTTTGTCT CTCACCTGCACTGTCTCTGGGTTCTCACT AACCAGCTATCATGTAAGCTGGGTTCGCC AGCCTCCAGGAAAAGGTCTGGAGTGGAT GGGAGCAATATGGACTGGTGGAAGCACA GCATATAATTCACTCTCAAATCCCGACT GAGCATCAGCAGGGACATCTCCAAGAGC CAAGTTTTCTTAAAAATGAACAGTCTGCAA ACTGAAGACACAGCCACTTACTACTGTGC CAGAGCCGATTTCTATGTTATGGATGCCT GGGGTCAAGGAGCTTCAGTCACTGTCTC CTCA |
| 67 | 137 Light Chain Variable Region amino acid sequence (kabat CDR underlined) | DIMLTQSPVTLSVSPGESISLSC<u>RASQSIST DLH</u>WYQQKPNESPRVLIK<u>YGSQTIS</u>GIPSRF SGSGSGTDFTLNINRVEPEDFSVYYC<u>QQSN SWPWT</u>FGGGTKLELK |
| 68 | 137 Light Chain Variable Region nucleotide sequence | ACATCATGCTGACTCAGTCTCCAGTTACC CTGTCTGTGTCTCCAGGAGAGAGCATCA |

TABLE 2 -continued

Rat variable region sequences

| SEQ ID NO: | |
|---|---|
| | GTCTCTCCTGCAGGGCCAGTCAGAGTATT<br>AGCACTGACTTGCATTGGTATCAGCAAAA<br>ACCAAATGAGTCTCCAAGGGTTCTCATCA<br>AATATGGTTCCCAGACCATCTCTGGAATC<br>CCCTCCAGGTTCAGTGGCAGTGGATCAG<br>GGACAGATTTCACTCTCAATATTAACAGA<br>GTAGAGCCTGAAGATTTTTCAGTTTATTAC<br>TGTCAGCAGAGTAATAGCTGGCCATGGA<br>CATTCGGTGGAGGCACCAAGCTGGAATT<br>GAAA |

D. Humanization of rat 438 and rat 351

Rat 438 and rat 351 were humanized and further developed to provide humanized monoclonal antibodies 438 and 351 (hereinafter "humanized 438" and "humanized 351", respectively). A human IgG1 heavy chain constant region with 3 mutations in the lower hinge region (L234A/L235A/G237A), that inactivate hIgG1's effector functions, and a human kappa light chain constant region were used as the constant region for the humanized 438 and humanized 351 antibodies. Humanization of rat 438 and rat 351 variable regions was performed using CDR graft strategy.

Table 3 provides the amino acid and nucleic acid sequences of various regions of humanized 438 and humanized 351 variants. The lead humanized 438 variant was determined to be VH1.1/VL1.8 after testing. Humanized 438 VH1.1/VL1.8 has a variable heavy chain as set forth in SEQ ID NO: 71 and a variable light chain as set forth in SEQ ID NO: 97. For humanized 438 variants, the CDR regions for variants VH 1.0 and 1.1 are the same and the CDR regions for variants VL 1.0, 1.1, 1.3, 1.4, 1.5, 1.6, 1.7, 1.8, 1.9, 1.10 and 1.11 are the same. The lead humanized 351 variant was determined to be VH1.0/VL1.1 after testing. Humanized 351 VH1.0/VL1.1 has a variable heavy chain as set forth in SEQ ID NO: 115 and a variable light chain as set forth in SEQ ID NO: 129. For humanized 351 variants, the CDR regions for variants VL 1.0, 1.1, 1.2, 1.3, 1.4, 1.5, 1.6, and 1.7 are the same.

TABLE 3

Humanized 438 and humanized 351 sequences

| SEQ ID NO: | | |
|---|---|---|
| 69 | 438 Heavy Chain Variable Region amino acid (VH1.0) | EVQLVESGGGLVQPGGSLRLSCAASGFTF<br>SSFAMAWVRQAPGKGLEWVASISYGGADT<br>YYRDSVKGRFTISRDNAKNSLYLQMNSLRA<br>EDTAVYYCARDLPYYGYTPFVMDAWGQGT<br>LVTVSS |
| 70 | 438 Heavy Chain Variable Region nucleotide sequence (VH1.0) | GAGGTGCAGCTGGTGGAGTCTGGGGGA<br>GGCTTGGTCCAGCCTGGGGGGTCCCTGA<br>GACTCTCCTGTGCAGCCTCTGGATTCACC<br>TTTAGTTCCTTCGCCATGGCCTGGGTCCG<br>CCAGGCTCCAGGGAAGGGGCTGGAGTG<br>GGTGGCCTCCATCTCCTATGGAGGCGCT<br>GACACCTACTACCGGGACTCCGTGAAGG<br>GCCGATTCACCATCTCCAGAGACAACGC<br>CAAGAACTCACTGTATCTGCAAATGAACA<br>GCCTGAGAGCCGAGGACACGGCTGTGTA<br>TTACTGTGCGAGAGATCTGCCCTACTACG<br>GCTACACCCCCTTCGTGATGGACGCCTG<br>GGGCCAGGGAACCCTGGTCACCGTCTCC<br>TCA |
| 71 | 438 Heavy Chain Variable Region amino acid sequence (VH 1.1) | EVQLVESGGGLVQPGGSLRLSCAASGFTF<br>SSFAMAWVRQAPGKGLEWVASISYGGADT<br>YYRDSVKGRFTISRDNAKNSLYLQMNSLRA<br>EDTAVYYCAKDLPYYGYTPFVMDAWGQGT<br>LVTVSS |
| 72 | 438 Heavy Chain Variable Region nucleotide sequence (VH1.1) | GAGGTGCAGCTGGTGGAGTCTGGGGGA<br>GGCTTGGTCCAGCCTGGGGGGTCCCTGA<br>GACTCTCCTGTGCAGCCTCTGGATTCACC<br>TTTAGTTCCTTCGCCATGGCCTGGGTCCG<br>CCAGGCTCCAGGGAAGGGGCTGGAGTG<br>GGTGGCCTCCATCTCCTATGGAGGCGCT<br>GACACCTACTACCGGGACTCCGTGAAGG<br>GCCGATTCACCATCTCCAGAGACAACGC<br>CAAGAACTCACTGTATCTGCAAATGAACA<br>GCCTGAGAGCCGAGGACACGGCTGTGTA<br>TTACTGTGCGAAGGATCTGCCCTACTACG |

TABLE 3 -continued

Humanized 438 and humanized 351 sequences

| SEQ ID NO: | | |
|---|---|---|
| | | GCTACACCCCTTCGTGATGGACGCCTG GGGCCAGGGAACCCTGGTCACCGTCTCC TCA |
| 73 | 438 Heavy Chain Variable Region CDR1 amino acid sequence (VH1.1) Kabat | SFAMA |
| 74 | 438 Heavy Chain Variable Region CDR1 amino acid sequence (VH1.1) Chothia | GFTFSSFAMA |
| 75 | 438 Heavy Chain Variable Region CDR1 nucleotide sequence (VH1.1) Kabat | TCCTTCGCCATGGCC |
| 76 | 438 Heavy Chain Variable Region CDR1 nucleotide sequence (VH1.1) Chothia | GGATTCACCTTTAGTTCCTTCGCCATGGC C |
| 77 | 438 Heavy Chain Variable Region CDR2 amino acid sequence (VH1.1) Kabat | SISYGGADTYYRDSVKG |
| 78 | 438 Heavy Chain Variable Region CDR2 amino acid sequence (VH1.1) Chothia | SYGGAD |
| 79 | 438 Heavy Chain Variable Region CDR2 nucleotide sequence (VH1.1) Kabat | TCCATCTCCTATGGAGGCGCTGACACCTA CTACCGGGACTCCGTGAAGGGC |
| 80 | 438 Heavy Chain Variable Region CDR2 nucleotide sequence (VH1.1) Chothia | CCTATGGAGGCGCTGAC |
| 81 | 438 Heavy Chain Variable Region CDR3 amino acid sequence (VH1.1) Kabat and Chothia | DLPYYGYTPFVMDA |
| 82 | 438 Heavy Chain Variable Region CDR3 nucleotide sequence (VH1.1) Kabat and Chotia | GATCTGCCCTACTACGGCTACACCCCCTT CGTGATGGACGCC |
| 83 | 438 Light Chain Variable Region amino acid sequence (VL1.0) | DIQMTQSPSSLSASVGDRVTITCRASQRINT DLHWYQQKPGKAPKLLIYFASQTISGVPSR FSGSGSGTDFTLTISSLQPEDFATYYCQQS NSWPYTFGQGTKLEIK |
| 84 | 438 Light Chain Variable Region nucleotide sequence (VL1.0) | GACATCCAGATGACCCAGTCTCCATCCTC CCTGTCTGCATCTGTAGGAGACAGAGTCA CCATCACTTGCCGGGCCTCCCAGCGGAT CAACACCGACCTGCACTGGTATCAGCAG AAACCAGGGAAAGCCCCTAAGCTCCTGAT CTATTTCGCCAGCCAGACCATCTCCGGG GTCCCATCAAGGTTCAGTGGCAGTGGAT CTGGGACAGATTTCACTCTCACCATCAGC AGTCTGCAACCTGAAGATTTTGCAACTTA CTACTGTCAGCAGTCCAACTCCTGGCCCT ACACCTTTGGCCAGGGGACCAAGCTGGA GATCAAA |
| 85 | 438 Light Chain Variable Region amino acid sequence (VL1.1) | DIQLTQSPSSLSASVGDRVTITCRASQRINT DLHWYQQKPGKAPKVLIKFASQTISGVPSR FSGSGSGTDFTLTISSLQPEDFATYYCQQS NSWPYTFGQGTKLEIK |
| 86 | 438 Light Chain Variable Region nucleotide sequence (VL1.1) | GACATCCAGCTGACCCAGTCTCCATCCTC CCTGTCTGCATCTGTAGGAGACAGAGTCA CCATCACTTGCCGGGCCTCCCAGCGGAT CAACACCGACCTGCACTGGTATCAGCAG AAACCAGGGAAAGCCCCTAAGGTGCTGA TCAAGTTCGCCAGCCAGACCATCTCCGG GGTCCCATCAAGGTTCAGTGGCAGTGGA TCTGGGACAGATTTCACTCTCACCATCAG |

TABLE 3 -continued

Humanized 438 and humanized 351 sequences

| SEQ ID NO: | | |
|---|---|---|
| | | CAGTCTGCAACCTGAAGATTTTGCAACTT ACTACTGTCAGCAGTCCAACTCCTGGCCC TACACCTTTGGCCAGGGGACCAAGCTGG AGATCAAA |
| 87 | 438 Light Chain Variable Region amino acid sequence (VL1.3) | DIQLTQSPSSLSASVGDRVTITCRASQRINT DLHWYQQKPGKAPKLLIYFASQTISGVPSR FSGSGSGTDFTLTISSLQPEDFATYYCQQS NSWPYTFGQGTKLEIK |
| 88 | 438 Light Chain Variable Region nucleotide sequence (VL1.3) | GACATCCAGCTGACCCAGTCTCCATCCTC CCTGTCTGCATCTGTAGGAGACAGAGTCA CCATCACTTGCCGGGCCTCCCAGCGGAT CAACACCGACCTGCACTGGTATCAGCAG AAACCAGGGAAAGCCCCTAAGCTCCTGAT CTATTTCGCCAGCCAGACCATCTCCGGG GTCCCATCAAGGTTCAGTGGCAGTGGAT CTGGGACAGATTTCACTCTCACCATCAGC AGTCTGCAACCTGAAGATTTTGCAACTTA CTACTGTCAGCAGTCCAACTCCTGGCCCT ACACCTTTGGCCAGGGGACCAAGCTGGA GATCAAA |
| 89 | 438 Light Chain Variable Region amino acid sequence (VL1.4) | DIQMTQSPSSLSASVGDRVTITCRASQRINT DLHWYQQKPGKAPKVLIYFASQTISGVPSR FSGSGSGTDFTLTISSLQPEDFATYYCQQS NSWPYTFGQGTKLEIK |
| 90 | 438 Light Chain Variable Region nucleotide sequence (VL1.4) | GACATCCAGATGACCCAGTCTCCATCCTC CCTGTCTGCATCTGTAGGAGACAGAGTCA CCATCACTTGCCGGGCCTCCCAGCGGAT CAACACCGACCTGCACTGGTATCAGCAG AAACCAGGGAAAGCCCCTAAGGTGCTGA TCTATTTCGCCAGCCAGACCATCTCCGGG GTCCCATCAAGGTTCAGTGGCAGTGGAT CTGGGACAGATTTCACTCTCACCATCAGC AGTCTGCAACCTGAAGATTTTGCAACTTA CTACTGTCAGCAGTCCAACTCCTGGCCCT ACACCTTTGGCCAGGGGACCAAGCTGGA GATCAAA |
| 91 | 438 Light Chain Variable Region amino acid sequence (VL1.5) | DIQMTQSPSSLSASVGDRVTITCRASQRINT DLHWYQQKPGKAPKLLIKFASQTISGVPSR FSGSGSGTDFTLTISSLQPEDFATYYCQQS NSWPYTFGQGTKLEIK |
| 92 | 438 Light Chain Variable Region nucleotide sequence (VL1.5) | GACATCCAGATGACCCAGTCTCCATCCTC CCTGTCTGCATCTGTAGGAGACAGAGTCA CCATCACTTGCCGGGCCTCCCAGCGGAT CAACACCGACCTGCACTGGTATCAGCAG AAACCAGGGAAAGCCCCTAAGCTCCTGAT CAAGTTCGCCAGCCAGACCATCTCCGGG GTCCCATCAAGGTTCAGTGGCAGTGGAT CTGGGACAGATTTCACTCTCACCATCAGC AGTCTGCAACCTGAAGATTTTGCAACTTA CTACTGTCAGCAGTCCAACTCCTGGCCCT ACACCTTTGGCCAGGGGACCAAGCTGGA GATCAAA |
| 93 | 438 Light Chain Variable Region amino acid sequence (VL1.6) | DIQLTQSPSSLSASVGDRVTITCRASQRINT DLHWYQQKPGKAPKVLIYFASQTISGVPSR FSGSGSGTDFTLTISSLQPEDFATYYCQQS NSWPYTFGQGTKLEIK |
| 94 | 438 Light Chain Variable Region nucleotide sequence (VL1.6) | GACATCCAGCTGACCCAGTCTCCATCCTC CCTGTCTGCATCTGTAGGAGACAGAGTCA CCATCACTTGCCGGGCCTCCCAGCGGAT CAACACCGACCTGCACTGGTATCAGCAG AAACCAGGGAAAGCCCCTAAGGTGCTGA TCTATTTCGCCAGCCAGACCATCTCCGGG GTCCCATCAAGGTTCAGTGGCAGTGGAT CTGGGACAGATTTCACTCTCACCATCAGC AGTCTGCAACCTGAAGATTTTGCAACTTA CTACTGTCAGCAGTCCAACTCCTGGCCCT |

US 9,127,060 B2

TABLE 3 -continued

Humanized 438 and humanized 351 sequences

| SEQ ID NO: | | |
|---|---|---|
| | | ACACCTTTGGCCAGGGGACCAAGCTGGA GATCAAA |
| 95 | 438 Light Chain Variable Region amino acid sequence (VL1.7) | DIQLTQSPSSLSASVGDRVTITCRASQRINT DLHWYQQKPGKAPKLLIKFASQTISGVPSR FSGSGSGTDFTLTISSLQPEDFATYYCQQS NSWPYTFGQGTKLEIK |
| 96 | 438 Light Chain Variable Region nucleotide sequence (VL1.7) | GACATCCAGCTGACCCAGTCTCCATCCTC CCTGTCTGCATCTGTAGGAGACAGAGTCA CCATCACTTGCCGGGCCTCCCAGCGGAT CAACACCGACCTGCACTGGTATCAGCAG AAACCAGGGAAAGCCCCTAAGCTCCTGAT CAAGTTCGCCAGCCAGACCATCTCCGGG GTCCCATCAAGGTTCAGTGGCAGTGGAT CTGGGACAGATTTCACTCTCACCATCAGC AGTCTGCAACCTGAAGATTTTGCAACTTA CTACTGTCAGCAGTCCAACTCCTGGCCCT ACACCTTTGGCCAGGGGACCAAGCTGGA GATCAAA |
| 97 | 438 Light Chain Variable Region amino acid sequence (VL1.8) | DIQMTQSPSSLSASVGDRVTITCRASQRINT DLHWYQQKPGKAPKVLIKFASQTISGVPSR FSGSGSGTDFTLTISSLQPEDFATYYCQQS NSWPYTFGQGTKLEIK |
| 98 | 438 Light Chain Variable Region nucleotide sequence (VL1.8) | GACATCCAGATGACCCAGTCTCCATCCTC CCTGTCTGCATCTGTAGGAGACAGAGTCA CCATCACTTGCCGGGCCTCCCAGCGGAT CAACACCGACCTGCACTGGTATCAGCAG AAACCAGGGAAAGCCCCTAAGGTGCTGA TCAAGTTCGCCAGCCAGACCATCTCCGG GGTCCCATCAAGGTTCAGTGGCAGTGGA TCTGGGACAGATTTCACTCTCACCATCAG CAGTCTGCAACCTGAAGATTTTGCAACTT ACTACTGTCAGCAGTCCAACTCCTGGCCC TACACCTTTGGCCAGGGGACCAAGCTGG AGATCAAA |
| 99 | 438 Light Chain Variable Region CDR1 amino acid sequence (VL1.8) Kabat and Chothia | RASQRINTDLH |
| 100 | 438 Light Chain Variable Region CDR1 nucleotide sequence (VL1.8) Kabat and Chothia | CGGGCCTCCCAGCGGATCAACACCGACC TGCAC |
| 101 | 438 Light Chain Variable Region CDR2 amino acid sequence (VL1.8) Kabat and Chothia | FASQTIS |
| 102 | 438 Light Chain Variable Region CDR2 nucleotide sequence (VL1.8) Kabat and Chothia | TTCGCCAGCCAGACCATCTCC |
| 103 | 438 Light Chain Variable Region CDR3 amino acid sequence (VL1.8) Kabat and Chothia | QQSNSWPYT |
| 104 | 438 Light Chain Variable Region CDR3 nucleotide sequence (VL1.8) Kabat and Chothia | CAGCAGTCCAACTCCTGGCCCTACACC |
| 105 | 438 Light Chain Variable Region amino acid sequence (VL1.9) | DIMLTQSPSSLSASVGDRVTITCRASQRINT DLHWYQQKPGKAPKVLIKFASQTISGVPSR FSGSGSGTDFTLTISSLQPEDFATYYCQQS NSWPYTFGQGTKLEIK |
| 106 | 438 Light Chain Variable Region nucleotide sequence (VL1.9) | GACATCATGCTGACCCAGTCTCCATCCTC CCTGTCTGCATCTGTAGGAGACAGAGTCA CCATCACTTGCCGGGCCTCCCAGCGGAT CAACACCGACCTGCACTGGTATCAGCAG AAACCAGGGAAAGCCCCTAAGGTGCTGA TCAAGTTCGCCAGCCAGACCATCTCCGG GGTCCCATCAAGGTTCAGTGGCAGTGGA |

TABLE 3 -continued

Humanized 438 and humanized 351 sequences

| SEQ ID NO: | | |
|---|---|---|
| | | TCTGGGACAGATTTCACTCTCACCATCAG CAGTCTGCAACCTGAAGATTTTGCAACTT ACTACTGTCAGCAGTCCAACTCCTGGCCC TACACCTTTGGCCAGGGGACCAAGCTGG AGATCAAA |
| 107 | 438 Light Chain Variable Region amino acid sequence (VL1.10) | DIQLTQSPSSLSASVGDRVTITCRASQRINT DLHWYQQKPGKAPRVLIKFASQTISGVPSR FSGSGSGTDFTLTISSLQPEDFATYYCQQS NSWPYTFGQGTKLEIK |
| 108 | 438 Light Chain Variable Region nucleotide sequence (VL1.10) | GACATCATGCTGACCCAGTCTCCATCCTC CCTGTCTGCATCTGTAGGAGACAGAGTCA CCATCACTTGCCGGGCCTCCCAGCGGAT CAACACCGACCTGCACTGGTATCAGCAG AAACCAGGGAAAGCCCCTAGGGTGCTGA TCAAGTTCGCCAGCCAGACCATCTCCGG GGTCCCATCAAGGTTCAGTGGCAGTGGA TCTGGGACAGATTTCACTCTCACCATCAG CAGTCTGCAACCTGAAGATTTTGCAACTT ACTACTGTCAGCAGTCCAACTCCTGGCCC TACACCTTTGGCCAGGGGACCAAGCTGG AGATCAAA |
| 109 | 438 Light Chain Variable Region amino acid sequence (VL1.11) | DIQMTQSPSSLSASVGDRVTITCRASQRINT DLHWYQQKPGKAPRVLIKFASQTISGVPSR FSGSGSGTDFTLTISSLQPEDFATYYCQQS NSWPYTFGQGTKLEIK |
| 110 | 438 Light Chain Variable Region nucleotide sequence (VL1.11) | GACATCCAGATGACCCAGTCTCCATCCTC CCTGTCTGCATCTGTAGGAGACAGAGTCA CCATCACTTGCCGGGCCTCCCAGCGGAT CAACACCGACCTGCACTGGTATCAGCAG AAACCAGGGAAAGCCCCTAGGGTGCTGA TCAAGTTCGCCAGCCAGACCATCTCCGG GGTCCCATCAAGGTTCAGTGGCAGTGGA TCTGGGACAGATTTCACTCTCACCATCAG CAGTCTGCAACCTGAAGATTTTGCAACTT ACTACTGTCAGCAGTCCAACTCCTGGCCC TACACCTTTGGCCAGGGGACCAAGCTGG AGATCAAA |
| 111 | 438 Heavy Chain amino acid sequence (VH1.1)-hIgG1-3M (CDRs underlined) | EVQLVESGGGLVQPGGSLRLSCAASGFTF SS<u>FAMA</u>WVRQAPGKGLEWVA<u>SISYGGADT YYRDSVKG</u>RFTISRDNAKNSLYLQMNSLRA EDTAVYYCAK<u>DLPYYGYTPFVMDA</u>WGQT LVTVSSASTKGPSVFPLAPSSKSTSGGTAA LGCLVKDYFPEPVTVSWNSGALTSGVHTFP AVLQSSGLYSLSSVVTVPSSSLGTQTYICNV NHKPSNTKVDKKVEPKSCDKTHTCPPCPA PEAAGAPSVFLFPPKPKDTLMISRTPEVTCV VVDVSHEDPEVKFNWYVDGVEVHNAKTKP REEQYNSTYRVVSVLTVLHQDWLNGKEYK CKVSNKALPAPIEKTISKAKGQPREPQVYTL PPSREEMTKNQVSLTCLVKGFYPSDIAVEW ESNGQPENNYKTTPPVLDSDGSFFLYSKLT VDKSRWQQGNVFSCSVMHEALHNHYTQK SLSLSPGK |
| 112 | 438 Heavy Chain nucleotide sequence (VH1.1)-hIgG1-3M | GAGGTGCAGCTGGTGGAGTCTGGGGGA GGCTTGGTCCAGCCTGGGGGGTCCCTGA GACTCTCCTGTGCAGCCTCTGGATTCACC TTTAGTTCCTTCGCCATGGCCTGGGTCCG CCAGGCTCCAGGGAAGGGGCTGGAGTG GGTGGCCTCCATCTCCTATGGAGGCGCT GACACCTACTACCGGGACTCCGTGAAGG GCCGATTCACCATCTCCAGAGACAACGC CAAGAACTCACTGTATCTGCAAATGAACA GCCTGAGAGCCGAGGACACGGCTGTGTA TTACTGTGCGAAGGATCTGCCCTACTACG GCTACACCCCCTTCGTGATGGACGCCTG GGGCCAGGGAACCCTGGTCACCGTCTCC TCAGCGTCGACCAAGGGCCCATCGGTCT TCCCCCTGGCACCCTCCTCCAAGAGCAC CTCTGGGGGCACAGCGGCCCTGGGCTG |

TABLE 3 -continued

Humanized 438 and humanized 351 sequences

| SEQ ID NO: | | |
|---|---|---|
| | | CCTGGTCAAGGACTACTTCCCCGAACCG GTGACGGTGTCGTGGAACTCAGGCGCCC TGACCAGCGGCGTGCACACCTTCCCGGC TGTCCTACAGTCCTCAGGACTCTACTCCC TCAGCAGCGTGGTGACCGTGCCCTCCAG CAGCTTGGGCACCCAGACCTACATCTGC AACGTGAATCACAAGCCAGCAACACCAA GGTGGACAAGAAAGTTGAGCCCAAATCTT GTGACAAAACTCACACATGCCCACCGTGC CCAGCACCTGAAGCCGCTGGGGCACCGT CAGTCTTCCTCTTCCCCCCAAAACCCAAG GACACCCTCATGATCTCCCGGACCCCTG AGGTCACATGCGTGGTGGTGGACGTGAG CCACGAAGACCCTGAGGTCAAGTTCAACT GGTACGTGGACGGCGTGGAGGTGCATAA TGCCAAGACAAAGCCGCGGGAGGAGCAG TACAACAGCACGTACCGTGTGGTCAGCG TCCTCACCGTCCTGCACCAGGACTGGCT GAATGGCAAGGAGTACAAGTGCAAGGTC TCCAACAAAGCCCTCCCAGCCCCCATCG AGAAAACCATCTCCAAAGCCAAAGGGCA GCCCCGAGAACCACAGGTGTACACCCTG CCCCCATCCCGGGAGGAGATGACCAAGA ACCAGGTCAGCCTGACCTGCCTGGTCAA AGGCTTCTATCCCAGCGACATCGCCGTG GAGTGGGAGAGCAATGGGCAGCCGGAG AACAACTACAAGACCACGCCTCCCGTGCT GGACTCCGACGGCTCCTTCTTCCTCTATA GCAAGCTCACCGTGGACAAGAGCAGGTG GCAGCAGGGGAACGTCTTCTCATGCTCC GTGATGCATGAGGCTCTGCACAACCACTA CACGCAGAAGAGCCTCTCCCTGTCCCCG GGTAAA |
| 113 | 438 Light Chain amino acid sequence (VL1.8)-hkappa (CDRs underlined) | DIQMTQSPSSLSASVGDRVTITC<u>RASQRINT DLH</u>WYQQKPGKAPKVLIK<u>FASQTIS</u>GVPSR FSGSGSGTDFTLTISSLQPEDFATYYC<u>QQS NSWPYT</u>FGQGTKLEIKRTVAAPSVFIFPPSD EQLKSGTASVVCLLNNFYPREAKVQWKVD NALQSGNSQESVTEQDSKDSTYSLSSTLTL SKADYEKHKVYACEVTHQGLSSPVTKSFNR GEC |
| 114 | 438 Light Chain nucleotide sequence (VL1.8)-hkappa | GACATCATGCTGACCCAGTCTCCATCCTC CCTGTCTGCATCTGTAGGAGACAGAGTCA CCATCACTTGCCGGGCCTCCCAGCGGAT CAACACCGACCTGCACTGGTATCAGCAG AAACCAGGGAAAGCCCCTAGGGTGCTGA TCAAGTTCGCCAGCCAGACCATCTCCGG GGTCCCATCAAGGTTCAGTGGCAGTGGA TCTGGGACAGATTTCACTCTCACCATCAG CAGTCTGCAACCTGAAGATTTTGCAACTT ACTACTGTCAGCAGTCCAACTCCTGGCCC TACACCTTTGGCCAGGGGACCAAGCTGG AGATCAAACGAACTGTGGCTGCACCATCT GTCTTCATCTTCCCGCCATCTGATGAGCA GTTGAAATCTGGAACTGCCTCTGTTGTGT GCCTGCTGAATAACTTCTATCCCAGAGAG GCCAAAGTACAGTGGAAGGTGGATAACG CCCTCCAATCGGGTAACTCCCAGGAGAG TGTCACAGAGCAGGACAGCAAGGACAGC ACCTACAGCCTCAGCAGCACCCTGACGC TGAGCAAAGCAGACTACGAGAAACACAAA GTCTACGCCTGCGAAGTCACCCATCAGG GCCTGAGCTCGCCCGTCACAAAGAGCTT CAACAGGGGAGAGTGT |
| 115 | 351 Heavy Chain Variable Region amino acid (VH1.0) | EVQLVESGGGLVQPGGSLRLSCAASGFTF SHYGMNWVRQAPGKGLEWVASISRSGSYI RYVDTVKGRFTISRDNAKNSLYLQMNSLRA EDTAVYYCAREGQFGDYFEYWGQGTLVTV SS |

TABLE 3 -continued

Humanized 438 and humanized 351 sequences

| SEQ ID NO: | | |
|---|---|---|
| 116 | 351 Heavy Chain Variable Region nucleotide sequence (VH1.0) | GAGGTGCAGCTGGTGGAGTCTGGGGGA GGCTTGGTCCAGCCTGGGGGGTCCCTGA GACTCTCCTGTGCAGCCTCTGGATTCACC TTTAGTCACTACGGCATGAACTGGGTCCG CCAGGCTCCAGGGAAGGGGCTGGAGTG GGTGGCCTCCATCTCCAGATCCGGCTCC TACATCAGATACGTGGACACCGTGAAGG GCCGATTCACCATCTCCAGAGACAACGC CAAGAACTCACTGTATCTGCAAATGAACA GCCTGAGAGCCGAGGACACGGCTGTGTA TTACTGTGCGAGAGAGGGCCAGTTCGGC GACTACTTCGAGTACTGGGGCCAGGGAA CCCTGGTCACCGTCTCCTCA |
| 117 | 351 Heavy Chain Variable Region CDR1 amino acid sequence (VH1.0) Kabat | HYGMN |
| 118 | 351 Heavy Chain Variable Region CDR1 amino acid sequence (VH1.0) Chothia | GFTFSHYGMN |
| 119 | 351 Heavy Chain Variable Region CDR1 nucleotide sequence (VH1.0) Kabat | CACTATGGAATGAAC |
| 120 | 351 Heavy Chain Variable Region CDR1 nucleotide sequence (VH1.0) Chothia | GGATTCACTTTCAGTCACTATGGAATGAA C |
| 121 | 351 Heavy Chain Variable Region CDR2 amino acid sequence (VH1.0) Kabat | SISRSGSYIRYVDTVKG |
| 122 | 351 Heavy Chain Variable Region CDR2 amino acid sequence (VH1.0) Chothia | SRSGSY |
| 123 | 351 Heavy Chain Variable Region CDR2 nucleotide sequence (VH1.0) Kabat | TCTATTAGTAGGAGTGGCAGTTACATCCG CTATGTAGACACAGTGAAGGGC |
| 124 | 351 Heavy Chain Variable Region CDR2 nucleotide sequence (VH 1.0) Chothia | AGTAGGAGTGGCAGTTAC |
| 125 | 351 Heavy Chain Variable Region CDR3 amino acid sequence (VH 1.0) Kabat and Chothia | EGQFGDYFEY |
| 126 | 351 Heavy Chain Variable Region CDR3 nucleotide sequence (VH 1.0) Kabat and Chotia | GAGGGACAATTCGGGGACTACTTTGAGTA C |
| 127 | 351 Light Chain Variable Region amino acid sequence (VL1.0) | DIQMTQSPSSLSASVGDRVTITCRASQKIST NLHWYQQKPGKAPKLLIYYASQTISGVPSR FSGSGSGTDFTLTISSLQPEDFATYYCQQT NSWPLTFGGGTKVEIK |
| 128 | 351 Light Chain Variable Region nucleotide sequence (VL1.0) | GACATCCAGATGACCCAGTCTCCATCCTC CCTGTCTGCATCTGTAGGAGACAGAGTCA CCATCACTTGCCGGGCCTCCCAGAAGAT CTCCACCAACCTGCACTGGTATCAGCAGA AACCAGGGAAAGCCCCTAAGCTCCTGAT CTATTACGCCTCTCAGACCATCTCCGGGG TCCCATCAAGGTTCAGTGGCAGTGGATCT GGGACAGATTTCACTCTCACCATCAGCAG TCTGCAACCTGAAGATTTTGCAACTTACTA CTGTCAGCAGACCAACTCCTGGCCCCTG ACCTTCGGCGGAGGGACCAAGGTGGAGA TCAAA |
| 129 | 351 Light Chain Variable Region amino acid sequence (VL1.1) | DIQMTQSPSSLSASVGDRVTITCRASQKIST NLHWYQQKPGKAPKILIKYASQTISGVPSRF |

TABLE 3 -continued

Humanized 438 and humanized 351 sequences

| SEQ ID NO: | | |
|---|---|---|
| | | SGSGSGTDFTLTISSLQPEDFATYYCQQTN SWPLTFGGGTKVEIK |
| 130 | 351 Light Chain Variable Region nucleotide sequence (VL1.1) | GACATCCAGATGACCCAGTCTCCATCCTC CCTGTCTGCATCTGTAGGAGACAGAGTCA CCATCACTTGCCGGGCCTCCCAGAAGAT CTCCACCAACCTGCACTGGTATCAGCAGA AACCAGGGAAAGCCCCTAAGATCCTGATC AAGTACGCCTCTCAGACCATCTCCGGGG TCCCATCAAGGTTCAGTGGCAGTGGATCT GGGACAGATTTCACTCTCACCATCAGCAG TCTGCAACCTGAAGATTTTGCAACTTACTA CTGTCAGCAGACCAACTCCTGGCCCCTG ACCTTCGGCGGAGGGACCAAGGTGGAGA TCAAA |
| 131 | 351 Light Chain Variable Region CDR1 amino acid sequence (VL1.1) Kabat and Chothia | RASQKISTNLH |
| 132 | 351 Light Chain Variable Region CDR1 nucleotide sequence (VL1.1) Kabat and Chothia | AGGGCCAGTCAGAAAATTAGCACTAACTT ACAT |
| 133 | 351 Light Chain Variable Region CDR2 amino acid sequence (VL1.1) Kabat and Chothia | YASQTIS |
| 134 | 351 Light Chain Variable Region CDR2 nucleotide sequence (VL1.1) Kabat and Chothia | TATGCTTCCCAGACCATCTCT |
| 135 | 351 Light Chain Variable Region CDR3 amino acid sequence (VL1.1) Kabat and Chothia | QQTNSWPLTT |
| 136 | 351 Light Chain Variable Region CDR3 nucleotide sequence (VL1.1) Kabat and Chothia | CAACAGACTAATAGTTGGCCGCTCACG |
| 137 | 351 Light Chain Variable Region amino acid sequence (VL1.2) | DIQLTQSPSSLSASVGDRVTITCRASQKIST NLHWYQQKPGKAPKLLIYYASQTISGVPSR FSGSGSGTDFTLTISSLQPEDFATYYCQQT NSWPLTFGGGTKVEIK |
| 138 | 351 Light Chain Variable Region nucleotide sequence (VL1.2) | GACATCCAGCTGACCCAGTCTCCATCCTC CCTGTCTGCATCTGTAGGAGACAGAGTCA CCATCACTTGCCGGGCCTCCCAGAAGAT CTCCACCAACCTGCACTGGTATCAGCAGA AACCAGGGAAAGCCCCTAAGCTCCTGAT CTATTACGCCTCTCAGACCATCTCCGGGG TCCCATCAAGGTTCAGTGGCAGTGGATCT GGGACAGATTTCACTCTCACCATCAGCAG TCTGCAACCTGAAGATTTTGCAACTTACTA CTGTCAGCAGACCAACTCCTGGCCCCTG ACCTTCGGCGGAGGGACCAAGGTGGAGA TCAAA |
| 139 | 351 Light Chain Variable Region amino acid sequence (VL1.3) | DIQMTQSPSSLSASVGDRVTITCRASQKIST NLHWYQQKPGKAPKILIYYASQTISGVPSRF SGSGSGTDFTLTISSLQPEDFATYYCQQTN SWPLTFGGGTKVEIK |
| 140 | 351 Light Chain Variable Region nucleotide sequence (VL1.3) | GACATCCAGATGACCCAGTCTCCATCCTC CCTGTCTGCATCTGTAGGAGACAGAGTCA CCATCACTTGCCGGGCCTCCCAGAAGAT CTCCACCAACCTGCACTGGTATCAGCAGA AACCAGGGAAAGCCCCTAAGATCCTGATC TATTACGCCTCTCAGACCATCTCCGGGGT CCCATCAAGGTTCAGTGGCAGTGGATCT GGGACAGATTTCACTCTCACCATCAGCAG TCTGCAACCTGAAGATTTTGCAACTTACTA CTGTCAGCAGACCAACTCCTGGCCCCTG ACCTTCGGCGGAGGGACCAAGGTGGAGA TCAAA |

TABLE 3 -continued

Humanized 438 and humanized 351 sequences

| SEQ ID NO: | | |
|---|---|---|
| 141 | 351 Light Chain Variable Region amino acid sequence (VL1.4) | DIQMTQSPSSLSASVGDRVTITCRASQKIST NLHWYQQKPGKAPKLLIKYASQTISGVPSR FSGSGSGTDFTLTISSLQPEDFATYYCQQT NSWPLTFGGGTKVEIK |
| 142 | 351 Light Chain Variable Region nucleotide sequence (VL1.4) | GACATCCAGATGACCCAGTCTCCATCCTC CCTGTCTGCATCTGTAGGAGACAGAGTCA CCATCACTTGCCGGGCCTCCCAGAAGAT CTCCACCAACCTGCACTGGTATCAGCAGA AACCAGGGAAAGCCCCTAAGCTCCTGAT CAAGTACGCCTCTCAGACCATCTCCGGG GTCCCATCAAGGTTCAGTGGCAGTGGAT CTGGGACAGATTTCACTCTCACCATCAGC AGTCTGCAACCTGAAGATTTTGCAACTTA CTACTGTCAGCAGACCAACTCCTGGCCC CTGACCTTCGGCGGAGGGACCAAGGTGG AGATCAAA |
| 143 | 351 Light Chain Variable Region amino acid sequence (VL1.5) | DIQLTQSPSSLSASVGDRVTITCRASQKIST NLHWYQQKPGKAPKILIYYASQTISGVPSRF SGSGSGTDFTLTISSLQPEDFATYYCQQTN SWPLTFGGGTKVEIK |
| 144 | 351 Light Chain Variable Region nucleotide sequence (VL1.5) | GACATCCAGCTGACCCAGTCTCCATCCTC CCTGTCTGCATCTGTAGGAGACAGAGTCA CCATCACTTGCCGGGCCTCCCAGAAGAT CTCCACCAACCTGCACTGGTATCAGCAGA AACCAGGGAAAGCCCCTAAGATCCTGATC TATTACGCCTCTCAGACCATCTCCGGGGT CCCATCAAGGTTCAGTGGCAGTGGATCT GGGACAGATTTCACTCTCACCATCAGCAG TCTGCAACCTGAAGATTTTGCAACTTACTA CTGTCAGCAGACCAACTCCTGGCCCCTG ACCTTCGGCGGAGGGACCAAGGTGGAGA TCAAA |
| 145 | 351 Light Chain Variable Region amino acid sequence (VL1.6) | DIQLTQSPSSLSASVGDRVTITCRASQKIST NLHWYQQKPGKAPKLLIKYASQTISGVPSR FSGSGSGTDFTLTISSLQPEDFATYYCQQT NSWPLTFGGGTKVEIK |
| 146 | 351 Light Chain Variable Region nucleotide sequence (VL1.6) | GACATCCAGCTGACCCAGTCTCCATCCTC CCTGTCTGCATCTGTAGGAGACAGAGTCA CCATCACTTGCCGGGCCTCCCAGAAGAT CTCCACCAACCTGCACTGGTATCAGCAGA AACCAGGGAAAGCCCCTAAGCTCCTGAT CAAGTACGCCTCTCAGACCATCTCCGGG GTCCCATCAAGGTTCAGTGGCAGTGGAT CTGGGACAGATTTCACTCTCACCATCAGC AGTCTGCAACCTGAAGATTTTGCAACTTA CTACTGTCAGCAGACCAACTCCTGGCCC CTGACCTTCGGCGGAGGGACCAAGGTGG AGATCAAA |
| 147 | 351 Light Chain Variable Region amino acid sequence (VL1.7) | DIQLTQSPSSLSASVGDRVTITCRASQKIST NLHWYQQKPGKAPKILIKYASQTISGVPSRF SGSGSGTDFTLTISSLQPEDFATYYCQQTN SWPLTFGGGTKVEIK |
| 148 | 351 Light Chain Variable Region nucleotide sequence (VL1.7) | GACATCCAGCTGACCCAGTCTCCATCCTC CCTGTCTGCATCTGTAGGAGACAGAGTCA CCATCACTTGCCGGGCCTCCCAGAAGAT CTCCACCAACCTGCACTGGTATCAGCAGA AACCAGGGAAAGCCCCTAAGATCCTGATC AAGTACGCCTCTCAGACCATCTCCGGGG TCCCATCAAGGTTCAGTGGCAGTGGATCT GGGACAGATTTCACTCTCACCATCAGCAG TCTGCAACCTGAAGATTTTGCAACTTACTA CTGTCAGCAGACCAACTCCTGGCCCCTG ACCTTCGGCGGAGGGACCAAGGTGGAGA TCAAA |

TABLE 3 -continued

Humanized 438 and humanized 351 sequences

| SEQ ID NO: | | |
|---|---|---|
| 149 | 351 Heavy Chain amino acid sequence (VH1.0)-hIgG1-3M (CDRs underlined) | EVQLVESGGGLVQPGGSLRLSCAASGFTF SHYGMNWVRQAPGKGLEWVASISRSGSYI RYVDTVKGRFTISRDNAKNSLYLQMNSLRA EDTAVYYCAREGQFGDYFEYWGQGTLVTV SSASTKGPSVFPLAPSSKSTSGGTAALGCL VKDYFPEPVTVSWNSGALTSGVHTFPAVLQ SSGLYSLSSVVTVPSSSLGTQTYICNVNHK PSNTKVDKKVEPKSCDKTHTCPPCPAPEAA GAPSVFLFPPKPKDTLMISRTPEVTCVVVDV SHEDPEVKFNWYVDGVEVHNAKTKPREEQ YNSTYRVVSVLTVLHQDWLNGKEYKCKVS NKALPAPIEKTISKAKGQPREPQVYTLPPSR EEMTKNQVSLTCLVKGFYPSDIAVEWESNG QPENNYKTTPPVLDSDGSFFLYSKLTVDKS RWQQGNVFSCSVMHEALHNHYTQKSLSLS PGK |
| 150 | 351 Heavy Chain nucleotide sequence (VH1.0)-hIgG1-3M | GAGGTGCAGCTGGTGGAGTCTGGGGGA GGCTTGGTCCAGCCTGGGGGGTCCCTGA GACTCTCCTGTGCAGCCTCTGGATTCACC TTTAGTCACTACGGCATGAACTGGGTCCG CCAGGCTCCAGGGAAGGGGCTGGAGTG GGTGGCCTCCATCTCCAGATCCGGCTCC TACATCAGATACGTGGACACCGTGAAGG GCCGATTCACCATCTCCAGAGACAACGC CAAGAACTCACTGTATCTGCAAATGAACA GCCTGAGAGCCGAGGACACGGCTGTGTA TTACTGTGCGAGAGAGGGCCAGTTCGGC GACTACTTCGAGTACTGGGGCCAGGGAA CCCTGGTCACCGTCTCCTCA |
| 151 | 351 Light Chain amino acid sequence (VL1.1)-hkappa (CDRs underlined) | DIQMTQSPSSLSASVGDRVTITCRASQKIST NLHWYQQKPGKAPKILIKYASQTISGVPSRF SGSGSGTDFTLTISSLQPEDFATYYCQQTN SWPLTFGGGTKVEIKRTVAAPSVFIFPPSDE QLKSGTASVVCLLNNFYPREAKVQWKVDN ALQSGNSQESVTEQDSKDSTYSLSSTLTLS KADYEKHKVYACEVTHQGLSSPVTKSFNR GEC |
| 152 | 351 Light Chain nucleotide sequence (VL1.1)-hkappa | GACATCCAGATGACCCAGTCTCCATCCTC CCTGTCTGCATCTGTAGGAGACAGAGTCA CCATCACTTGCCGGGCCTCCCAGAAGAT CTCCACCAACCTGCACTGGTATCAGCAGA AACCAGGGAAAGCCCCTAAGATCCTGATC AAGTACGCCTCTCAGACCATCTCCGGGG TCCCATCAAGGTTCAGTGGCAGTGGATCT GGGACAGATTTCACTCTCACCATCAGCAG TCTGCAACCTGAAGATTTTGCAACTTACTA CTGTCAGCAGACCAACTCCTGGCCCCTG ACCTTCGGCGGAGGGACCAAGGTGGAGA TCAAA | cDNAs containing human acceptor framework, DP54 for heavy chain and DPK9 for light chain, with relevant CDR donor sequences were synthesized by GeneArt, AG. Synthesized cDNA products were subcloned and fused in frame with human IgG1-3m constant region for the heavy chain, or human kappa for the light chain in mammalian expression vectors pSMED2 and pSMN2, respectively. Alignment of the VHs and VLs of human acceptor framework, rat 438 and humanized 438 variants, along with rat 351 and humanized 351 variants are shown in Table 4 below. The CDRs of Kabat scheme are underlined. For 351VH and 351VL, the lower case text in framework region indicates the difference in residues between rat 351 and humanized 351 variants.

There is significant homology between human acceptor framework and that of rat 438 variable region, 78% for VH and 61% for VL. Also, there is significant homology between human acceptor framework and rat 351 variable regions, 76% for VH and 61% for VL.

TABLE 4

Alignment of human acceptor framework, rat 438 and humanized 438 variants,
along with rat 351 and humanized 351 variants. (CDRs of Kabat scheme are underlined)

438VH:

```
DP54_JH4    EVQLVESGGGLVQPGGSLRLSCAASGPITSSYWMSWVRQAPGKGLEWVANIKQDGSEKYYVDSVKGRFTISRDNAKNSLY 80
Rat438VH    AVQLVESGGGLVQPGRSLKLSCTASGPITSSFAMAWVRQAPTKGLEWVASISYGGADTYYRDSVKGRFTISRDNAKSSLY 80
438VH1.0    EVQLVESGGGLVQPGGSLRLSCAASGPITSSFAMAWVRQAPGKGLEWVASISYGGADTYYRDSVKGRFTISRDNAKNSLY 80
438VH1.1    EVQLVESGGGLVQPGGSLRLSCAASGPITSSFAMAWVRQAPGKGLEWVASISYGGADTYYRDSVKGRFTISRDNAKNSLY 80

DP54_JH4    LQMNSLRAEDTAVYYCAR---YFDY-------WGQGTLVTVSS 113
Rat438VH    LQMDSLRSEDTSTYYCAKDLPYYGYTPFVMDAWGQGTSVIVSS 123
438VH1.0    LQMNSLRAEDTAVYYCARDLPYYGYTPFVMDAWGQGTLVTVSS 123
438VH1.1    LQMNSLRAEDTAVYYCAKDLPYYGYTPFVMDAWGQGTLVTVSS 123
```

438VL:

```
DPK9_Jk2    DIQMTQSPSSLSASVGDRVTITCRASQSISSYLNWYQQKPGKAPKLLIYAASSLQSGVPSRFSGSGSGTDFTLTISSLQP 80
Rat438VL    DIMLTQSPPTLSVTPGETISLSCRASQRINTDLHWYQQKPNESPRVLIKFASQTISGVPSRFSGSGSGTDFTLNINRVEP 80
438VL1.0    DIQMTQSPSSLSASVGDRVTITCRASQRINTDLHWYQQKPGKAPKLLIYFASQTISGVPSRFSGSGSGTDFTLTISSLQP 80
438VL1.8    DIQMTQSPSSLSASVGDRVTITCRASQRINTDLHWYQQKPGKAPKVLIKFASQTISGVPSRFSGSGSGTDFTLTISSLQP 80

DPK9_Jk2    EDFATYYCQQSYSTPYTFGQGTKLEIK 107
Rat438VL    EDFSVYYCQQSNSWPYTFGAGTKLELK 107
438VL1.0    EDFATYYCQQSNSWPYTFGQGTKLEIK 107
438VL1.8    EDFATYYCQQSNSWPYTFGQGTKLEIK 107
```

351VH:

```
DP54_JH4    EVQLVESGGGLVQPGgSLrlSCaASGFTFSSYWMSWvRQAPGKGLeWVANIKQDGSEKYYVDSVKGRFTISRDnAKNsLY 80
Rat351VH    EVQLVESGGGLVQPGRSLKVSCLASGFTFSHYGMNWIRQAPGKGLDWVASISRSGSYIRYVDTVKGRFTVSRDIAKNTLY 80
351VH1.0    EVQLVESGGGLVQPGGSLRLSCAASGFTFSHYGMNWVRQAPGKGLEWVASISRSGSYIRYVDTVKGRFTISRDNAKNSLY 80

DP54_JH4    LQMnSLRaEDTAvYYCAR------YFDYWGQGtIVTVSS 113
Rat351VH    LQMTSLRSEDTALYYCAREGQFGDYFEYWGQGVMVTVSS 119
351VH1.0    LQMNSLRAEDTAVYYCAREGQFGDYFEYWGQGTLVTVSS 119
```

351VL:

```
DPK9_Jk4    DIqmTQSPssLSasvGdRvtitCRASQSISSYLNWYQQKPgkaPklLIYAASSLQSGvPSRFSGSGSGTDFTLtIsslqP 80
Rat351VL    DIMLTQSPATLSVTPGERISLSCRASQKISTNLHWYQQKPNESPRILIKYASQTISGIPSRFSGSGSGTDFTLHINTVEP 80
351VL1.0    DIQMTQSPSSLSASVGDRVTITCRASQKISTNLHWYQQKPGKAPKLLIYYASQTISGVPSRFSGSGSGTDFTLTISSLQP 80
351VL1.1    DIQMTQSPSSLSASVGDRVTITCRASQKISTNLHWYQQKPGKAPKILIKYASQTISGVPSRFSGSGSGTDFTLTISSLQP 80

DPK9_Jk4    EDF atYYCQQSYSTPLTFGgGTKvEIK 107
Rat351VL    EDF SVYYCQQTNSWPLTFGSGTKLEIK 107
351VL1.0    EDF ATYYCQQTNSWPLTFGGGTKVEIK 107
351VL1.1    EDF ATYYCQQTNSWPLTFGGGTKVEIK 107
```

During humanization, CDR grafted antibodies may result in a loss of activity of the original antibody. Differences in the framework region may account for the altered conformation of the resulting humanized 438 and humanized 351 antibodies, and selected back mutations in the human acceptor framework to that of original antibody were introduced to recover the activity and binding epitope. Table 5 shows selected back mutations in the human acceptor framework to rat 438 and rat 351 residues at the corresponding positions to optimize the activity and binding epitope.

TABLE 5

Back mutations in VH and VL of humanized 438 and humanized 351 variants.

| 438 VH Variant | 1.0 | 1.1 | | | | | | |
|---|---|---|---|---|---|---|---|---|
| VH back mutation | none | R94K | | | | | | |

| 438 VL Variant | 1.0 | 1.1 | 1.3 | 1.4 | 1.5 | 1.6 | 1.7 | 1.8 | 1.9 |
|---|---|---|---|---|---|---|---|---|---|
| VL back mutation | none | M4L L46V Y49K | M4L | L46V | Y49K | M4L L46V | M4L Y49K | L46V Y49K | Q3M M4L L46V Y49K |

TABLE 5-continued

Back mutations in VH and VL of humanized 438 and humanized 351 variants.

| 351 VH Variant | 1.0 | | | | | | | |
|---|---|---|---|---|---|---|---|---|
| VH back mutation | none | | | | | | | |
| 351 VL Variant | 1.0 | 1.1 | 1.2 | 1.3 | 1.4 | 1.5 | 1.6 | 1.7 |
| VL back mutation | none | L46V Y49K | M4L | L46I | Y49K | M4L L46I | M4L Y49K | M4L L46V Y49K |

Example 3

Characterization of Anti-Notch1 Inhibitory Antibodies
A. Expression and Binding to Notch1

Relative expression yields of humanized 438 and humanized 351 variants were tested in a transient expression assay in COS cells.

As shown in Table 6, a number of humanized 438 variants, including humanized 438 VH1.1/ VL1.8, and a number of humanized 351 variants, including humanized 351 VH1.0/ VL1.1, demonstrated significant yields.

TABLE 6

Relative expression yields in conditioned media of humanized 438 variants and humanized 351 variants in transient expression in COS cells.

| 438 Variant | VH1.0/ VL1.3 | VH1.0/ VL1.4 | VH1.0/ VL1.5 | VH1.0/ VL1.6 | VH1.0/ VL1.7 | VH1.0/ VL1.8 | VH1.0/ VL1.9 | VH1.0/ VL1.10 | VH1.0/ VL1.11 |
|---|---|---|---|---|---|---|---|---|---|
| 438 Yield (µg/ml) | 41.51 | 41.63 | 85.73 | 35.11 | 36.94 | 40.08 | 51.9 | 62.58 | 45.86 |
| 438 Variant | VH1.1/ VL1.3 | VH1.1/ VL1.4 | VH1.1/ VL1.5 | VH1.1/ VL1.6 | VH1.1/ VL1.7 | VH1.1/ VL1.8 | VH1.1/ VL1.9 | VH1.1/ VL1.10 | VH1.1/ VL1.11 |
| 438 Yield (µg/ml) | 23.2 | 49.47 | 65.93 | 47.72 | 31.95 | 66.65 | 14.12 | 36.7 | 37.54 |
| 351 Variant | VH1.0/ VL1.0 | VH1.0/ VL1.1 | VH1.0/ VL1.2 | VH1.0/ VL1.3 | VH1.0/ VL1.4 | VH1.0/ VL1.5 | VH1.0/ VL1.6 | VH1.0/ VL1.7 | |
| 351 Yield (µg/ml) | 33.5 | 26.66 | 24.52 | 25.1 | 35.20 | 29.25 | 28.93 | 33.54 | |

Total expression levels of IgGs in conditioned media were measured by quantitative IgG ELISA, as described in Example 2. Table 7 shows EC50 (nM) values calculated from cell surface Notch1 binding ELISAs for humanized 438 variants and rat 438, along with humanized 351 variants and rat 351.

The data demonstrates that multiple variants of humanized 438, including humanized 438 VH1.1/VL1.8, are similar to rat 438 in binding to full-length human Notch1 expressed on the cell surface of U-2 OS cells. Furthermore, Table 7 shows that both humanized 438 VH1.1/VL1.8 and VH1.1/VL1.3 fully retained rat 438's cross-reactivity to mouse Notch1 expressed on the cell surface of U-2 OS cells.

The data further demonstrates that humanized 351 VH1.0/VL1.1 and VH1.1/VL1.4, are similar to rat 351 in binding to full-length human Notch1 expressed on the cell surface of U-2 OS cells. Table 7 further shows that humanized 351 VH1.0/VL1.1 and VH1.1/VL1.4 fully retained rat 351's cross-reactivity to mouse Notch1 expressed on the cell surface of U-2 OS cells.

TABLE 7

EC50 (nM) values of cell surface Notch1 binding ELISAs for humanized 438 variants and rat 438, along with humanized 351 variants and rat 351.

| | EC50 (nM) | | | | | | | |
|---|---|---|---|---|---|---|---|---|
| | Antibody | | | | | | | |
| | Rat 438 | VH1.0/ VL1.1 | VH1.1/ VL1.0 | VH1.1/ VL1.1 | VH1.1/ VL1.3 | VH1.1/ VL1.5 | VH1.1/ VL1.8 | VH1.1/ VL1.9 |
| Human Notch1 | 0.2132 | 0.305 | 0.2956 | 0.1773 | 0.1516 | 0.2189 | 0.2025 | 0.1776 |

TABLE 7-continued

EC50 (nM) values of cell surface Notch1 binding ELISAs for humanized 438
variants and rat 438, along with humanized 351 variants and rat 351.

| | EC50 (nM) | | | | | | | |
|---|---|---|---|---|---|---|---|---|
| Mouse Notch1 | 0.1725 | 0.2287 | 0.1437 | 0.1291 | 0.09337 | 0.1457 | 0.1489 | 0.1374 |

| | Antibody | | |
|---|---|---|---|
| | Rat 351 | VH1.0/ VL1.1 | VH1.0/ VL1.4 |
| Human Notch1 | 0.10 | 0.15 | 0.10 |
| Mouse Notch1 | 0.07 | 0.08 | 0.07 |

B. Competition ELISA

Competition ELISAs between humanized 438 variants and biotinylated rat 438, along with humanized 351 variants and biotinylated rat 351, on recombinant or cell surface expressed full length human Notch1 was performed. In a similar manner as described for recombinant protein or cell based ELISAs, 96 well cell culture plates were either coated with Notch1 NRR-Avi_His protein (hi-bound co-Star plates), or seeded with full length Notch1 expressing U-2 OS cells (cell culture plate, Co-star), respectively. Serially diluted (1:3 in blocking buffer) antibody solutions or cell culture conditioned media, in the presence of 0.8 nM of biotinylated rat 438 or biotinylated rat 351 antibody were applied to the plate.

After incubation for 2 hours, the plates were washed, as described above, and HRP-conjugated streptavidin (Southern Biotech) diluted 1:5000 in blocking buffer was applied. Incubation with streptavidin was allowed for 30 min before the plates were washed again and developed with TMB solution for 10 minutes. Developing reaction was stopped by adding 0.18M $H_2SO_4$ and absorbance at 450 nM was measured. Data plotting and analyses were performed with Microsoft Excel and Graphpad-Prizm software.

Table 8 shows EC50 (nM) values of competition ELISA of humanized 438 variants with biotinylated rat 438 antibody for binding to recombinant human Notch1 NRR immunogen. The data shows that multiple variants of humanized 438, including humanized 438 VH1.1/VL1.8, had EC50 values similar to the unlabelled rat 438 in the competition ELISA. This demonstrates that the humanized 438 variants compete as well as unlabelled rat 438 with biotinylated rat 438 for the binding to Notch1 NRR immunogen. These results indicate that humanized 438 variants bind to the same or similar epitope on the immunogen as the rat 438 antibody.

Table 8 further shows EC50 (nM) values of the competition ELISA of humanized 438 variants with biotinylated rat 438 antibody for binding to full-length human Notch1 expressed on the cell surface of U-2 OS cells. The data shows that multiple variants of humanized 438, including humanized 438 VH1.1/VL1.8, had EC50 values similar to the unlabelled rat 438 in the competition ELISA. This demonstrates that the humanization 438 variants compete as well as unlabelled rat 438 with biotinylated rat 438 for the binding to full length human Notch1 expressed on cell surface of U-2 OS cells. These results indicate that humanized 438 variants bind to the same or similar epitope on full-length human Notch1 expressed on the cell surface of U-2 OS cells as the rat 438 antibody.

TABLE 8

EC50 (nM) values of competition ELISAs between humanized 438 variants and biotinylated
rat 438 on recombinant or cell surface expressed full-length human Notch1

| | Antibody | | | | | | | | |
|---|---|---|---|---|---|---|---|---|---|
| | Rat 438-mIgG | VH1.0/ VL1.1 | VH1.1/ VL1.0 | VH1.1/ VL1.1 | VH1.1/ VL1.3 | VH1.1/ VL1.9 | VH1.0/ VL1.8 | VH1.1/ VL1.8 | VH1.1/ VL1.5 | Rat 438-hIgG |
| Recombinant human Notch 1 | 1.5 | 0.7 | 1.1 | 0.6 | 2.5 | 0.4 | 2.1 | 1.2 | 7.0 | 2.1 |
| Cell surface full-length human Notch 1 | 3.6 | 4.0 | 2.8 | 2.4 | 2.8 | 2.2 | 11.6 | 3.2 | 3.3 | 4.4 |

Table 9 shows EC50 (nM) values of the competition ELISA of humanized 351 variants and biotinylated rat 351 antibody for binding to full-length human Notch1 expressed on the cell surface of U-2 OS cells. The data shows that multiple variants of humanized 351, including humanized 351 VH1.0/VL1.1, had EC50 values similar to the unlabelled rat 351 in the competition ELISA. This demonstrates that humanized 351 variants compete as well as unlabelled rat 351 with biotinylated rat 351 for the binding to full length human Notch1 expressed on cell surface. These results indicate that humanized 351 variants bind to the same, or similar, epitope on full length human Notch1 expressed on the cell surface of U-2 OS cells as the rat 351 antibody.

TABLE 9

EC50 (nM) values of competition ELISAs between humanized 351 variants and biotinylated rat 351 on cell surface expressed full-length human Notch1

| Antibody | Rat 351 | VH1.0/ VL1.1 | VH1.0/ VL1.4 | Anti-*E. Tenella* |
|---|---|---|---|---|
| Cell surface full-length human Notch1 | 4.43 | 2.75 | 2.11 | non-competing |

C. Specificity of Binding to Other Human Notch Homologues

Other members of the Notch receptor family play important roles in biological processes. For example, Notch2 deficiency leads to embryonic death in mouse models. In contrast, Notch3 deficiency leads to only mild phenotype in distal arteries and Notch4 deficiency results in no detectable phenotype in mouse models. The closest homologues of the Notch1 NRR region are Notch2 and Notch3 (~50% homology), and Notch4 is a more distant homologue (34% homology). Crossreactivity of anti-Notch1 antibodies to other members of the Notch family, especially Notch2, may lead to undesired effects in patients. Therefore, the potential cross-reactivity of rat 438 and humanized 438, along with rat 351 and humanized 351 antibodies to other Notch family members were assessed.

Expression constructs encoding human Notch2 and Notch3 NRR regions, fused with human IgG1 Fc fragment were stably introduced into CHO-PACE cells. Conditioned media from these cells expressing NRR-Fc fusions were collected. Human Notch2 NRR-Fc and human and mouse Notch3 NRR-Fc were purified by protein A affinity followed by size exclusion chromatography (SEC). Purified preparations were dialysed into TBS with 1 mM CaCl$_2$ and analyzed on analytical SEC to be >99% in purity.

As shown in Table 10, rat 438 lacked detectable binding to human Notch2 NRR-Fc fusion protein. Further shown in Table 10, humanized 438 variants lacked detectable binding to full-length human Notch3 expressed on U-2 OS cell surface, demonstrating that 438 did not cross-react with Notch3.

TABLE 10

Binding of rat-mIgG1 and humanized 438 variants to Notch2 NRR-Fc and Notch3 U-2 OS cells (N/B represents non-binding).

| | Binding to Notch2 NRR-Fc | | Binding to Notch3 U2-OS cells |
|---|---|---|---|
| Rat 438-mIgG1 | N/B | Rat438-mIgG | N/B |
| Humanized 438VH1.0/VL1.1 | N/B | A2 | N/B |
| Humanized 438VH1.1/VL1.0 | N/B | | |
| Humanized 438VH1.1/VL1.3 | N/B | | |
| Humanized 438VH1.1/VL1.5 | N/B | | |
| Humanized 438VH1.1/VL1.8 | N/B | | |
| Humanized 438VHH1.1/VL1.9 | N/B | | |
| A2 | N/B | | |

As shown in Table 11, humanized 351 VH1.0/VL1.1 lacked detectable binding to human Notch2 NRR-Fc fusion protein, and to both human and mouse Notch3 NRR-Fc fusion proteins. However, humanized 351 VH1.0/VL1.1 cross-reacted with human, mouse and cyno-Notch1 NRR.

TABLE 11

Binding of humanized 351 VH1.0/VL1.1 to recombinant human, mouse and cyno-Notch1; human Notch2; and human and mouse Notch3 NRR-Fc fusion proteins (N/B represents non-binding).

| | IC50 (nM) | | | | | |
|---|---|---|---|---|---|---|
| | Human Notch1 NRR-Fc | Mouse Notch1 NRR-Fc | Cynomulgus Notch1 NRR-Fc | Human Notch2 NRR-Fc | Human Notch3 NRR-Fc | Mouse Notch3 NRR-Fc |
| Humanized 351 VH1.0/VL1.1 | 0.249 | 0.27 | 0.26 | N/B | N/B | N/B |

D. Binding Affinity to Human Notch1 NRR

The kinetic constants of the anti-Notch1 NRR interactions were determined by surface plasmon resonance (Biacore® T100, Biacore Inc., Piscataway, N.J.). Flow cells of a CM5 chip were immobilized with approximately 10,000 Resonance Unit (RU) of anti-human IgG-Fc (Biacore®) in 10 mM Glycine, pH 5.0 at 10 µl/min for 600 seconds. 10 µg/ml of anti-Notch1 humanized 438 variants and humanized 351 variants diluted in TBS with 1 mM CaCl$_2$ were captured at 10 µl/min. Association of four concentrations of human Notch1 NRR_Avi_His recombinant protein (from 3.7-100 nM) and a zero concentration (running buffer) at 100 µl/min were recorded for 3 minutes in TBS with 1 mM CaCl$_2$. Dissociation of the complexes was measured for 10 minutes. The surface of the chip was regenerated by injecting 3M MgCl$_2$ with 3 mM EGTA for 60 seconds at 10 µl/min. Curves obtained after subtraction of the reference and buffer signals were fitted to a 1:1 Langmuir binding model with Biacore® T100 Evaluation Software (Biacore®).

The binding affinity of selected humanized 438 variants and humanized 351 variants, and A2 antibody (Wu, Y. et al., Nature 464:1052-1057, 2010) to human Notch1 NRR protein was determined and shown in Table 12. Kinetic analysis by Biacore® showed similar ka (on) and kd (off) rates for selected humanized 438 variants, including VH1.1/VL1.8 and VH1.1/VL1.3, compared to the A2 antibody.

Kinetic analysis by Biacore® further showed higher ka (on) and kd (off) rates for rat 351 and selected humanized 351 variants, including VH1.0/VL1.1 and VH1.1/VL1.4, compared to the A2 antibody. Although the resulting $K_D$ values for rat 351 and selected humanized 351 variants were similar, the differences demonstrated in the ka (on) and kd (off) rates may play a role in the distinct neutralizing activities against Notch1 dependent signaling described in Examples below.

TABLE 12

Biacore® analysis of rat 438 and humanized 438 variants, along with rat 351 and humanized 351 variants to recombinant human Notch1 NRR protein, in comparison to control A2 antibody.
(N/A represents not applicable).

| 438 | ka (1/Ms) | kd (1/s) | $K_D$ (M) | $K_D$ (nM) | Fold difference from rat 438 |
|---|---|---|---|---|---|
| Rat 438-hIG1 | 5.27E+04 | 2.29E−4 | 4.34E−09 | 4.34 | 1.00 |
| 438 VH1.1/VL1.3 | 2.42E+05 | 4.42E−04 | 1.83E−09 | 1.83 | 0.42 |
| 438 VH1.1/VL1.8 | 2.14E+05 | 4.49E−04 | 2.10E−09 | 2.10 | 0.48 |
| 438 VH1.0/VL1.1 | 6.05E+04 | 3.89E−04 | 6.42E−09 | 6.4 | 1.47 |
| 438 VH1.1/VL1.0 | 4.74E+04 | 1.03E−03 | 2.18E−08 | 21.8 | 5.02 |
| 438 VH1.1/VL1.1 | 4.37E+04 | 4.22E−04 | 9.65E−09 | 9.6 | 2.21 |

| 351 | ka (1/Ms) | kd (1/s) | $K_D$ (M) | $K_D$ (nM) | Fold difference from rat 351 |
|---|---|---|---|---|---|
| Rat 351 | 4.39E+05 | 1.02E−03 | 2.33E−09 | 2.3 | 1.00 |
| 351 VH1.0/VL1.1 | 4.92E+05 | 1.55E−03 | 3.14E−09 | 3.1 | 1.35 |
| 351 VH1.0/VL1.4 | 4.58E+05 | 2.23E−03 | 4.88E−09 | 4.9 | 2.10 |
| A2 | 1.20E+05 | 3.53E−04 | 2.94E−09 | 2.94 | N/A |

(N/A represents not applicable).

D. Thermal Stability

Thermal stability of a protein or protein domain positively correlates with the stability of the protein or protein domain. A higher melting point of a protein or protein domain often provides improved manufacturability and longer shelf life. Differential scanning calorimetry (DSC) was used for assessing the thermal stability of humanized 438 variants and rat 438-mIgG1. Protein samples were diluted in PBS to 0.3 mg/ml in a volume of 250 µl. The corresponding formulation buffer blank was used for the reference sample. Both samples were thoroughly degassed using a MicroCal ThermoVac Sample Degassing and Thermostat (Microcal, Inc., Northampton, Mass.) set to 8° C. Samples were dispensed into the appropriate cells of a MicroCal VP-DSC Capillary Cell MicroCalorimter (MicroCal, Inc., Northampton, Mass.). Samples were equilibrated for 4 minutes at 15° C. and then scanned up to 100° C. at a rate of 100° C. per hour. A filtering period of 20 seconds was selected. Raw data was baseline corrected and the protein concentration was normalized. Origin Software (OriginLab Corporation, Northampton, Mass.) was used to fit the data to an MN2-State Model with an appropriate number of transitions.

As shown in Table 13 below, all humanized 438 variants had higher thermostability, as displayed by higher melting point, in their Fab region (all above 77° C.) compared to rat 438-mIgG1.

TABLE 13

Thermal Stability (DSC) analysis of humanized 438 variants and rat 438-mIgG1.

| | Tm (° C.) | | | |
|---|---|---|---|---|
| | CH2 | Fab | CH3 | ΔT Fab |
| Rat 438-mIgG1 | 71.82 | | 81.92 | — |
| VH1.0/VL1.8 | | 75.33 | 84.65 | 3.5 |
| VH1.0/VL1.1 | 73.28 | 77.34 | 84.59 | 5.5 |
| VH1.1/VL1.8 | 72.90 | 79.26 | 85.50 | 7.4 |
| VH1.1/VL1.1 | 72.96 | 80.79 | 85.84 | 9.0 |
| VH1.1/VL1.5 | 71.91 | 80.97 | 86.21 | 9.2 |
| VH1.1/VL1.0 | 72.79 | 82.90 | | 11.1 |
| VH1.1/VH1.3 | 72.84 | 84.00 | | 12.2 |

Example 4

Figure 2:
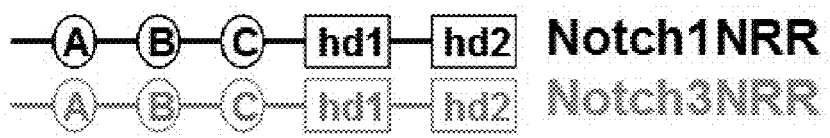
FIG. 2 shows recombinant human Notch1 NRR and Notch3 NRR domain swap chimeric constructs for epitope mapping of the anti-Notch1 antibodies rat 351-mIgG1, rat 438-mIgG1 and A2.

Identification of Anti-Notch1 Inhibitory Antibodies Binding Epitopes on Notch1 NRR A. Domain Swap Chimeric Constructs As described in Example 3, humanized 438 and humanized 351 variants lacked cross-reactivity with the Notch3 protein. Domain swap chimeric constructs for Notch1 and Notch3 NRR were prepared for epitope mapping of the anti-Notch1 rat 438-mIgG1, rat 351-mIgG1 and A2 antibodies. Expression constructs encoding human Notch3-Notch1 (herein termed Notch3-1) NRR region domain swap chimera with C-terminal Fc fusion (human IgG1 Fc fragment) were individually transfected into CHO-PACE and stable pools expressing each chimera were established. Conditioned media from each stable pool were applied to protein A affinity chromatography, followed by size exclusion chromatography (SEC) for the purification of the chimeric fusion protein. Purified preparations were then dialysed into TBS with 1 mM $CaCl_2$ and analyzed on analytical SEC. FIG. 2 shows recombinant human Notch1 NRR and Notch3 NRR domain swap chimeric constructs for epitope mapping rat 351-mIgG1, rat 438-mIgG1 and A2. As shown in FIG. 2, the recombinant NRR chimeric proteins consist of various Notch3 (shown in grey) and Notch1 (shown in black) domains fused to human Fc (not shown).

Relative binding capacities of rat 438-mIgG1 and rat 351-mIgG1 to Notch3-1 NRR domain swap chimeras were tested with Biacore® SPR technology and the relative Resonance Units (RU) binding capacity of the antibody being tested. The binding of rat 438-mIgG1 and rat 351-mIgG1 to Notch3-1 NRR chimeras by SPR was determined by surface plasmon resonance (Biacore® 3000, BIAcore Inc., Piscataway, N.J.). Flow cells of a CM5 chip were immobilized with approximately 10,000 RU each of anti-murine IgG (goat) and goat IgG as a control in 10 mM Glycine, pH 5.0 at 10 µl/min for 600 seconds. Rat 438-mIgG1 and rat 351-mIgG1 antibodies diluted to 1 µg/ml in HBS-P with 0.1 mM $CaCl_2$ were captured at 10 µl/min for 300 seconds. Approximate capture for each antibody was 150 RU (response 1). Next, 10 µg/ml Notch3-1 NRR chimeras were injected at 10 µl/ml for 300 seconds in the same buffer on the captured rat 438-mIgG1 and rat 351-mIgG1 antibodies and the captured Notch3-1 NRR was measured (response 2). Dissociation of the complexes after each cycle was achieved using 10 mM Ac pH 1.5 at 30 µl/min for 20 seconds.

As shown in FIG. 2, the epitope binding profile of rat 438-mIgG1 and rat 351-mIgG1 to domains of Notch1 NRR are distinct from the binding profile of A2 to domains of Notch1 NRR. More specifically, the binding of A2 to the NRR is more dependent on the LNR-B domain than rat 438-mIgG1. In addition, the binding of rat 351-mIgG1 to the Notch1 NRR is less dependent on the LNR-A and LNR-B domains compared to A2. The differences in domain binding profiles, combined with more detailed information on the differences in the contact residues in Notch1 NRR, and the distinct orientation of the Notch1 NRR in association with rat 438-mIgG1 and A2, as revealed by co-crystal structures described below, demonstrates that rat 438-mIgG1 interacts with Notch1 NRR in a different manner than A2.

B. X-Ray Crystallographic Analysis

Rat 438 and rat 351 were expressed and purified as described above in Example 2. Fab (antigen-binding fragment) was generated from rat 438 and rat 351 using the PIERCE Fab Preparation Kit (immobilized papain), product # 44685. Rat 438 and rat 351 were incubated with immobilized papain for 24 hours at 37° C. The Fab was purified by desalting with a ZEBA column (PIERCE) equilibrated with 50 mM Tris pH 8.0. The Fab was collected in the flow-through from Q FF column equilibrated with 50 mM Tris pH 8.0.

The resulting Fab fragment was mixed with the human Notch1 NRR protein at a molar ratio of 1:1.2 with the addition of 0.9 mM $CaCl_2$ and incubated on ice for 30 minutes before purification on an S200 size exclusion column equilibrated with 25 mM Tris pH 8.0, 150 mM NaCl, and 0.9 mM $CaCl_2$. Fractions from the predominant peak containing the Fab:NRR complex were pooled and concentrated to 11 mg/ml using a 10 $K_D$ cutoff VIVASPIN HY concentrator (Sartorius). The Fab:NRR complex was crystallized using the hanging drop vapor diffusion method.

For rat 438, limited proteolysis of the complex using chymotrypsin was required in order to obtain crystals. The complex was first mixed with chymotrypsin to a final concentration of 2 ug/ml and then combined with an equal volume of well solution consisting of 100 mM sodium cacodylate pH 5.5, 14-20% PEG 8000, 100-200 mM calcium acetate. Crystals appeared within a week and continued to grow for 3 weeks. For rat 351, the complex was combined with an equal volume of well solution consisting of 20% PEG 3350, 200 mM sodium sulfate. Crystals appeared after one week and continued to grow for 3 weeks.

Crystals were cryo-protected by swiping through well solution with the addition of 25% glycerol. X-ray data was collected at SER-CAT beamline 22BM for rat 438 and 22ID for rat 351 at the Advanced Photon Source and processed to a resolution of 2.6 Angstrom using the HKL-2000 (HKL Software) software package. The structure was solved by molecular replacement using Phaser software. The search models were taken from pdb id 3L95 for the Notch1 NRR, 2HRP for the heavy chain and 1xgp for the light chain of rat 438, and 1 BM3 for the heavy chain and 3L95 for the light chain of rat 351. The resulting model was rebuilt and refined using coot and BUSTER (Global Phasing, Ltd.) including soft NCS restraints. The structure was validated using molprobity. Residues involved in interactions were determined using the pymol and PISA.

Figure 3:
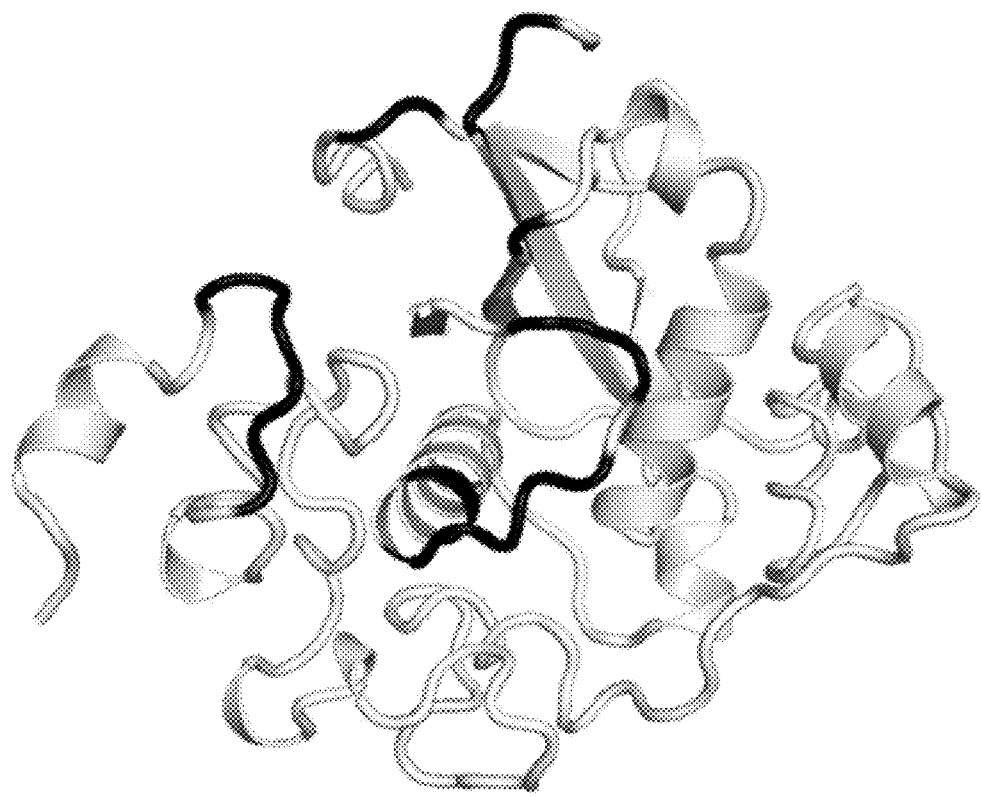
FIG. 3 shows a structural view of the rat 438 epitope on the human Notch1 NRR.
Figure 4:
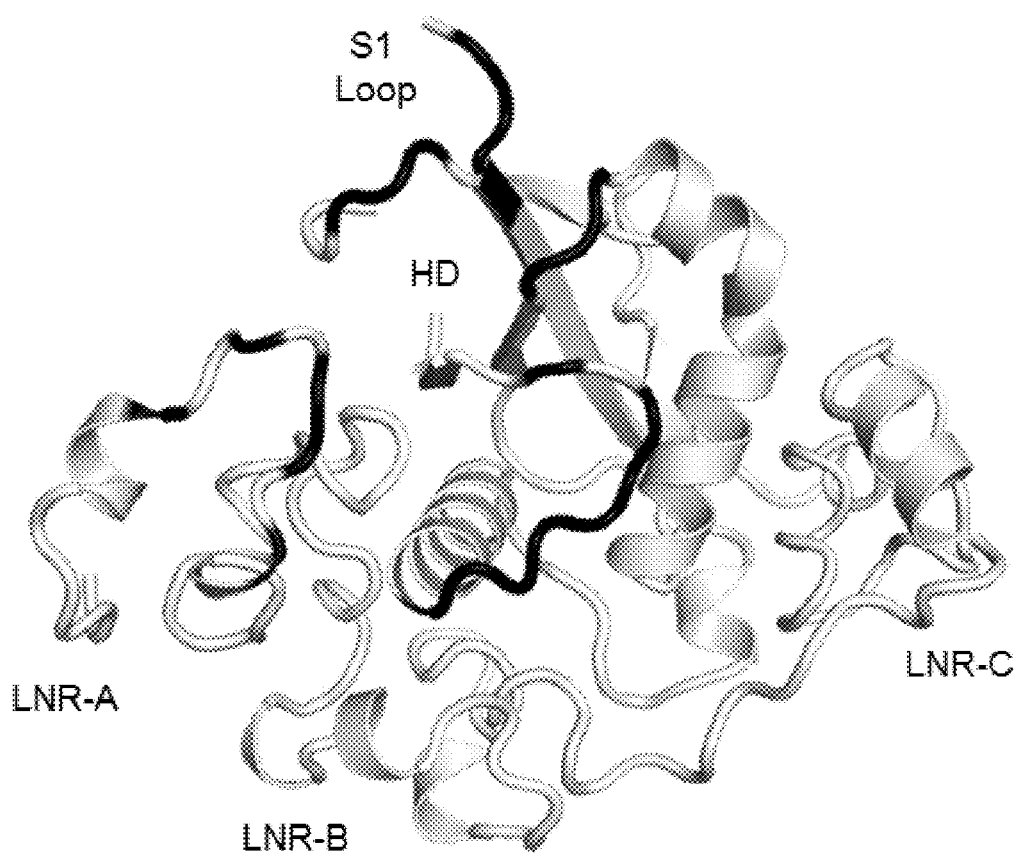
FIG. 4 shows a structural view of the rat 351 epitope on the human Notch1 NRR.
Figure 5:
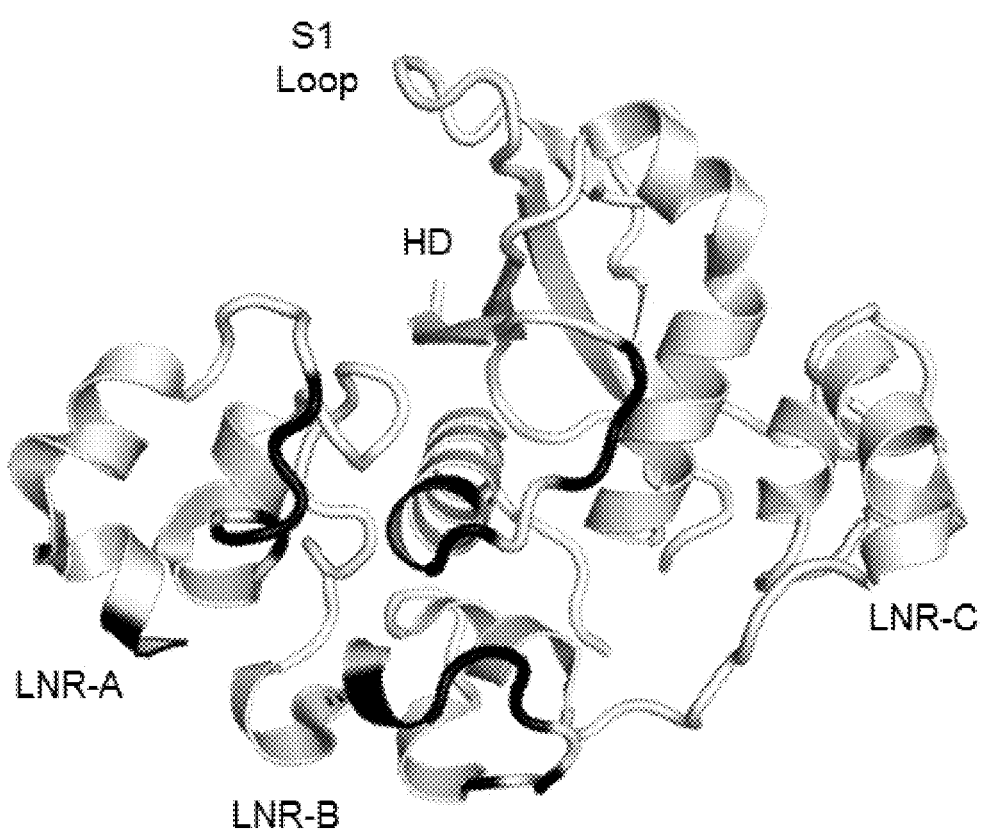
FIG. 5 shows a structural view of the A2 epitope on the human Notch1 NRR.

A structural view of the rat 438 epitope on the human Notch1 NRR is shown in FIG. 3. and the rat 351 epitope on the human Notch1 NRR is shown in FIG. 4. A similar X-ray crystallographic analysis was completed using published data for the A2 antibody and FIG. 5 shows the structural view of the A2 epitope on the human Notch1 NRR. For FIGS. 3-5, amino acid residues within 3.8 angstroms of the antibody are shown in black. Table 14 below provides the residues involved in Notch1 NRR antibody interactions for rat 438, rat 351 and A2.

The data shows that rat 438 and A2 bind overlapping but distinct surfaces within the Notch1 NRR. Both epitopes include the central HD domain. Rat 438 and A2 interact with LNR-A, however rat 438 interacts with a larger surface. Only rat 438 interacts with the S1 loop region and only A2 interacts with LNR-B. More specifically, the data shows that rat 438 binds to human Notch1 NRR residues Asn 1461, Lys 1462, Val 1463, Cys 1464, Leu 1466, Leu 1580, Tyr 1621, Gly 1622, Met 1670, Asp 1671, Val 1672, Arg 1673, Leu 1707, Ala 1708, Leu 1710, Gly 1711, Ser 1712, Leu 1713, Pro 1716 and Lys 1718.

The data also shows that rat 351 and A2 bind overlapping but distinct surfaces within the Notch1 NRR. In particular, only rat 351 interacts with the S1 loop region and only A2 interacts with LNR-B. Rat 351 and A2 both interact with LNR-A, however rat 351 interacts with a distinct subset of LNR-A amino acids. More specifically, the data shows that rat 351 binds to the human Notch1 NRR residues Asp 1458, Asn 1461, Val 1463, Cys 1464, Leu 1466, Leu 1580, Met 1581, Pro 1582, Tyr 1621, Gly 1622, Arg 1623, Asp 1671, Val 1672, Arg 1673, Gly 1674, Leu 1710, Gly 1711, Ser 1712, Leu 1713, Asn 1714, Ile 1715, Pro 1716, Lys 1718.

The x-ray crystal structure of rat 438 and rat 351 residues binding to Notch1 NRR were further analyzed using the program PISA. The data shows that rat 438 formed strong electrostatic interactions (salt bridges) with the residues Lys1718 and Arg1673. Notch1 NRR residues that formed hydrogen bonds with the rat 438 antibody were Asn1461, Asp1671, Arg1673, Leu1713, Lys1718, Cys1464, Ala1708, and Ser1712. The Notch1 NRR residues that contribute more than 40 $Angstrom^2$ of buried surface area upon formation of the complex with rat 438 antibody were Arg1673, Val1463, Lys1462, Gly1622, Asp1671 from the interaction with the heavy chain, and Leu1466, Lys1718, Gly1711, Cys1464, Pro1716, and Val1463 from the interaction with the light chain. Of the residues identified, rat 438 binds to human Notch1 NRR at least at residues Asn1461, Val1463, Lys1462, Asp1671, Arg1673, Leu1713, and Lys1718.

The data shows that rat 351 forms strong electrostatic interactions (salt bridges) with residues Asp1458 and Arg1673. Notch1 NRR residues that formed hydrogen bonds with the rat 351 antibody were Asp1458, Val1463, Cys1464, Ser1465, Tyr1621, Asp1671, Val1672, Arg1673, Gly1711, Ser1712, Leu1713, and Asn1714. The Notch1 NRR residues that contribute more than 40 $Angstrom^2$ of buried surface area upon formation of the complex with rat 351 were Val1463, Cys1464, Leu1466, Gly1711, Asn1714, Pro1716, and Lys1718 from the interaction with the light chain, and Asn1461, Leu1580, Asp1671, and Arg1673 from interactions with the heavy chain. Of the residues identified, rat 351 binds to human Notch1 NRR at least at residues Asp1458, Val1463, Tyr1621, Asp1671, Val1672, Arg1673, Ser1712, and Leu1713. Further, A2 does not interact with residues Asp1458, Val1463, Tyr1621, Asp1671, Val1672, Arg1673, Ser1712, and Leu1713.

TABLE 14

Residues of rat 438 and rat 351 involved in human Notch1 NRR antibody interactions

| | Human Notch1 NRR Residue | | Rat 351 Residue | | Rat 438 Residue | | A2 Residue | |
|---|---|---|---|---|---|---|---|---|
| LNR-A | ASP | 1458 | ARG | 58 | H | | | |
| | ASN | 1461 | ARG | 58 | H | TYR | 58 | H |
| | | | TRP | 94 | L | | | |

TABLE 14-continued

Residues of rat 438 and rat 351 involved in human Notch1 NRR antibody interactions

Figure 6:
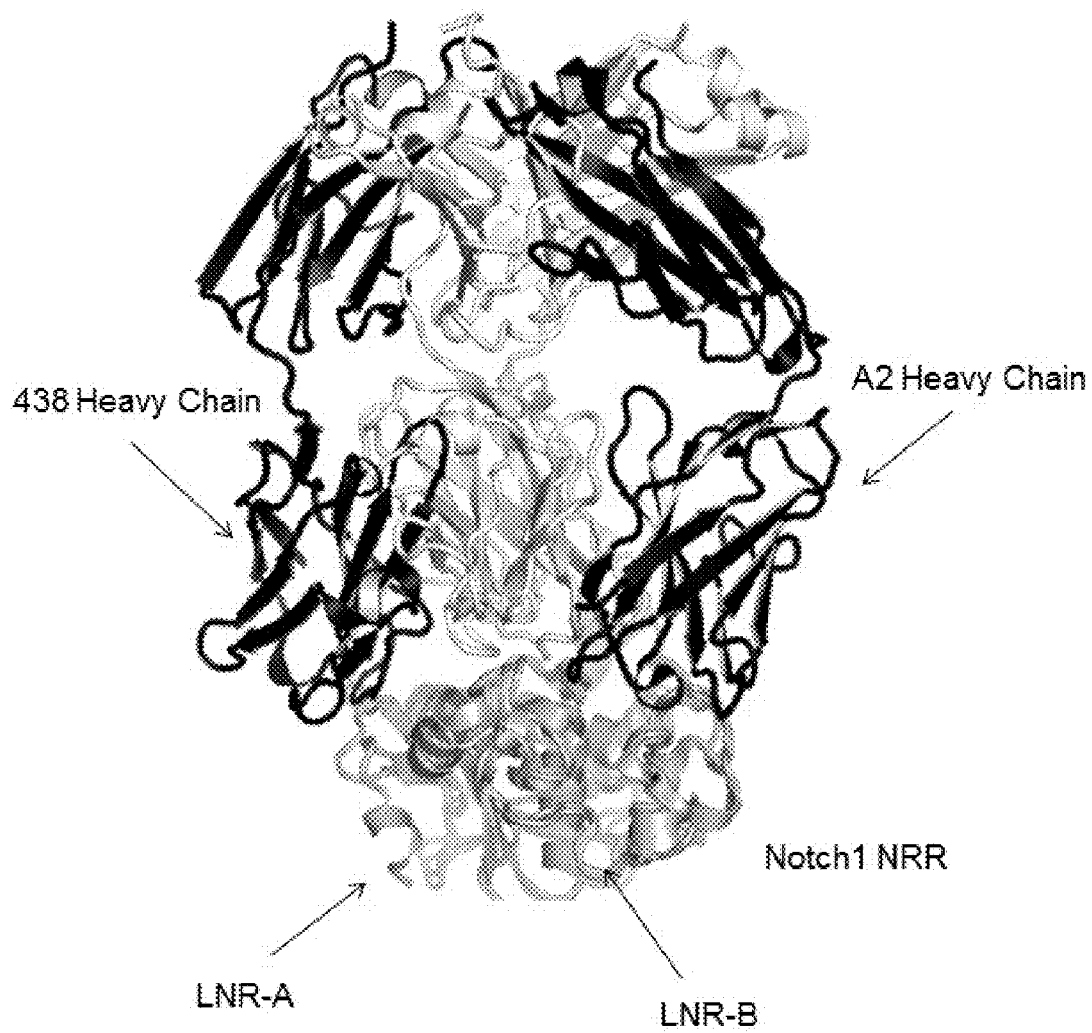
FIG. 6 shows the superposition of the structures of Notch1 NRR bound to rat 438 and A2 antibodies
Figure 7:
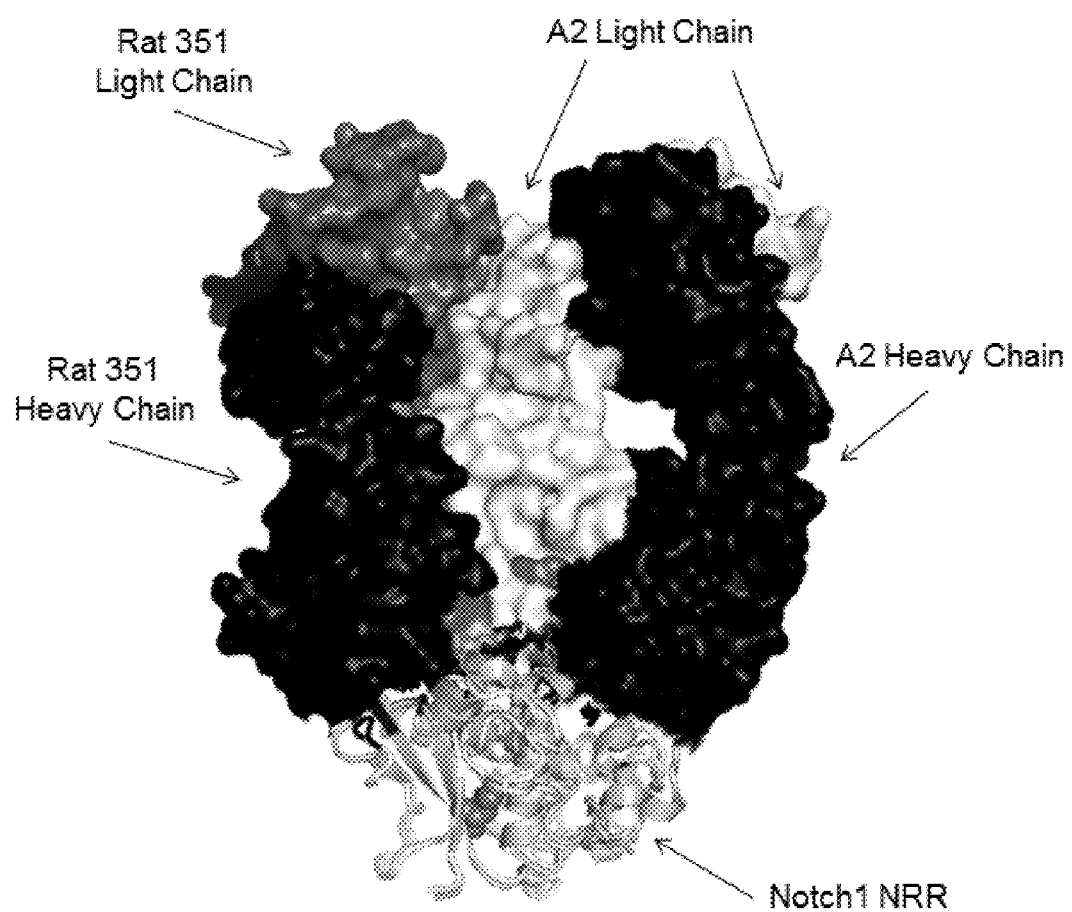
FIG. 7 shows the superposition of the structures of Notch1 NRR (shown as ribbons) bound to rat 351 and A2 antibodies (shown as molecular surfaces).

| | Human Notch1 NRR Residue | | Rat 351 Residue | | | Rat 438 Residue | | | A2 Residue | | |
|---|---|---|---|---|---|---|---|---|---|---|---|
| | LYS | 1462 | | | | TYR | 58 | H | | | |
| | | | | | | TYR | 100A | H | | | |
| | VAL | 1463 | TRP | 94 | L | TYR | 58 | H | | | |
| | | | | | | THR | 100B | H | | | |
| | CYS | 1464 | ASN | 92 | L | ASN | 92 | L | TYR | 49 | L |
| | | | SER | 93 | L | SER | 93 | L | PHE | 53 | L |
| | | | TRP | 94 | L | TRP | 94 | L | | | |
| | SER | 1465 | | | | TRP | 94 | L | TYR | 49 | L |
| | LEU | 1466 | ILE | 2 | L | ASP | 1 | L | SER | 96 | H |
| | | | GLN | 27 | L | ILE | 2 | L | PHE | 98 | H |
| | | | SER | 93 | L | GLN | 27 | L | TYR | 49 | L |
| | | | | | | SER | 93 | L | | | |
| | | | | | | TRP | 94 | L | | | |
| | GLN | 1467 | | | | | | | SER | 56 | L |
| | ASN | 1469 | | | | | | | PHE | 98 | H |
| LNR-B | LYS | 1499 | | | | | | | SER | 30 | H |
| | | | | | | | | | SER | 31 | H |
| | | | | | | | | | ASN | 52 | H |
| | TYR | 1500 | | | | | | | PRO | 53 | H |
| | | | | | | | | | ASN | 54 | H |
| | PHE | 1501 | | | | | | | ARG | 99 | H |
| | SER | 1502 | | | | | | | ARG | 99 | H |
| | ASP | 1503 | | | | | | | ARG | 50 | H |
| | | | | | | | | | ASN | 52 | H |
| | | | | | | | | | ASN | 54 | H |
| | | | | | | | | | SER | 56 | H |
| | | | | | | | | | ARG | 99 | H |
| | HIS | 1505 | | | | | | | ASN | 54 | H |
| | | | | | | | | | SER | 56 | H |
| | ASP | 1507 | | | | | | | ASN | 54 | H |
| S1 Loop | LEU | 1580 | PHE | 98 | H | PRO | 97 | H | | | |
| | MET | 1581 | GLN | 53 | L | | | | | | |
| | PRO | 1582 | PHE | 98 | H | | | | | | |
| | TYR | 1621 | ARG | 52A | H | TYR | 99 | H | | | |
| | GLY | 1622 | ARG | 52A | H | TYR | 99 | H | | | |
| | ARG | 1623 | ARG | 52A | H | | | | | | |
| | ASP | 1671 | TYR | 32 | H | TYR | 98 | H | | | |
| | | | GLN | 97 | H | TYR | 99 | H | | | |
| | | | | | | GLY | 100 | H | | | |
| | VAL | 1672 | GLN | 97 | H | PRO | 97 | H | | | |
| | | | PHE | 98 | H | TYR | 98 | H | | | |
| | | | | | | TYR | 99 | H | | | |
| | | | | | | GLY | 100 | H | | | |
| | ARG | 1673 | HIS | 31 | H | PRO | 97 | H | | | |
| | | | TYR | 32 | H | TYR | 98 | H | | | |
| | | | ARG | 52A | H | TYR | 99 | H | | | |
| | | | GLU | 95 | H | GLY | 100 | H | | | |
| | | | GLY | 96 | H | | | | | | |
| | | | GLN | 97 | H | | | | | | |
| | | | PHE | 98 | H | | | | | | |
| | GLY | 1674 | PHE | 98 | H | | | | | | |
| HD Core | LEU | 1707 | | | | ASN | 30 | L | | | |
| | ALA | 1708 | | | | ASN | 30 | L | PHE | 98 | H |
| | SER | 1709 | | | | | | | GLY | 97 | H |
| | | | | | | | | | PHE | 98 | H |
| | LEU | 1710 | LYS | 28 | L | ARG | 28 | L | GLY | 97 | H |
| | | | | | | | | | PHE | 98 | H |
| | | | | | | | | | ARG | 99 | H |
| | GLY | 1711 | LYS | 28 | L | ARG | 28 | L | PHE | 98 | H |
| | | | SER | 30 | L | ASN | 30 | L | | | |
| | | | | | | GLY | 68 | L | | | |
| | SER | 1712 | LYS | 28 | L | ARG | 28 | L | | | |
| | | | SER | 30 | L | ASN | 30 | L | | | |
| | LEU | 1713 | SER | 30 | L | ASN | 30 | L | | | |
| | ASN | 1714 | SER | 30 | L | ASN | 30 | L | PHE | 91 | L |
| | | | SER | 67 | L | SER | 67 | L | TYR | 92 | L |
| | | | GLY | 68 | L | | | | | | |
| | ILE | 1715 | THR | 31 | L | | | | TYR | 92 | L |
| | PRO | 1716 | GLN | 53 | L | GLN | 53 | L | ASP | 28 | L |
| | | | | | | | | | TYR | 92 | L |
| | TYR | 1717 | | | | GLN | 53 | L | | | |
| | LYS | 1718 | ASN | 32 | L | ASP | 32 | L | ALA | 99 | H |
| | | | TYR | 50 | L | PHE | 50 | L | TYR | 100 | H |
| | | | GLN | 53 | L | GLN | 53 | L | | | |

FIG. 6 shows the superposition of the structures of human Notch1 NRR bound to rat 438 and A2 antibodies; the human Notch1 NRR is at the bottom. The heavy chains of rat 438 and A2 are shown in black and the light chains, in grey, are in between the two heavy chains. As shown in FIG. 6, the orientation of rat 438 and A2 antibodies relative to the NRR is rotated by almost 180 degrees so that the light chain N-terminus of rat 438 points towards LNR-A whereas the light chain of A2 points towards LNR-C (in back region of Notch1 NRR). This places the heavy chains on opposite sides of the two light chains from the point of view of the NRR. The A2 heavy chain is therefore on the opposite side of the light chain from the S1 loop FIG. 7 shows the superposition of the structures of human Notch1 NRR (shown as ribbons) bound to rat 351 and A2 antibodies (shown as molecular surfaces). The heavy chains of rat 351 and A2 are shown in black. The light chain of rat 351 is shown in dark grey and the light chain of A2 is shown in light grey. FIG. 7 shows that rat 351 and A2 antibodies bind in opposite orientations confirming their association with unique epitopes.

Example 5

Functional Characterization of Anti-Notch1 Inhibitory Antibodies in Cell-based Assays A. EDTA-Treatment in Notch1 Reporter Gene Assay In the absence of ligand, the heterodimeric S1-cleaved Notch1 receptor remains inactive at the cell membrane. The Notch1 NRR domains adopt an auto-inhibitory conformation by burying cleavage site 2 (S2), thus preventing access to metalloproteases. The Notch1 NRR domains associate through non-covalent interactions that are stabilized by divalent cations such as calcium. However, the inhibitory interactions of the Notch1 NRR domains can be disrupted by the chelating agent EDTA. Calcium chelation by EDTA results in rapid shedding of the extracellular domain from the cell membrane and is sufficient to activate Notch1 signaling (Rand et al., Mol. Cell. Biol. 20(5):1825-35, 2000).

To determine whether anti-Notch1 inhibitory antibodies stabilize the Notch1 NRR in an inactive conformation upon chelation of divalent cations, Notch1-reporter cells (see section B below) were pre-incubated with rat 438-mIgG1, rat 351-mIgG1 or A2 antibodies, and control anti-*E.tenella* antibody and then treated with 5 mM EDTA. Human Notch1 reporter cells were plated in white-walled 96 well plates at 40,000 cells per well and cultured overnight in McCoy's 5A medium, 10% FBS, Pen/Strep/Glutamine. Medium was removed by aspiration and replaced with medium containing rat 438-mIgG1, rat 351-mIgG1 or A2 antibodies, and control anti-*E.tenella* antibody at 0, 0.01, 0.1, 1, 10 and 30 µg/ml for 1 hour at room temperature. Following the 1 hour antibody pre-treatments, EDTA was added to the cells at a final concentration of 5 mM and incubated at 37° C. in 5% $CO_2$ for 6 hours. The DUAL-GLO Luciferase Assay System (Promega) was used to measure the activities of the 8xCSL Firefly-Luciferase (Notch1-induced) and Renilla-luciferase (constitutive) reporters. The luminescent readings from Firefly-luciferase were divided by the Renilla-luciferase readings to calculate the levels of Notch1 signaling. An average of 3 replicates from each treatment was calculated and plotted along with standard deviations.

Table 15 shows the Notch1 reporter gene assay performed with increasing concentrations of rat 438-mIgG1, rat 351-mIgG1 and A2 antibodies, and control anti-*E. tenella* antibody, in the presence of the chelating agent EDTA and absence of ligand. The data shows that the addition of EDTA alone to the Notch1-reporter cell line stimulates activation of the Firefly-luciferase reporter gene (see 0 µg/ml condition). As expected, the control anti-*E. tenella* antibody did not inhibit Notch1 signaling. In contrast, pre-treatment of the cells with increasing concentrations of rat 438-mIG1, rat 351-mIgG1 and A2 antibodies each inhibited activation of the Firefly-luciferase reporter gene in a dose-dependent manner in the presence of EDTA. At 1 µg/ml, 10 µg/ml and 30 µg/ml concentrations, the Firefly to *Renilla*-luciferase ratios of the rat 351-mIgG1, rat 438-mIgG1 and A2 treatments were significantly lower than control anti-*E. tenella*, indicating inhibition of Notch1 signaling.

TABLE 15

Notch1 reporter gene assay performed with increasing concentrations of rat 438-mIg1, rat 351-mIgG1 or A2 antibodies, and control anti-*E. tenella* antibody in the presence of the chelating agent EDTA and absence of ligand.

| | Firefly/*Renilla* Luminescence Antibody Concentration | | | | | |
|---|---|---|---|---|---|---|
| | 0 µg/mL | 0.01 µg/mL | 0.1 µg/mL | 1 µg/mL | 10 µg/mL | 30 µg/mL |
| rat 351-mIgG1 | 315.2 | 303.9 | 202.1 | 84.8 | 62.1 | 57.0 |
| rat 438-mIgG1 | 333.5 | 338.2 | 245.5 | 116.9 | 54.3 | 46.9 |
| A2 | 307.1 | 312.3 | 172.5 | 89.9 | 63.5 | 55.2 |
| ANTI-*E. TENELLA* | 266.7 | 267.2 | 299.0 | 278.4 | 257.1 | 229.0 |
| | Standard Deviations | | | | | |
| rat 351-mIgG1 | 37.3 | 23.7 | 33.6 | 6.6 | 2.0 | 4.8 |
| rat 438-mIgG1 | 20.5 | 13.2 | 9.9 | 14.5 | 9.0 | 9.0 |
| A2 | 25.0 | 17.7 | 10.7 | 14.9 | 7.8 | 8.0 |
| ANTI-*E. TENELLA* | 16.5 | 34.1 | 48.4 | 27.0 | 23.1 | 6.2 |

B. Cell Line Construction for Notch1 Reporter Gene Co-Culture Assay

The inhibitory activities of anti-Notch1 humanized 438 and humanized 351 antibodies were tested in a Notch1 reporter gene co-culture assay, described in Example 2. Humanized 438 and humanized 351 antibodies were pre-incubated with Notch1 reporter cells and then co-cultured with DLL4-HEK293 cells to activate Notch1 signaling or with parental HEK293 cells as a control.

To generate the Notch1 reporter cell line, a series of three sequential, stable transfections were performed in the U-2 OS human osteosarcoma cell line (ATCC, Manassas, Va.). The first transfection used a vector for expression of full-length human Notch1 or mouse Notch1 based on the pCMV6-Entry-Myc-Flag backbone (Origene), and in both the correct DNA sequences of the Notch1 inserts were confirmed. Following transfection with the TransIT-LT1 transfection reagent (Mirus, Madison, Wis.), U-2 OS cells were selected in G418 and clonal lines were isolated. Second, stable Notch1-expressing U-2 OS clones were re-transfected with the pGL4.27 [luc2P/minP/Hygro] vector (Promega, Madison, Wis.) containing eight tandem copies of the CSL enhancer sequence (CGTGG-GAAAAT), selected in Hygromycin B plus G418 and clonal lines were isolated. The 8xCSL Firefly-luciferase reporter construct is responsive to activated Notch1 signaling (for example, see, Jeffries et al., Mol. Cell. Biol. 22(11):3927-3941, 2002). Thirdly, the Notch1-pGL4.27 U-2 OS cells were re-transfected with pGL4.74 [hRluc/TK] vector (Promega) plus the Linear Puromycin Marker (Clontech, Mountain View, Calif.), selected in Puromycin, Hygromycin B and G418, and clonal lines were isolated. The pGL4.74 vector encoded the *Renilla*-luciferase gene that is constitutively expressed from an HSV-TK promoter and served as an internal control. The triple stable transfected U-2 OS line (termed "Notch1 reporter cells" herein) was maintained in McCoy's 5A medium (Gibco, Grand Island, N.Y.) containing 10% FBS, 1× Penicillin/Streptomycin/L-Glutamine (Gibco), 0.25 mg/ml G418 sulfate, 0.3 mg/ml Hygromycin B and 0.001 mg/ml Puromycin.

To generate the ligand-expressing cells, HEK293 cells (ATCC) were transfected with vectors for expression of human DLL4 or mouse DLL4. Both vectors were based on the pCMV6-AC-HA-His backbone (Origene, Rockville, Md.), and the correct DNA sequences of the DLL4 inserts were confirmed. Following transfection, HEK293 cells were selected in 0.5 mg/ml G418, and clonal lines were isolated, expanded and analyzed for DLL4 expression. Clones with high DLL4 expression and high induction of Notch1 reporter activity in the U-2 OS cells were used to assess the inhibitory effect of anti-Notch1 antibodies.

The luminescent readings from Firefly-luciferase were divided by the internal control *Renilla*-luciferase reading to normalize the signals (termed "FIR ratio" herein). To calculate the fold-induction of Notch1 signaling, the F/R ratios generated from the DLL4-HEK293 co-culture reporter assays were divided by the F/R ratios from the parental HEK293 co-cultures and termed relative luciferase unit (RLU) or activity.

Figure 8:
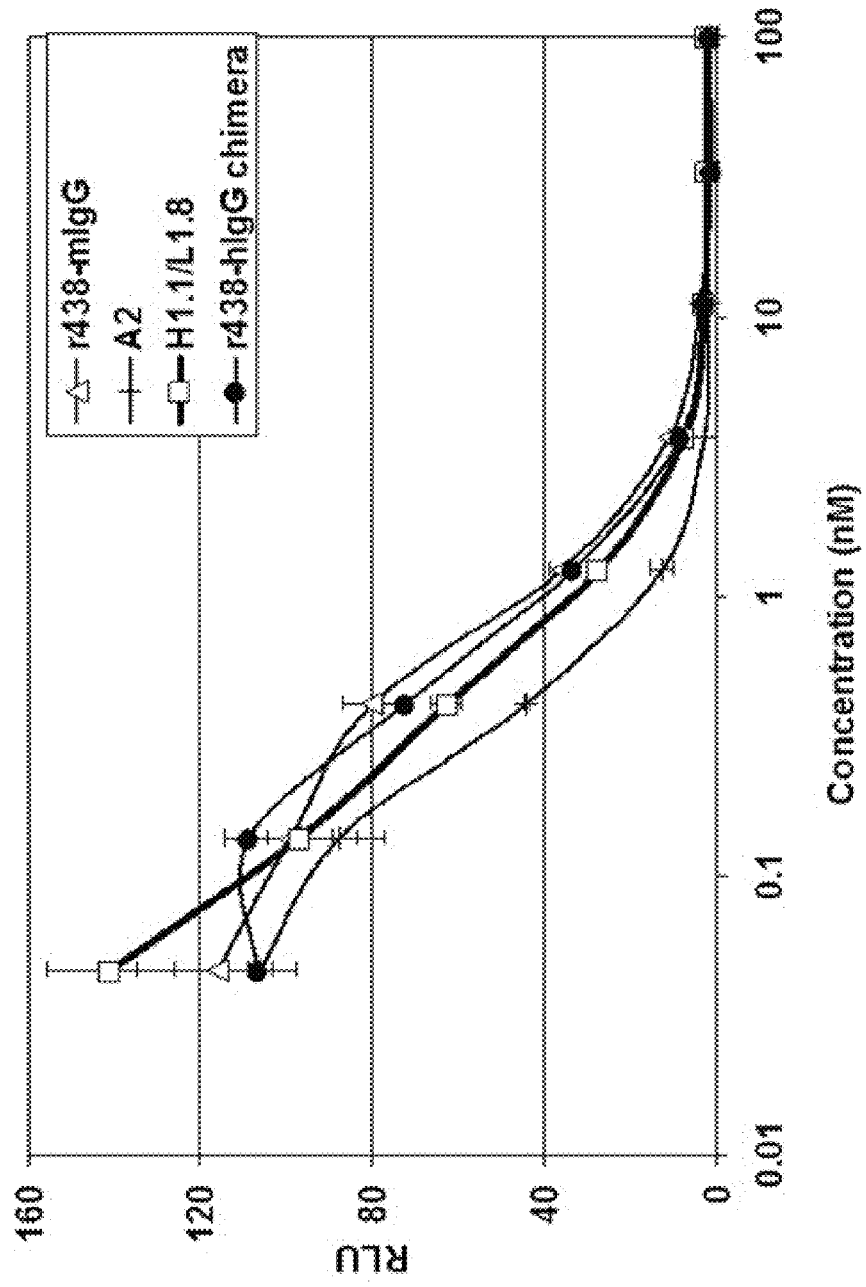
FIG. 8 shows the neutralizing activity of humanized 438 VH1.1/VL1.8, rat 438-mIgG1 and A2 antibodies against Notch1 dependent signaling in human Notch1 reporter cells.
Figure 9:
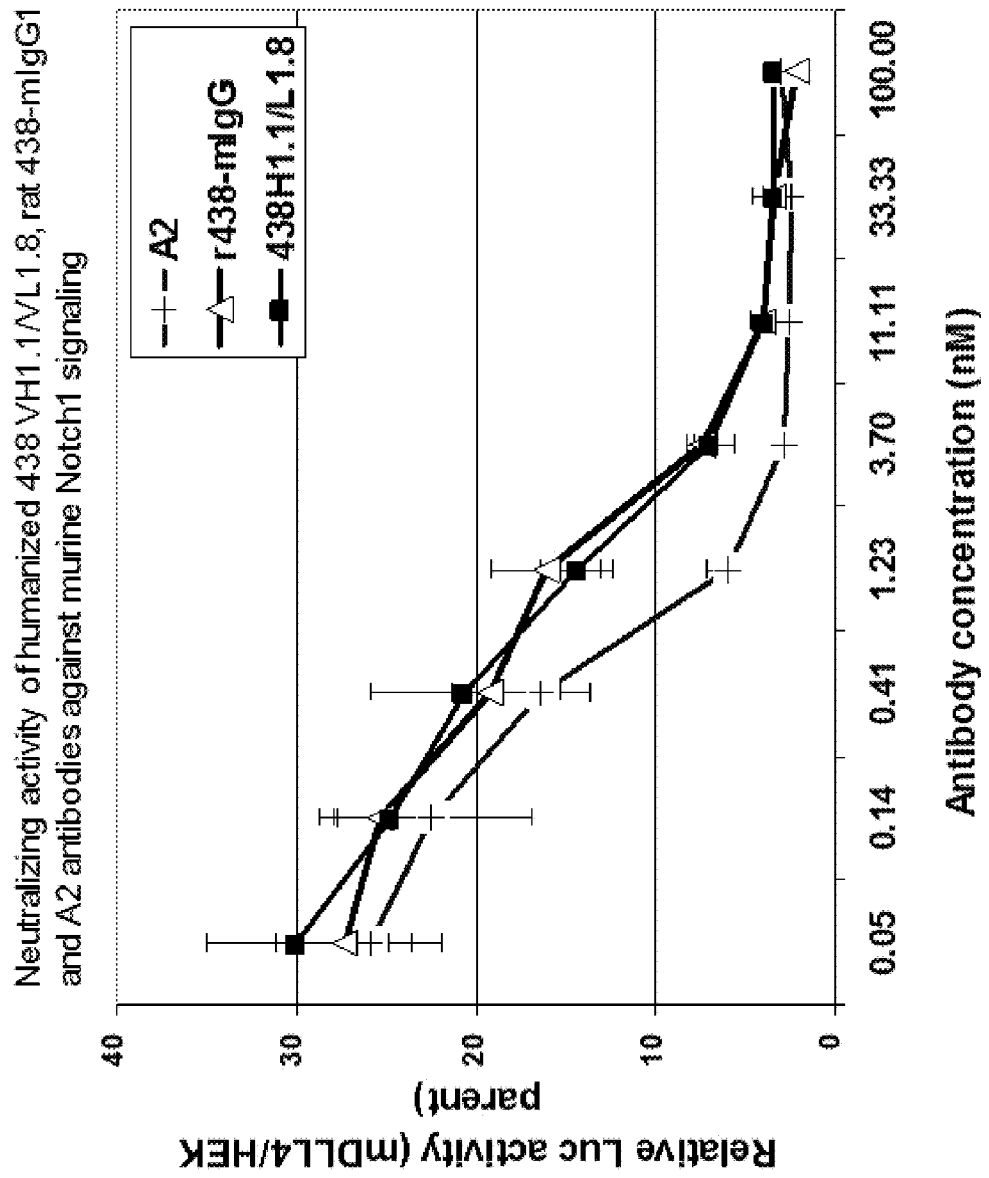
FIG. 9 shows the neutralizing activity of humanized 438 VH1.1/VL1.8, rat 438-mIgG1 and A2 antibodies against Notch1 dependent signaling in mouse Notch1 reporter cells.

A titration of humanized 438 VH1.1/VL1.8 and A2 in the human and murine Notch1 reporter co-culture assays demonstrated potent inhibition of Notch1 signaling in a dose-dependent manner. FIGS. 8 and 9 show the neutralizing activity of humanized 438 VH1.1/VL1.8 and rat 438 antibodies against Notch1 dependent signaling in human and mouse Notch1 reporter cells, respectively. Humanized 438 VH1.1/VL1.8 showed equivalent neutralizing activity to that of rat 438, in both human and mouse Notch1 dependent signaling reporter assays. Therefore, humanized 438 VH1.1/VL1.8 fully retained the neutralizing activity of rat 438.

The IC50 (nM) values of rat 438-mIgG1 and humanized 438 variants were calculated from the inhibition of Notch1 dependent signaling from the Notch1 reporter gene co-culture assays, as provided in Table 16 below. Humanized 438 VH1.1/VL1.8 showed the most significant level of inhibition against both human and mouse Notch1 signaling, as represented by the lowest IC50 values among all humanization 438 variants.

TABLE 16

IC50 (nM) values of rat 438-mIgG1 and humanization 438 variants.

| | Antibody | | | | | | | | | | |
|---|---|---|---|---|---|---|---|---|---|---|---|
| | A2 | r438-mIgG | VH1.0/VL1.1 | VH1.1/VL1.0 | VH1.1/VL1.1 | VH1.1/VL1.3 | VH1.1/VL1.9 | VH1.0/VL1.8 | VH1.1/VL1.8 | VH1.1/VL1.5 | r438-hIgG |
| Human Notch 1 | 0.31 | 0.68 | 1.19 | 0.46 | 0.657 | 0.45 | 0.38 | 1.87 | 0.17 | 0.35 | 0.65 |
| Mouse Notch 1 | 0.32 | 0.71 | nd | nd | nd | 0.62 | nd | 1.37 | 0.46 | 0.50 | nd |

(n.d = not determined)

The inhibitory effects of rat 351 and A2 anti-Notch1 antibodies on the co-culture reporter assay were examined by adding increasing concentrations of antibody over a range from about 0.01 nM to 200 nM. To calculate the percent (%) inhibition of anti-Notch1 antibody treated co-cultures, the RLU from increasing concentrations of antibody treatments were divided by an untreated control using the formula (1−(treated/untreated)*100).

Figure 10:
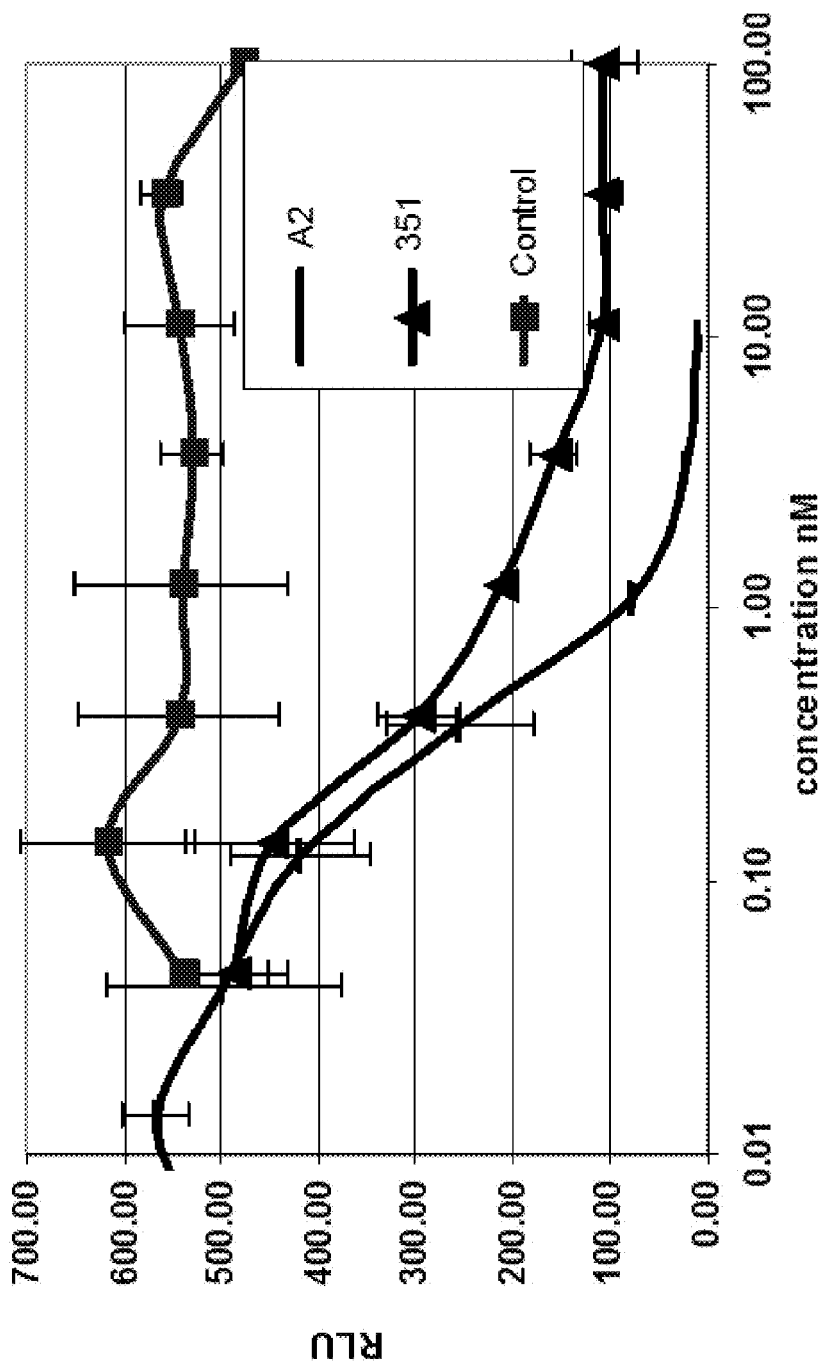
FIG. 10 shows the neutralizing activity of rat 351 and A2 antibodies against human Notch1 signaling.
Figure 11:
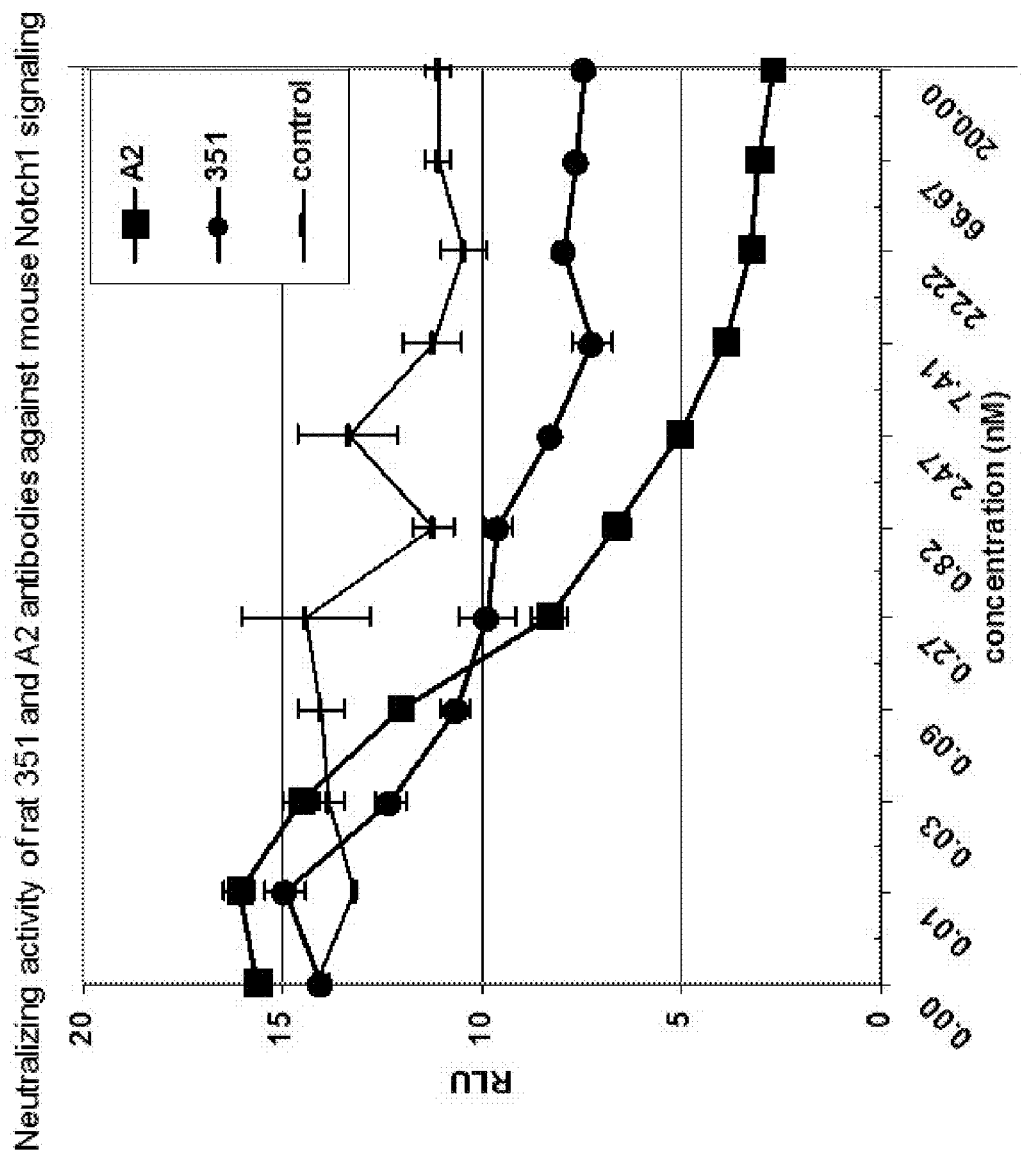
FIG. 11 shows the neutralizing activity of rat 351 and A2 antibodies against mouse Notch1 signaling.

A titration of rat 351 and A2 antibodies in human and murine Notch1 reporter co-culture assays demonstrated rat 351's unique neutralizing activity against Notch1 signaling. As shown in FIGS. 10, 11 and Table 17, both rat 351 and A2 inhibited Notch1 signaling in a dose-dependent manner and had similar IC50 values calculated from the Notch1 reporter co-culture assays. FIG. 10 and Table 17 show that A2 achieved a maximal inhibition (plateau inhibition) of Notch1 signaling at about 100% in human Notch1 reporter co-culture assays when antibody concentrations were greater than 20 times the IC50 value. In contrast, rat 351 achieved a maximal inhibition of only about 85%, which was lower than the maximal inhibition observed for A2. Rat 351 failed to achieve 100% maximal inhibition even when antibody concentrations were 250 times the IC50 value. FIG. 11 and Table 17 show that similar results were observed for the mouse Notch1 reporter co-culture assays. A2 achieved a maximal inhibition of Notch1 signaling at about 86% in mouse Notch1 reporter co-culture assays. In contrast, rat 351 achieved a maximal inhibition of only about 55%, which is lower than the 86% maximal inhibition observed for A2.

TABLE 17

Neutralizing activity of rat 351 and A2 antibodies against human and murine Notch1-dependent signaling in a reporter gene assay

| | Neutralization activity (Human RGA) | | Neutralization activity (murine RGA) | |
|---|---|---|---|---|
| Antibody | IC50 (nM) | % Inhibition | IC50 (nM) | % Inhibition |
| Rat 351 | 0.4 | ~85% | 0.3 | 55% |
| A2 | 0.3 | ~100% | 0.2 | 86% |

Figure 12:
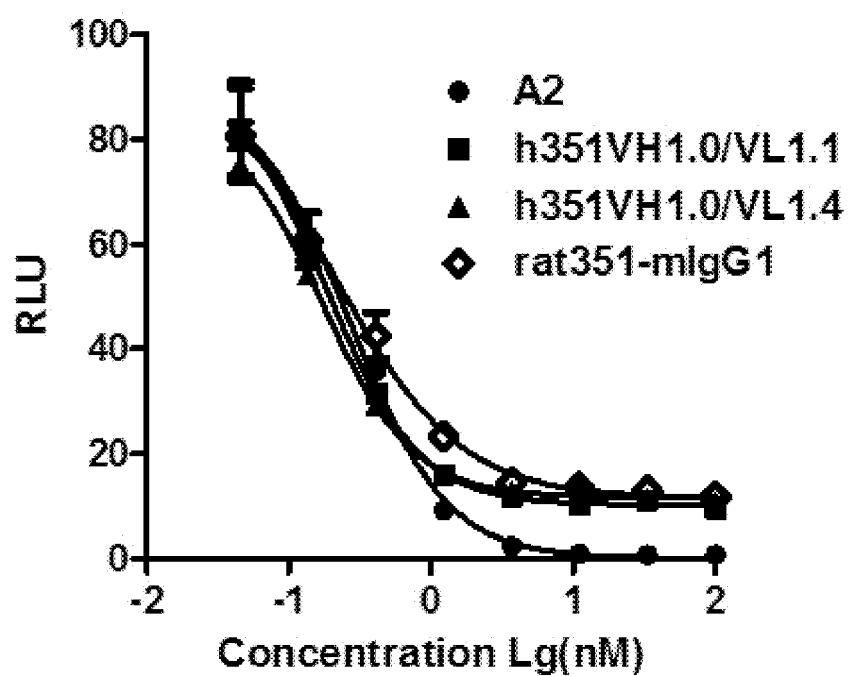
FIG. 12 shows the neutralizing activity of humanized 351 variants, rat 351-mIgG1 and A2 antibodies against Notch1 dependent signaling in human Notch1 reporter cells.
Figure 13:
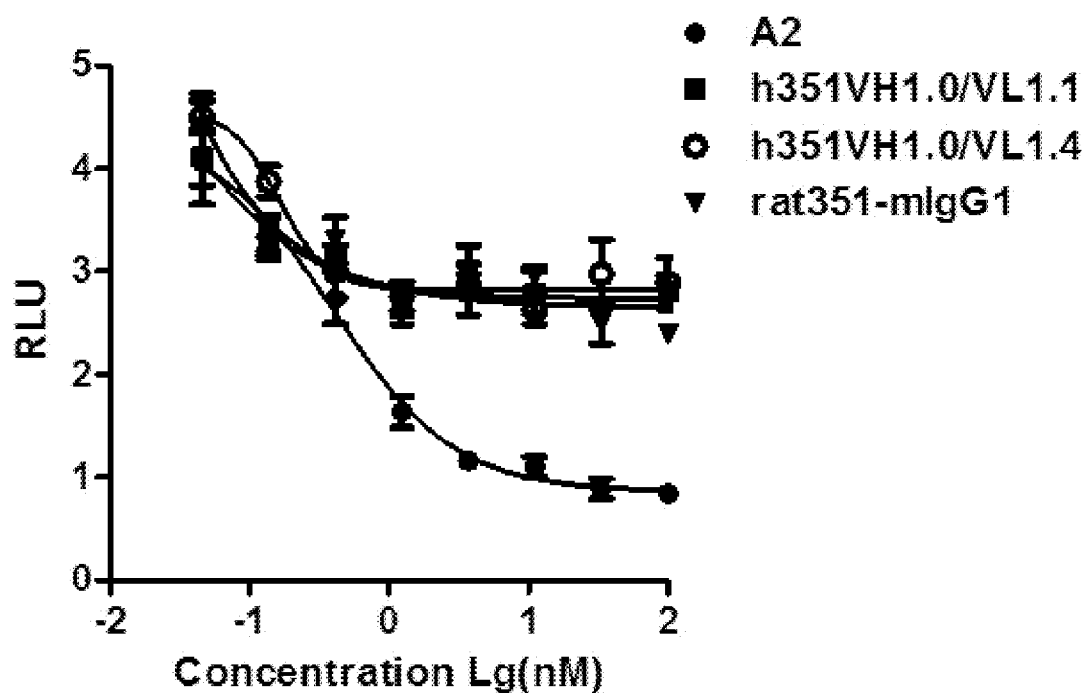
FIG. 13 shows the neutralizing activity of humanized 351 variants, rat 351-mIgG1 and A2 antibodies against Notch1 dependent signaling in mouse Notch1 reporter cells.

FIGS. 12 and 13 show the neutralizing activity of humanized 351 variants and rat 351-mIgG1 in both human and mouse Notch1 dependent signaling reporter assays, respectively. Table 18 provides the IC50 (nM) values of humanized 351 variants, rat 351-mIgG1 and A2 calculated from the inhibition of Notch1 dependent signaling from the Notch1 reporter gene co-culture assays. The data shows that humanized 351 VH1.0/VL1.1 exhibited a neutralizing activity profile that is similar to rat 351-mIgG1 and rat 351. Humanized 351 VH1.0/VL1.1 achieved a maximal inhibition of Notch1 signaling at about ~87.4%, which is lower than the maximal inhibition observed for A2.

TABLE 18

Neutralizing activity of rat 351-mIgG1 and humanized 351 variants against human and murine Notch1-dependent signaling in a reporter gene assay

| Antibody | Neutralization activity (Human RGA) | | Neutralization activity (murine RGA) | |
|---|---|---|---|---|
| | IC50 (nM) | % Inhibition | IC50 (nM) | % Inhibition |
| Rat 351-mIgG1 | 0.22 | ~85.4% | 0.42 | ~51% |
| Humanized 351 VH1.0/VL1.1 | 0.19 | ~87.4% | 0.38 | ~48% |
| Humanized 351 VH1.0/VL1.4 | 0.17 | ~85.4% | 0.49 | ~46% |
| A2 | 0.27 | ~99.1% | 0.36 | ~82% |

Example 6

Structural and Functional Basis for Neutralizing Activity of Clone 351

A $Ca^{2+}$ bound in each of the LNR-A, B, and C domains of the Notch1 NRR is required for maintaining the integrity of the Notch1 NRR structure. Removal of $Ca^{2+}$, for example, by addition of EDTA to the media of Notch1 expressing cells, leads to the destabilization of the Notch1 NRR structure. This results in the exposure of the S2 metalloproteinase cleavage site in the Notch1 NRR and activation of Notch1 signaling (Rand et al., Mol. Cell. Biol. 20(5):1825-35, 2000).

Figure 14A:
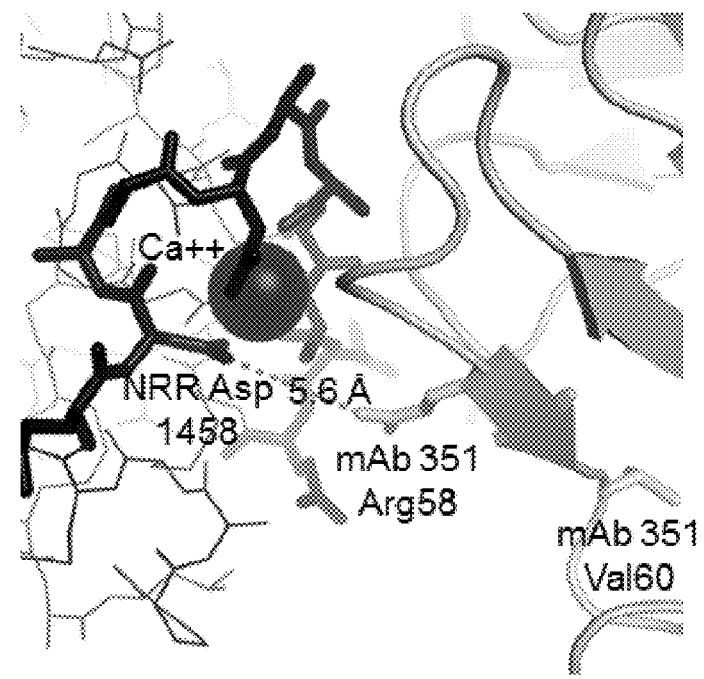
FIGS. 14A and 14B show structural views of the interaction interface between rat 351 and Notch1 NRR in the LNR-A region.
Figure 14B:
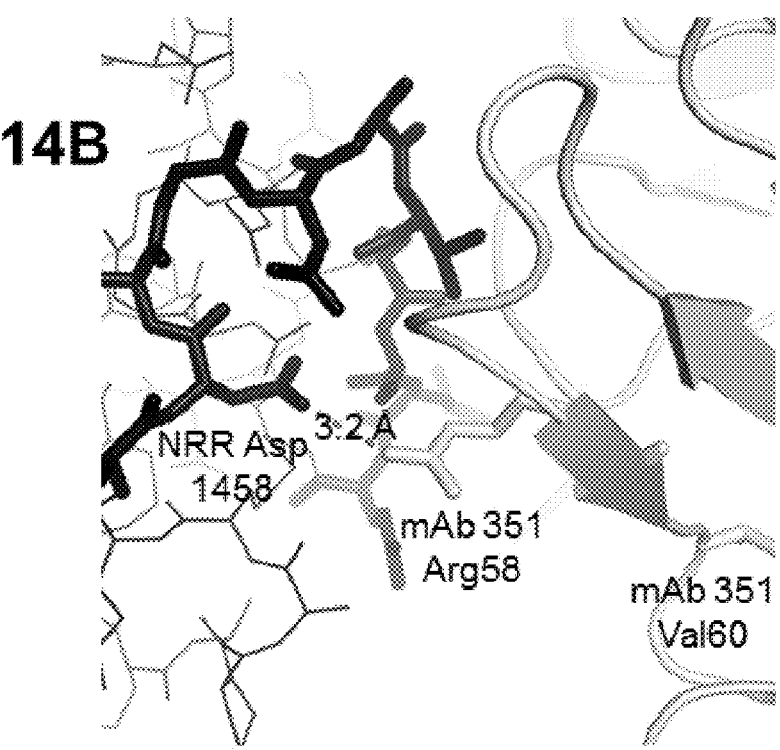

The co-crystal structure of rat 351 Fab with human Notch1 NRR has four independent complexes in a single crystal. However, only one of the four complexes contained the expected $Ca^{2+}$ bound to the LNR-A. FIG. 14A shows the interaction of rat 351 and human Notch1 NRR in the LNR-A region of complex 1. In this structure, a negatively charged residue in Notch1 NRR, Asp1458, had an ionic interaction with the calcium present in the structure. FIG. 14B shows the interaction of rat 351 and human Notch1 NRR in the LNR-A region of Complex 2. Complex 2 is a representative image of Complexes 2-4. In Complexes 2-4, instead of having an ionic interaction with calcium, the Asp1458 of the human Notch1 NRR formed a salt bridge with a positively charged residue in the rat 351 VH CDR2, Arg58. This indicated that the positively charged Arg58 of rat 351 is competing with the positively charged $Ca^{2+}$ for binding to the negatively charged Asp1458 of the human Notch1 NRR.

Figure 15:
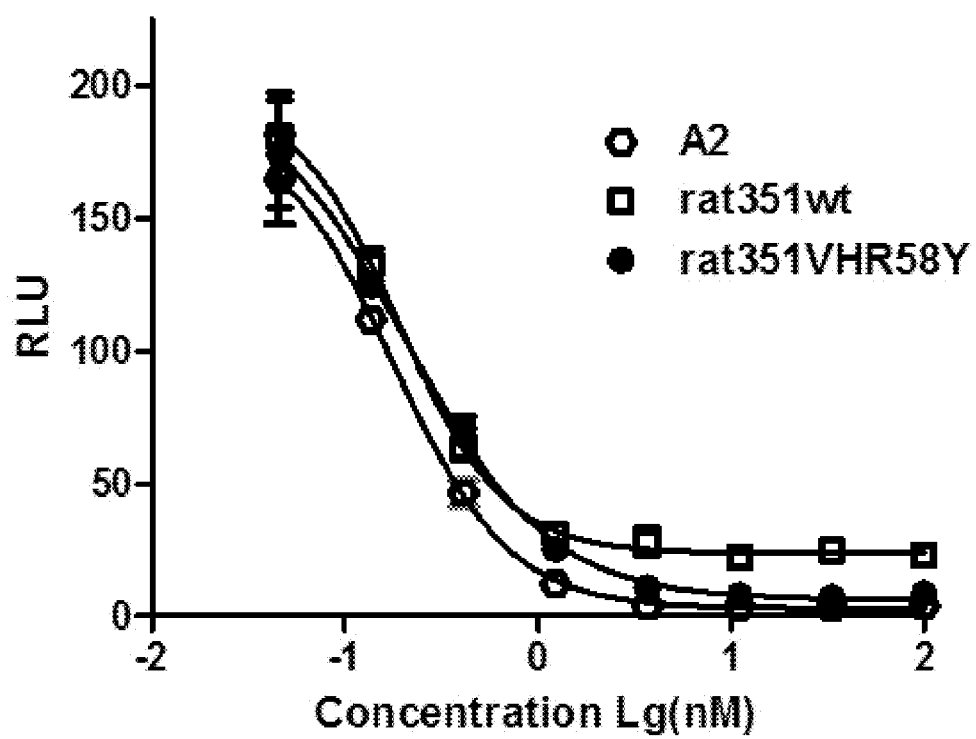
FIG. 15 shows the neutralization activity of rat 351, mutant rat 351 and A2 in co-culture reporter gene assays.

To demonstrate the significance of the positively charged residue Arg58 in the functional properties of rat 351, mutant rat 351-mIgG1 antibodies were generated in which the Arg58 in the VH was mutated to a neutral residue, Tyr (as well as Arg58-Tyr in combination with Val60-Ala or Arg). The mutant rat 351-mIgG1 antibodies were tested in Notch1 signaling inhibition reporter assays and the results are shown in FIG. 15 and Table 19. As shown, rat 351 achieved a maximal inhibition of only about 87%, while mutant rat 351-mIgG1 and A2 achieved a higher maximal inhibition of ~95% and ~98%, respectively.

TABLE 19

IC50 (nM) and maximal inhibition(%) values for rat 351, mutant rat 351 and A2

| | Antibody | | | | |
|---|---|---|---|---|---|
| | A2 | Rat 351 wt | Rat 351 VH R58Y | Rat 351 VH R58Y/V60A | Rat 351 VH R58Y/V60R |
| IC50 (nM) | 0.18 | 0.19 | 0.21 | 0.16 | 0.11 |
| Maximal Inhibition (%) | 97.7% | 87.5% | 95.3% | 95.3% | 95.3% |

Example 7

Effects of Anti-Notch1 Inhibitory Antibodies on Endothelial Cell Sprouting, Angiogenesis and Vascularization A. In vitro Evaluation of Anti-Notch1 Inhibitory Antibodies The effect of anti-Notch1 inhibitory antibodies on angiogenesis was examined in an in vitro model of endothelial cell sprouting using a human umbilical vein endothelial cell (HUVEC) fibrin gel bead assay (FGBA) (also termed the HUVEC-FGBA herein). A modified version of the HUVEC-FGBA was performed essentially as described by Nakatsu, et al. (*Microvasc. Res.* 66 (2):102-112, 2003), except primary human lung tumor-associated fibroblasts (LTAFs) were substituted for Detroit 551 skin fibroblasts. HUVEC sprouts were examined 10-15 days after addition of fibroblasts.

Human lung tumor tissue (sample 87852A1; Asterand, Detroit, Mich.) was mechanically and enzymatically disaggregated. Cells were sieved through a 40 μm cell strainer to obtain a single cell suspension. Viable cells were isolated following treatment with red blood cell lysis buffer (Roche, Indianapolis, Ind.) and magnetic separation from dead cells (Miltenyi Biotec, Auburn, Calif.). Primary lung tumor-associated fibroblasts were established and maintained in RPMI medium containing 20% FBS.

Figure 16:
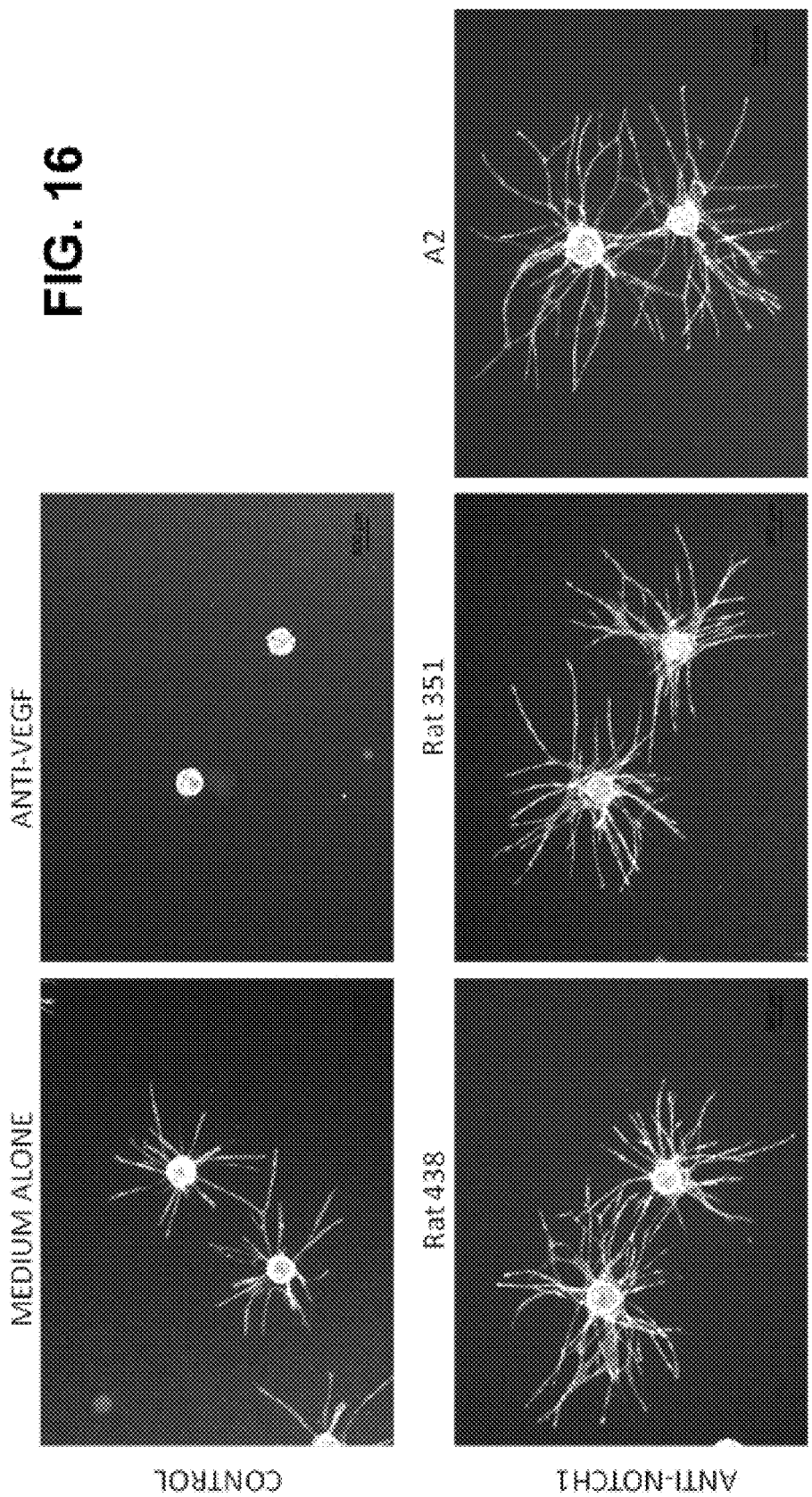
FIG. 16 shows representative epifluorescent images of CD31-Cy3 immunostaining of HUVEC-sprouts at day 10 of treatment with rat 438, rat 351 and A2, and control medium alone and anti-VEGF antibody.

The LTAF-containing HUVEC-FGBAs were treated with rat 438, rat 351 or A2 antibodies. Medium alone (untreated) and anti-VEGF inhibitor AVASTIN (Genentech, So. San Francisco, Calif.) control treatments were also included. FIG. 16 shows representative epifluorescent images of CD31-Cy3 immunostaining at day 10 of rat 438, rat 351 and A2 treated HUVEC-sprouts. An increase was demonstrated in HUVEC sprouting and vessel lengths of rat 438 and rat 351 treatment compared to the medium alone (untreated) control. In contrast, treatment with anti-VEGF inhibitor AVASTIN prevented HUVEC sprouting altogether. Thus, inhibition of Notch1 signaling with rat 438 and rat 351 de-regulated angiogenesis in a manner distinct from anti-VEGF inhibitors, such as AVASTIN.

Furthermore, Table 20 shows that rat 438 and rat 351 increased the average number of sprout branch points per bead compared to control anti-*E. tenella* antibody in a HUVEC-FGBA on day 6 and day 12 of treatment. However, the effect of rat 351 on the average number of branch points per bead was lower on day 6 compared to rat 438 and A2. By day 12, both rat 438 and rat 351, as well as A2, induce a similar number of branch points per bead. During angiogenesis, active Notch1 signaling negatively regulates the number of endothelial tip cells and thus modulates the levels of branching and sprouting (Hellstrom, M. et al., Nature 445 (7129):776-780, 2007).

TABLE 20

Average number of branch points/bead in rat 351, rat 438 and A2 treatment in a HUVEC-FGBA.

|  | Rat 351 | Rat 438 | A2 | ANTI-E. TENELLA |
|---|---|---|---|---|
| Day 6 | | | | |
| Average number of branch points/bead | 2.7 | 6.1 | 5.9 | 1.3 |
| Standard deviation | 1.3 | 1.8 | 2.1 | 1.1 |
| Day 12 | | | | |
| Average number of branch points/bead | 9.3 | 11.2 | 10.6 | 1.2 |
| Standard deviation | 1.8 | 2.6 | 2.3 | 1.1 |

B. In vivo Evaluation of Anti-Notch1 Inhibitory Antibodies

The effect of anti-Notch1 inhibitory antibodies was further examined in an in vivo mouse assay of angiogenesis and vascularization. The neonatal retina is a well-characterized model of angiogenesis and has been used to study the role of the Notch pathway in this process. There is extensive angiogenesis in the mouse retina starting at birth. As in the human retina, the vasculature originates from the optic nerve and spreads to form a network of vessels which then sprout downward to establish a secondary network. Genetic and pharmacological manipulation of Notch signaling has demonstrated that proper Notch signaling is required for angiogenesis in the neonatal retina (Hellstrom, M. et al., Nature 445(7129):776-780, 2007).

Pregnant CD-1 mice were housed individually and monitored regularly for the birth of the litter. For rat 438-mIgG1, pups were dosed 1 and 3 days after birth with either 10 mg/kg of control anti-E. tenella antibody, 10 mg/kg of rat 438-mIgG1 or 10 mg/kg of A2. For rat 351-mIgG1, pups are dosed at 1 and 3 days after birth with either 30 mg/kg of control anti-E. tenella antibody, 30 mg/kg of rat 351-mIgG1 or 30 mg/kg of A2.

Figure 17:
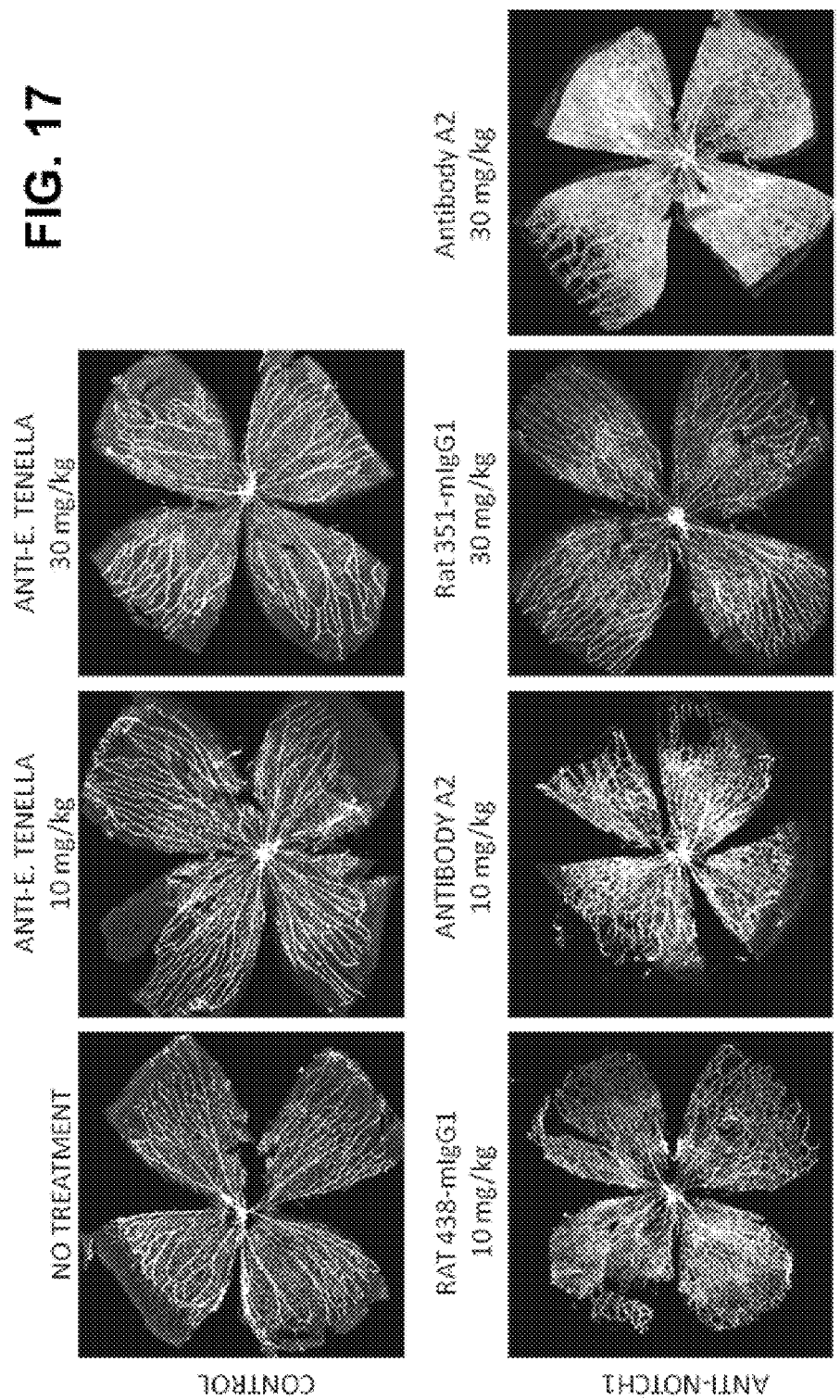
FIG. 17 shows representative confocal images of Isolectin B4-ALEXA488 staining in a mouse retinal model of angiogenesis after treatment with rat 438-mIgG1, rat 351-mIgG1 and A2 antibodies, and controls anti-*E.tenella* antibody and no treatment.

On day 5 after birth, pups were euthanized and the eyes were harvested and fixed overnight in 2% formaldehyde. The following day, the eyes were transferred to PBS and the retinas were isolated. To stain the retinas, Isolectin B4 (Sigma, St. Louis, MO) was conjugated to ALEXA FLUOR 488 with a labeling kit (Invitrogen, Carlsbad, CA) and used at 15 mg/ml in PBS with 10% goat serum, 1% Triton X-100, 0.1% sodium azide, and 0.1 mM each of $CaCl_2$, $MgCl_2$ and $MnCl_2$. Retinas were washed 5 times in PBS with 1% TRITON X-100, 0.1% sodium azide, and 0.1 mM each of $CaCl_2$, $MgCl_2$ and $MnCl_2$ and a final time in PBS with 0.1% sodium azide, and 0.1 mM each of $CaCl_2$, $MgCl_2$ and $MnCl_2$. Retinas were cut and mounted with FLUORMOUNT-G (EMS, Hatfield, PA) and imaged on a Zeiss LSM510 confocal microscope (Carl Zeiss MicroImaging, LLC, Thornwood, NY). FIG. 17 shows representative confocal images of Isolectin B4-ALEXA488 staining in a mouse retinal model of angiogenesis after treatment with rat 438-mIG1, rat 351-mIgG1 and A2. Anti-E.tenella antibody and no treatment controls were also included.

As shown in FIG. 17, the retina from a mouse pup in the rat 438-mIgG1 treatment group had different vasculature compared to the retinas from mouse pups in the anti-E. Tenella antibody and no treatment control groups. This indicates that rat 438-mIgG1 antibody disrupted angiogenesis in vivo. In particular, the retinas from rat 438-mIgG1 treatment group showed more extensive vasculature, similar to that previously reported after genetic and pharmacological manipulation of Notch signaling (Hellstrom, M. et al., Nature 445 (7129):776-780, 2007). This indicates that inhibition of Notch1 signaling with rat 438-mIgG1 directly impacted angiogenesis in the mouse neonatal retina.

Further shown in FIG. 17, the retina from a mouse pup in the rat 351-mIGg1 treatment group had similar vasculature compared to the retinas from mouse pups in the anti-E. Tenella antibody and no treatment control groups. In contrast, the retina from the A2 group showed more extensive vasculature, similar to that previously reported after genetic and pharmacological manipulation of Notch signaling (Hellstrom, M. et al., Nature 445 (7129):776-780, 2007). This demonstrates that, in contrast to A2, rat 351-mIgG1 antibody did not significantly disrupt murine angiogenesis in vivo or that the potential effect of rat 351-mIgG1 on the murine vasculature was not observed at the chosen time point or with the tested dosing regimen.

Example 8

Effects of Anti-Notch1 Inhibitory Antibodies on Cell Lines Having Native and Mutant Notch1 Receptors A. Effects of Anti-Notch1 Inhibitory Antibodies on Notch1 Activation in Human Fibroblast Cell Line CCD1076SK Having Native Notch1 Receptors Notch1 signaling is activated by ligand binding which induces conformational changes within the extracellular Notch1 NRR domains thereby exposing metalloprotease and gamma-Secretase cleavage sites. Proteolysis results in the release of the Notch1 intracellular domain (Notch1$^{ICD}$), a transcriptional activator, from the cell membrane. Notch1 activation and Notch1$^{ICD}$ release were examined by Western blot analysis of protein extracts generated from the human fibroblast cell line CCD1076SK that was plated on recombinant human DLL4 ligand treated with increasing concentrations of rat 438, rat 351 or A2 antibodies, and control anti-E. tenella antibody for 24 hours. Released Notch1$^{ICD}$ molecules initiating at a Valine residue were detected with the D3B8 antibody (anti-Notch1$^{ICD}$) (Cell Signaling Technology, Danvers, Mass.).

To activate Notch1 signaling, the CCD1076SK skin fibroblasts were cultured in the presence of DLL4 ligand. Six-well plates were coated with 2 μg/ml of recombinant human DLL4 (R&D Systems, Minneapolis, MN) in 1X DPBS containing $CaCl_2$ and $MgCl_2$. The 2×10E6 CCD1076SK skin fibroblasts in DMEM medium containing 10%FBS were added to the recombinant human DLL4-coated wells in the presence of 0, 0.001, 0.01, 0.1, 1 and 10 μg/ml of rat 438, rat 351 and A2 antibodies, and control anti-E.tenella antibody. Cells were incubated with the antibodies for 24 hours at 37° C. in 5% $CO_2$. Cells were lysed in 1% NP40, 0.5% sodium deoxycholate, 5 mM EDTA, 0.25 M NaCl, 0.025 M Tris-HCl, pH 7.5, containing COMPLETE MINI Protease inhibitor cocktail (Roche) and 0.4 mM PMSF. Extracts were resolved by SDS-PAGE on a 7.5% polyacrylamide gel and transferred to nitrocellulose paper using an IBLOT Gel transfer system (Invitrogen). The released Notch1$^{ICD}$ molecules initiating at a Valine a residue were detected with anti-Notch1$^{ICD}$ and, as a loading control, anti-beta-actin using standard western blot procedures. Densitometric analysis was performed on films that were scanned with a BioRad GS-800 Calibrated Densitometer and analyzed with Quantity One version 4.6.9 software (BioRad). Notch1$^{ICD}$ levels were normalized to beta-actin control in each sample and then compared to the untreated control.

Figure 18:
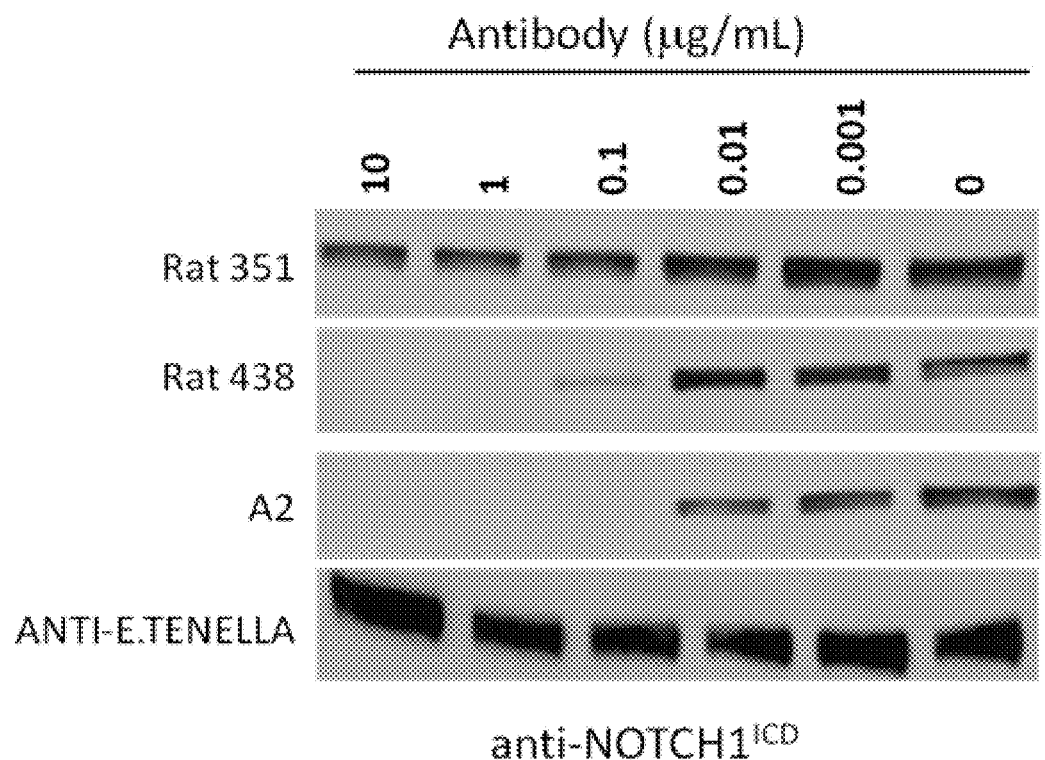
FIG. 18 shows a Western blot analysis of protein extracts generated from CCD1076SK human fibroblasts plated on recombinant human DLL4 ligand and treated with increasing concentrations of rat 351, rat 438 and A2, and control anti-*E. tenella* antibody.

As shown in FIG. 18, titration of rat 438 potently inhibited Notch1 activation in a dose-dependent manner, as indicated by the levels of released Notch1$^{ICD}$ detected. Further shown in FIG. 18 and in Table 21, titration of rat 351 up to 10 μg/mL demonstrated lower inhibition of Notch1 activation of a native Notch1 receptor compared to A2, as indicated by the levels of released Notch1$^{ICD}$ detected. At all concentrations, and in particular beginning at 0.1 μg/mL, rat 351 demonstrated higher levels of released Notch1$^{ICD}$ compared to A2.

TABLE 21

Densitometric analysis of Notch1$^{ICD}$ levels from Western blot of FIG. 18

| Ab, μg/ml | Normalized Notch1$^{ICD}$ levels | |
|---|---|---|
| | Rat 351 | A2 |
| 0 | 1.000 | 1.000 |
| 0.001 | 0.826 | 0.748 |
| 0.01 | 0.848 | 0.402 |
| 0.1 | 0.554 | 0.003 |
| 1 | 0.393 | 0.003 |
| 10 | 0.302 | 0.006 |

B. Effects of Anti-Notch1 Inhibitory Antibodies on Notch1 Activation in T-Cell Acute Lymphoblastic Leukemia (T-ALL) Cells Line Having Mutant Notch1 Receptors Constitutive Notch1 activation and release of the Notch1 intracellular domain (Notch1$^{ICD}$) is reported in a subset of T-cell acute lymphoblastic leukemia (T-ALL) patients and T-ALL cell lines that harbor mutations within the NRR domain of the Notch1 receptor (Weng et al., Science 306:269-271, 2004). These mutations are categorized into 3 major classes. Class 1 mutations are single amino acid substitutions and small in-frame deletions or insertion in HD1. Class 2 mutations are longer insertions in the distal region of HD2 that relocate the S2-metalloprotease cleavage site beyond the auto-inhibitory NRR domain. Class 3 mutations, also called Juxtamembrane Expansion Mutations (JMEs), displace the NRR away from the cell membrane.

T-ALL cell lines with Notch1 receptor class 1 mutations tested include HPB-ALL cells with a leucine to proline mutation at amino acid 1575 (L1575P), ALL-SIL cells with a leucine to proline mutation at amino acid 1594 (L1594P), MOLT-4 cells with a leucine to proline mutation at amino acid 1601 (L1601P) and DND-41 cells with compound class 1 mutations of leucine to proline at amino acid position 1594 and aspartic acid to valine at amino acid position 1610 (L1594P/D1610V). The CCRF-CEM cell line harbors a class 2 mutation and possesses a 12 amino acid insertion at position 1595. The Jurkat cell line harbors a class 3 JEM mutation that inserts 17 amino acids at position 1740.

Notch1 activation and Notch1$^{ICD}$ release was examined by Western blot analysis of protein extracts generated from the T-ALL cell lines treated with increasing concentrations of rat 438-mIgG1, humanized 438 VH1.1/VL1.8, rat 351-mIgG1 or A2 antibodies, and control anti-E.tenella antibody. Released Notch1$^{ICD}$ molecules initiating at a Valine residue are specifically detected with D3B8 antibody (anti-Notch1$^{ICD}$).

The T-ALL cell lines HPB-ALL, ALL-SIL, CCRF-CEM, MOLT-4, DND-41 and Jurkat cells were used instead of CCD1076SK fibroblasts as described above. Since T-ALL cells possess constitutively released Notch1$^{ICD}$, no exogenous DLL4 ligand was required. Suspension cultures of 2×10E6 T-ALL cells were mixed with 0, 0.001, 0.01, 0.1, 1 and 10 μg/ml of rat 438-mIgG1, humanized 438 VH1.1/VH1.8, rat 351-mIgG1 or A2 antibodies, and control anti-E.tenella antibody in RPMI 1640 medium containing 10% FBS, Pen/Strep/Glutamine. Cells were incubated with the antibodies for 24 hours at 37° C. in 5% $CO_2$. Cells were harvested by centrifugation and medium was removed by aspiration. Cell pellets were lysed in 1% NP40, 0.5% sodium deoxycholate, 5 mM EDTA, 0.25 M NaC1, 0.025 M Tris-HC1, pH 7.5, containing COMPLETE MINI Protease inhibitor cocktail (Roche). Extracts were resolved by SDS-PAGE on a 7.5% polyacrylamide gel and transferred to nitrocellulose paper using an IBLOT Gel transfer system (Invitrogen). The released Notch1$^{ICD}$ molecules initiating at a Valine residue are detected with anti-Notch1$^{ICD}$ and, as a loading control, anti-beta-actin using standard western blot procedures. Densitometric analysis was performed on films that were scanned with a BioRad GS-800 Calibrated Densitometer and analyzed with Quantity One version 4.6.9 software (BioRad). Notch1$^{ICD}$ levels were normalized to beta-actin in each sample and then compared to the untreated control.

Figure 19:
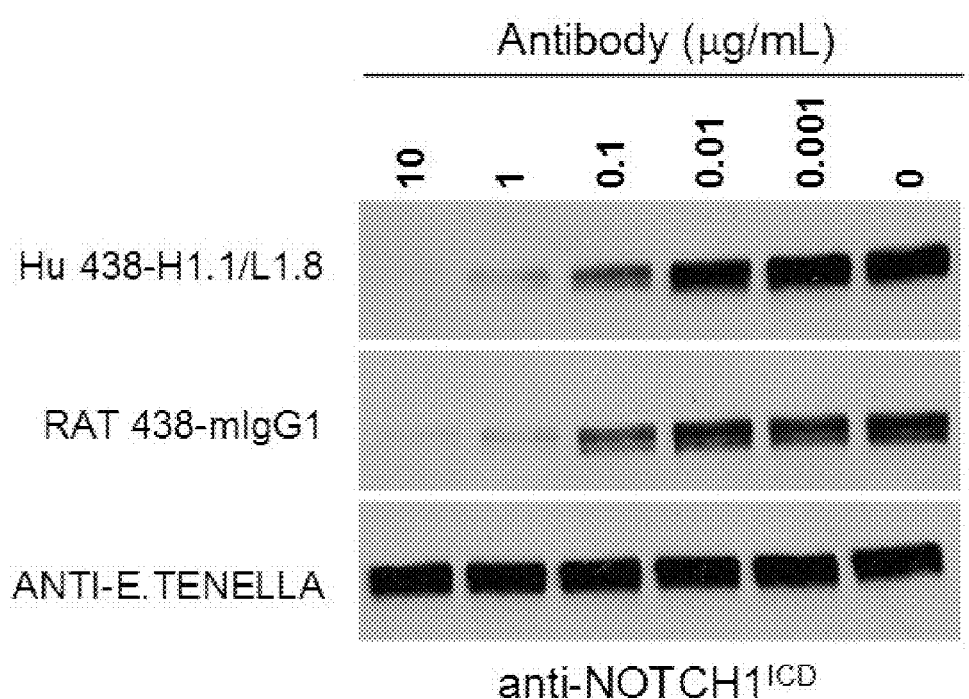
FIG. 19 shows a Western blot analysis of protein extracts generated from HBP-ALL cells treated with increasing concentrations of humanized 438 VH1.1/VL1.8, rat 438-mIgG1, and control anti-*E. tenella* antibody.

As shown in FIG. 19, treatment of HBP-ALL cells with increasing concentrations of rat 438-mIgG1 and humanized 438 VH1.1/VL1.8 significantly inhibited constitutive Notch1 activation, as indicated by the levels of released Notch1$^{ICD}$ detected. Thus, mutation of leucine to proline at position 1575 did not affect the ability of rat 438-mIgG1 and humanized 438 VH1.1/VL1.8 antibodies to inhibit Notch1 activation. This is consistent with Table 14 demonstrating that the rat 438 antibody did not interact with the amino acid at position 1575 in the wild-type NRR-antibody co-crystal structure.

Figure 20:
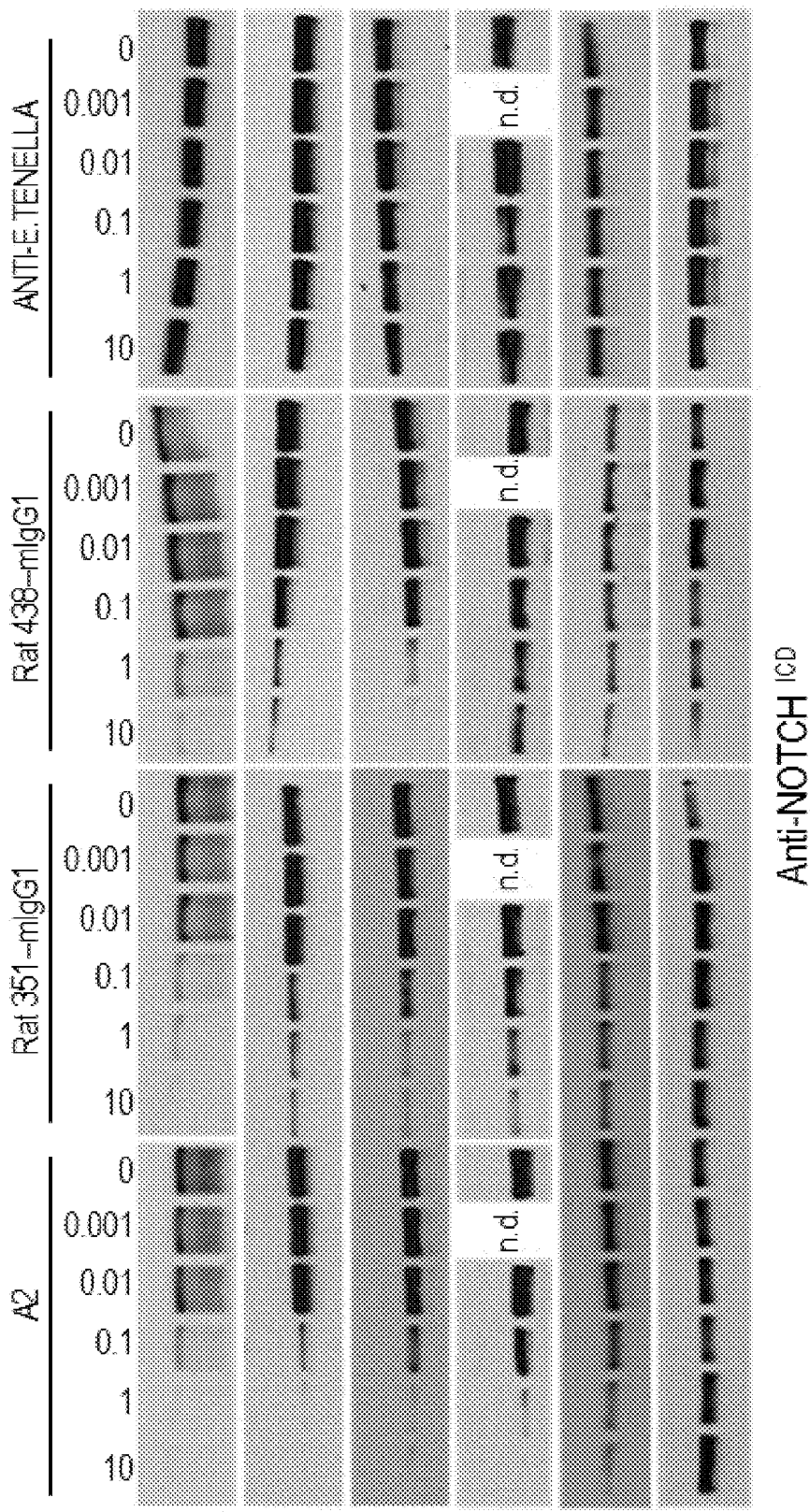
FIG. 20 shows a Western blot analysis of protein extracts generated from T-ALL cell lines treated with increasing concentrations of rat 351-mIgG1, rat 438-mIgG1 and A2, and control anti-*E. tenella* antibody.

As shown in FIG. 20 and Table 22, treatment of T-ALL cell lines HPB-ALL, ALL-SIL, CCRF-CEM, MOLT-4 and DND-41 cells with increasing concentrations of rat 438-mIgG1, rat 351-mIgG1 and A2 inhibited Notch1 activation in a dose dependent manner, as indicated by the decreased detection of released Notch1$^{ICD}$ by western blot and densitometric analysis. In contrast, treatment of Jurkat cells with increasing concentrations of rat 351-mIgG1 and A2 failed to inhibit Notch1 activation, as indicated by the detection of released Notch1$^{ICD}$ by western blot analysis. As expected, the control anti-E. tenella antibody demonstrated no effect on the levels of released Notch1$^{ICD}$ in any of the T-ALL cell lines.

Rat 438-mIgG1, rat 351-mIgG1 and A2 antibodies similarly inhibited Notch1 activation and release of the Notch1$^{ICD}$ in certain T-ALL cell lines with class 1 (HPB-ALL cells with L1575P, ALL-SIL cells with L1594P, MOLT-4 cells with L1601P, and DND-41 cells with compound class 1 mutations L1594P/D1610V) and class 2 (CCRF-CEM cell line with an 12 amino acid insertion at position 1595) NRR mutations, and rat 35'-mIgG1 and A2 failed to inhibit cleavage of the Notch1 receptor and release of the Notch1$^{ICD}$ in Jurkat cells with a class 3 JEM mutation. Furthermore, rat 351-mIgG1 demonstrated higher inhibition of Notch1 activation of a mutant Notch1 receptor, as shown in FIG. 20 and Table 22, compared to the inhibition of Notch1 activation of a native Notch1 receptor by rat 351, as shown in FIG. 18 and Table 21.

TABLE 22

Densitometric analysis of Notch1$^{ICD}$ levels from the Western blot of FIG. 20

Normalized Notch1$^{ICD}$ levels

| Ab, µg/ml | HPB-ALL A2 | HPB-ALL Rat 351-mIgG1 | ALL-SIL A2 | ALL-SIL Rat 351-mIgG1 | CCRF-CEM A2 | CCRF-CEM Rat 351-mIgG1 | MOLT-4 A2 | MOLT-4 Rat 351-mIgG1 | DND-41 A2 | DND-41 Rat 351-mIgG1 | Jurkat A2 | Jurkat Rat 351-mIgG1 |
|---|---|---|---|---|---|---|---|---|---|---|---|---|
| 0 | 1.000 | 1.000 | 1.000 | 1.000 | 1.000 | 1.000 | 1.000 | 1.000 | 1.000 | 1.000 | 1.000 | 1.000 |
| 0.001 | 0.852 | 0.833 | 1.565 | 0.982 | 1.119 | 0.982 | n.d. | n.d. | 0787 | 1.020 | 1.197 | 1.535 |
| 0.01 | 1.145 | 0.886 | 1.310 | 0.712 | 1.276 | 1.038 | 0.962 | 1.525 | 0.840 | 0.988 | 1.165 | 1.435 |
| 0.1 | 0.330 | 0.156 | 0.068 | 0.080 | 0.424 | 0.413 | 0.644 | 0.751 | 0.479 | 0.367 | 0.983 | 1.406 |
| 1 | 0.038 | 0.075 | 0.033 | 0.030 | 0.048 | 0.043 | 0.075 | 0.284 | 0.199 | 0.322 | 1.152 | 1.078 |
| 10 | 0.041 | 0.020 | 0.043 | 0.019 | 0.027 | 0.034 | 0.043 | 0.082 | 0.114 | 0.219 | 1.586 | 1.204 |

(n.d = not determined)

C. Effects of Anti-Notch1 Inhibitory Antibodies on Viability of T-Cell Acute Lymphoblastic Leukemia (T-ALL) Cells Line Having Mutant Notch1 Receptors The effects of anti-Notch1 antibodies on HBP-ALL cells were further assessed using an MTS cellular viability indicator (Promega, Madison, Wis.) to determine the percent viable cells after treatment. The MTS reagent was converted into a product that can be measured at an optical density of 490 nanometers (O.D. 490 nm) by metabolically active living, but not dead cells. HBP-ALL cells (1×10E4 cells/well) in RPMI 1640 medium containing 10% FBS, Pen/Strep/Glutamine were incubated with 0, 0.47, 1.88, 7.5 and 30 µg/ml of humanized 438 VH1.1/VL1.8, rat 438-mIgG1, rat 351-mIgG1 and A2 antibodies, and control anti-E. tenella antibody for 7 days and then assayed with MTS reagent according to manufacturer's instructions.

Table 23 shows the MTS viability assay of anti-Notch1 inhibitory antibody treatments of HPB-ALL cells with increasing concentration of rat 438-mIgG1, rat 351-mIgG1 and A2 antibodies, and control anti-E. tenella antibody. As a result, HBP-ALL cells treated with increasing concentrations of rat 438-mIgG1, 351-mIgG1 and A2 up to 30 µg/ml displayed lower levels of the converted MTS reagent at O.D. 490 nm than control anti-E. tenella treatments. This indicates fewer cells were present in the rat 438-mIgG1, rat 351-mIgG1 and A2 treated cells, a result of increased cell death and/or decreased proliferation.

TABLE 23

MTS viability assay of HPB-ALL leukemia cells treated with rat 438-mIgG1, rat 351-mIgG1, and A2, and control anti-E. tenella antibodies

| | Antibody concentration | | | | |
|---|---|---|---|---|---|
| | 0 µg/mL | 0.47 µg/mL | 1.88 µg/mL | 7.5 µg/mL | 30 µg/mL |
| | O.D. 490 nm | | | | |
| Rat 438-mIgG1 | 0.361 | 0.394 | 0.284 | 0.180 | 0.110 |
| Rat 351-mIgG1 | 0.366 | 0.267 | 0.175 | 0.119 | 0.082 |
| A2 | 0.355 | 0.271 | 0.167 | 0.107 | 0.076 |
| ANTI-E. TENELLA | 0.366 | 0.425 | 0.440 | 0.427 | 0.445 |
| | Standard Deviations | | | | |
| Rat 438-mIgG1 | 0.003 | 0.004 | 0.007 | 0.019 | 0.010 |
| Rat 351-mIgG1 | 0.009 | 0.015 | 0.015 | 0.011 | 0.006 |
| A2 | 0.002 | 0.018 | 0.004 | 0.008 | 0.013 |
| ANTI-E. TENELLA | 0.012 | 0.004 | 0.056 | 0.024 | 0.010 |

Similar results were observed for humanized 438 VH1.1/VL1.8 as shown in Table 24, which illustrates a MTS assay of anti-Notch1 inhibitory antibody treatments of HPB-ALL cells with increasing concentration of humanized 438 VH1.1/VL1.8, rat 438-mIgG1 and control anti-E. tenella. Thus, in addition to inhibiting Notch1 activation, humanized 438 VH1.1/VL1.8 antibodies also inhibited growth of cancer cells with a mutation in the NRR domain of Notch1, a common feature in T-ALL patients.

TABLE 24

MTS viability assay of HPB-ALL leukemia cells treated with humanized 438VH1.1/VH1.8, rat 438-mIgG1 and control anti-E. tenella antibodies

| | Antibody concentration | | | | |
|---|---|---|---|---|---|
| | 0 µg/mL | 0.47 µg/mL | 1.88 µg/mL | 7.5 µg/mL | 30 µg/mL |
| | O.D. 490 nm | | | | |
| Humanized 438 VH1.1/VL1.8 | 0.464 | 0.427 | 0.306 | 0.204 | 0.162 |
| Rat 438-mIgG1 | 0.456 | 0.478 | 0.373 | 0.259 | 0.190 |
| ANTI-E. TENELLA | 0.457 | 0.488 | 0.428 | 0.524 | 0.525 |
| | Standard Deviations | | | | |
| Humanized 438 VH1.1/VL1.8 | 0.016 | 0.014 | 0.011 | 0.009 | 0.003 |
| Rat 438-mIgG1 | 0.012 | 0.038 | 0.051 | 0.034 | 0.004 |
| ANTI-E. TENELLA | 0.008 | 0.003 | 0.099 | 0.029 | 0.013 |

To demonstrate the in vitro activity of mutant rat 351 antibodies, HPB-ALL cells were treated with increasing concentration of either rat 351-mIgG1, rat 351(R58Y)-mIgG1, rat 351(R58Y/V60A)-mIgG1, 438 humanized VH1.1/VL1.8, A2 antibodies or control anti-E. tenella antibody. Table 25 shows a MTS assay of anti-Notch1 inhibitory antibody treatments and their resulting IC50 values. Both rat 351(R58Y)-mIgG1 and rat 351(R58Y/V60A)-mIgG1 antibodies inhibited HPB-ALL growth, but in a manner more similar to humanized 438 VH1.1/VL1.8 than the wild-type rat 351-mIgG1 antibody as determined by their IC50 values. Thus, the Arg58 residue in rat 351-mIgG1 contributed to its potent inhibitory activity against a Notch1 receptor with a mutant NRR.

TABLE 25

MTS viability assay of HPB-ALL leukemia cells treated with mutant rat 351-mIgG1 antibodies and IC50 (nM) values.

| | Antibody concentration | | | | | | |
|---|---|---|---|---|---|---|---|
| | 0 µg/mL | 0.0391 µg/mL | 0.1563 µg/mL | 0.625 µg/mL | 2.5 µg/mL | 10 µg/mL | IC50, nM |
| | O.D. 490 nm | | | | | | |
| Rat 351-mIgG1 | 0.755 | 0.726 | 0.514 | 0.311 | 0.235 | 0.192 | 1.27 |
| Rat 351-R58Y-mIgG1 | 0.697 | 0.715 | 0.582 | 0.345 | 0.236 | 0.184 | 2.17 |
| Rat 351 R58Y/V60A-mIgG1 | 0.697 | 0.775 | 0.667 | 0.363 | 0.265 | 0.184 | 2.49 |
| 438 Humanized VH1.1/VL1.8 | 0.694 | 0.702 | 0.601 | 0.339 | 0.223 | 0.198 | 2.26 |
| A2 | 0.755 | 0.706 | 0.568 | 0.325 | 0.204 | 0.178 | 1.85 |
| ANTI-*E. TENELLA* | 0.694 | 0.735 | 0.758 | 0.759 | 0.772 | 0.774 | n.a. |
| | Standard Deviations | | | | | | |
| Rat 351-mIgG1 | 0.017 | 0.032 | 0.018 | 0.014 | 0.015 | 0.005 | |
| Rat 351-R58Y | 0.020 | 0.008 | 0.024 | 0.012 | 0.019 | 0.006 | |
| Rat 351-R58Y/V60A | 0.020 | 0.024 | 0.025 | 0.017 | 0.014 | 0.007 | |
| 438 Humanized VH1.1/VL1.8 | 0.022 | 0.006 | 0.023 | 0.016 | 0.014 | 0.008 | |
| A2 | 0.017 | 0.012 | 0.029 | 0.010 | 0.009 | 0.017 | |
| ANTI-*E. TENELLA* | 0.022 | 0.023 | 0.024 | 0.009 | 0.034 | 0.054 | |

Example 9

Effects of Anti-Notch1 Inhibitory Antibodies on In vivo Growth of Human Tumor Xenografts A. Notch1 and Jagged1 Co-immunohistochemistry The effects of anti-Notch1 inhibitory antibodies were tested in pre-clinical models with Notch1 expression in both xenografted tumor and host stromal cells in order to maximize their potential efficacy. To identify a pre-clinical model that expresses Notch1 and one of its ligand, Jagged1, immunohistochemistry using anti-Notch1 and anti-Jagged1 antibodies was performed on the 37622A1 non-small cell lung cancer (NSCLC) patient-derived xenograft (PDX), termed hereinafter "37622A1 NSCLC PDX." A tissue fragment from the 37622A1 NSCLC PDX was formalin-fixed and paraffin embedded (FFPE) using standard histological procedures. Five micron FFPE sections were cut, dewaxed and hydrated to distilled water. Antigens were retrieved in pH 6.0 citrate buffer in a pressure cooker. Endogenous peroxidase was blocked with 0.3% H2O2 for 15 minutes. Sections were incubated with DAKO Protein block for 20 minutes. Endogenous biotin was blocked by an avidin/biotin block kit (Vector). A 1:50 dilution of rabbit anti-Notch1 (ab52627; Abcam) was applied to the sections for 1 hour at room temperature. Anti-rabbit IgG-biotin (JacksonImmuno) was applied to the sections for 30 minutes at room temperature. Streptavidin-HRP was added to the sections for 30 minutes at room temperature. DAB was used to develop color for 5 minutes. Sections were heated at 98° C. for 10 minutes in pH 6.0 citrate buffer to destroy bound anti-Notch1 primary and anti-rabbit IgG secondary antibodies from the first reaction. Sections were blocked in DAKO Protein block for 20 minutes and incubated with a 1:100 dilution of rabbit anti-Jagged 1 antibody (Santa Cruz) for 2 hours at room temperature. An anti-rabbit IgG-HRP polymer (DAKO) was applied for 30 minutes at room temperature. IMMPACT VIP substrate was used to develop color for 7 minutes. Sections were briefly counterstained in Mayer's hematoxylin, dehydrated, cleared and coverslipped.

Figure 21:
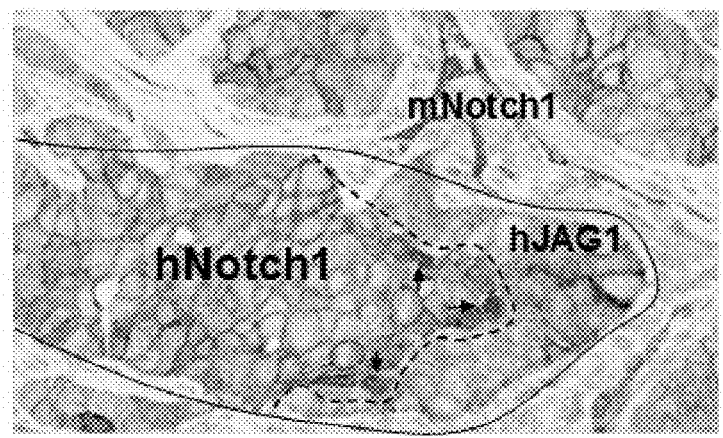
FIG. 21 shows immunohistochemical detection of Notch1 receptors and Jagged1 ligand in the 37622A1 NSCLC patient derived xenograft.

As shown in FIG. 21, the 37622A1 NSCLC PDX had heterogeneous expression of the human Notch1 receptor (left of dashed line) and human Jagged1 ligand (right of dashed line) within clusters of tumor cells (demarcated with a solid line). Nuclear Notch1$^{ICD}$ (arrows) was also detected at the interface of human Notch1 and human Jagged1 tumor cells indicating active Notch1 signaling. Within the mouse stroma, murine Notch1 was also detected in the PDX-associated vasculature, consistent with the previous finding that Notch1 signaling regulates angiogenesis in the murine neonatal retina. The expression pattern of Notch1 and Jagged1 in the 37622A1 NSCLC PDX indicated that it is a relevant model to examine the in vivo effects of anti-Notch1 antibodies.

In NSCLC, K-ras is a frequently mutated oncogene that promotes tumor growth. Thus, the K-ras gene from the 37622A1 NSCLC PDX was sequenced to determine if it contained wild-type or mutant K-ras. Genomic DNA was isolated from a fragment of the 37622A1 NSCLC PDX using the PREPGEM Kit according to manufacturer's instructions (ZyGEM, Solana Beach, CA). K-ras DNA sequences were amplified with KOD polymerase (EMD Chemicals, Gibbstown, NJ) using forward and reverse primers. PCR cycling conditions: 1 cycle at 75° C. for 15 minutes, 1 cycle at 95° C. for 5 minutes, 1 cycle at 96° C. for 1 minute, and 35 cycles at 96° C. for 15 seconds, 60° C. for 15 seconds and 72° C. for 40 seconds, and 1 cycle at 72° C. for 1 minute and 20 seconds. Amplified PCR product of 496 basepairs was purified with QIAQUICK PCR Purification kit (Qiagen, Valencia, CA) and DNA sequencing was performed with the BigDye Terminator v1.1 Cycle sequencing Kit (ABI, Foster City, CA) according to manufacturer's instructions.

Figure 22:
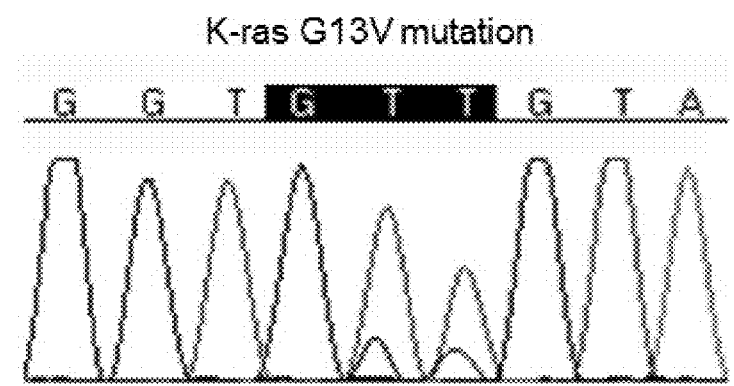
FIG. 22 shows a chromatogram indicating that the 37622A1 NSCLC patient derived xenograft possessed a G13V mutation in the human K-ras gene.

As shown in FIG. 22, DNA sequence analysis indicated that the 37622A1 NSCLC PDX possesses a glycine to valine (encoded by the DNA sequence GTT) mutation at amino acid 13 (G13V) in the human K-ras gene.

B. In vivo Growth Inhibition Studies for NSCLC Xenografts

The effects of anti-Notch1 inhibitory antibodies were examined in immunodeficient mice on the in vivo growth of human tumor xenografts that were established from fragments of freshly resected NSCLC tumors obtained in accordance with appropriate consent procedures (Asterand). The 87393A1 NSCLC patient-derived xenografts and 37622A NSCLC patient-derived xenografts (termed hereinafter "87393A1 NSCLC PDX" and "37622A1 NSCLC PDX", respectively) were passaged in vivo as fragments from animal to animal in NOD-SCID and nude (Nu/Nu) female mice, respectively.

When the tumors reached a volume of 200 to 400 mm³, they were staged to ensure uniformity of the tumor size among various treatment groups prior to the administration of anti-Notch1 and control anti-E. tenella antibodies. The 37622A1 NSCLC PDX model was dosed i.p. once a week for 3 weeks with 10 mg/kg of rat 438-mIgG1 and A2, and control anti-E. tenella antibody. The 87393A1 NSCLC PDX model is dosed i.p. twice a week for 4 weeks with 20 mg/kg of rat 351-mIgG1 and control anti-E. tenella antibody. Tumors were measured at least once a week and their volume was calculated with the formula: tumor volume (mm³)=0.5×(tumor width²)(tumor length). From 8-11 animals, mean tumor volumes (±SEM) for each treatment group were calculated and compared to the control-treated.

Table 26 shows the efficacy of rat 438-mIgG1 and A2 antibodies in 37622A1 NSCLC patient derived xenografts with G13V mutation in K-ras compared to control anti-E. tenella antibody. Growth inhibition of 37622A1 PDXs by rat 438-mIgG1 indicates that NSCLCs with activated Notch1 and/or mutations in the K-ras oncogene might be sensitive to Notch1 pathway inhibitors.

TABLE 26

Efficacy of rat 438-mIgG1 and A2 antibodies in 37622A1 NSCLC patient derived xenografts with G13V mutation in K-ras.

| | Control ANTI-E. TENELLA | | | | | |
|---|---|---|---|---|---|---|
| | Day 0 | Day 3 | Day 7 | Day 10 | Day 14 | Day 16 |
| Tumor Volume (mm³) | 341.5 | 547.5 | 901.0 | 1128.4 | 1606.3 | 1860.5 |
| S.E.M. | 40.0 | 67.1 | 103.2 | 151.6 | 231.3 | 275.8 |
| | Day 0 | Day 1 | Day 4 | Day 8 | Day 11 | Day 14 |
| | Rat 438-mIgG1 | | | | | |
| Tumor Volume (mm³) | 336.5 | 584.5 | 498.4 | 429.9 | 502.5 | 539.2 |
| S.E.M. | 44.6 | 76.4 | 81.8 | 87.1 | 97.3 | 126.9 |
| | A2 | | | | | |
| Tumor Volume (mm³) | 344.3 | 533.7 | 523.9 | 428.7 | 536.2 | 622.8 |
| S.E.M. | 45.6 | 72.7 | 72.1 | 63.0 | 117.0 | 147.5 |

Table 27 shows the efficacy of rat 351-mIgG1 in 87393A1 NSCLC PDX compared to control anti-E. tenella antibody. Treatment with rat 351-mIgG1 resulted in 29% tumor growth inhibition compared to control anti-E. tenella treated tumors at day 28.

TABLE 27

Efficacy of rat 351-mIgG1 in 87393A1 NSCLC patient derived xenografts.

| | Day 0 | Day 7 | Day 14 | Day 20 | Day 26 | Day 28 |
|---|---|---|---|---|---|---|
| | Control Anti-E. tenella | | | | | |
| Tumor Volume (mm³) | 312.4 | 456.5 | 596.8 | 695.6 | 880.4 | 836.6 |
| S.E.M. | 7.7 | 37.4 | 45.6 | 33.3 | 61.1 | 41.8 |
| | Rat 351-mIgG1 | | | | | |
| Tumor Volume (mm³) | 275.4 | 299.5 | 433.3 | 466.2 | 529.5 | 590.4 |
| S.E.M. | 5.1 | 35.5 | 57.8 | 62.2 | 89.6 | 93.5 |

To confirm Notch1 activation was inhibited, western blot analysis using the D3B8 antibody (anti-Notch1$^{ICD}$) was performed on protein extracts generated from xenografts at the end of the study. Xenografts from the rat 438-mIgG1, A2, and control anti-E.tenella treated 37622A1 NSCLC PDX model, and xenografts from the rat 3511-mIgG1 and control anti-E.tenella treated 873931A1 NSCLC PDX models were harvested at the end of the study. Tumor tissue was lysed in 1% NP40, 0.51% sodium deoxycholate, 5 mM EDTA, 0.25 M NaC1, 0.025 M Tris-HC1, pH 7.51, containing COMPLETE MINI Protease inhibitor cocktail (Roche). Extracts were resolved by SDS-PAGE on a 7.51% polyacrylamide gel and transferred to nitrocellulose paper using an IBLOT Gel transfer system (Invitrogen). Released Notch1$^{ICD}$ molecules initiating at a Valine residue were detected with the D3B8 antibody (anti-Notch1$^{ICD}$) and total levels of the Notch1 C-terminal domain were detected with D1E11 (anti-Notch1) (Cell Signaling Technologies) using standard western blot procedures. β-Actin is shown as a loading control.

Figure 23:
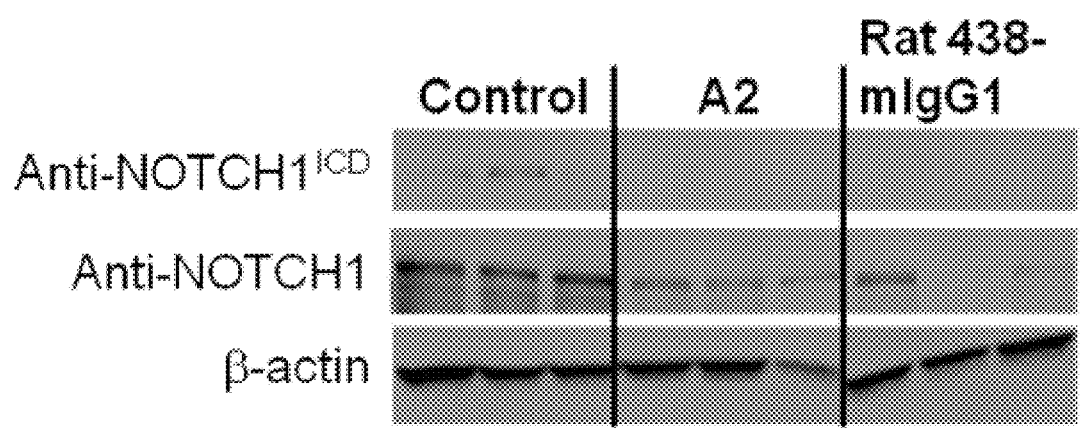
FIG. 23 shows western blot analysis of protein extracts generated from 37622A1 NSCLC patient derived xenografts treated with rat 438-mIgG1, A2 and control anti-*E. tenella* antibodies.
Figure 24:
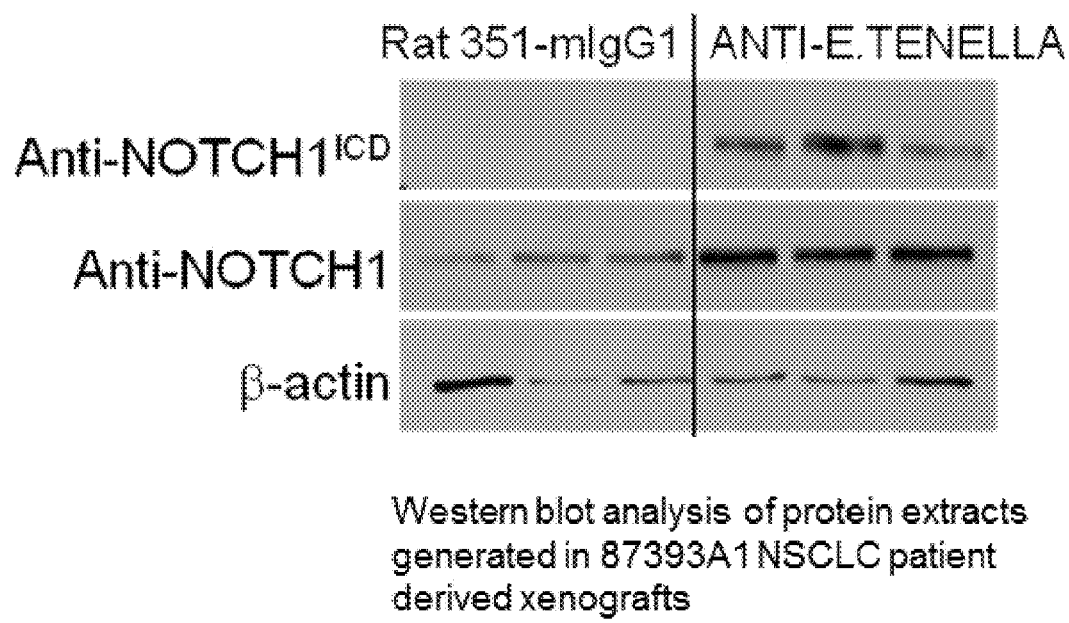
FIG. 24 shows a Western blot analysis of protein extracts generated in 87393A1 NSCLC patient derived xenografts treated with rat 351-mIgG1 and control anti-*E. tenella* antibodies.

FIG. 23 shows western blot analysis of protein extracts generated from 37622A1 NSCLC PDXs treated with rat 438-mIgG1 and A2. Detection of released Notch1$^{ICD}$ was observed in control anti-E. tenella treated tumors but not in rat 438-mIgG1 treated tumors, indicating inhibition of Notch1 activation. FIG. 24 shows western blot analysis of protein extracts generated from 87393A1 NSCLC PDXs treated with rat 351-mIgG1 and control anti-E. tenella antibodies. Detection of released Notch1$^{ICD}$ was observed in control anti-E. tenella treated tumors but not in rat 351-mIgG1 treated tumors, indicating inhibition of Notch1 activation.

Figure 25:
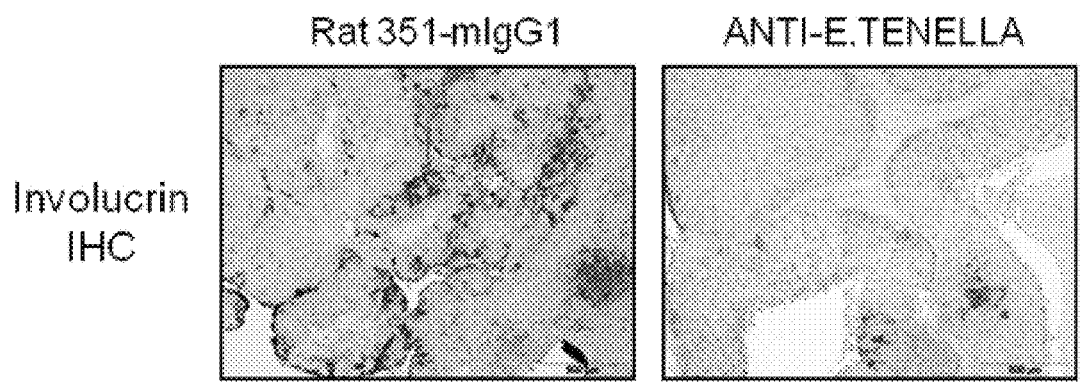
FIG. 25 shows immunohistochemical detection of involucrin expression in 87393A1 NSCLC patient derived xenografts after treatment with rat 351-mIgG1 and control anti-*E. tenella* antibodies.
Figure 26:
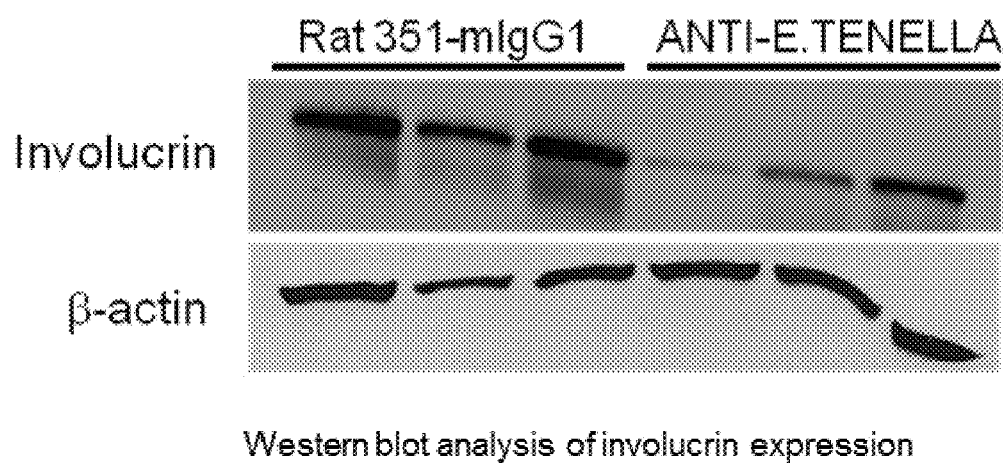
FIG. 26 shows a Western blot analysis of involucrin expression in 87393A1 NSCLC patient derived xenografts after treatment with rat 351-mIgG1 and control anti-*E. tenella* antibodies.

Donor clinical information from the original 87393A1 NSCLC PDX specimen indicated that the patient's tumor was an invasive poorly differentiated squamous cell carcinoma of the lung. Involucrin is a marker for squamous cell differentiation in lung tumors (Said, J. W., et. al., Laboratory Investigation, 1983, volume 49, 563-568). To determine whether inhibition of Notch1 activation had an effect on 87393A1 NSCLC PDX tumor cell differentiation, involucrin expression was analyzed by immunohistochemistry and western blot analysis. FIGS. 25 and 26 show involucrin immunohistochemisty and western blot analysis of rat 351-mIgG1 and control anti-*E. tenella* treated tumors, respectively. Inhibition of Notch1 activation in 87393A1 NSCLC PDX resulted in increased expression levels of involucrin as demonstrated by immunohistochemistry and western blot analysis. Thus, in addition to reducing tumor size, anti-Notch1 treatment also increased tumor cell differentiation.

D16A antibody, 2 times a week for 2 weeks. Tumors were measured at least once a week and their volume was calculated with the formula: tumor volume $(mm^3)=0.5\times$(tumor width$^2$)(tumor length). From 8-11 animals, mean tumor masses (±SEM) for each treatment group were calculated and comnared to the control-treated.

Table 29 shows the efficacy of rat 438-mIgG1, rat 351-mIgG1 and A2 antibodies in HPB-ALL xenografts with L1575P mutation in Notch1 NRR. The data demonstrates that treatment with rat 438-mIgG1 and treatment rat 351-mIgG1 both inhibited in vivo growth of HPB-ALL cells compared to control D16A antibody, thus slowing tumor growth.

TABLE 29

Efficacy of rat 351-mIgG1, rat 438-mIgG1 and A2 antibodies in HPB-ALL xenografts with L1575P mutation in Notch1 NRR.

|  | Day 0 | Day 1 | Day 4 | Day 8 | Day 11 | Day 14 |
| --- | --- | --- | --- | --- | --- | --- |
| Control D16A | | | | | | |
| Tumor Volume (mm$^3$) | 175.3 | 201.9 | 261.2 | 522.0 | 735.9 | 1003.4 |
| S.E.M. | 6.4 | 4.4 | 11.4 | 44.1 | 82.3 | 162.2 |
| Rat 351-mIgG1 | | | | | | |
| Tumor Volume (mm$^3$) | 166.1 | 198.6 | 244.1 | 267.0 | 231.0 | 251.0 |
| S.E.M. | 8.3 | 5.5 | 12.0 | 21.6 | 21.3 | 36.2 |
| Rat 438-mIgG1 | | | | | | |
| Tumor Volume (mm$^3$) | 165.1 | 194.7 | 225.0 | 244.3 | 176.9 | 179.2 |
| S.E.M. | 4.9 | 5.0 | 7.3 | 25.6 | 21.6 | 25.9 |
| A2 | | | | | | |
| Tumor Volume (mm$^3$) | 174.5 | 197.9 | 218.5 | 201.4 | 157.5 | 146.3 |
| S.E.M. | 2.8 | 4.6 | 7.4 | 12.5 | 13.2 | 13.9 |

To determine whether inhibition of Notch1 activation alone effected body weight, mice were weighed during in vivo efficacy studies. Table 28 shows that the average mouse body weights (minus tumor weights) of rat 351-mIgG and control anti-*E. tenella* antibody treated groups over the course of the study were not significantly different in the 87393A1 NSCLC PDXs.

TABLE 28

Average mouse body weights (minus tumor weights) in 87393A1 NSCLC PDXs after treatment with rat 351-mIgG1.

| | Average Mouse Body Weights in grams (minus tumor weights) | | | | |
| --- | --- | --- | --- | --- | --- |
| Antibody | Day 0 | Day 7 | Day 14 | Day 20 | Day 26 |
| Control Anti-*E. tenella* | 23.9 | 23.1 | 23.4 | 23.3 | 22.9 |
| Rat 351-mIgG1 | 23.4 | 23.0 | 23.1 | 23.3 | 23.5 |

C. In vivo Growth Inhibition Studies for HPB-ALL Xenografts

Similar in vivo experiments were performed with the mutant Notch1 HPB-ALL cell line as performed with the 37622A1 NSCLC PDX and 87393A1 NSCLC PDX described above. To generate xenografts, nude female mice (Nu/Nu) were implanted subcutaneously with 8×10E6 HPB-ALL cells in 50% MATRIGEL (BD Biosciences). When the tumors reached a volume of 200 to 400 mm$^3$, the tumors were staged to ensure uniformity of the tumor mass among various treatment groups prior to the administration of anti-Notch1 and control D16A antibodies. The HPB-ALL model was dosed s.c. at 20 mg/kg of rat 438-mIgG1, 351-mIgG1, A2 or D. In vivo Growth Inhibition Studies for Calu-6 NSCLC Xenografts Similar experiments were performed with the Calu-6 NSCLC cell line as performed with the HPB-ALL cells above for in vivo studies. Calu-6 xenografts were initially established in nude female mice (Nu/Nu) from 2×10E6 in vitro cultured cells in 50% MATRIGEL (BD Biosciences) and then serially passaged in vivo as tumor fragments from animal to animal. When the tumors reached the volume of 200 to 400 mm$^3$, the tumors were staged to ensure uniformity of the tumor size among various treatment groups prior to the administration of anti-Notch1 and control antibodies. The Calu-6 model was dosed i.p. at 3, 10 and 30 mg/kg of rat 438-mIgG1 or A2, or 10 mg/kg of control anti-E.tenella, 2 times a week for2 weeks Tumors were measured at least once a week and their volume was calculated with the formula: volume (mm$^3$) =0.5×(tumor width$^2$)(tumor length). From 8-11 animals, mean tumor volumes (±SEM) for each treatment group were calculated and compared to the control-treated.

The Calu-6 model was chosen because it was previously demonstrated to respond to Notch pathway inhibitors such as anti-DLL4 (Ridgeway et al., Nature 444:1083-1087, 2006) and A2 antibodies. Table 30 shows the efficacy of rat 438-mIgG1 and A2 in Calu-6 lung cancer model. Treatment with 3 mg/kg, 10 mg/kg and 30 mg/kg of the rat 438-mIgG1 resulted in a dose-dependent decrease in tumor growth. However, efficient (>50%) growth reduction of Calu-6 xenografts only occurred at the 30 mg/kg dose, which was 3 times higher than the dose required to inhibit the growth of the 37622A1 PDXs to a similar level.

TABLE 30

Efficacy of rat 438-mIgG1 and A2 in Calu-6 lung cancer model.

|  | Day 0 | Day 6 | Day 9 | Day 13 | Day 16 | Day 19 |
|---|---|---|---|---|---|---|
| Anti-E. tenella (10 mg/kg) | 258 ± 17 | 491 ± 34 | 740 ± 64 | 1156 ± 140 | 1260 ± 171 | 1613 ± 222 |
| Rat 438-mIgG1 (3 mg/kg) | 250 ± 29 | 362 ± 58 | 465 ± 88 | 742 ± 127 | 888 ± 171 | 1279 ± 219 |
| Rat 438-mIgG1 (10 mg/kg) | 263 ± 26 | 383 ± 40 | 448 ± 51 | 566 ± 68 | 667 ± 87 | 904 ± 129 |
| Rat 438-mIgG1 (30 mg/kg) | 242 ± 27 | 343 ± 58 | 445 ± 82 | 566 ± 106 | 601 ± 120 | 720 ± 152 |
| A2 (3 mg/kg) | 238 ± 29 | 349 ± 42 | 450 ± 58 | 603 ± 74 | 664 ± 91 | 851 ± 113 |
| A2 (10 mg/kg) | 250 ± 34 | 297 ± 35 | 348 ± 47 | 444 ± 64 | 480 ± 70 | 603 ± 101 |
| A2 (30 mg/kg) | 241 ± 26 | 376 ± 52 | 486 ± 68 | 598 ± 115 | 622 ± 121 | 779 ± 168 |

To determine if inhibition of Notch1 signaling alone effects body weight, mice were weighed during in vivo efficacy studies. Table 31 shows that the average mouse body weights (minus tumor weights) of rat 438-mIgG1 and A2, and control anti-E. tenella treated groups over the course of the study, were not significantly different

TABLE 31

Average mouse body weights (minus tumor weights) of rat 438-mIgG1 and A2, and control anti-E. tenella treatments in Calu-6 model (n = 10-11).

|  | Day 6 | Day 9 | Day 13 | Day 16 | Day 19 |
|---|---|---|---|---|---|
| E. tenella (10 mg/kg) | 24.6 ± 1.56 | 25.2 ± 1.42 | 24.3 ± 1.64 | 24.7 ± 1.74 | 24.0 ± 1.77 |
| Rat 438-mIgG1 (3 mg/kg) | 24.5 ± 2.18 | 25.8 ± 1.74 | 25.8 ± 1.67 | 26.4 ± 1.60 | 25.7 ± 1.66 |
| Rat 438-mIgG1 (10 mg/kg) | 25.1 ± 2.06 | 25.1 ± 2.21 | 24.6 ± 1.88 | 25.1 ± 1.71 | 24.5 ± 1.54 |
| Rat 438-mIgG1 (30 mg/kg) | 24.7 ± 2.21 | 25.7 ± 2.10 | 25.2 ± 2.48 | 25.8 ± 2.18 | 25.3 ± 2.23 |
| A2 (3 mg/kg) | 24.7 ± 2.39 | 26.1 ± 2.06 | 26.1 ± 2.05 | 27.1 ± 1.99 | 26.4 ± 1.82 |
| A2 (10 mg/kg) | 24.5 ± 1.63 | 25.2 ± 1.74 | 25.1 ± 1.86 | 25.3 ± 1.79 | 24.7 ± 1.69 |
| A2 (30 mg/kg) | 25.8 ± 1.61 | 26.4 ± 1.54 | 26.2 ± 1.73 | 26.8 ± 1.99 | 26.0 ± 2.07 |

E. In vivo Growth Inhibition Studies for Breast Cancer Xenografts

The effects of humanized 438 VH1.1/VL1.8 was examined on the in vivo growth in triple negative breast cancer xenografts models, Sum149 and MDA-MB-231. Athymic female mice (Nu/Nu, 6-8 weeks) were obtained from Charles River Laboratories and housed in specific pathogen-free conditions, according to the guidelines of the Association for the Assessment and Accreditation for Laboratory Animal Care, International. Animals were provided sterile rodent chow and water ad libitum.

Cells for implantation into athymic mice were harvested and pelleted by centrifugation at 450×g for 5-10 minutes. The cell pellets were washed once and re-suspended in sterile serum-free medium. Tumor cells were supplemented with 50% MATRIGEL (BD Biosciences) to facilitate tumor take and growth of selected tumor cells as xenografts. Cells (2-3× $10^6$ in 100 µL) were implanted subcutaneously into the hind flank region of the mouse and allowed to grow to the designated size prior to the administration of compound for each experiment.

For anti-tumor efficacy, animals bearing tumors of 150-300 $mm^3$ in size were randomly divided into groups that received either control antibody (26H6) or humanized 438 VH1.1/VL1.8 and dosed by s.c. injection weekly. Docetaxel was dosed by i.p. injection weekly. Tumor measurements were obtained every 2-3 days. Tumor volume ($mm^3$) was measured with Vernier calipers and calculated using the formula: length (mm)×width (mm)×width (mm)×0.52, shown in Tables 32 and 33.

TABLE 32

Efficacy of humanized 438 VH1.1/VL1.8 in triple negative breast cancer xenografts model, SUM149.

| Day post implant | Vehicle + 26H6 | Docetaxel, 6 mgk I.P weekly | Humanized 438 VH1.1/ VL1.8, 5 mgk SC weekly | Humanized 438 VH1.1/VL1.8 + Docetaxel |
|---|---|---|---|---|
| | Mean tumor volume (mm3) | | | |
| 36 | 220 | 225 | 214 | 223 |
| 41 | 266 | 239 | 166 | 181 |
| 46 | 408 | 282 | 153 | 149 |
| 49 | 543 | 486 | 150 | 125 |
| 53 | 529 | 458 | 135 | 104 |
| 56 | 711 | 587 | 177 | 144 |
| 60 | 796 | 638 | 179 | 129 |
| 63 | 937 | 769 | 239 | 187 |
| 67 | 1271 | 962 | 244 | 185 |
| | SE | | | |
| 36 | 8 | 6 | 8 | 6 |
| 41 | 12 | 7 | 6 | 9 |
| 46 | 21 | 18 | 16 | 12 |
| 49 | 34 | 45 | 18 | 9 |
| 53 | 38 | 39 | 17 | 10 |
| 56 | 45 | 41 | 19 | 14 |
| 60 | 68 | 44 | 18 | 12 |
| 63 | 100 | 53 | 23 | 24 |
| 67 | 125 | 62 | 22 | 26 |

TABLE 33

Efficacy of humanized 438 VH1.1/VL1.8 in triple negative breast cancer xenografts model, MDA-MB-231

| Day post implant | vehicle + 26H6 | Docetaxel, 10 mgk I.P weekly | Humanized 438 VH1.1/VL1.8, 5 mgk SC weekly | Humanized 438 VH1.1/VL1.8 + Docetaxel |
|---|---|---|---|---|
| Mean tumor volume (mm3) | | | | |
| 50 | 413 | 431 | 409 | 428 |
| 52 | 462 | 478 | 510 | 441 |
| 57 | 697 | 535 | 451 | 339 |
| 62 | 1204 | 717 | 466 | 354 |
| 65 | 1716 | 1326 | 694 | 506 |
| 69 | 2291 | 1396 | 768 | 486 |
| SE | | | | |
| 50 | 33 | 25 | 21 | 21 |
| 52 | 38 | 30 | 22 | 26 |
| 57 | 45 | 33 | 25 | 17 |
| 62 | 62 | 41 | 27 | 30 |
| 65 | 145 | 109 | 69 | 56 |
| 69 | 216 | 128 | 73 | 34 |

Percent (%) inhibition values were measured on the final day of study for drug-treated compared with vehicle-treated mice and are calculated as $100-\{1-[(\text{Treated}_{Final\ day}-\text{Treated}_{Day\ 1})/(\text{Control}_{Final\ day}-\text{Control}_{Day\ 1})]\}$. For all tumor growth inhibition experiments, 8 to 10 mice per dose group were used. A Student's t test was used to determine the P value. Table 34 shows the efficacy of humanized 438 VH1.1/VL1.8 in triple negative breast cancer xenografts models.

TABLE 34

Efficacy of humanized 438 VH1.1/VL1.8 and in triple negative breast cancer xenografts models.

| Tumor model | Agent | % TGI |
|---|---|---|
| Sum149 | Vehicle + 26H6 | 0 |
| | Docetaxel, 6 mpk | 30 |
| | Humanized 438 VH1.1/VL1.8, 5 mgk | 97 |
| | Humanized 438 VH1.1/VL1.8 + Docetaxel | 104 |
| MDA-MB-231 | Vehicle + 26H6 | 0 |
| | Docetaxel, 10 mpk | 49 |
| | Humanized 438 VH1.1/VL1.8, 5 mgk | 81 |
| | Humanized 438 VH1.1/VL1.8 + Docetaxel | 97 |

Example 10

Effect of Anti-Notch1 Inhibitory Antibodies on the Differentiation and Proliferation of Intestinal Cells Pharmacological and genetic inhibition of Notch signaling converts proliferative progenitor cells within intestinal crypts into secretory goblet cells (van Es et al., Nature 435:959-963, 2005). The effects of anti-Notch1 inhibitory antibodies on the proliferation and differentiation of cells in the mouse intestine were examined on tissues collected from the Calu-6 and 87393A1 NSCLC PDX efficacy studies of Example 9. Immunohistochemistry using Alcian blue stain for mucins (ie, secretory goblet cells) and anti-Ki67 for proliferation was performed on intestinal samples.

Mouse small intestines were harvested from the Calu-6 and 87393A1 NSCLC PDX efficacy studies, trimmed longitudinally, formalin fixed and held in 70% ETOH. The tissue was then embedded in paraffin. An Alcian Blue stain was performed for mucosubstances according to manufacturer's instructions. Immunohistochemistry using an anti-Ki67 antibody (SP6, Abcam, Cambridge, MA) was performed on a DAKO Auto Stainer (Dako, Carpinteria, CA) to demonstrate cell proliferation according to manufacturer's instructions.

1. Image Capture

Stained tissue sections were scanned on a Nanozoomer Slide Scanner (Hamamatsu, Bridgewater, N.J.) using a 20Xobj setting. Images were scanned and saved into the ndp file format. Virtual images were opened in Aperio Image Scope Software (Aperio Technologies, Vista, Calif.). Two images from opposite sides of the intestine lumen were captured at 10× virtual magnification and saved as Tiff images.

Figure 27:
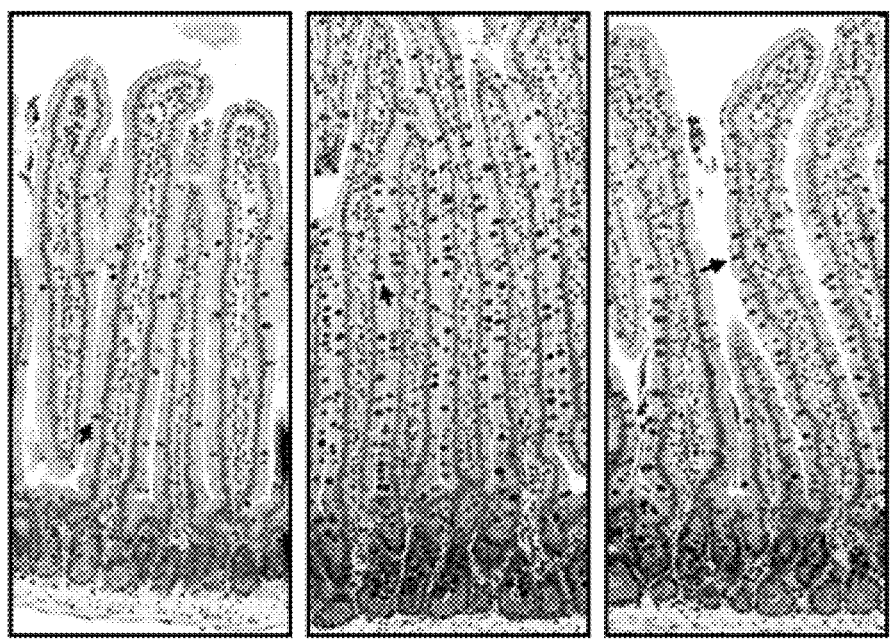
FIG. 27 shows histochemical identification of secretory goblet cells using Alcian Blue stain on the ileum section of mouse intestines from Calu-6 efficacy study treated with rat 438-mIgG1, A2, and control anti-*E. tenella* antibody.

FIG. 27 shows histochemical identification of secretory goblet cells using Alcian Blue stain on the ileum section of mouse intestines from Calu-6 efficacy study treated with either 10 mg/kg rat 438-mIgG1, A2 or control anti-E. tenella antibody. Representative images of intestinal villi and crypts are shown. Goblet cells are demarcated with arrows, and for simplicity, only 1 cell in each image is highlighted as an example. Although anti-Notch1 antibodies did not cause weight loss during the study, treatment with either rat 438-mIgG1 or A2 induced differentiation of secretory goblet cells as evidenced by increased alcian blue staining in villi as well as in the crypts. Thus inhibition of Notch1 signaling alone increased goblet cell differentiation, however not to a level that significantly impacted body weight.

2. Image Analysis

Virtual images were opened in Image Pro-Plus Software (Media Cybernetics, Bethesda, Md.). A manual outline Area of Interest (AOI) was created that included the intestinal tissue (crypt and villi), but excluded the smooth muscle, artifacts, folds, and debris. A threshold was created to identify Alcian Blue stain area and tissue area. The thresholds were applied to the AOIs and range statistics were exported to an Excel spreadsheet. In Excel, a mean Alcian Blue stain ratio was calculated for each animal from the two collected stain ratios to provide a single calculated Alcian Blue Stain Ratio per animal. A mean Alcian Blue Stain Ratio and standard deviation were created for each group. Statistics were performed using the JMP statistical software (JMP, Cary, N.C.).

Table 35 shows an image quantitation of Alcian Blue stain ratio of rat 438-mIgG1 and A2, and control anti-E. tenella antibody treated mouse intestines in Calu-6 efficacy study. Compared to anti-E. tenella control at 10 mg/kg, there was a significant increase in the Alcian Blue stain ratio in rat 438-mIgG1 dosed at 10 mg/kg and 30 mg/kg. The quantitative image analysis of alcian blue stain confirms the increased differentiation of goblet cells over a larger region of the ileum in comparison to the region shown in FIG. 27.

TABLE 35 shows an image quantitation of Alcian Blue stain ratio of rat 438-mIgG1 and A2, and control anti-E. tenella antibody treated mouse intestines in Calu-6 efficacy study.

| Treatment Group | Alcian Blue Stain Ratio | S.E.M. |
|---|---|---|
| ANTI-E. TENELLA, 10 mg/kg | 2.71 | 0.23 |
| Rat 438-mIgG1, 3 mg/kg | 3.97 | 0.59 |
| Rat 438-mIgG1, 10 mg/kg | 7.64 | 0.79 |
| Rat 438-mIgG1, 30 mg/kg | 8.24 | 0.63 |
| A2, 3 mg/kg | 7.38 | 1.44 |
| A2, 10 mg/kg | 14.13 | 2.32 |
| A2, 30 mg/kg | 11.63 | 1.07 |

Figure 29:
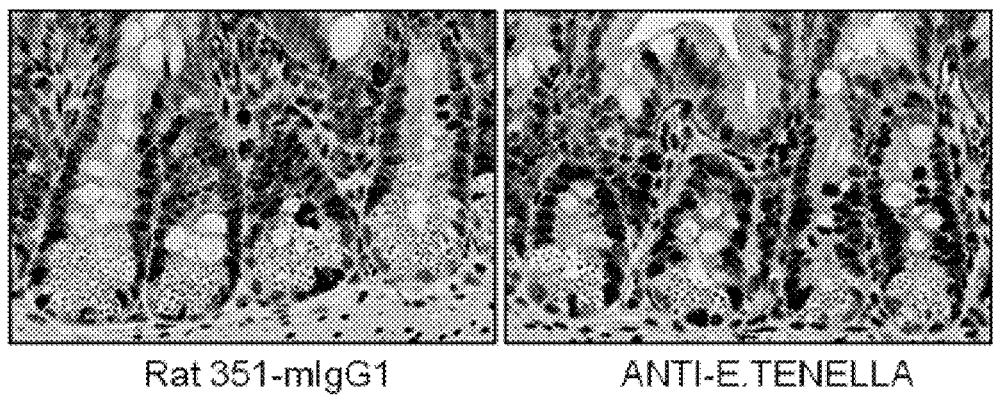
FIG. 29 shows anti-Ki67 immunohistochemistry on mouse intestinal crypts from 87393A1 patient derived xenograft efficacy study treated with rat 351-mIgG1 and control anti-*E. tenella* antibodies.

Statistical analysis of pairwise comparisons between the average or mean Alcian Blue stain ratios from each treatment group are shown in Table 36. Ratios for each pair were determined using Student's t test. Positive values show pairs of means that are significantly different. Unlike A2, rat 438-mIgG1 dosed at 3 mg/kg did not induce a significant increase in the Alcian Blue stain ratio compared to control anti-*E. tenella* antibody. Furthermore, A2 dosed at 10 mg/kg induced a significant increase in the alcian blue stain ratio compared to rat 438-mIgG1 dosed at 10 mg/kg suggesting that rat 438-mIgG1 caused less cellular differentiation in intestinal cells than A2.

crypts from the 87393A1 NSCLC PDX efficacy study treated with either rat 351-mIgG1 or control anti-*E. tenella* antibodies. FIG. 29 shows representative images of Ki67-stained intestinal crypts indicating that Ki67-staining was reduced at the base of the crypts in the rat 351-mIgG1 treated animals, but not in the control anti-*E. tenella* treated animals.

Consistent with this observation, Table 38 shows image quantitation of Ki67 stain ratios of rat 351-mIgG1 and control

TABLE 36

Statistical analysis of mean comparisons of alcian blues stain.
t 2.03452
Alpha 0.05

| Abs(Dif)-LSD | A2 10mpk | A2 30mpk | Rat 438-mIgG1 30mpk | Rat 438-mIgG1 10mpk | A2 3mpk | Rat 438-mIgG1 3mpk | Anti *E-tenella* 10mpk |
|---|---|---|---|---|---|---|---|
| A2 10mpk | −3.48282 | −0.9733 | 2.409854 | 2.84528 | 3.268058 | 6.512037 | 7.942685 |
| A2 30mpk | −0.9733 | −3.48282 | −0.09967 | 0.335759 | 0.758538 | 4.002516 | 5.433165 |
| Rat 438-mIgG1 30mpk | 2.409854 | −0.09967 | −3.48282 | −3.0474 | −2.62462 | 0.619362 | 2.05001 |
| Rat 438-mIgG1 10mpk | 2.84528 | 0.335759 | −3.0474 | −3.81524 | −3.40003 | −0.14848 | 1.2746 |
| A2 3mpk | 3.268058 | 0.758538 | −2.62462 | −3.40003 | −3.48282 | −0.23884 | 1.191806 |
| Rat 438-mIgG1 3mpk | 6.512037 | 4.002516 | 0.619362 | −0.14848 | −0.23884 | −3.81524 | −2.39216 |
| Anti *E-tenella* 10mpk | 7.942685 | 5.433165 | 2.05001 | 1.2746 | 1.191806 | −2.39216 | −3.48282 |

Figure 28:
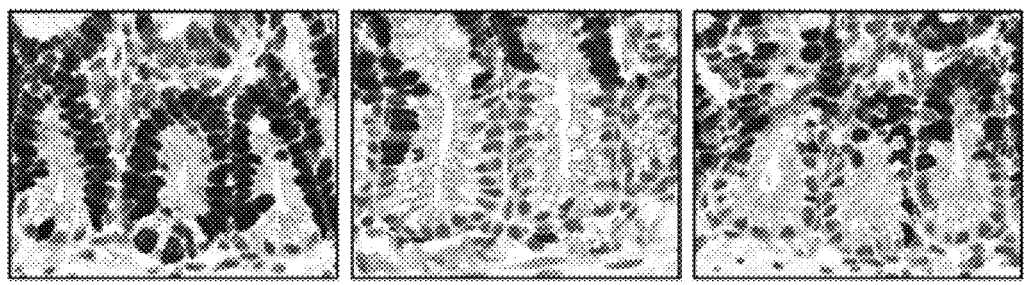
FIG. 28 shows anti-Ki67 immunohistochemistry on mouse intestinal crypts from Calu-6 efficacy study treated with rat 438-mIgG1, A2 and control anti-*E. tenella* antibody.

FIG. 28 shows anti-Ki67 immunohistochemistry on mouse intestinal crypts from Calu-6 efficacy study treated with either 10 mg/kg of rat 438-mIgG1, A2, or control anti-*E. tenella* antibody. Representative images of Ki67-stained intestinal crypts are shown. Ki67-staining was reduced at the base of the crypts in the rat 438-mIgG1 treated animals, but not the control anti-*E. tenella* treated animals. Loss of Ki67-stained proliferative crypt cells was consistent with the conversion to post-mitotic goblet cells that was observed by alcian blue staining.

Table 37 shows an image quantitation of Alcian Blue stain ratio of rat 351-mIgG1 and control anti-*E. tenella* antibody treated mouse intestines in the 87393A1 NSCLC PDX efficacy study. Compared to anti-*E. tenella* control, there was no significant difference in the Alcian Blue stain ratio in rat 351-mIgG1 treated mice (p=0.22). The quantitative image analysis of Alcian blue stain indicated that rat 351-mIgG1 did not induce goblet cell hyperplasia like other Notch pathway inhibitors. Thus, the inhibition of Notch1 signaling with rat 351-mIgG1 did not increase goblet cell differentiation.

TABLE 37

Quantitation of Alcian Blue stain ratio of rat 351-mIgG1 and anti-*E. tenella* treated mouse intestines in a 87393A1 NSCLC PDX efficacy study.

|  | Rat 351-mIgG1 | Anti-*E. tenella* |
|---|---|---|
| Alcian Blue Stain Ratio | 3.06 | 2.53 |
| Standard Deviation | 0.61 | 0.81 |

FIG. 29 and Table 38 show anti-Ki67 immunohistochemistry and quantitation of Ki67 stain ratio on mouse intestinal anti-*E. tenella* antibody treated mouse intestines. The data indicated that there is a small, but statically significant (p=0.023) decrease in Ki67 stain ratios in rat 351-mIgG1 compared to control anti-E. tenella antibody treatments. The quantitative analysis of Ki67 stain ratios showed a decrease in proliferation of cells at the base of crypts as demonstrated by a reduction in the relative levels of Ki67 staining over a larger region of the ileum in comparison to the region shown in the upper panels of FIG. 29. Thus, the inhibition of Notch1 signaling with rat 351-mIgG1 decreased proliferation.

TABLE 38

Quantitation of Ki67 stain ratio on mouse intestinal crypts from 87393A1 NSCLC PDXs treated with rat 351-mIgG1 and control Anti-*E. tenella* antibodies.

|  | Rat 351-mIgG1 | Anti-*E. tenella* |
|---|---|---|
| Ki67 Stain Ratio | 5.66 | 7.39 |
| Standard Deviation | 0.34 | 1.47 |

Example 11

Pharmacokinetics and Pharmacodynamics of Anti-Notch1 Inhibitory Antibody

1. Iodination Procedure

Iodination was performed using the IODO-BEADS method according to manufacturer's instructions (Pierce, Rockford, IL). Briefly, ~200 µg of test article were used per 2 mCi of 125-Iodine (Perkin-Elmer) and were incubated for 15-25 minutes at ambient temperature with 2 IODO-BEADS and ~200 µL of PBS. The reaction mixture was separated from the IODO-BEADS by filtration (CENTRICON-10 from Millipore, Billerica, MA).

2. Preparation and Characterization of Dosing Solution

For rat 438-mIgG1, a dosing solution was prepared by mixing unlabeled test article rat 438-mIgG1, a trace amount of $^{125}$I-labeled test article and a formulation buffer (PBS) for a final protein concentrations of 2 mg/mL to enable a dosing volume of 10 mL/kg dosing in mice. For rat 351-mIgG1, three dosing solutions were prepared by mixing unlabeled test article of rat 351-mIgG1, a trace amount of $^{125}$I-labeled test article and a formulation buffer (PBS) for a final protein concentrations of 2, 0.5 and 2.4 mg/mL to enable a dosing volume of 2.5, 10 and 12.5 mL/kg dosing in mice for group I (5 mg/kg i.v.), II (5 mg/kg i.p.) and III (30 mg/kg i.p.), respectively.

The fraction of radioactivity in a dosing solution accounted for by free iodine ("% free iodine") was determined using trichloroacetic acid (TCA)-precipitation. Dosing solution aliquots (5 µL) were mixed with mouse serum (45 µL) and were counted (in triplicate) for total radioactivity (Model 1480 WIZARD™, Wallac Inc., Gaithersburg, Md. or Model 2470 Perkin Elmer, Waltham Mass.). TCA (50 µL of 20% stock) was added to the samples. Samples were centrifuged at approximately 3000 g for 10 minutes. An aliquot of 50 µL of resultant supernatant was counted for soluble counts per minute (cpm). The fraction of free iodine in the dosing solution was calculated using the formula: [2*average soluble elution cpm/average total elution cpm*100%]. The specific activity of the dosing solution (µCi/mg) was calculated by the formula: [average total cpm−2*average soluble cpm]/[dosing solution concentration (mg/mL)*dosing solution volume (mL)*2,200,000 cpm/µCi].

The purity of the dosing solution was also qualitatively analyzed using SDS-PAGE and confirmed as a predominately single band under non-reducing conditions and as double bands under reducing conditions.

3. Determination of Radioactive Equivalent Concentrations in Serum and Tissues

The total radioactivity in serum samples (50 µL, in duplicates) was determined by gamma counting. An equivalent volume of 20% TCA was added into each serum aliquot and samples were spun at ~12000 rpm for 10 minutes. TCA-soluble radioactivity in 50 µL supernatant aliquot was determined by gamma-counting. TCA-precipitable radioactivity (cpm) in a given sample (Total cpm−2*TCA-soluble cpm), the specific activity of the dosing solution (TCA-precipitable cpm per mg of protein), as well as dates of sample (tS) and dosing solution (tD) measurements, were used to calculate the test article concentration in a given sample, using the formula: [average TCA-precipitable cpm/EXP(−0.693/60.2* (tS−tD))]/[specific activity (in cpm/mg)*sample volume (in mL)].

The quantitation of radioactive equivalent tissue concentration (µg eq./g) of $^{125}$I-labeled test article was based on the total radioactivity in tissues and the specific activity of the dosing solution after a correction for half-life of $^{125}$I using the formula: [sample cpm/EXP(−0.693/60.2×(tS−tD))]/[specific activity (in cpm/mg)×sample weight (in mg)]. TCA-precipitation for tissue samples was not performed. Tissue to serum concentration ratios (T/S) for tissue sample at a given timepoint were calculated using the ratio of radioactive equivalent concentration in tissue (µg eq./g) to that in serum (µg eq./mL).

4. Pharmacokinetic Calculations

Pharmacokinetic calculations were based on mean serum or tissue concentrations in mice. A non-compartmental analysis module (Model 201 and 200 for analysis of serum data after IV and IP administration, respectively) of the pharmacokinetic software package WinNonlin, ver. 5.1 (Pharsight) was used. The area under the serum concentration versus time curve (AUC) was calculated using the linear trapezoidal method. The slope of the apparent terminal phase was estimated by log-linear regression using at least 3 data points and the terminal rate constant (λ) was derived from the slope. AUC0-∞ was estimated as the sum of the AUC0-t (where t is the time of the last measurable concentration) and Ct/λ. The apparent terminal half-life (t½) was calculated as 0.693/λ.

Table 39 shows the serum and tissue exposures of non-tumor bearing nude mice to rat 438-mIgG1 antibodies that were measured at the indicated time points after a single 5 mg/kg i.p. injection of $^{125}$Iodine-labeled rat 438-mIgG1 antibody. Highest radioactive equivalent (RE) concentrations and exposure (AUC0-INF) were found in serum at all time points examined, followed by liver, skin, kidney, large intestines, small intestines, lungs and eyes. Radioactivity in tissues declined with time, as shown in Table 39. Despite the known expression and essential role of Notch1 signaling in the gastrointestinal tract of mice, rat 438-mIgG1 did not preferentially accumulate in the large or small intestines compared to other tissues tested.

TABLE 39

Serum and tissue concentrations of $^{125}$Iodine-labeled rat 438-mIgG1 antibody after a single i.p. injection of 5 mg/kg to nude mice.

| | 1 hour | 3 hours | 6 hours | 24 hours | 72 hours | 120 hours | 168 hours | 240 hours | 336 hours |
|---|---|---|---|---|---|---|---|---|---|
| serum | 4855 ± 5992 | 16439 ± 9789 | 15834 ± 1287 | 6640 ± 539 | 2983 ± 886 | 1618 ± 332 | 1006 ± 291 | 690 ± 129 | 111 ± 147 |
| eyes | | | 832 ± 141 | 302 ± 22 | 155 ± 41 | 142 ± 36 | 46.0 ± 40.6 | | |
| kidneys | | | 2121 ± 375 | 798 ± 95 | 486 ± 235 | 373 ± 166 | 216 ± 40 | | 87.4 ± 8.8 |
| large intestine | | | 2093 ± 156 | 514 ± 107 | 154 ± 46 | 94.2 ± 16.9 | 54.9 ± 0.8 | | |
| liver | | | 7590 ± 925 | 1677 ± 225 | 704 ± 501 | 541 ± 158 | 322 ± 59 | | 97.9 ± 61.1 |
| lung | | | 1047 ± 633 | 227 ± 111 | 253 ± 149 | 178 ± 46 | 124 ± 100 | | 25.3 ± 14.8 |
| skin | | | 2688 ± 429 | 1688 ± 192 | 513 ± 30 | 430 ± 160 | 171 ± 54 | | 70.3 ± 46.0 |
| small intestine | | | 1855 ± 232 | 353 ± 78 | 195 ± 40 | 114 ± 18 | 55.1 ± 6.5 | | 16.0 ± 9.6 |

The ratios of tissue to serum concentrations were calculated and the Mean tissue/serum concentration ratios after a single 5 mg/kg i.p. dose of rat 438-mIgG1 to nude mice are shown in Table 40. The tissue to serum concentration ratios remained relatively constant through the time points examined, indicating equilibrium between serum and tissues. The serum concentrations of rat 438-mIgG1 were higher than tissue concentrations, such that T/S ratios were low (<1 in general) and within the typical range observed for a mIgG1.

TABLE 40

Mean tissue/serum concentration ratios after a single 5 mg/kg i.p. dose of rat 438-mIgG1 to nude mice.

|  | 6 hours | 24 hours | 72 hours | 120 hours | 168 hours |
| --- | --- | --- | --- | --- | --- |
| Eyes | 0.053 ± 0.007 | 0.046 ± 0.001 | 0.052 ± 0.004 | 0.092 ± 0.034 | 0.056 ± 0.058 |
| Kidneys | 0.133 ± 0.016 | 0.121 ± 0.022 | 0.158 ± 0.035 | 0.224 ± 0.053 | 0.220 ± 0.028 |
| Large intestine | 0.133 ± 0.012 | 0.077 ± 0.010 | 0.052 ± 0.003 | 0.059 ± 0.006 | 0.058 ± 0.020 |
| Liver | 0.478 ± 0.023 | 0.255 ± 0.053 | 0.212 ± 0.127 | 0.331 ± 0.040 | 0.332 ± 0.064 |
| Lung | 0.065 ± 0.036 | 0.034 ± 0.016 | 0.086 ± 0.044 | 0.117 ± 0.051 | 0.123 ± 0.079 |
| Skin | 0.172 ± 0.040 | 0.256 ± 0.045 | 0.185 ± 0.067 | 0.269 ± 0.103 | 0.173 ± 0.033 |
| Small intestine | 0.117 ± 0.008 | 0.053 ± 0.007 | 0.067 ± 0.007 | 0.071 ± 0.008 | 0.057 ± 0.0.14 |

After administration of $^{125}$I-labeled rat 438-mIgG1, Cmax was calculated to be 16.4 μg eq./mL, with a Tmax achieved at 3 hr. Elimination t½ was 58 hrs and exposure (AUC0-∞) was 788 μg eq.*hr/mL, as shown in Table 41. The half life of rat 438-mIgG1 after a single 5 mg/kg i.p. dose is relatively short (~2.4 d).

TABLE 41

Pharmacokinetics parameters of anti-Notch1 inhibitory antibody rat 438-mIgG1 in female nude mice after a single i.p. does of 5 mg/kg.

| Cmax (ug/mL) | Tmax (hr) | t½ (hr) | AUClast (hr*ug/mL) | AUC0-inf (hr*ug/mL) | AUC0-inf/Dose (hr*kg*ug/mL/mg) | AUC Extrap (%) | MRT (hr) |
| --- | --- | --- | --- | --- | --- | --- | --- |
| 16.4 | 3 | 58 | 779 | 788 | 158 | 1.2 | 67 |

Note:
PK parameters were generated from mean plasma concentrations (n = 3 per time point)

Serum exposures of rat 351-mIgG1 were measured in non-tumor bearing nude mice after a single 5 mg/kg i.v, 5 mg/kg i.p. or 30 mg/kg i.p. injection of $^{125}$I-labeled rat 351-mIgG1 antibody. The observed serum concentration values were used to calculate multiple pharmacokinetic parameters, as shown in Table 42 and Table 43.

Table 42 shows pharmacokinetic parameters after the i.v. administration of 5 mg/kg of $^{125}$I-labeled rat 351-mIgG1 to female nude mice. The elimination t½ and systemic clearance of rat 351-mIgG1 were ~3 days (70.2 hrs) and 1.74 mL/hr/kg, respectively. The volume of distribution at steady state (Vdss) was 177 mL/kg. The exposure (AUC0-INF) was 2871 μg eq·hr/mL.

TABLE 42

Pharmacokinetic parameters of $^{125}$I-labeled rat 351-mIgG1 in female nude mice following i.v. administration of a single 5 mg/kg dose.

| Dose mg/kg | $C_0$ μg eq./mL | $AUC_{0-last}$ μg eq. hr/mL | $AUC_{0-\infty}$ μg eq. hr/mL | $AUC_{0-\infty}$/Dose μgeq.*hr/mL/ mg/kg | $AUC_{\%Extrap}$ % | $t_{1/2}$ hrs | CL mL/hr/ kg | Vdss mL/kg |
| --- | --- | --- | --- | --- | --- | --- | --- | --- |
| 5 | 50.6 | 2766 | 2871 | 574 | 3.68 | 70.2 | 1.74 | 177 |

Table 43 shows pharmacokinetic parameters after the i.p. administration of 5 and 30 mg/kg of $^{125}$I-labeled rat 351-mIgG1 to female nude mice. The Cmax was 30 and 151 µg eq./mL, respectively, and the Tmax was achieved at 6 hours for both dose groups. Elimination t½ was 93 and 163 hours (~4-7 days) and exposure (AUC0-INF) was 2754 and 24080 µg eq.*hr/mL, following the 5 and 30 mg/kg, respectively. The dose normalized AUC ratio (F) between i.p. and i.v. administration was ~1.4, suggesting that absorption after i.p. administration of 30 mg/kg was complete in mice.

TABLE 43

Pharmacokinetic parameters of $^{125}$I-labeled rat 351-mIgG1 antibody in female nude mice following i.p. administration of 5 mg/kg and 30 mg/kg.

| Dose mg/kg | $C_{max}$ µg eq./mL | $T_{max}$ hrs | $T_{1/2}$ hrs | $AUC_{0-last}$ µg eq.*hr/mL | $AUC_{0-\infty}$ µg eq.* hr/mL | $AUC_{0-\infty}$/Dose µg eq.* hr/mL/mg/kg | $AUC_{\%Extrap}$ % | MRT hrs | F % |
|---|---|---|---|---|---|---|---|---|---|
| 5 | 29.7 | 6 | 93.2 | 2572 | 2754 | 551 | 6.64 | 117 | 95.9 |
| 30 | 151 | 6 | 163 | 18687 | 24080 | 803 | 22.4 | 221 | complete |

Serum and tissue exposures of non-tumor bearing nude mice to rat 351-mIgG1 were measured after a single 5 and 30 mg/kg i.p. injection of $^{125}$I-labeled rat 351-mIgG1. For the 5 mg/kg i.p. dose, the highest radioactive equivalent (RE) concentrations and exposure (AUC0-INF) were found in serum at all time points examined, followed by liver, spleen, skin, kidneys, small intestine, large intestine, lung and eyes, as shown in Table 44. For the 30 mg/kg i.p. dose, the highest radioactive equivalent (RE) concentrations and exposure (AUC0-INF) were found in serum at all time points examined, followed by liver, skin, spleen, small intestine, lung, kidneys, eyes and large intestine, as shown in Table 45. The data shows that rat 351-mIgG1 did not preferentially accumulate in the large or small intestines compared to other tissues tested for both the 5 mg/kg and 30 mg/kg i.p. doses.

TABLE 44

Mean tissue and serum concentrations (µg eq./g tissue) of $^{125}$I-labeled rat 351-mIgG1 in nude mice following a single i.p. dose of 5 mg/kg (n = 3 per time point).

| Time, hrs | 6 | 24 | 72 | 120 | 168 | 240 | 336 |
|---|---|---|---|---|---|---|---|
| eyes | 920 | 631 | 510 | 439 | 235 | 162 | 75 |
| kidneys | 2052 | 1167 | 1128 | 1029 | 304 | 229 | 89 |
| L. intestine | 1147 | 545 | 378 | 316 | 131 | 99 | 41 |
| liver | 12228 | 3417 | 1223 | 1135 | 501 | 599 | 140 |
| lung | 990 | 1294 | 1264 | 726 | 183 | 464 | 193 |
| skin | 2761 | 3435 | 2023 | 1480 | 665 | 430 | 192 |
| S. intestine | 1888 | 767 | 459 | 389 | 171 | 144 | 50 |
| spleen | 2897 | 1411 | 1189 | 888 | 349 | 323 | 103 |
| Serum | 29664 | 16894 | 12303 | 9014 | 4724 | 2858 | 1359 |

TABLE 45

Mean tissue and serum concentrations (µg eq./g tissue) of $^{125}$I-labeled rat 351-mIgG1 in nude mice following i.p. administration of 30 mg/kg (n = 3 per time point).

| Time, hrs | 6 | 24 | 72 | 120 | 168 | 240 | 336 |
|---|---|---|---|---|---|---|---|
| Eyes | 8451 | 9733 | 3733 | 2183 | 2534 | 1899 | 1223 |
| kidneys | 9423 | 6487 | 8693 | 2722 | 4870 | 4315 | 967 |
| L. intestine | 5225 | 3175 | 2644 | 1448 | 1133 | 968 | 493 |
| Liver | 56856 | 20363 | 11979 | 5497 | 4843 | 3614 | 1456 |
| Lung | 10237 | 7091 | 2496 | 1749 | 2902 | 3002 | 1925 |
| Skin | 22323 | 17707 | 15125 | 8381 | 7287 | 4439 | 3011 |
| S. intestine | 10496 | 4505 | 3523 | 1956 | 1956 | 1491 | 638 |
| Spleen | 14353 | 6805 | 7346 | 3314 | 3454 | 3135 | 1111 |
| Serum | 150928 | 101971 | 80782 | 53137 | 46925 | 35299 | 22982 |

What is claimed is:

1. An antibody that binds to Notch1, wherein the antibody comprises:
   (a) a heavy chain CDR1 as set forth in SEQ ID NO: 73,
   (b) a heavy chain CDR2 as set forth in SEQ ID NO: 77,
   (e) a heavy chain CDR3 as set forth in SEQ ID NO: 81,
   (d) a light chain CDR1 as set forth in SEQ ID NO: 99,
   (e) a light chain CDR2 as set forth in SEQ ID NO: 101, and
   (f) a light chain CDR3 as set forth in SEQ ID NO: 103.

2. The antibody according to claim 1, comprising:
   a heavy chain variable region selected from the group consisting of SEQ ID NO: 69 and 71, and
   a light chain variable region selected from the group consisting of SEQ ID NO: 83, 85, 87, 89, 91, 93, 95, 97, 105, 107 and 109.

3. The antibody according to claim 1, comprising:
   a heavy chain variable region amino acid sequence that is at least 90% identical to SEQ ID NO: 71; and
   a light chain variable region amino acid sequence that is at least 90% identical to SEQ ID NO: 97.

4. The antibody according to claim 3, comprising:
   a heavy chain amino acid sequence that is at least 90% identical to SEQ ID NO: 111; and
   a light chain amino acid sequence that is at least 90% identical to SEQ ID NO: 113.

5. An isolated antibody that binds to human Notch1, wherein the antibody binds an epitope comprising amino acid residues Asn 1461, Lys 1462, Val 1463, Asp 1671, Arg 1673, Leu 1713 and Lys 1718.

6. The antibody according to claim 3, comprising:
   a heavy chain variable region amino acid sequence as set forth in SEQ ID NO: 71; and
   a light chain variable region amino acid sequence as set forth in SEQ ID NO: 97.

7. The antibody according to claim 4, comprising:
   a heavy chain amino acid sequence as set forth in SEQ ID NO: 111; and
   a light chain amino acid sequence as set forth in SEQ ID NO: 113.

8. A pharmaceutical composition comprising the antibody of claim 1 and a pharmaceutically acceptable carrier.

9. A method of treating a disorder in a subject in need thereof, comprising administering to the subject the antibody according to claim 1, wherein the disorder is selected from the group consisting of T-cell acute lymphoblastic leukemia (T-ALL), non-small cell lung cancer (NSCLC) and breast cancer.

* * * * *

SEQUENCE LISTING

<160> NUMBER OF SEQ ID NOS: 152

<210> SEQ ID NO 1

```
<211> LENGTH: 351
<212> TYPE: PRT
<213> ORGANISM: Artificial Sequence
<220> FEATURE:
<223> OTHER INFORMATION: Synthetic peptide sequence

<400> SEQUENCE: 1

Met Pro Leu Leu Leu Leu Leu Leu Leu Pro Ser Pro Leu His Pro
1               5                   10                  15

Gly Gly Ala Gly Arg Asp Ile Pro Pro Leu Ile Glu Glu Ala Cys
            20                  25                  30

Glu Leu Pro Glu Cys Gln Glu Asp Ala Gly Asn Lys Val Cys Ser Leu
            35                  40                  45

Gln Cys Asn Asn His Ala Cys Gly Trp Asp Gly Gly Asp Cys Ser Leu
50                  55                  60

Asn Phe Asn Asp Pro Trp Lys Asn Cys Thr Gln Ser Leu Gln Cys Trp
65                  70                  75                  80

Lys Tyr Phe Ser Asp Gly His Cys Asp Ser Gln Cys Asn Ser Ala Gly
                85                  90                  95

Cys Leu Phe Asp Gly Phe Asp Cys Gln Arg Ala Glu Gly Gln Cys Asn
            100                 105                 110

Pro Leu Tyr Asp Gln Tyr Cys Lys Asp His Phe Ser Asp Gly His Cys
            115                 120                 125

Asp Gln Gly Cys Asn Ser Ala Glu Cys Glu Trp Asp Gly Leu Asp Cys
130                 135                 140

Ala Glu His Val Pro Glu Arg Leu Ala Ala Gly Thr Leu Val Val Val
145                 150                 155                 160

Val Leu Met Pro Pro Glu Gln Leu Arg Asn Ser Ser Phe His Phe Leu
            165                 170                 175

Arg Glu Leu Ser Arg Val Leu His Thr Asn Val Val Phe Lys Arg Asp
            180                 185                 190

Ala His Gly Gln Gln Met Ile Phe Pro Tyr Tyr Gly Arg Glu Glu Glu
            195                 200                 205

Leu Arg Lys His Pro Ile Lys Arg Ala Ala Glu Gly Trp Ala Ala Pro
210                 215                 220

Asp Ala Leu Leu Gly Gln Val Lys Ala Ser Leu Leu Pro Gly Gly Ser
225                 230                 235                 240

Glu Gly Gly Arg Arg Arg Arg Glu Leu Asp Pro Met Asp Val Arg Gly
            245                 250                 255

Ser Ile Val Tyr Leu Glu Ile Asp Asn Arg Gln Cys Val Gln Ala Ser
            260                 265                 270

Ser Gln Cys Phe Gln Ser Ala Thr Asp Val Ala Ala Phe Leu Gly Ala
            275                 280                 285

Leu Ala Ser Leu Gly Ser Leu Asn Ile Pro Tyr Lys Ile Glu Ala Val
            290                 295                 300

Gln Ser Glu Thr Val Glu Pro Pro Pro Ala Gln Leu His Phe Met
305                 310                 315                 320

Gly Gly Gly Ser Gly Gly Leu Asn Asp Ile Phe Glu Ala Gln Lys
            325                 330                 335

Ile Glu Trp His Glu Gly Gly Pro Pro His His His His His
            340                 345                 350

<210> SEQ ID NO 2
<211> LENGTH: 304
<212> TYPE: PRT
<213> ORGANISM: Homo sapiens
```

<400> SEQUENCE: 2

Gly Gly Ala Gly Arg Asp Ile Pro Pro Leu Ile Glu Glu Ala Cys
1               5                   10                  15

Glu Leu Pro Glu Cys Gln Glu Asp Ala Gly Asn Lys Val Cys Ser Leu
            20                  25                  30

Gln Cys Asn Asn His Ala Cys Gly Trp Asp Gly Gly Asp Cys Ser Leu
        35                  40                  45

Asn Phe Asn Asp Pro Trp Lys Asn Cys Thr Gln Ser Leu Gln Cys Trp
    50                  55                  60

Lys Tyr Phe Ser Asp Gly His Cys Asp Ser Gln Cys Asn Ser Ala Gly
65              70                  75                  80

Cys Leu Phe Asp Gly Phe Asp Cys Gln Arg Ala Glu Gly Gln Cys Asn
            85                  90                  95

Pro Leu Tyr Asp Gln Tyr Cys Lys Asp His Phe Ser Asp Gly His Cys
            100                 105                 110

Asp Gln Gly Cys Asn Ser Ala Glu Cys Glu Trp Asp Gly Leu Asp Cys
        115                 120                 125

Ala Glu His Val Pro Glu Arg Leu Ala Ala Gly Thr Leu Val Val Val
    130                 135                 140

Val Leu Met Pro Pro Glu Gln Leu Arg Asn Ser Ser Phe His Phe Leu
145                 150                 155                 160

Arg Glu Leu Ser Arg Val Leu His Thr Asn Val Val Phe Lys Arg Asp
                165                 170                 175

Ala His Gly Gln Gln Met Ile Phe Pro Tyr Tyr Gly Arg Glu Glu Glu
            180                 185                 190

Leu Arg Lys His Pro Ile Lys Arg Ala Ala Glu Gly Trp Ala Ala Pro
        195                 200                 205

Asp Ala Leu Leu Gly Gln Val Lys Ala Ser Leu Leu Pro Gly Gly Ser
    210                 215                 220

Glu Gly Gly Arg Arg Arg Arg Glu Leu Asp Pro Met Asp Val Arg Gly
225                 230                 235                 240

Ser Ile Val Tyr Leu Glu Ile Asp Asn Arg Gln Cys Val Gln Ala Ser
                245                 250                 255

Ser Gln Cys Phe Gln Ser Ala Thr Asp Val Ala Ala Phe Leu Gly Ala
            260                 265                 270

Leu Ala Ser Leu Gly Ser Leu Asn Ile Pro Tyr Lys Ile Glu Ala Val
        275                 280                 285

Gln Ser Glu Thr Val Glu Pro Pro Pro Pro Ala Gln Leu His Phe Met
    290                 295                 300

<210> SEQ ID NO 3
<211> LENGTH: 1053
<212> TYPE: DNA
<213> ORGANISM: Artificial Sequence
<220> FEATURE:
<223> OTHER INFORMATION: Synthetic nucleotide sequence

<400> SEQUENCE: 3
atgcctctcc tcctcttgct gctcctgctg ccaagcccct tacacgcggg tggggccggg    60
cgcgacatcc ccccgccgct gatcgaggag gcgtgcgagc tgcccgagtg ccaggaggac   120
gcgggcaaca aggtctgcag cctgcagtgc aacaaccacg cgtgcggctg ggacggcggt   180
gactgctccc tcaacttcaa tgaccccctgg aagaactgca cgcagtctct gcagtgctgg   240
aagtacttca gtgacggcca ctgtgacagc cagtgcaact cagccggctg cctcttcgac   300

```
ggctttgact gccagcgtgc ggaaggccag tgcaaccccc tgtacgacca gtactgcaag    360
gaccacttca gcgacgggca ctgcgaccag ggctgcaaca gcgcggagtg cgagtgggac    420
gggctggact gtgcggagca tgtacccgag aggctggcgg ccggcacgct ggtggtggtg    480
gtgctgatgc cgccggagca gctgcgcaac agctccttcc acttcctgcg ggagctcagc    540
cgcgtgctgc acaccaacgt ggtcttcaag cgtgacgcac acggccagca gatgatcttc    600
ccctactacg gccgcgagga ggagctgcgc aagcacccca tcaagcgtgc cgccgagggc    660
tgggccgcac ctgacgccct gctgggccag gtgaaggcct cgctgctccc tggtggcagc    720
gagggtgggc ggcggcggag ggagctggac cccatggacg tccgcggctc catcgtctac    780
ctggagattg acaaccggca gtgtgtgcag gcctcctcgc agtgcttcca gagtgccacc    840
gacgtggccg cattcctggg agcgctcgcc tcgctgggca gcctcaacat cccctacaag    900
atcgaggccg tgcagagtga gaccgtggag ccgcccccgc cggcgcagct gcacttcatg    960 ggaggggga  gcgaggcgg actgaacgac atcttcgagg ctcagaaaat cgaatggcac   1020
gaaggtggcc caccacatca tcatcatcat cac                               1053

<210> SEQ ID NO 4
<211> LENGTH: 912
<212> TYPE: DNA
<213> ORGANISM: Homo sapiens

<400> SEQUENCE: 4
ggtggggccg ggcgcgacat ccccccgccg ctgatcgagg aggcgtgcga gctgcccgag     60
tgccaggagg acgcgggcaa caaggtctgc agcctgcagt gcaacaacca cgcgtgcggc    120
tgggacggcg tgactgctc cctcaacttc aatgacccct ggaagaactg cacgcagtct    180
ctgcagtgct ggaagtactt cagtgacggc cactgtgaca gccagtgcaa ctcagccggc    240
tgcctcttcg acggctttga ctgccagcgt gcggaaggcc agtgcaaccc cctgtacgac    300
cagtactgca aggaccactt cagcgacggg cactgcgacc agggctgcaa cagcgcggag    360
tgcgagtggg acgggctgga ctgtgcggag catgtacccg agaggctggc ggccggcacg    420
ctggtggtgg tggtgctgat gccgccggag cagctgcgca acagctcctt ccacttcctg    480
cgggagctca gccgcgtgct gcacaccaac gtggtcttca gcgtgacgc  acacggccag    540 cagatgatct tcccctacta cggccgcgag gaggagctgc gcaagcaccc catcaagcgt    600
gccgccgagg gctgggccgc acctgacgcc ctgctgggcc aggtgaaggc ctcgctgctc    660
cctggtggca gcgagggtgg gcggcggcgg agggagctgg accccatgga cgtccgcggc    720
tccatcgtct acctggagat tgacaaccgg cagtgtgtgc aggcctcctc gcagtgcttc    780
cagagtgcca ccgacgtggc cgcattcctg ggagcgctcg cctcgctggg cagcctcaac    840
atcccctaca agatcgaggc cgtgcagagt gagaccgtgg agccgccccc gccggcgcag    900
ctgcacttca tg                                                        912

<210> SEQ ID NO 5
<211> LENGTH: 341
<212> TYPE: PRT
<213> ORGANISM: Artificial Sequence
<220> FEATURE:
<223> OTHER INFORMATION: Synthetic peptide sequence

<400> SEQUENCE: 5

Met Pro Leu Leu Leu Leu Leu Leu Leu Leu Pro Ser Pro Leu His Pro
1               5                   10                  15
```

Gly Gly Ala Gly Arg Asp Ile Pro Pro Gln Ile Glu Glu Ala Cys
            20                  25                  30

Glu Leu Pro Glu Cys Gln Val Asp Ala Gly Asn Lys Val Cys Asn Leu
        35                  40                  45

Gln Cys Asn Asn His Ala Cys Gly Trp Asp Gly Gly Asp Cys Ser Leu
    50                  55                  60

Asn Phe Asn Asp Pro Trp Lys Asn Cys Thr Gln Ser Leu Gln Cys Trp
65                  70                  75                  80

Lys Tyr Phe Ser Asp Gly His Cys Asp Ser Gln Cys Asn Ser Ala Gly
                85                  90                  95

Cys Leu Phe Asp Gly Phe Asp Cys Gln Leu Thr Glu Gly Gln Cys Asn
            100                 105                 110

Pro Leu Tyr Asp Gln Tyr Cys Lys Asp His Phe Ser Asp Gly His Cys
        115                 120                 125

Asp Gln Gly Cys Asn Ser Ala Glu Cys Glu Trp Asp Gly Leu Asp Cys
    130                 135                 140

Ala Glu His Val Pro Glu Arg Leu Ala Ala Gly Thr Leu Val Leu Val
145                 150                 155                 160

Val Leu Leu Pro Pro Asp Gln Leu Arg Asn Asn Ser Phe His Phe Leu
                165                 170                 175

Arg Glu Leu Ser His Val Leu His Thr Asn Val Val Phe Lys Arg Asp
            180                 185                 190

Ala Gln Gly Gln Gln Met Ile Phe Pro Tyr Tyr Gly His Glu Glu Glu
        195                 200                 205

Leu Arg Lys His Pro Ile Lys Arg Ser Thr Val Gly Trp Ala Thr Ser
    210                 215                 220

Ser Leu Leu Pro Gly Thr Ser Gly Gly Arg Gln Arg Arg Glu Leu Asp
225                 230                 235                 240

Pro Met Asp Ile Arg Gly Ser Ile Val Tyr Leu Glu Ile Asp Asn Arg
                245                 250                 255

Gln Cys Val Gln Ser Ser Ser Gln Cys Phe Gln Ser Ala Thr Asp Val
            260                 265                 270

Ala Ala Phe Leu Gly Ala Leu Ala Ser Leu Gly Ser Leu Asn Ile Pro
        275                 280                 285

Tyr Lys Ile Glu Ala Val Lys Ser Glu Pro Val Glu Pro Pro Leu Pro
    290                 295                 300

Ser Gln Leu His Leu Met Gly Gly Ser Gly Gly Leu Asn Asp
305                 310                 315                 320

Ile Phe Glu Ala Gln Lys Ile Glu Trp His Gly Gly Pro Pro His
                325                 330                 335

His His His His
        340

<210> SEQ ID NO 6
<211> LENGTH: 294
<212> TYPE: PRT
<213> ORGANISM: Mus musculus

<400> SEQUENCE: 6

Gly Gly Ala Gly Arg Asp Ile Pro Pro Gln Ile Glu Glu Ala Cys
1               5                   10                  15

Glu Leu Pro Glu Cys Gln Val Asp Ala Gly Asn Lys Val Cys Asn Leu
        20                  25                  30

Gln Cys Asn Asn His Ala Cys Gly Trp Asp Gly Gly Asp Cys Ser Leu

```
                35                  40                  45
Asn Phe Asn Asp Pro Trp Lys Asn Cys Thr Gln Ser Leu Gln Cys Trp
 50                  55                  60

Lys Tyr Phe Ser Asp Gly His Cys Asp Ser Gln Cys Asn Ser Ala Gly
 65                  70                  75                  80

Cys Leu Phe Asp Gly Phe Asp Cys Gln Leu Thr Glu Gly Gln Cys Asn
                 85                  90                  95

Pro Leu Tyr Asp Gln Tyr Cys Lys Asp His Phe Ser Asp Gly His Cys
            100                 105                 110

Asp Gln Gly Cys Asn Ser Ala Glu Cys Glu Trp Asp Gly Leu Asp Cys
        115                 120                 125

Ala Glu His Val Pro Glu Arg Leu Ala Ala Gly Thr Leu Val Leu Val
    130                 135                 140

Val Leu Leu Pro Pro Asp Gln Leu Arg Asn Asn Ser Phe His Phe Leu
145                 150                 155                 160

Arg Glu Leu Ser His Val Leu His Thr Asn Val Val Phe Lys Arg Asp
                165                 170                 175

Ala Gln Gly Gln Gln Met Ile Phe Pro Tyr Tyr Gly His Glu Glu Glu
            180                 185                 190

Leu Arg Lys His Pro Ile Lys Arg Ser Thr Val Gly Trp Ala Thr Ser
        195                 200                 205

Ser Leu Leu Pro Gly Thr Ser Gly Gly Arg Gln Arg Arg Glu Leu Asp
    210                 215                 220

Pro Met Asp Ile Arg Gly Ser Ile Val Tyr Leu Glu Ile Asp Asn Arg
225                 230                 235                 240

Gln Cys Val Gln Ser Ser Ser Gln Cys Phe Gln Ser Ala Thr Asp Val
                245                 250                 255

Ala Ala Phe Leu Gly Ala Leu Ala Ser Leu Gly Ser Leu Asn Ile Pro
            260                 265                 270

Tyr Lys Ile Glu Ala Val Lys Ser Glu Pro Val Glu Pro Pro Leu Pro
        275                 280                 285

Ser Gln Leu His Leu Met
    290

<210> SEQ ID NO 7
<211> LENGTH: 1023
<212> TYPE: DNA
<213> ORGANISM: Artificial Sequence
<220> FEATURE:
<223> OTHER INFORMATION: Synthetic nucleotide sequence

<400> SEQUENCE: 7
atgcctctcc tcctcttgct gctcctgctg ccaagcccct tacacgcggg tggcgctggg      60
cgcgacattc ccccaccgca gattgaggag gcctgtgagc tgcctgagtg ccaggtggat     120
gcaggcaata aggtctgcaa cctgcagtgt aataatcacg catgtggctg ggatggtggc     180
gactgctccc tcaacttcaa tgaccccctgg aagaactgca cgcagtctct acagtgctgg     240
aagtatttta gcgacggcca ctgtgacagc cagtgcaact cggccggctg cctctttgat     300
ggcttcgact gccagctcac cgagggacag tgcaaccccc tgtatgacca gtactgcaag     360
gaccacttca gtgatggcca ctgcgaccag ggctgtaaca gtgccgaatg tgagtgggat     420
ggcctagact gtgctgagca tgtacccgag cggctggcag ccggcaccct ggtgctggtg     480
gtgctgcttc cacccgacca gctacggaac aactccttcc actttctgcg ggagctcagc     540
cacgtgctgc acaccaacgt ggtcttcaag cgtgatgcgc aaggccagca gatgatcttc     600
```

```
ccgtactatg gccacgagga agagctgcgc aagcacccaa tcaagcgctc tacagtgggt    660
tgggccacct cttcactgct tcctggtacc agtggtgggc gccagcgcag ggagctggac    720
cccatggaca tccgtggctc cattgtctac ctggagatcg acaaccggca atgtgtgcag    780
tcatcctcgc agtgcttcca gagtgccacc gatgtggctg ccttcctagg tgctcttgcg    840
tcacttggca gcctcaatat tccttacaag attgaggccg tgaagagtga gccggtggag    900
cctccgctgc cctcgcagct gcacctcatg ggaggggaa gcggaggcgg actgaacgac    960
atcttcgagg ctcagaaaat cgaatggcac gaaggtggcc caccacatca tcatcatcat   1020
cac                                                                 1023

<210> SEQ ID NO 8
<211> LENGTH: 882
<212> TYPE: DNA
<213> ORGANISM: Mus musculus

<400> SEQUENCE: 8
ggtggcgctg ggcgcgacat tcccccaccg cagattgagg aggcctgtga gctgcctgag     60
tgccaggtgg atgcaggcaa taaggtctgc aacctgcagt gtaataatca cgcatgtggc    120
tgggatggtg gcgactgctc cctcaacttc aatgaccccc ggaagaactg cacgcagtct    180
ctacagtgct ggaagtattt tagcgacggc cactgtgaca gccagtgcaa ctcggccggc    240
tgcctctttg atggcttcga ctgccagctc accgagggac agtgcaaccc cctgtatgac    300
cagtactgca aggaccactt cagtgatggc cactgcgacc agggctgtaa cagtgccgaa    360
tgtgagtggg atggcctaga ctgtgctgag catgtacccg agcggctggc agccggcacc    420
ctggtgctgg tggtgctgct tccacccgac cagctacgga caactccctt ccactttctg    480
cgggagctca gccacgtgct gcacaccaac gtggtcttca gcgtgatgc gcaaggccag    540 cagatgatct tcccgtacta tggccacgag gaagagctgc gcaagcaccc aatcaagcgc    600
tctacagtgg gttgggccac ctcttcactg cttcctggta ccagtggtgg gcgccagcgc    660
agggagctgg accccatgga catccgtggc tccattgtct acctggagat cgacaaccgg    720
caatgtgtgc agtcatcctc gcagtgcttc agagtgccac cgatgtggc tgccttccta    780 ggtgctcttg cgtcacttgg cagcctcaat attccttaca agattgaggc cgtgaagagt    840
gagccggtga gcctccgct gccctcgcag ctgcacctca tg                        882

<210> SEQ ID NO 9
<211> LENGTH: 564
<212> TYPE: PRT
<213> ORGANISM: Artificial Sequence
<220> FEATURE:
<223> OTHER INFORMATION: Synthetic peptide sequence

<400> SEQUENCE: 9

Met Gly Trp Ser Cys Ile Ile Leu Phe Leu Val Ala Thr Ala Thr Gly
1               5                   10                  15

Ala His Ser Gly Gly Ala Gly Arg Asp Ile Pro Pro Leu Ile Glu
            20                  25                  30

Glu Ala Cys Glu Leu Pro Glu Cys Gln Glu Asp Ala Gly Asn Lys Val
        35                  40                  45

Cys Ser Leu Gln Cys Asn Asn His Ala Cys Gly Trp Asp Gly Gly Asp
    50                  55                  60

Cys Ser Leu Asn Phe Asn Asp Pro Trp Lys Asn Cys Thr Gln Ser Leu
65                  70                  75                  80
```

```
Gln Cys Trp Lys Tyr Phe Ser Asp Gly His Cys Asp Ser Gln Cys Asn
                 85                  90                  95
Ser Ala Gly Cys Leu Phe Asp Gly Phe Asp Cys Gln Arg Ala Glu Gly
            100                 105                 110
Gln Cys Asn Pro Leu Tyr Asp Gln Tyr Cys Lys Asp His Phe Ser Asp
        115                 120                 125
Gly His Cys Asp Gln Gly Cys Asn Ser Ala Glu Cys Glu Trp Asp Gly
    130                 135                 140
Leu Asp Cys Ala Glu His Val Pro Glu Arg Leu Ala Ala Gly Thr Leu
145                 150                 155                 160
Val Val Val Val Leu Met Pro Pro Glu Gln Leu Arg Asn Ser Ser Phe
                165                 170                 175
His Phe Leu Arg Glu Leu Ser Arg Val Leu His Thr Asn Val Val Phe
            180                 185                 190
Lys Arg Asp Ala His Gly Gln Gln Met Ile Phe Pro Tyr Tyr Gly Arg
        195                 200                 205
Glu Glu Glu Leu Arg Lys His Pro Ile Lys Arg Ala Ala Glu Gly Trp
    210                 215                 220
Ala Ala Pro Glu Ala Leu Leu Gly Gln Val Lys Ala Ser Leu Leu Pro
225                 230                 235                 240
Gly Gly Gly Gly Gly Arg Arg Arg Glu Leu Asp Pro Met Asp
                245                 250                 255
Val Arg Gly Ser Ile Val Tyr Leu Glu Ile Asp Asn Arg Gln Cys Val
                260                 265                 270
Gln Ala Ser Ser Gln Cys Phe Gln Ser Ala Thr Asp Val Ala Ala Phe
            275                 280                 285
Leu Gly Ala Leu Ala Ser Leu Gly Ser Leu Asn Ile Pro Tyr Lys Ile
        290                 295                 300
Glu Ala Val Gln Ser Glu Thr Val Glu Pro Pro Pro Ala Gln Leu
305                 310                 315                 320
His Phe Met Gly Gly Gly Ser Gly Gly Gly Glu Pro Lys Ser
                325                 330                 335
Ser Asp Lys Thr His Thr Cys Pro Pro Cys Pro Ala Glu Leu Leu
            340                 345                 350
Gly Gly Pro Ser Val Phe Leu Phe Pro Pro Lys Pro Lys Asp Thr Leu
        355                 360                 365
Met Ile Ser Arg Thr Pro Glu Val Thr Cys Val Val Val Asp Val Ser
    370                 375                 380
His Glu Asp Pro Glu Val Lys Phe Asn Trp Tyr Val Asp Gly Val Glu
385                 390                 395                 400
Val His Asn Ala Lys Thr Lys Pro Arg Glu Glu Gln Tyr Asn Ser Thr
                405                 410                 415
Tyr Arg Val Val Ser Val Leu Thr Val Leu His Gln Asp Trp Leu Asn
            420                 425                 430
Gly Lys Glu Tyr Lys Cys Lys Val Ser Asn Lys Ala Leu Pro Ala Pro
        435                 440                 445
Ile Glu Lys Thr Ile Ser Lys Ala Lys Gly Gln Pro Arg Glu Pro Gln
    450                 455                 460
Val Tyr Thr Leu Pro Pro Ser Arg Glu Glu Met Thr Lys Asn Gln Val
465                 470                 475                 480
Ser Leu Thr Cys Leu Val Lys Gly Phe Tyr Pro Ser Asp Ile Ala Val
                485                 490                 495
```

-continued

```
Glu Trp Glu Ser Asn Gly Gln Pro Glu Asn Asn Tyr Lys Thr Thr Pro
            500                 505                 510

Pro Val Leu Asp Ser Asp Gly Ser Phe Phe Leu Tyr Ser Lys Leu Thr
        515                 520                 525

Val Asp Lys Ser Arg Trp Gln Gln Gly Asn Val Phe Ser Cys Ser Val
    530                 535                 540

Met His Glu Ala Leu His Asn His Tyr Thr Gln Lys Ser Leu Ser Leu
545                 550                 555                 560

Ser Pro Gly Lys

<210> SEQ ID NO 10
<211> LENGTH: 304
<212> TYPE: PRT
<213> ORGANISM: Macaca fascicularis

<400> SEQUENCE: 10

Gly Gly Ala Gly Arg Asp Ile Pro Pro Leu Ile Glu Glu Ala Cys
1               5                   10                  15

Glu Leu Pro Glu Cys Gln Glu Asp Ala Gly Asn Lys Val Cys Ser Leu
            20                  25                  30

Gln Cys Asn Asn His Ala Cys Gly Trp Asp Gly Gly Asp Cys Ser Leu
        35                  40                  45

Asn Phe Asn Asp Pro Trp Lys Asn Cys Thr Gln Ser Leu Gln Cys Trp
    50                  55                  60

Lys Tyr Phe Ser Asp Gly His Cys Asp Ser Gln Cys Asn Ser Ala Gly
65                  70                  75                  80

Cys Leu Phe Asp Gly Phe Asp Cys Gln Arg Ala Glu Gly Gln Cys Asn
                85                  90                  95

Pro Leu Tyr Asp Gln Tyr Cys Lys Asp His Phe Ser Asp Gly His Cys
            100                 105                 110

Asp Gln Gly Cys Asn Ser Ala Glu Cys Glu Trp Asp Gly Leu Asp Cys
        115                 120                 125

Ala Glu His Val Pro Glu Arg Leu Ala Ala Gly Thr Leu Val Val Val
    130                 135                 140

Val Leu Met Pro Pro Glu Gln Leu Arg Asn Ser Ser Phe His Phe Leu
145                 150                 155                 160

Arg Glu Leu Ser Arg Val Leu His Thr Asn Val Val Phe Lys Arg Asp
                165                 170                 175

Ala His Gly Gln Gln Met Ile Phe Pro Tyr Tyr Gly Arg Glu Glu Glu
            180                 185                 190

Leu Arg Lys His Pro Ile Lys Arg Ala Ala Glu Gly Trp Ala Ala Pro
        195                 200                 205

Glu Ala Leu Leu Gly Gln Val Lys Ala Ser Leu Leu Pro Gly Gly Gly
    210                 215                 220

Gly Gly Gly Arg Arg Arg Arg Glu Leu Asp Pro Met Asp Val Arg Gly
225                 230                 235                 240

Ser Ile Val Tyr Leu Glu Ile Asp Asn Arg Gln Cys Val Gln Ala Ser
                245                 250                 255

Ser Gln Cys Phe Gln Ser Ala Thr Asp Val Ala Ala Phe Leu Gly Ala
            260                 265                 270

Leu Ala Ser Leu Gly Ser Leu Asn Ile Pro Tyr Lys Ile Glu Ala Val
        275                 280                 285

Gln Ser Glu Thr Val Glu Pro Pro Pro Ala Gln Leu His Phe Met
    290                 295                 300
```

<210> SEQ ID NO 11
<211> LENGTH: 1692
<212> TYPE: DNA
<213> ORGANISM: Artificial Sequence
<220> FEATURE:
<223> OTHER INFORMATION: Synthetic nucleotide sequence

<400> SEQUENCE: 11

```
atgggatgga gctgtatcat cctcttcttg gtagcaacag ctacaggcgc gcactccggt    60
ggggccgggc gcgacatccc ccgccgctg atcgaggagg cgtgcgagct gcccgagtgc   120
caggaggacg cgggcaacaa ggtctgcagc ctgcagtgca acaaccacgc gtgcggctgg   180
gacggcggtg actgctccct caacttcaat gacccctgga agaactgcac gcagtctctg   240
cagtgctgga agtacttcag tgacggccac tgtgacagcc agtgcaactc agccggctgc   300
ctcttcgacg gctttgactg ccagcgtgcg gaaggccagt gcaaccccct gtacgaccag   360
tactgcaagg accacttcag cgacgggcac tgcgaccagg ctgcaacag cgcggagtgc   420
gagtgggacg ggctggactg tgcggagcat gtacccgaga ggctggcggc cggcacgctg   480
gtggtggtgg tgctgatgcc gccggagcag ctgcgcaaca gctccttcca cttcctgcgg   540
gagctcagcc gcgtgctgca caccaacgtg gtcttcaagc gtgacgcaca cggccagcag   600
atgatcttcc cctactacgg ccgcgaggag gagctgcgca agcacccat caagcgtgcc   660
gccgagggct gggccgcacc tgaagccctg ctgggccagt gaaggcctc gctgctccct   720
ggtggcggtg gaggtgggcg gcggcggagg gagctggacc ccatggacgt ccgcggctcc   780
atcgtctacc tggagattga caaccggcag tgtgtgcagg cctcctcgca gtgcttccag   840
agtgccaccg acgtggccgc attcctggga gcgctcgcct cgctgggcag cctcaacatc   900
ccctacaaga tcgaggccgt gcagagtgag accgtggagc cgcccccgcc ggcgcagctg   960
cacttcatgg aggggggcgg atccggcgga ggcggagagc ccaaatcttc tgacaaaact  1020
cacacatgcc caccgtgccc agcacctgaa ctcctggggg gaccgtcagt cttcctcttc  1080
cccccaaaac ccaaggacac cctcatgatc tcccggaccc ctgaggtcac atgcgtggtg  1140
gtggacgtga gccacgaaga ccctgaggtc aagttcaact ggtacgtgga cggcgtggag  1200
gtgcataatg ccaagacaaa gccgcgggag gagcagtaca acagcacgta ccgtgtggtc  1260
agcgtcctca ccgtcctgca ccaggactgg ctgaatggca aggagtacaa gtgcaaggtc  1320
tccaacaaag ccctcccagc ccccatcgag aaaaccatct ccaaagccaa agggcagccc  1380
cgagaaccac aggtgtacac cctgccccca tcccgggagg agatgaccaa gaaccaggtc  1440
agcctgacct gcctggtcaa aggcttctat cccagcgaca tcgccgtgga gtgggagagc  1500
aatgggcagc cggagaacaa ctacaagacc acgcctcccg tgctggactc cgacggctcc  1560
ttcttcctct atagcaagct caccgtggac aagagcaggt ggcagcaggg gaacgtcttc  1620
tcatgctccg tgatgcatga ggctctgcac aaccactaca cgcagaagag cctctccctg  1680
tccccgggta aa                                                      1692
```

<210> SEQ ID NO 12
<211> LENGTH: 912
<212> TYPE: DNA
<213> ORGANISM: Macaca fascicularis

<400> SEQUENCE: 12

```
ggtggggccg gcgcgacat cccccgccg ctgatcgagg aggcgtgcga gctgcccgag    60
tgccaggagg acgcgggcaa caaggtctgc agcctgcagt gcaacaacca cgcgtgcggc   120
```

```
tgggacggcg gtgactgctc cctcaacttc aatgacccct ggaagaactg cacgcagtct    180
ctgcagtgct ggaagtactt cagtgacggc cactgtgaca gccagtgcaa ctcagccggc    240
tgcctcttcg acggctttga ctgccagcgt gcggaaggcc agtgcaaccc cctgtacgac    300
cagtactgca aggaccactt cagcgacggg cactgcgacc agggctgcaa cagcgcggag    360
tgcgagtggg acgggctgga ctgtgcggag catgtacccg agaggctggc ggccggcacg    420
ctggtggtgg tggtgctgat gccgccggag cagctgcgca cagctccctt ccacttcctg    480
cgggagctca gccgcgtgct gcacaccaac gtggtcttca gcgtgacgc acacggccag     540 cagatgatct tccccctacta cggccgcgag gaggagctgc gcaagcaccc catcaagcgt    600
gccgccgagg gctgggccgc acctgaagcc ctgctgggcc aggtgaaggc ctcgctgctc    660
cctggtggcg gtggaggtgg gcggcggcg agggagctgg accccatgga cgtccgcggc     720
tccatcgtct acctggagat tgacaaccgg cagtgtgtgc aggcctcctc gcagtgcttc    780
cagagtgcca ccgacgtggc cgcattcctg ggagcgctcg cctcgctggg cagcctcaac    840
atcccctaca agatcgaggc cgtgcagagt gagaccgtgg agccgccccc gccggcgcag    900
ctgcacttca tg                                                        912

<210> SEQ ID NO 13
<211> LENGTH: 123
<212> TYPE: PRT
<213> ORGANISM: Artificial Sequence
<220> FEATURE:
<223> OTHER INFORMATION: Synthetic peptide sequence

<400> SEQUENCE: 13

Ala Val Gln Leu Val Glu Ser Gly Gly Gly Leu Val Gln Pro Gly Arg
1               5                   10                  15

Ser Leu Lys Leu Ser Cys Thr Ala Ser Gly Phe Thr Phe Ser Ser Phe
            20                  25                  30

Ala Met Ala Trp Val Arg Gln Ala Pro Thr Lys Gly Leu Glu Trp Val
        35                  40                  45

Ala Ser Ile Ser Tyr Gly Gly Ala Asp Thr Tyr Tyr Arg Asp Ser Val
    50                  55                  60

Lys Gly Arg Phe Thr Ile Ser Arg Asp Asn Ala Lys Ser Ser Leu Tyr
65                  70                  75                  80

Leu Gln Met Asp Ser Leu Arg Ser Glu Asp Thr Ser Thr Tyr Tyr Cys
                85                  90                  95

Ala Lys Asp Leu Pro Tyr Tyr Gly Tyr Thr Pro Phe Met Asp Ala
            100                 105                 110

Trp Gly Gln Gly Thr Ser Val Thr Val Ser Ser
        115                 120

<210> SEQ ID NO 14
<211> LENGTH: 369
<212> TYPE: DNA
<213> ORGANISM: Artificial Sequence
<220> FEATURE:
<223> OTHER INFORMATION: Synthetic nucleotide sequence

<400> SEQUENCE: 14
gcggtacagt tggtggagtc tgggggaggc ttagtgcagc ctggaaggtc cttgaaactc     60
tcctgtacag cctctggatt cactttcagt agctttgcaa tggcctgggt ccgccaggct    120
ccaacgaagg ggctggagtg ggtcgcatcc attagttatg gtggtgctga cacttactat    180
```

```
cgagactccg tgaagggccg attcactatc tccagagata atgcaaaaag cagcctatat      240
ttgcaaatgg acagtctgag gtctgaggac acgtccactt attactgtgc aaaagacctt      300
ccatactacg gatatacccc ctttgttatg gatgcctggg gtcagggaac ttcagtcact      360
gtctcctca                                                              369

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 15

Ser Phe Ala Met Ala
1               5

<210> SEQ ID NO 16
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 16

Gly Phe Thr Phe Ser Ser Phe Ala Met Ala
1               5                   10

<210> SEQ ID NO 17
<211> LENGTH: 15
<212> TYPE: DNA
<213> ORGANISM: Artificial Sequence
<220> FEATURE:
<223> OTHER INFORMATION: Synthetic nucleotide sequence

<400> SEQUENCE: 17
tccttcgcca tggcc                                                       15

<210> SEQ ID NO 18
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 18
ggattcacct ttagttcctt cgccatggcc                                       30

<210> SEQ ID NO 19
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 19

Ser Ile Ser Tyr Gly Gly Ala Asp Thr Tyr Tyr Arg Asp Ser Val Lys
1               5                   10                  15
Gly

<210> SEQ ID NO 20
<211> LENGTH: 6
<212> TYPE: PRT
<213> ORGANISM: Artificial Sequence
<220> FEATURE:
```

<223> OTHER INFORMATION: Synthetic peptide sequence

<400> SEQUENCE: 20

Ser Tyr Gly Gly Ala Asp
1               5

<210> SEQ ID NO 21
<211> LENGTH: 51
<212> TYPE: DNA
<213> ORGANISM: Artificial Sequence
<220> FEATURE:
<223> OTHER INFORMATION: Synthetic nucleotide sequence

<400> SEQUENCE: 21
tccatctcct atggaggcgc tgacacctac taccgggact ccgtgaaggg c        51

<210> SEQ ID NO 22
<211> LENGTH: 17
<212> TYPE: DNA
<213> ORGANISM: Artificial Sequence
<220> FEATURE:
<223> OTHER INFORMATION: Synthetic nucleotide sequence

<400> SEQUENCE: 22
cctatggagg cgctgac                                               17

<210> SEQ ID NO 23
<211> LENGTH: 14
<212> TYPE: PRT
<213> ORGANISM: Artificial Sequence
<220> FEATURE:
<223> OTHER INFORMATION: Synthetic peptide sequence

<400> SEQUENCE: 23

Asp Leu Pro Tyr Tyr Gly Tyr Thr Pro Phe Val Met Asp Ala
1               5                   10

<210> SEQ ID NO 24
<211> LENGTH: 42
<212> TYPE: DNA
<213> ORGANISM: Artificial Sequence
<220> FEATURE:
<223> OTHER INFORMATION: Synthetic nucleotide sequence

<400> SEQUENCE: 24
gatctgccct actacggcta cacccccttc gtgatggacg cc                   42

<210> SEQ ID NO 25
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 25

Asp Ile Met Leu Thr Gln Ser Pro Pro Thr Leu Ser Val Thr Pro Gly
1               5                   10                  15

Glu Thr Ile Ser Leu Ser Cys Arg Ala Ser Gln Arg Ile Asn Thr Asp
            20                  25                  30

Leu His Trp Tyr Gln Gln Lys Pro Asn Glu Ser Pro Arg Val Leu Ile
        35                  40                  45

Lys Phe Ala Ser Gln Thr Ile Ser Gly Val Pro Ser Arg Phe Ser Gly
    50                  55                  60

Ser Gly Ser Gly Thr Asp Phe Thr Leu Asn Ile Asn Arg Val Glu Pro

```
                65                  70                  75                  80
Glu Asp Phe Ser Val Tyr Tyr Cys Gln Gln Ser Asn Ser Trp Pro Tyr
                    85                  90                  95
Thr Phe Gly Ala Gly Thr Lys Leu Glu Leu Lys
            100                 105
```

<210> SEQ ID NO 26
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 26

```
gacatcatgc tgactcagtc tccacctacc ctgtctgtaa ctccaggaga gaccatcagt      60
ctctcctgca gggccagtca gagaattaac actgacttac attggtatca gcaaaaacca    120
aatgagtctc caagggttct catcaaattt gcttcccaga ccatctctgg agtcccctcc    180
aggttcagtg gcagtggatc aggacagat ttcactctca atattaacag agtagagcct     240
gaagattttt cagtttatta ctgtcaacag agtaatagct ggccatacac gtttggcgct    300
gggaccaagc tggaactgaa a                                              321
```

<210> SEQ ID NO 27
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 27

```
Arg Ala Ser Gln Arg Ile Asn Thr Asp Leu His
1               5                   10
```

<210> SEQ ID NO 28
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 28

```
cgggcctccc agcggatcaa caccgacctg cac                                  33
```

<210> SEQ ID NO 29
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 29

```
Phe Ala Ser Gln Thr Ile Ser
1               5
```

<210> SEQ ID NO 30
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 30

```
ttcgccagcc agaccatctc c                                               21
```

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 31

Gln Gln Ser Asn Ser Trp Pro Tyr Thr
1               5

<210> SEQ ID NO 32
<211> LENGTH: 27
<212> TYPE: DNA
<213> ORGANISM: Artificial Sequence
<220> FEATURE:
<223> OTHER INFORMATION: Synthetic nucleotide sequence

<400> SEQUENCE: 32
cagcagtcca actcctggcc ctacacc                                           27

<210> SEQ ID NO 33
<211> LENGTH: 119
<212> TYPE: PRT
<213> ORGANISM: Artificial Sequence
<220> FEATURE:
<223> OTHER INFORMATION: Synthetic peptide sequence

<400> SEQUENCE: 33

Glu Val Gln Leu Val Glu Ser Gly Gly Gly Leu Val Gln Pro Gly Arg
1               5                   10                  15

Ser Leu Lys Val Ser Cys Leu Ala Ser Gly Phe Thr Phe Ser His Tyr
            20                  25                  30

Gly Met Asn Trp Ile Arg Gln Ala Pro Gly Lys Gly Leu Asp Trp Val
        35                  40                  45

Ala Ser Ile Ser Arg Ser Gly Ser Tyr Ile Arg Tyr Val Asp Thr Val
    50                  55                  60

Lys Gly Arg Phe Thr Val Ser Arg Asp Ile Ala Lys Asn Thr Leu Tyr
65                  70                  75                  80

Leu Gln Met Thr Ser Leu Arg Ser Glu Asp Thr Ala Leu Tyr Tyr Cys
                85                  90                  95

Ala Arg Glu Gly Gln Phe Gly Asp Tyr Phe Glu Tyr Trp Gly Gln Gly
            100                 105                 110

Val Met Val Thr Val Ser Ser
        115

<210> SEQ ID NO 34
<211> LENGTH: 357
<212> TYPE: DNA
<213> ORGANISM: Artificial Sequence
<220> FEATURE:
<223> OTHER INFORMATION: Synthetic nucleotide sequence

<400> SEQUENCE: 34
gaggtgcagc tggtggagtc tggaggaggc ttagtgcagc ctggaaggtc cctgaaagtc      60
tcctgtttag cctctggatt cactttcagt cactatggaa tgaactggat tcgccaggct     120
ccagggaagg ggctggactg ggttgcatct attagtagga gtggcagtta catccgctat     180
gtagacacag tgaagggccg attcaccgtc tccagagaca ttgccaagaa caccctgtac     240
ctgcaaatga ccagtctgag gtctgaagac actgccttgt attactgtgc aagagaggga     300

```
caattcgggg actactttga gtactggggc caaggagtca tggtcacagt ctcctca        357
```

<210> SEQ ID NO 35
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 35

His Tyr Gly Met Asn
1               5

<210> SEQ ID NO 36
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 36

Gly Phe Thr Phe Ser His Tyr Gly Met Asn
1               5                   10

<210> SEQ ID NO 37
<211> LENGTH: 15
<212> TYPE: DNA
<213> ORGANISM: Artificial Sequence
<220> FEATURE:
<223> OTHER INFORMATION: Synthetic nucleotide sequence

<400> SEQUENCE: 37

```
cactatggaa tgaac                                                       15
```

<210> SEQ ID NO 38
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 38

```
ggattcactt tcagtcacta tggaatgaac                                       30
```

<210> SEQ ID NO 39
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 39

Ser Ile Ser Arg Ser Gly Ser Tyr Ile Arg Tyr Val Asp Thr Val Lys
1               5                   10                  15

Gly

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 40

Ser Arg Ser Gly Ser Tyr

```
<210> SEQ ID NO 41
<211> LENGTH: 51
<212> TYPE: DNA
<213> ORGANISM: Artificial Sequence
<220> FEATURE:
<223> OTHER INFORMATION: Synthetic nucleotide sequence

<400> SEQUENCE: 41
tctattagta ggagtggcag ttacatccgc tatgtagaca cagtgaaggg c          51

<210> SEQ ID NO 42
<211> LENGTH: 18
<212> TYPE: DNA
<213> ORGANISM: Artificial Sequence
<220> FEATURE:
<223> OTHER INFORMATION: Synthetic nucleotide sequence

<400> SEQUENCE: 42
agtaggagtg gcagttac                                               18

<210> SEQ ID NO 43
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 43

Glu Gly Gln Phe Gly Asp Tyr Phe Glu Tyr
1               5                   10

<210> SEQ ID NO 44
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 44
gagggacaat tcggggacta ctttgagtac                                  30

<210> SEQ ID NO 45
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 45

Asp Ile Met Leu Thr Gln Ser Pro Ala Thr Leu Ser Val Thr Pro Gly
1               5                   10                  15

Glu Arg Ile Ser Leu Ser Cys Arg Ala Ser Gln Lys Ile Ser Thr Asn
            20                  25                  30

Leu His Trp Tyr Gln Gln Lys Pro Asn Glu Ser Pro Arg Ile Leu Ile
        35                  40                  45

Lys Tyr Ala Ser Gln Thr Ile Ser Gly Ile Pro Ser Arg Phe Ser Gly
    50                  55                  60

Ser Gly Ser Gly Thr Asp Phe Thr Leu His Ile Asn Thr Val Glu Pro
65                  70                  75                  80

Glu Asp Phe Ser Val Tyr Tyr Cys Gln Gln Thr Asn Ser Trp Pro Leu
                85                  90                  95
```

Thr Phe Gly Ser Gly Thr Lys Leu Glu Ile Lys
            100                 105

<210> SEQ ID NO 46
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 46
gacatcatgc tgactcagtc tccagctacc ctgtctgtaa ctccaggaga gagaatcagt    60
ctctcctgca gggccagtca gaaaattagc actaacttac attggtatca gcaaaagcca   120
aatgagtctc caaggattct catcaaatat gcttcccaga ccatctctgg aatcccctcc   180
aggttcagtg gcagtggatc agggacagat ttcactctcc atattaacac agtgagagcct   240 gaagattttt cagtttatta ctgtcaacag actaatagtt ggccgctcac gttcggttct   300
gggaccaagc tggagatcaa g                                              321

<210> SEQ ID NO 47
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 47

Arg Ala Ser Gln Lys Ile Ser Thr Asn Leu His
1               5                   10

<210> SEQ ID NO 48
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 48
agggccagtc agaaaattag cactaactta cat                                 33

<210> SEQ ID NO 49
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 49

Tyr Ala Ser Gln Thr Ile Ser
1               5

<210> SEQ ID NO 50
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 50
tatgcttccc agaccatctc t                                              21

<210> SEQ ID NO 51
<211> LENGTH: 9
<212> TYPE: PRT

<213> ORGANISM: Artificial Sequence
<220> FEATURE:
<223> OTHER INFORMATION: Synthetic peptide sequence

<400> SEQUENCE: 51

Gln Gln Thr Asn Ser Trp Pro Leu Thr
1               5

<210> SEQ ID NO 52
<211> LENGTH: 27
<212> TYPE: DNA
<213> ORGANISM: Artificial Sequence
<220> FEATURE:
<223> OTHER INFORMATION: Synthetic nucleotide sequence

<400> SEQUENCE: 52
caacagacta atagttggcc gctcacg                                       27

<210> SEQ ID NO 53
<211> LENGTH: 119
<212> TYPE: PRT
<213> ORGANISM: Artificial Sequence
<220> FEATURE:
<223> OTHER INFORMATION: Synthetic peptide sequence

<400> SEQUENCE: 53

Glu Val Gln Leu Val Glu Ser Gly Gly Gly Leu Val Gln Pro Gly Arg
1               5                   10                  15

Ser Leu Lys Leu Ser Cys Leu Ala Ser Gly Phe Thr Phe Ser His Tyr
            20                  25                  30

Gly Val Asn Trp Ile Arg Gln Ala Pro Gly Lys Gly Leu Glu Trp Ile
        35                  40                  45

Ala Ser Ile Ser Arg Ser Ser Ser Tyr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Leu Thr Ser Leu Arg Ser Glu Asp Thr Ala Leu Tyr Tyr Cys
                85                  90                  95

Ala Arg Glu Gly Gln Phe Gly Asp Tyr Phe Glu Tyr Trp Gly Arg Gly
            100                 105                 110

Val Met Val Thr Val Ser Ser
        115

<210> SEQ ID NO 54
<211> LENGTH: 357
<212> TYPE: DNA
<213> ORGANISM: Artificial Sequence
<220> FEATURE:
<223> OTHER INFORMATION: Synthetic nucleotide sequence

<400> SEQUENCE: 54
gaggtgcagc tagtggagtc tggaggaggc ttagtgcagc ctggaaggtc cctgaaactc      60
tcctgtttag cctctggatt cactttcagt cactatggag tgaactggat tcgccaggct    120
ccagggaagg ggctggaatg gattgcatct attagtagaa gtagcagtta catctactat    180
gcagacacag tgaagggccg attcaccatc tccagagaca tgccaagaa caccctgttc     240 ctgcaattga ccagtctgag gtctgaagac actgccttgt attactgtgc aagagagggg    300
caattcgggg actactttga atactggggc cgaggagtca tggtcacagt ctcctca       357

<210> SEQ ID NO 55

<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 55

Asp Ile Ile Leu Thr Gln Ser Pro Ala Ala Leu Ser Val Thr Pro Gly
1               5                   10                  15
Glu Ser Ile Ser Leu Ser Cys Arg Ala Ser Gln Ser Ile Asn Thr Asn
            20                  25                  30
Leu His Trp Tyr Gln Gln Lys Pro Asn Glu Ser Pro Arg Val Leu Ile
        35                  40                  45
Lys Tyr Ala Ser Gln Thr Ile Ser Gly Ile Pro Ser Arg Phe Ser Gly
    50                  55                  60
Ser Gly Ser Gly Thr Asp Phe Thr Leu Asn Ile Asn Arg Val Glu Pro
65                  70                  75                  80
Glu Asp Phe Ser Val Tyr Tyr Cys Gln Gln Ser Asn Ser Trp Pro Leu
                85                  90                  95
Thr Phe Gly Ser Gly Thr Lys Leu Glu Ile Lys
            100                 105

<210> SEQ ID NO 56
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 56
gacatcatac tgactcagtc tccagctgcc ctgtctgtaa ctccaggaga gagcatcagt      60
ctctcctgca gggccagtca gagtattaac actaacttgc attggtatca gcaaaaacca     120
aatgagtctc caagggttct catcaaatat gcttcccaga ccatctctgg aatccccctcc   180
aggttcagtg gcagtggatc aggacagat ttcactctca atattaacag agtagagcct     240
gaagattttt cagtttatta ctgtcaacag agtaatagct ggccgctcac gttcggttct    300
gggaccaagc tggagatcaa a                                              321

<210> SEQ ID NO 57
<211> LENGTH: 119
<212> TYPE: PRT
<213> ORGANISM: Artificial Sequence
<220> FEATURE:
<223> OTHER INFORMATION: Synthetic peptide sequence

<400> SEQUENCE: 57

Glu Val Gln Leu Val Glu Ser Gly Gly Gly Leu Val Gln Pro Gly Arg
1               5                   10                  15
Ser Leu Lys Leu Ser Cys Leu Ala Ser Gly Phe Thr Phe Ser His Tyr
            20                  25                  30
Gly Met Asn Trp Ile Arg Gln Ala Pro Gly Lys Gly Leu Glu Trp Ile
        35                  40                  45
Thr Ser Ile Thr Ser Ser Ser Tyr Ile Tyr Tyr Ala Asp Thr Val
    50                  55                  60
Lys Gly Arg Phe Thr Ile Ser Arg Asp Asn Ala Lys Asn Thr Leu Tyr
65                  70                  75                  80
Leu Gln Met Thr Ser Leu Arg Ser Glu Asp Thr Ala Leu Tyr Tyr Cys
                85                  90                  95

Ala Arg Glu Gly Gln Phe Gly Asp Tyr Phe Asp Tyr Trp Gly Gln Gly
            100                 105                 110

Val Met Val Thr Val Ser Ser
        115

<210> SEQ ID NO 58
<211> LENGTH: 357
<212> TYPE: DNA
<213> ORGANISM: Artificial Sequence
<220> FEATURE:
<223> OTHER INFORMATION: Synthetic nucleotide sequence

<400> SEQUENCE: 58
gaggtgcagc tggtggagtc tggaggaggc ttagtgcagc ctggaaggtc cctgaaactc        60
tcctgtttag cctctggatt cactttcagt cactatggaa tgaactggat tcgccaggct       120
ccagggaagg ggctggagtg gattacatct attactagta gtagcagtta catctactat       180
gcagacacag tgaagggccg attcaccatc tccagagaca atgccaagaa caccctgtac       240
ctgcaaatga ccagtctgag gtctgaagac actgccttgt attactgtgc aagagagggg       300
caattcgggg actactttga ttactggggc caaggagtca tggtcacagt ctcctca         357

<210> SEQ ID NO 59
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 59

Asp Ile Met Leu Thr Gln Ser Pro Ala Thr Leu Ser Val Thr Pro Gly
1               5                   10                  15

Glu Ser Ile Ser Leu Ser Cys Arg Ala Ser Gln Ser Ile Asn Thr Asn
            20                  25                  30

Leu His Trp Tyr Gln Gln Lys Pro Asn Glu Ser Pro Arg Val Leu Ile
        35                  40                  45

Lys Tyr Ala Ser Gln Thr Ile Ser Gly Ile Pro Ser Arg Phe Ser Gly
    50                  55                  60

Ser Gly Ser Gly Thr Asp Phe Thr Leu Asn Ile Asn Arg Val Glu Pro
65                  70                  75                  80

Glu Asp Phe Ser Val Tyr Tyr Cys Gln Gln Ser Asn Ser Trp Pro Leu
                85                  90                  95

Thr Phe Gly Ser Gly Thr Lys Leu Glu Ile Lys
            100                 105

<210> SEQ ID NO 60
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 60
gacatcatgc tgactcagtc tccagctacc ctgtctgtaa ctccaggaga gagcatcagt        60
ctctcctgca gggccagtca gagtattaac actaacttac attggtatca gcaaaaacca       120
aatgagtctc caagggttct catcaaatat gcttcccaga ccatctctgg aatcccctcc       180
aggttcagtg gcagtggatc aggacagat tcactctca atattaacag agtagagcct         240
gaagattttt cagtttatta ctgtcaacag agtaatagct ggccgctcac gttcggttct       300

```
gggaccaagc tggagatcaa a                                              321
```

<210> SEQ ID NO 61
<211> LENGTH: 119
<212> TYPE: PRT
<213> ORGANISM: Artificial Sequence
<220> FEATURE:
<223> OTHER INFORMATION: Synthetic peptide sequence

<400> SEQUENCE: 61

```
Glu Val Gln Leu Val Glu Ser Gly Gly Gly Leu Val Gln Pro Gly Arg
1               5                   10                  15

Ser Leu Lys Leu Ser Cys Leu Ala Ser Gly Phe Thr Phe Ser His Tyr
            20                  25                  30

Gly Met Asn Trp Ile Arg Gln Ala Pro Gly Lys Gly Leu Glu Trp Ile
        35                  40                  45

Thr Ser Ile Thr Ser Ser Ser Tyr Ile Tyr Tyr Ala Asp Thr Val
    50                  55                  60

Lys Gly Arg Phe Thr Ile Ser Arg Asp Asn Ala Lys Asn Thr Leu Tyr
65                  70                  75                  80

Leu Gln Met Thr Ser Leu Arg Ser Glu Asp Thr Ala Leu Tyr Tyr Cys
                85                  90                  95

Ala Arg Glu Gly Gln Phe Gly Asp Tyr Phe Asp Tyr Trp Gly Gln Gly
            100                 105                 110

Val Met Val Thr Val Ser Ser
        115
```

<210> SEQ ID NO 62
<211> LENGTH: 357
<212> TYPE: DNA
<213> ORGANISM: Artificial Sequence
<220> FEATURE:
<223> OTHER INFORMATION: Synthetic nucleotide sequence

<400> SEQUENCE: 62

```
gaggtgcagc tggtggagtc tggaggaggc ttagtgcagc ctggaaggtc cctgaaactc    60
tcctgtttag cctctggatt cactttcagt cactatggaa tgaactggat tcgccaggct   120
ccagggaagg ggctggagtg gattacatct attactagta gtagcagtta catctactat   180
gcagacacag tgaagggccg attcaccatc tccagagaca atgccaagaa caccctgtac   240
ctgcaaatga ccagtctgag gtctgaagac actgccttgt attactgtgc aagagagggg   300
caattcgggg actactttga ttactggggc caaggagtca tggtcacagt ctcctca      357
```

<210> SEQ ID NO 63
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 63

```
Asp Ile Met Leu Thr Gln Ser Pro Ala Thr Leu Ser Val Thr Pro Gly
1               5                   10                  15

Glu Ser Ile Ser Leu Ser Cys Arg Ala Ser Gln Ser Ile Asn Thr Asn
            20                  25                  30

Leu His Trp Tyr Gln Gln Lys Pro Asn Glu Ser Pro Arg Val Leu Ile
        35                  40                  45

Lys Tyr Ala Ser Gln Thr Ile Ser Gly Ile Pro Ser Arg Phe Ser Gly
    50                  55                  60
```

Ser Gly Ser Gly Thr Asp Phe Thr Leu Asn Ile Asn Arg Val Glu Pro
65                  70                  75                  80

Glu Asp Phe Ser Val Tyr Tyr Cys Gln Gln Ser Asn Ser Trp Pro Leu
                85                  90                  95

Thr Phe Gly Ser Gly Thr Lys Leu Glu Ile Lys
            100                 105

<210> SEQ ID NO 64
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 64
gacatcatgc tgactcagtc tccagctacc ctgtctgtaa ctccaggaga gagcatcagt    60
ctctcctgca gggccagtca gagtattaac actaacttac attggtatca gcaaaaacca   120
aatgagtctc caaggggttct catcaaatat gcttcccaga ccatctctgg aatcccctcc   180
aggttcagtg gcagtggatc agggacagat ttcactctca atattaacag agtagagcct   240
gaagattttt cagtttatta ctgtcaacag agtaatagct ggccgctcac gttcggttct   300
gggaccaagc tggagatcaa a                                            321

<210> SEQ ID NO 65
<211> LENGTH: 116
<212> TYPE: PRT
<213> ORGANISM: Artificial Sequence
<220> FEATURE:
<223> OTHER INFORMATION: Synthetic peptide sequence

<400> SEQUENCE: 65

Gln Val Gln Val Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

His Val Ser Trp Val Arg Gln Pro Pro Gly Lys Gly Leu Glu Trp Met
        35                  40                  45

Gly Ala Ile Trp Thr Gly Gly Ser Thr Ala Tyr Asn Ser Leu Leu Lys
    50                  55                  60

Ser Arg Leu Ser Ile Ser Arg Asp Ile Ser Lys Ser Gln Val Phe Leu
65                  70                  75                  80

Lys Met Asn Ser Leu Gln Thr Glu Asp Thr Ala Thr Tyr Tyr Cys Ala
                85                  90                  95

Arg Ala Asp Phe Tyr Val Met Asp Ala Trp Gly Gln Gly Ala Ser Val
            100                 105                 110

Thr Val Ser Ser
        115

<210> SEQ ID NO 66
<211> LENGTH: 348
<212> TYPE: DNA
<213> ORGANISM: Artificial Sequence
<220> FEATURE:
<223> OTHER INFORMATION: Synthetic nucleotide sequence

<400> SEQUENCE: 66
caggtgcagg tgaaggagtc aggacctggt ctggtgcagc cctcacagac tttgtctctc    60
acctgcactg tctctgggtt ctcactaacc agctatcatg taagctgggt tcgccagcct   120

```
ccaggaaaag gtctggagtg gatgggagca atatggactg gtggaagcac agcatataat    180
tcacttctca aatcccgact gagcatcagc agggacatct ccaagagcca agttttctta    240
aaaatgaaca gtctgcaaac tgaagacaca gccacttact actgtgccag agccgatttc    300
tatgttatgg atgcctgggg tcaaggagct tcagtcactg tctcctca                 348
```

<210> SEQ ID NO 67
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 67

Asp Ile Met Leu Thr Gln Ser Pro Val Thr Leu Ser Val Ser Pro Gly
1               5                   10                  15

Glu Ser Ile Ser Leu Ser Cys Arg Ala Ser Gln Ser Ile Ser Thr Asp
            20                  25                  30

Leu His Trp Tyr Gln Gln Lys Pro Asn Glu Ser Pro Arg Val Leu Ile
        35                  40                  45

Lys Tyr Gly Ser Gln Thr Ile Ser Gly Ile Pro Ser Arg Phe Ser Gly
    50                  55                  60

Ser Gly Ser Gly Thr Asp Phe Thr Leu Asn Ile Asn Arg Val Glu Pro
65                  70                  75                  80

Glu Asp Phe Ser Val Tyr Tyr Cys Gln Gln Ser Asn Ser Trp Pro Trp
                85                  90                  95

Thr Phe Gly Gly Gly Thr Lys Leu Glu Leu Lys
            100                 105

<210> SEQ ID NO 68
<211> LENGTH: 320
<212> TYPE: DNA
<213> ORGANISM: Artificial Sequence
<220> FEATURE:
<223> OTHER INFORMATION: Synthetic nucleotide sequence

<400> SEQUENCE: 68

```
acatcatgct gactcagtct ccagttaccc tgtctgtgtc tccaggagag agcatcagtc    60
tctcctgcag ggccagtcag agtattagca ctgacttgca ttggtatcag caaaaaccaa   120
atgagtctcc aagggttctc atcaaatatg gttcccagac catctctgga atcccctcca   180
ggttcagtgg cagtggatca gggacagatt tcactctcaa tattaacaga gtagagcctg   240
aagatttttc agtttattac tgtcagcaga gtaatagctg gccatggaca ttcggtggag   300
gcaccaagct ggaattgaaa                                                320
```

<210> SEQ ID NO 69
<211> LENGTH: 123
<212> TYPE: PRT
<213> ORGANISM: Artificial Sequence
<220> FEATURE:
<223> OTHER INFORMATION: Synthetic peptide sequence

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ala Trp Val Arg Gln Ala Pro Gly Lys Gly Leu Glu Trp Val

```
                  35                  40                  45
Ala Ser Ile Ser Tyr Gly Gly Ala Asp Thr Tyr Tyr Arg Asp Ser Val
         50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Asp Leu Pro Tyr Tyr Gly Tyr Thr Pro Phe Val Met Asp Ala
            100                 105                 110
Trp Gly Gln Gly Thr Leu Val Thr Val Ser Ser
            115                 120
```

<210> SEQ ID NO 70
<211> LENGTH: 369
<212> TYPE: DNA
<213> ORGANISM: Artificial Sequence
<220> FEATURE:
<223> OTHER INFORMATION: Synthetic nucleotide sequence

<400> SEQUENCE: 70

```
gaggtgcagc tggtggagtc tgggggaggc ttggtccagc ctggggggtc cctgagactc      60
tcctgtgcag cctctggatt cacctttagt tccttcgcca tggcctgggt ccgccaggct     120
ccagggaagg gctggagtg gtggcctcc atctcctatg gaggcgctga cacctactac       180
cgggactccg tgaagggccg attcaccatc tccagagaca cgccaagaa ctcactgtat      240
ctgcaaatga acagcctgag agccgaggac acggctgtgt attactgtgc gagagatctg     300
ccctactacg gctacacccc cttcgtgatg gacgcctggg gccagggaac cctggtcacc     360
gtctcctca                                                             369
```

<210> SEQ ID NO 71
<211> LENGTH: 123
<212> TYPE: PRT
<213> ORGANISM: Artificial Sequence
<220> FEATURE:
<223> OTHER INFORMATION: Synthetic peptide sequence

<400> SEQUENCE: 71

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Phe
             20                  25                  30
Ala Met Ala Trp Val Arg Gln Ala Pro Gly Lys Gly Leu Glu Trp Val
         35                  40                  45
Ala Ser Ile Ser Tyr Gly Gly Ala Asp Thr Tyr Tyr Arg Asp Ser Val
     50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Lys Asp Leu Pro Tyr Tyr Gly Tyr Thr Pro Phe Val Met Asp Ala
            100                 105                 110
Trp Gly Gln Gly Thr Leu Val Thr Val Ser Ser
            115                 120
```

<210> SEQ ID NO 72
<211> LENGTH: 369
<212> TYPE: DNA

<213> ORGANISM: Artificial Sequence
<220> FEATURE:
<223> OTHER INFORMATION: Synthetic nucleotide sequence

<400> SEQUENCE: 72

```
gaggtgcagc tggtggagtc tgggggaggc ttggtccagc ctgggggtc cctgagactc      60 tcctgtgcag cctctggatt cacctttagt tccttcgcca tggcctgggt ccgccaggct    120
ccagggaagg ggctggagtg ggtggcctcc atctcctatg gaggcgctga cacctactac    180
cgggactccg tgaagggccg attcaccatc tccagagaca acgccaagaa ctcactgtat    240
ctgcaaatga acagcctgag agccgaggac acggctgtgt attactgtgc gaaggatctg    300
ccctactacg gctacacccc cttcgtgatg gacgcctggg gccagggaac cctggtcacc    360
gtctcctca                                                            369
```

<210> SEQ ID NO 73
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 73

Ser Phe Ala Met Ala
1               5

<210> SEQ ID NO 74
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 74

Gly Phe Thr Phe Ser Ser Phe Ala Met Ala
1               5                   10

<210> SEQ ID NO 75
<211> LENGTH: 15
<212> TYPE: DNA
<213> ORGANISM: Artificial Sequence
<220> FEATURE:
<223> OTHER INFORMATION: Synthetic nucleotide sequence

<400> SEQUENCE: 75

```
tccttcgcca tggcc                                                      15
```

<210> SEQ ID NO 76
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 76

```
ggattcacct ttagttcctt cgccatggcc                                      30
```

<210> SEQ ID NO 77
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 77

```
Ser Ile Ser Tyr Gly Gly Ala Asp Thr Tyr Tyr Arg Asp Ser Val Lys
1               5                   10                  15
Gly

<210> SEQ ID NO 78
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 78

Ser Tyr Gly Gly Ala Asp
1               5

<210> SEQ ID NO 79
<211> LENGTH: 51
<212> TYPE: DNA
<213> ORGANISM: Artificial Sequence
<220> FEATURE:
<223> OTHER INFORMATION: Synthetic nucleotide sequence

<400> SEQUENCE: 79
tccatctcct atggaggcgc tgacacctac taccgggact ccgtgaaggg c          51

<210> SEQ ID NO 80
<211> LENGTH: 17
<212> TYPE: DNA
<213> ORGANISM: Artificial Sequence
<220> FEATURE:
<223> OTHER INFORMATION: Synthetic nucleotide sequence

<400> SEQUENCE: 80
cctatggagg cgctgac                                                17

<210> SEQ ID NO 81
<211> LENGTH: 14
<212> TYPE: PRT
<213> ORGANISM: Artificial Sequence
<220> FEATURE:
<223> OTHER INFORMATION: Synthetic peptide sequence

<400> SEQUENCE: 81

Asp Leu Pro Tyr Tyr Gly Tyr Thr Pro Phe Val Met Asp Ala
1               5                   10

<210> SEQ ID NO 82
<211> LENGTH: 42
<212> TYPE: DNA
<213> ORGANISM: Artificial Sequence
<220> FEATURE:
<223> OTHER INFORMATION: Synthetic nucleotide sequence

<400> SEQUENCE: 82
gatctgccct actacggcta cacccccttc gtgatggacg cc                    42

<210> SEQ ID NO 83
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 83

Asp Ile Gln Met Thr Gln Ser Pro Ser Ser Leu Ser Ala Ser Val Gly
```

```
              1               5                  10                 15
Asp Arg Val Thr Ile Thr Cys Arg Ala Ser Gln Arg Ile Asn Thr Asp
                20                  25                 30

Leu His Trp Tyr Gln Gln Lys Pro Gly Lys Ala Pro Lys Leu Leu Ile
            35                  40                 45

Tyr Phe Ala Ser Gln Thr Ile Ser Gly Val Pro Ser Arg Phe Ser Gly
        50                  55                 60

Ser Gly Ser Gly Thr Asp Phe Thr Leu Thr Ile Ser Ser Leu Gln Pro
65                  70                 75                 80

Glu Asp Phe Ala Thr Tyr Tyr Cys Gln Gln Ser Asn Ser Trp Pro Tyr
                85                 90                 95

Thr Phe Gly Gln Gly Thr Lys Leu Glu Ile Lys
                100                 105
```

<210> SEQ ID NO 84
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 84
gacatccaga tgacccagtc tccatcctcc ctgtctgcat ctgtaggaga cagagtcacc    60
atcacttgcc gggcctccca gcggatcaac accgacctgc actggtatca gcagaaacca   120
gggaaagccc ctaagctcct gatctatttc gccagccaga ccatctccgg ggtcccatca   180
aggttcagtg gcagtggatc tgggacagat ttcactctca ccatcagcag tctgcaacct   240
gaagattttg caacttacta ctgtcagcag tccaactcct ggccctacac ctttggccag   300
gggaccaagc tggagatcaa a                                             321

<210> SEQ ID NO 85
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 85

```
Asp Ile Gln Leu Thr Gln Ser Pro Ser Ser Leu Ser Ala Ser Val Gly
1               5                  10                 15

Asp Arg Val Thr Ile Thr Cys Arg Ala Ser Gln Arg Ile Asn Thr Asp
                20                  25                 30

Leu His Trp Tyr Gln Gln Lys Pro Gly Lys Ala Pro Lys Val Leu Ile
            35                  40                 45

Lys Phe Ala Ser Gln Thr Ile Ser Gly Val Pro Ser Arg Phe Ser Gly
        50                  55                 60

Ser Gly Ser Gly Thr Asp Phe Thr Leu Thr Ile Ser Ser Leu Gln Pro
65                  70                 75                 80

Glu Asp Phe Ala Thr Tyr Tyr Cys Gln Gln Ser Asn Ser Trp Pro Tyr
                85                 90                 95

Thr Phe Gly Gln Gly Thr Lys Leu Glu Ile Lys
                100                 105
```

<210> SEQ ID NO 86
<211> LENGTH: 321
<212> TYPE: DNA
<213> ORGANISM: Artificial Sequence
<220> FEATURE:

<223> OTHER INFORMATION: Synthetic nucleotide sequence

<400> SEQUENCE: 86

```
gacatccagc tgacccagtc tccatcctcc ctgtctgcat ctgtaggaga cagagtcacc    60
atcacttgcc gggcctccca gcggatcaac accgacctgc actggtatca gcagaaacca   120
gggaaagccc ctaaggtgct gatcaagttc gccagccaga ccatctccgg ggtcccatca   180
aggttcagtg gcagtggatc tgggacagat ttcactctca ccatcagcag tctgcaacct   240
gaagattttg caacttacta ctgtcagcag tccaactcct ggccctacac ctttggccag   300
gggaccaagc tggagatcaa a                                              321
```

<210> SEQ ID NO 87
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 87

```
Asp Ile Gln Leu Thr Gln Ser Pro Ser Ser Leu Ser Ala Ser Val Gly
 1               5                  10                  15
Asp Arg Val Thr Ile Thr Cys Arg Ala Ser Gln Arg Ile Asn Thr Asp
                20                  25                  30
Leu His Trp Tyr Gln Gln Lys Pro Gly Lys Ala Pro Lys Leu Leu Ile
            35                  40                  45
Tyr Phe Ala Ser Gln Thr Ile Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ser Asn Ser Trp Pro Tyr
                85                  90                  95
Thr Phe Gly Gln Gly Thr Lys Leu Glu Ile Lys
            100                 105
```

<210> SEQ ID NO 88
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 88

```
gacatccagc tgacccagtc tccatcctcc ctgtctgcat ctgtaggaga cagagtcacc    60
atcacttgcc gggcctccca gcggatcaac accgacctgc actggtatca gcagaaacca   120
gggaaagccc ctaagctcct gatctatttc gccagccaga ccatctccgg ggtcccatca   180
aggttcagtg gcagtggatc tgggacagat ttcactctca ccatcagcag tctgcaacct   240
gaagattttg caacttacta ctgtcagcag tccaactcct ggccctacac ctttggccag   300
gggaccaagc tggagatcaa a                                              321
```

<210> SEQ ID NO 89
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 89

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Asn Thr Asp
            20                  25                  30

Leu His Trp Tyr Gln Gln Lys Pro Gly Lys Ala Pro Lys Val Leu Ile
        35                  40                  45

Tyr Phe Ala Ser Gln Thr Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Tyr
                85                  90                  95

Thr Phe Gly Gln Gly Thr Lys Leu Glu Ile Lys
            100                 105
```

<210> SEQ ID NO 90
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 90

```
gacatccaga tgacccagtc tccatcctcc ctgtctgcat ctgtaggaga cagagtcacc    60
atcacttgcc gggcctccca gcggatcaac accgacctgc actggtatca gcagaaacca   120
gggaaagccc ctaaggtgct gatctatttc gccagccaga ccatctccgg ggtcccatca   180
aggttcagtg gcagtggatc tgggacagat ttcactctca ccatcagcag tctgcaacct   240
gaagattttg caacttacta ctgtcagcag tccaactcct ggccctacac ctttggccag   300
gggaccaagc tggagatcaa a                                             321
```

<210> SEQ ID NO 91
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 91

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Asn Thr Asp
            20                  25                  30

Leu His Trp Tyr Gln Gln Lys Pro Gly Lys Ala Pro Lys Leu Leu Ile
        35                  40                  45

Lys Phe Ala Ser Gln Thr Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Tyr
                85                  90                  95

Thr Phe Gly Gln Gly Thr Lys Leu Glu Ile Lys
            100                 105
```

<210> SEQ ID NO 92
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 92

```
gacatccaga tgacccagtc tccatcctcc ctgtctgcat ctgtaggaga cagagtcacc    60
atcacttgcc gggcctccca gcggatcaac accgacctgc actggtatca gcagaaacca   120
gggaaagccc ctaagctcct gatcaagttc gccagccaga ccatctccgg ggtcccatca   180
aggttcagtg gcagtggatc tgggacagat ttcactctca ccatcagcag tctgcaacct   240
gaagattttg caacttacta ctgtcagcag tccaactcct ggccctacac ctttggccag   300
gggaccaagc tggagatcaa a                                             321
```

<210> SEQ ID NO 93
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 93

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Arg Ile Asn Thr Asp
            20                  25                  30

Leu His Trp Tyr Gln Gln Lys Pro Gly Lys Ala Pro Lys Val Leu Ile
        35                  40                  45

Tyr Phe Ala Ser Gln Thr Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Tyr
                85                  90                  95

Thr Phe Gly Gln Gly Thr Lys Leu Glu Ile Lys
            100                 105
```

<210> SEQ ID NO 94
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 94

```
gacatccagc tgacccagtc tccatcctcc ctgtctgcat ctgtaggaga cagagtcacc    60
atcacttgcc gggcctccca gcggatcaac accgacctgc actggtatca gcagaaacca   120
gggaaagccc ctaaggtgct gatctatttc gccagccaga ccatctccgg ggtcccatca   180
aggttcagtg gcagtggatc tgggacagat ttcactctca ccatcagcag tctgcaacct   240
gaagattttg caacttacta ctgtcagcag tccaactcct ggccctacac ctttggccag   300
gggaccaagc tggagatcaa a                                             321
```

<210> SEQ ID NO 95
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 95

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Arg Ile Asn Thr Asp
                20                  25                  30

Leu His Trp Tyr Gln Gln Lys Pro Gly Lys Ala Pro Lys Leu Leu Ile
            35                  40                  45

Lys Phe Ala Ser Gln Thr Ile Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Tyr
                85                  90                  95

Thr Phe Gly Gln Gly Thr Lys Leu Glu Ile Lys
            100                 105
```

<210> SEQ ID NO 96
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 96

```
gacatccagc tgacccagtc tccatcctcc ctgtctgcat ctgtaggaga cagagtcacc      60
atcacttgcc gggcctccca gcggatcaac accgacctgc actggtatca gcagaaacca     120
gggaaagccc ctaagctcct gatcaagttc gccagccaga ccatctccgg ggtcccatca     180
aggttcagtg gcagtggatc tgggacagat ttcactctca ccatcagcag tctgcaacct     240
gaagattttg caacttacta ctgtcagcag tccaactcct ggccctacac ctttggccag     300
gggaccaagc tggagatcaa a                                               321
```

<210> SEQ ID NO 97
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 97

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Asn Thr Asp
                20                  25                  30

Leu His Trp Tyr Gln Gln Lys Pro Gly Lys Ala Pro Lys Val Leu Ile
            35                  40                  45

Lys Phe Ala Ser Gln Thr Ile Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Tyr
                85                  90                  95

Thr Phe Gly Gln Gly Thr Lys Leu Glu Ile Lys
            100                 105
```

<210> SEQ ID NO 98
<211> LENGTH: 321
<212> TYPE: DNA

```
<213> ORGANISM: Artificial Sequence
<220> FEATURE:
<223> OTHER INFORMATION: Synthetic nucleotide sequence

<400> SEQUENCE: 98
gacatccaga tgacccagtc tccatcctcc ctgtctgcat ctgtaggaga cagagtcacc      60
atcacttgcc gggcctccca gcggatcaac accgacctgc actggtatca gcagaaacca     120
gggaaagccc ctaaggtgct gatcaagttc gccagccaga ccatctccgg ggtcccatca     180
aggttcagtg gcagtggatc tgggacagat ttcactctca ccatcagcag tctgcaacct     240
gaagattttg caacttacta ctgtcagcag tccaactcct ggccctacac ctttggccag     300
gggaccaagc tggagatcaa a                                              321

<210> SEQ ID NO 99
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 99

Arg Ala Ser Gln Arg Ile Asn Thr Asp Leu His
1               5                   10

<210> SEQ ID NO 100
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 100
cgggcctccc agcggatcaa caccgacctg cac                                  33

<210> SEQ ID NO 101
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 101

Phe Ala Ser Gln Thr Ile Ser
1               5

<210> SEQ ID NO 102
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 102
ttcgccagcc agaccatctc c                                               21

<210> SEQ ID NO 103
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 103

Gln Gln Ser Asn Ser Trp Pro Tyr Thr
```

<210> SEQ ID NO 104
<211> LENGTH: 27
<212> TYPE: DNA
<213> ORGANISM: Artificial Sequence
<220> FEATURE:
<223> OTHER INFORMATION: Synthetic nucleotide sequence

<400> SEQUENCE: 104
cagcagtcca actcctggcc ctacacc                                        27

<210> SEQ ID NO 105
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 105

Asp Ile Met Leu Thr Gln Ser Pro Ser Ser Leu Ser Ala Ser Val Gly
1               5                   10                  15

Asp Arg Val Thr Ile Thr Cys Arg Ala Ser Gln Arg Ile Asn Thr Asp
            20                  25                  30

Leu His Trp Tyr Gln Gln Lys Pro Gly Lys Ala Pro Lys Val Leu Ile
        35                  40                  45

Lys Phe Ala Ser Gln Thr Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Tyr
                85                  90                  95

Thr Phe Gly Gln Gly Thr Lys Leu Glu Ile Lys
            100                 105

<210> SEQ ID NO 106
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 106
gacatcatgc tgacccagtc tccatcctcc ctgtctgcat ctgtaggaga cagagtcacc        60
atcacttgcc gggcctccca gcggatcaac accgacctgc actggtatca gcagaaacca       120
gggaaagccc ctaaggtgct gatcaagttc gccagccaga ccatctccgg ggtcccatca       180
aggttcagtg gcagtggatc tgggacagat ttcactctca ccatcagcag tctgcaacct       240
gaagattttg caacttacta ctgtcagcag tccaactcct ggccctacac ctttggccag       300
gggaccaagc tggagatcaa a                                                321

<210> SEQ ID NO 107
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 107

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Arg Ile Asn Thr Asp
                 20                  25                  30

Leu His Trp Tyr Gln Gln Lys Pro Gly Lys Ala Pro Arg Val Leu Ile
             35                  40                  45

Lys Phe Ala Ser Gln Thr Ile Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Ser Trp Pro Tyr
                 85                  90                  95

Thr Phe Gly Gln Gly Thr Lys Leu Glu Ile Lys
            100                 105

<210> SEQ ID NO 108
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 108
gacatcatgc tgacccagtc tccatcctcc ctgtctgcat ctgtaggaga cagagtcacc     60
atcacttgcc gggcctccca gcggatcaac accgacctgc actggtatca gcagaaacca    120
gggaaagccc ctagggtgct gatcaagttc gccagccaga ccatctccgg ggtcccatca    180
aggttcagtg gcagtggatc tgggacagat ttcactctca ccatcagcag tctgcaacct    240
gaagattttg caacttacta ctgtcagcag tccaactcct ggccctacac ctttggccag    300
gggaccaagc tggagatcaa a                                              321

<210> SEQ ID NO 109
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 109

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Arg Ile Asn Thr Asp
                 20                  25                  30

Leu His Trp Tyr Gln Gln Lys Pro Gly Lys Ala Pro Arg Val Leu Ile
             35                  40                  45

Lys Phe Ala Ser Gln Thr Ile Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asn Ser Trp Pro Tyr
                 85                  90                  95

Thr Phe Gly Gln Gly Thr Lys Leu Glu Ile Lys
            100                 105

<210> SEQ ID NO 110
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 110

```
gacatccaga tgacccagtc tccatcctcc ctgtctgcat ctgtaggaga cagagtcacc    60
atcacttgcc gggcctccca gcggatcaac accgacctgc actggtatca gcagaaacca   120
gggaaagccc ctaggtgct gatcaagttc gccagccaga ccatctccgg ggtcccatca   180
aggttcagtg gcagtggatc tgggacagat ttcactctca ccatcagcag tctgcaacct   240
gaagattttg caacttacta ctgtcagcag tccaactcct ggccctacac ctttggccag   300
gggaccaagc tggagatcaa a                                             321
```

<210> SEQ ID NO 111
<211> LENGTH: 453
<212> TYPE: PRT
<213> ORGANISM: Artificial Sequence
<220> FEATURE:
<223> OTHER INFORMATION: Synthetic peptide sequence

<400> SEQUENCE: 111

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ala Trp Val Arg Gln Ala Pro Gly Lys Gly Leu Glu Trp Val
        35                  40                  45

Ala Ser Ile Ser Tyr Gly Gly Ala Asp Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Pro Tyr Tyr Gly Tyr Thr Pro Phe Val Met Asp Ala
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Ala Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285
```

```
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Glu Glu Met Thr Lys Asn Gln
        355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro Gly Lys
    450
```

<210> SEQ ID NO 112
<211> LENGTH: 1359
<212> TYPE: DNA
<213> ORGANISM: Artificial Sequence
<220> FEATURE:
<223> OTHER INFORMATION: Synthetic nucleotide sequence

<400> SEQUENCE: 112

```
gaggtgcagc tggtggagtc tgggggaggc ttggtccagc ctggggggtc cctgagactc      60
tcctgtgcag cctctggatt cacctttagt tccttcgcca tggcctgggt ccgccaggct     120
ccagggaagg gctgagtg gtggcctcc atctcctatg gaggcgctga cacctactac     180
cgggactccg tgaagggccg attcaccatc tccagagaca cgccaagaa ctcactgtat     240
ctgcaaatga acagcctgag agccgaggac acggctgtgt attactgtgc gaaggatctg     300
ccctactacg gctacacccc cttcgtgatg gacgcctggg gccagggaac cctggtcacc     360
gtctcctcag cgtcgaccaa gggcccatcg gtcttcccc tggcacccct ctccaagagc     420
acctctgggg gcacagcggc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca caccaaggt ggacaagaaa     660
gttgagccca atcttgtga caaaactcac acatgcccac cgtgcccagc acctgaagcc     720
gctgggcac cgtcagtctt cctcttcccc ccaaaaccca aggacaccct catgatctcc     780
cggacccctg aggtcacatg cgtggtggtg gacgtgagcc acgaagaccc tgaggtcaag     840
ttcaactggt acgtggacgg cgtggaggtg cataatgcca agacaaagcc gcggaggag     900
cagtacaaca gcacgtaccg tgtggtcagc gtcctcaccg tcctgcacca ggactggctg     960
aatggcaagg agtacaagtg caaggtctcc aacaaagccc tcccagcccc catcgagaaa    1020
accatctcca aagccaaagg gcagccccga gaaccacagg tgtacaccct gcccccatcc    1080
```

```
cgggaggaga tgaccaagaa ccaggtcagc ctgacctgcc tggtcaaagg cttctatccc    1140
agcgacatcg ccgtggagtg ggagagcaat gggcagccgg agaacaacta caagaccacg    1200
cctcccgtgc tggactccga cggctccttc ttcctctata gcaagctcac cgtggacaag    1260
agcaggtggc agcaggggaa cgtcttctca tgctccgtga tgcatgaggc tctgcacaac    1320
cactacacgc agaagagcct ctccctgtcc ccgggtaaa                           1359

<210> SEQ ID NO 113
<211> LENGTH: 214
<212> TYPE: PRT
<213> ORGANISM: Artificial Sequence
<220> FEATURE:
<223> OTHER INFORMATION: Synthetic peptide sequence

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Asn Thr Asp
            20                  25                  30

Leu His Trp Tyr Gln Gln Lys Pro Gly Lys Ala Pro Lys Val Leu Ile
        35                  40                  45

Lys Phe Ala Ser Gln Thr Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 114
<211> LENGTH: 642
<212> TYPE: DNA
<213> ORGANISM: Artificial Sequence
<220> FEATURE:
<223> OTHER INFORMATION: Synthetic nucleotide sequence

<400> SEQUENCE: 114
gacatcatgc tgacccagtc tccatcctcc ctgtctgcat ctgtaggaga cagagtcacc    60
atcacttgcc gggcctccca gcggatcaac accgacctgc actggtatca gcagaaacca    120
gggaaagccc ctagggtgct gatcaagttc gccagccaga ccatctccgg ggtcccatca    180
aggttcagtg gcagtggatc tgggacagat ttcactctca ccatcagcag tctgcaacct    240
```

```
gaagattttg caacttacta ctgtcagcag tccaactcct ggccctacac ctttggccag    300
gggaccaagc tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga aaaacacaaa gtctacgcct gcgaagtcac ccatcagggc    600
ctgagctcgc ccgtcacaaa gagcttcaac aggggagagt gt                      642
```

<210> SEQ ID NO 115
<211> LENGTH: 119
<212> TYPE: PRT
<213> ORGANISM: Artificial Sequence
<220> FEATURE:
<223> OTHER INFORMATION: Synthetic peptide sequence

<400> SEQUENCE: 115

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
            20                  25                  30

Gly Met Asn Trp Val Arg Gln Ala Pro Gly Lys Gly Leu Glu Trp Val
        35                  40                  45

Ala Ser Ile Ser Arg Ser Gly Ser Tyr Ile Arg Tyr Val Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gln Phe Gly Asp Tyr Phe Glu Tyr Trp Gly Gln Gly
            100                 105                 110

Thr Leu Val Thr Val Ser Ser
        115
```

<210> SEQ ID NO 116
<211> LENGTH: 357
<212> TYPE: DNA
<213> ORGANISM: Artificial Sequence
<220> FEATURE:
<223> OTHER INFORMATION: Synthetic nucleotide sequence

<400> SEQUENCE: 116

```
gaggtgcagc tggtggagtc tgggggaggc ttggtccagc ctggggggtc cctgagactc     60
tcctgtgcag cctctggatt cacctttagt cactacggca tgaactgggt ccgccaggct    120
ccagggaagg gctggagtg gtggcctcc atctccagat ccggctccta catcagatac    180
gtggacaccg tgaagggccg attcaccatc tccagagaca cgccaagaa ctcactgtat    240 ctgcaaatga acagcctgag agccgaggac acggctgtgt attactgtgc gagagagggc    300
cagttcggcg actacttcga gtactggggc cagggaaccc tggtcaccgt ctcctca      357
```

<210> SEQ ID NO 117
<211> LENGTH: 5
<212> TYPE: PRT
<213> ORGANISM: Artificial Sequence
<220> FEATURE:
<223> OTHER INFORMATION: Synthetic peptide sequence

```
<400> SEQUENCE: 117

His Tyr Gly Met Asn
1               5

<210> SEQ ID NO 118
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 118

Gly Phe Thr Phe Ser His Tyr Gly Met Asn
1               5                   10

<210> SEQ ID NO 119
<211> LENGTH: 15
<212> TYPE: DNA
<213> ORGANISM: Artificial Sequence
<220> FEATURE:
<223> OTHER INFORMATION: Synthetic nucleotide sequence

<400> SEQUENCE: 119
cactatggaa tgaac                                                      15

<210> SEQ ID NO 120
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 120
ggattcactt tcagtcacta tggaatgaac                                      30

<210> SEQ ID NO 121
<211> LENGTH: 17
<212> TYPE: PRT
<213> ORGANISM: Artificial Sequence
<220> FEATURE:
<223> OTHER INFORMATION: Synthetic peptide sequence

<400> SEQUENCE: 121

Ser Ile Ser Arg Ser Gly Ser Tyr Ile Arg Tyr Val Asp Thr Val Lys
1               5                   10                  15

Gly

<210> SEQ ID NO 122
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 122

Ser Arg Ser Gly Ser Tyr
1               5

<210> SEQ ID NO 123
<211> LENGTH: 51
<212> TYPE: DNA
<213> ORGANISM: Artificial Sequence
<220> FEATURE:
<223> OTHER INFORMATION: Synthetic nucleotide sequence

<400> SEQUENCE: 123
```
tctattagta ggagtggcag ttacatccgc tatgtagaca cagtgaaggg c    51

<210> SEQ ID NO 124
<211> LENGTH: 18
<212> TYPE: DNA
<213> ORGANISM: Artificial Sequence
<220> FEATURE:
<223> OTHER INFORMATION: Synthetic nucleotide sequence

<400> SEQUENCE: 124
agtaggagtg gcagttac    18

<210> SEQ ID NO 125
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 125

Glu Gly Gln Phe Gly Asp Tyr Phe Glu Tyr
1               5                   10

<210> SEQ ID NO 126
<211> LENGTH: 30
<212> TYPE: DNA
<213> ORGANISM: Artificial Sequence
<220> FEATURE:
<223> OTHER INFORMATION: Synthetic nucleotide sequence

<400> SEQUENCE: 126
gagggacaat tcggggacta ctttgagtac    30

<210> SEQ ID NO 127
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Thr Asn
            20                  25                  30

Leu His Trp Tyr Gln Gln Lys Pro Gly Lys Ala Pro Lys Leu Leu Ile
        35                  40                  45

Tyr Tyr Ala Ser Gln Thr Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Trp Pro Leu
                85                  90                  95

Thr Phe Gly Gly Gly Thr Lys Val Glu Ile Lys
            100                 105

<210> SEQ ID NO 128
<211> LENGTH: 321
<212> TYPE: DNA
<213> ORGANISM: Artificial Sequence
<220> FEATURE:
<223> OTHER INFORMATION: Synthetic nucleotide sequence

```
<400> SEQUENCE: 128
gacatccaga tgacccagtc tccatcctcc ctgtctgcat ctgtaggaga cagagtcacc    60
atcacttgcc gggcctccca agatctcc accaacctgc actggtatca gcagaaacca    120
gggaaagccc ctaagctcct gatctattac gcctctcaga ccatctccgg ggtcccatca    180
aggttcagtg gcagtggatc tgggacagat ttcactctca ccatcagcag tctgcaacct    240
gaagattttg caacttacta ctgtcagcag accaactcct ggcccctgac cttcggcgga    300
gggaccaagg tggagatcaa a                                              321

<210> SEQ ID NO 129
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Thr Asn
            20                  25                  30

Leu His Trp Tyr Gln Gln Lys Pro Gly Lys Ala Pro Lys Ile Leu Ile
        35                  40                  45

Lys Tyr Ala Ser Gln Thr Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Trp Pro Leu
                85                  90                  95

Thr Phe Gly Gly Gly Thr Lys Val Glu Ile Lys
            100                 105

<210> SEQ ID NO 130
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 130
gacatccaga tgacccagtc tccatcctcc ctgtctgcat ctgtaggaga cagagtcacc    60
atcacttgcc gggcctccca agatctcc accaacctgc actggtatca gcagaaacca    120
gggaaagccc ctaagatcct gatcaagtac gcctctcaga ccatctccgg ggtcccatca    180
aggttcagtg gcagtggatc tgggacagat ttcactctca ccatcagcag tctgcaacct    240
gaagattttg caacttacta ctgtcagcag accaactcct ggcccctgac cttcggcgga    300
gggaccaagg tggagatcaa a                                              321

<210> SEQ ID NO 131
<211> LENGTH: 11
<212> TYPE: PRT
<213> ORGANISM: Artificial Sequence
<220> FEATURE:
<223> OTHER INFORMATION: Synthetic peptide sequence

<400> SEQUENCE: 131

Arg Ala Ser Gln Lys Ile Ser Thr Asn Leu His
1               5                   10
```

<210> SEQ ID NO 132
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 132
agggccagtc agaaaattag cactaactta cat                                    33

<210> SEQ ID NO 133
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 133

Tyr Ala Ser Gln Thr Ile Ser
1               5

<210> SEQ ID NO 134
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 134
tatgcttccc agaccatctc t                                                 21

<210> SEQ ID NO 135
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 135

Gln Gln Thr Asn Ser Trp Pro Leu Thr Thr
1               5                   10

<210> SEQ ID NO 136
<211> LENGTH: 27
<212> TYPE: DNA
<213> ORGANISM: Artificial Sequence
<220> FEATURE:
<223> OTHER INFORMATION: Synthetic nucleotide sequence

<400> SEQUENCE: 136
caacagacta atagttggcc gctcacg                                           27

<210> SEQ ID NO 137
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 137

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Lys Ile Ser Thr Asn
            20                  25                  30

```
Leu His Trp Tyr Gln Gln Lys Pro Gly Lys Ala Pro Lys Leu Leu Ile
         35                  40                  45

Tyr Tyr Ala Ser Gln Thr Ile Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Asn Ser Trp Pro Leu
                 85                  90                  95

Thr Phe Gly Gly Gly Thr Lys Val Glu Ile Lys
            100                 105
```

<210> SEQ ID NO 138
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 138

```
gacatccagc tgacccagtc tccatcctcc ctgtctgcat ctgtaggaga cagagtcacc    60
atcacttgcc gggcctccca gaagatctcc accaacctgc actggtatca gcagaaacca   120
gggaaagccc ctaagctcct gatctattac gcctctcaga ccatctccgg ggtcccatca   180
aggttcagtg gcagtggatc tgggacagat ttcactctca ccatcagcag tctgcaacct   240
gaagattttg caacttacta ctgtcagcag accaactcct ggcccctgac cttcggcgga   300
gggaccaagg tggagatcaa a                                             321
```

<210> SEQ ID NO 139
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 139

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Lys Ile Ser Thr Asn
                 20                  25                  30

Leu His Trp Tyr Gln Gln Lys Pro Gly Lys Ala Pro Lys Ile Leu Ile
         35                  40                  45

Tyr Tyr Ala Ser Gln Thr Ile Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Asn Ser Trp Pro Leu
                 85                  90                  95

Thr Phe Gly Gly Gly Thr Lys Val Glu Ile Lys
            100                 105
```

<210> SEQ ID NO 140
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 140

```
gacatccaga tgacccagtc tccatcctcc ctgtctgcat ctgtaggaga cagagtcacc    60
```

```
atcacttgcc gggcctccca gaagatctcc accaacctgc actggtatca gcagaaacca    120
gggaaagccc ctaagatcct gatctattac gcctctcaga ccatctccgg ggtcccatca    180
aggttcagtg gcagtggatc tgggacagat ttcactctca ccatcagcag tctgcaacct    240
gaagattttg caacttacta ctgtcagcag accaactcct ggcccctgac cttcggcgga    300
gggaccaagg tggagatcaa a    321
```

<210> SEQ ID NO 141
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 141

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Lys Ile Ser Thr Asn
            20                  25                  30

Leu His Trp Tyr Gln Gln Lys Pro Gly Lys Ala Pro Lys Leu Leu Ile
        35                  40                  45

Lys Tyr Ala Ser Gln Thr Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Trp Pro Leu
                85                  90                  95

Thr Phe Gly Gly Gly Thr Lys Val Glu Ile Lys
            100                 105
```

<210> SEQ ID NO 142
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 142

```
gacatccaga tgacccagtc tccatcctcc ctgtctgcat ctgtaggaga cagagtcacc     60
atcacttgcc gggcctccca gaagatctcc accaacctgc actggtatca gcagaaacca    120
gggaaagccc ctaagctcct gatcaagtac gcctctcaga ccatctccgg ggtcccatca    180
aggttcagtg gcagtggatc tgggacagat ttcactctca ccatcagcag tctgcaacct    240
gaagattttg caacttacta ctgtcagcag accaactcct ggcccctgac cttcggcgga    300
gggaccaagg tggagatcaa a    321
```

<210> SEQ ID NO 143
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 143

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Lys Ile Ser Thr Asn
            20                  25                  30
```

```
Leu His Trp Tyr Gln Gln Lys Pro Gly Lys Ala Pro Lys Ile Leu Ile
            35                  40                  45

Tyr Tyr Ala Ser Gln Thr Ile Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Asn Ser Trp Pro Leu
                 85                  90                  95

Thr Phe Gly Gly Gly Thr Lys Val Glu Ile Lys
            100                 105
```

<210> SEQ ID NO 144
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 144

```
gacatccagc tgacccagtc tccatcctcc ctgtctgcat ctgtaggaga cagagtcacc    60
atcacttgcc gggcctccca gaagatctcc accaacctgc actggtatca gcagaaacca   120
gggaaagccc ctaagatcct gatctattac gcctctcaga ccatctccgg ggtcccatca   180
aggttcagtg gcagtggatc tgggacagat ttcactctca ccatcagcag tctgcaacct   240
gaagattttg caacttacta ctgtcagcag accaactcct ggcccctgac cttcggcgga   300
gggaccaagg tggagatcaa a                                             321
```

<210> SEQ ID NO 145
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 145

```
Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Lys Ile Ser Thr Asn
             20                  25                  30

Leu His Trp Tyr Gln Gln Lys Pro Gly Lys Ala Pro Lys Leu Leu Ile
            35                  40                  45

Lys Tyr Ala Ser Gln Thr Ile Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Asn Ser Trp Pro Leu
                 85                  90                  95

Thr Phe Gly Gly Gly Thr Lys Val Glu Ile Lys
            100                 105
```

<210> SEQ ID NO 146
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 146

```
gacatccagc tgacccagtc tccatcctcc ctgtctgcat ctgtaggaga cagagtcacc    60
atcacttgcc gggcctccca gaagatctcc accaacctgc actggtatca gcagaaacca   120
gggaaagccc ctaagctcct gatcaagtac gcctctcaga ccatctccgg ggtcccatca   180
aggttcagtg gcagtggatc tgggacagat ttcactctca ccatcagcag tctgcaacct   240
gaagattttg caacttacta ctgtcagcag accaactcct ggcccctgac cttcggcgga   300
gggaccaagg tggagatcaa a                                             321
```

<210> SEQ ID NO 147
<211> LENGTH: 107
<212> TYPE: PRT
<213> ORGANISM: Artificial Sequence
<220> FEATURE:
<223> OTHER INFORMATION: Synthetic peptide sequence

<400> SEQUENCE: 147

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Lys Ile Ser Thr Asn
                20                  25                  30

Leu His Trp Tyr Gln Gln Lys Pro Gly Lys Ala Pro Lys Ile Leu Ile
            35                  40                  45

Lys Tyr Ala Ser Gln Thr Ile Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Trp Pro Leu
                85                  90                  95

Thr Phe Gly Gly Gly Thr Lys Val Glu Ile Lys
            100                 105
```

<210> SEQ ID NO 148
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 148

```
gacatccagc tgacccagtc tccatcctcc ctgtctgcat ctgtaggaga cagagtcacc    60
atcacttgcc gggcctccca gaagatctcc accaacctgc actggtatca gcagaaacca   120
gggaaagccc ctaagatcct gatcaagtac gcctctcaga ccatctccgg ggtcccatca   180
aggttcagtg gcagtggatc tgggacagat ttcactctca ccatcagcag tctgcaacct   240
gaagattttg caacttacta ctgtcagcag accaactcct ggcccctgac cttcggcgga   300
gggaccaagg tggagatcaa a                                             321
```

<210> SEQ ID NO 149
<211> LENGTH: 449
<212> TYPE: PRT
<213> ORGANISM: Artificial Sequence
<220> FEATURE:
<223> OTHER INFORMATION: Synthetic peptide sequence

<400> SEQUENCE: 149

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
```

-continued

```
                20                  25                  30
Gly Met Asn Trp Val Arg Gln Ala Pro Gly Lys Gly Leu Glu Trp Val
                35                  40                  45

Ala Ser Ile Ser Arg Ser Gly Ser Tyr Ile Arg Tyr Val Asp Thr Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Gln Phe Gly Asp Tyr Phe Glu Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Ala Ala Gly Ala Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445
```

Lys

<210> SEQ ID NO 150
<211> LENGTH: 357
<212> TYPE: DNA
<213> ORGANISM: Artificial Sequence
<220> FEATURE:
<223> OTHER INFORMATION: Synthetic nucleotide sequence

<400> SEQUENCE: 150

```
gaggtgcagc tggtggagtc tgggggaggc ttggtccagc ctggggggtc cctgagactc      60
tcctgtgcag cctctggatt cacctttagt cactacggca tgaactgggt ccgccaggct     120
ccagggaagg gctggagtg gtggcctcc atctccagat ccggctccta catcagatac     180
gtggacaccg tgaagggccg attcaccatc tccagagaca cgccaagaa ctcactgtat     240
ctgcaaatga acagcctgag agccgaggac acggctgtgt attactgtgc gagagagggc     300
cagttcggcg actacttcga gtactggggc cagggaaccc tggtcaccgt ctcctca       357
```

<210> SEQ ID NO 151
<211> LENGTH: 214
<212> TYPE: PRT
<213> ORGANISM: Artificial Sequence
<220> FEATURE:
<223> OTHER INFORMATION: Synthetic peptide sequence

<400> SEQUENCE: 151

Asp Ile Gln Met Thr Gln Ser Pro Ser Leu Ser Ala Ser Val Gly
1               5                   10                  15

Asp Arg Val Thr Ile Thr Cys Arg Ala Ser Gln Lys Ile Ser Thr Asn
                20                  25                  30

Leu His Trp Tyr Gln Gln Lys Pro Gly Lys Ala Pro Lys Ile Leu Ile
            35                  40                  45

Lys Tyr Ala Ser Gln Thr Ile Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 152

-continued

```
<211> LENGTH: 321
<212> TYPE: DNA
<213> ORGANISM: Artificial Sequence
<220> FEATURE:
<223> OTHER INFORMATION: Synthetic nucleotide sequence

<400> SEQUENCE: 152
gacatccaga tgacccagtc tccatcctcc ctgtctgcat ctgtaggaga cagagtcacc      60
atcacttgcc gggcctccca gaagatctcc accaacctgc actggtatca gcagaaacca     120
gggaaagccc ctaagatcct gatcaagtac gcctctcaga ccatctccgg ggtcccatca     180
aggttcagtg gcagtggatc tgggacagat ttcactctca ccatcagcag tctgcaacct     240
gaagattttg caacttacta ctgtcagcag accaactcct ggcccctgac cttcggcgga     300
gggaccaagg tggagatcaa a                                               321
```